(12) United States Patent
Bi et al.

(10) Patent No.: US 12,083,118 B2
(45) Date of Patent: Sep. 10, 2024

(54) SUBSTITUTED 1,1'-BIPHENYL COMPOUNDS, ANALOGUES THEREOF, AND METHODS USING SAME

(71) Applicant: Arbutus Biopharma Corporation, Burnaby (CA)

(72) Inventors: Yingzhi Bi, Plainsboro, NJ (US); Bruce D. Dorsey, Ambler, PA (US); Yi Fan, Doylestown, PA (US); Christopher Brooks Moore, Jamison, PA (US); Duyan Nguyen, Ambler, PA (US)

(73) Assignee: Arbutus Biopharma Corporation, Vancouver (CA)

( * ) Notice: Subject to any disclaimer, the term of this patent is extended or adjusted under 35 U.S.C. 154(b) by 0 days.

(21) Appl. No.: 16/982,842

(22) PCT Filed: Mar. 29, 2019

(86) PCT No.: PCT/US2019/024896
§ 371 (c)(1),
(2) Date: Sep. 21, 2020

(87) PCT Pub. No.: WO2019/191624
PCT Pub. Date: Oct. 3, 2019

(65) Prior Publication Data
US 2021/0052585 A1  Feb. 25, 2021

Related U.S. Application Data

(60) Provisional application No. 62/662,032, filed on Apr. 24, 2018, provisional application No. 62/650,054, filed on Mar. 29, 2018.

(51) Int. Cl.
| | |
|---|---|
| *A61K 31/506* | (2006.01) |
| *A61K 31/137* | (2006.01) |
| *A61K 31/277* | (2006.01) |
| *A61K 31/4164* | (2006.01) |
| *A61K 31/444* | (2006.01) |
| *A61K 31/445* | (2006.01) |
| *A61K 31/4545* | (2006.01) |
| *A61K 31/505* | (2006.01) |
| *A61K 45/06* | (2006.01) |
| *C07C 217/58* | (2006.01) |
| *C07C 255/61* | (2006.01) |
| *C07D 211/60* | (2006.01) |
| *C07D 233/26* | (2006.01) |
| *C07D 239/06* | (2006.01) |
| *C07D 401/12* | (2006.01) |
| *C07D 401/14* | (2006.01) |

(52) U.S. Cl.
CPC .......... *A61K 31/506* (2013.01); *A61K 31/137* (2013.01); *A61K 31/277* (2013.01); *A61K 31/4164* (2013.01); *A61K 31/444* (2013.01); *A61K 31/445* (2013.01); *A61K 31/4545* (2013.01); *A61K 31/505* (2013.01); *A61K 45/06* (2013.01); *C07C 217/58* (2013.01); *C07C 255/61* (2013.01); *C07D 211/60* (2013.01); *C07D 233/26* (2013.01); *C07D 239/06* (2013.01); *C07D 401/12* (2013.01); *C07D 401/14* (2013.01)

(58) Field of Classification Search
CPC .. C07D 401/14; C07D 401/12; C07D 239/06; C07D 233/26; C07D 211/60; C07C 255/61; A61K 31/505
USPC .......................................................... 514/210
See application file for complete search history.

(56) References Cited

U.S. PATENT DOCUMENTS

| | | | |
|---|---|---|---|
| 4,263,319 A | 4/1981 | Engel | |
| 4,346,251 A | 8/1982 | Engel | |
| 4,636,508 A | 1/1987 | Brewer et al. | |
| 4,879,276 A | 11/1989 | Brewer | |
| 5,663,368 A | 9/1997 | Flisak et al. | |
| 6,806,272 B2 | 10/2004 | Bauer et al. | |
| 7,875,614 B2 | 1/2011 | Buchstaller et al. | |
| 8,383,623 B2 | 2/2013 | Zhu et al. | |
| 8,633,182 B2 | 1/2014 | Hamprecht et al. | |
| 8,642,585 B2 | 2/2014 | Eckhardt et al. | |
| 9,403,763 B2 | 8/2016 | Sodroski et al. | |
| 9,617,251 B2 | 4/2017 | Eckhardt et al. | |
| 9,957,219 B2 | 5/2018 | Bara et al. | |
| 9,988,343 B2 | 6/2018 | Mazitschek et al. | |
| 10,125,101 B2 | 11/2018 | Eckhardt et al. | |
| 10,144,706 B2 * | 12/2018 | Yeung | C07C 235/08 |
| 10,335,388 B2 | 7/2019 | Josey et al. | |
| 10,392,405 B2 | 8/2019 | Malathong et al. | |
| 10,550,127 B1 | 2/2020 | Eckhardt et al. | |

(Continued)

FOREIGN PATENT DOCUMENTS

| | | |
|---|---|---|
| CN | 108395443 A | 8/2018 |
| CN | 108727453 A | 11/2018 |

(Continued)

OTHER PUBLICATIONS

Machine translation WO 2017202275.*

(Continued)

*Primary Examiner* — Ana Z Muresan
(74) *Attorney, Agent, or Firm* — Saul Ewing LLP; Domingos J. Silva; Kevin T. O'Brien

(57) ABSTRACT

The present invention includes substituted 3,3'bis(phenoxymethyl)-1,1'-biphenyl compounds, analogues thereof, and compositions comprising the same, that can be used to treat or prevent hepatitis B virus (HBV) and/or hepatitis D virus (HDV) infections in a patient.

26 Claims, No Drawings

(56) References Cited

U.S. PATENT DOCUMENTS

| | | | |
|---|---|---|---|
| 10,568,874 B2 | 2/2020 | Lange et al. | |
| 10,639,284 B2 | 5/2020 | Lange et al. | |
| 10,774,071 B2 | 9/2020 | Aktoudianakis et al. | |
| 10,807,948 B2 | 10/2020 | Dixon et al. | |
| 10,919,852 B2 | 2/2021 | Lange et al. | |
| 2006/0035938 A1 | 2/2006 | Bladh et al. | |
| 2010/0022482 A1 | 1/2010 | Baumann et al. | |
| 2014/0243196 A1 | 8/2014 | Deshmukh et al. | |
| 2015/0291549 A1 | 10/2015 | Chupak et al. | |
| 2016/0171150 A1 | 6/2016 | Walensky et al. | |
| 2017/0107202 A1 | 4/2017 | Yeung et al. | |
| 2017/0107216 A1 | 4/2017 | Wu et al. | |
| 2017/0143737 A1 | 5/2017 | Soong | |
| 2017/0144996 A1 | 5/2017 | Chen et al. | |
| 2017/0144997 A1 | 5/2017 | Chen et al. | |
| 2017/0145025 A1 | 5/2017 | Li et al. | |
| 2017/0174679 A1 | 6/2017 | Lajkiewicz et al. | |
| 2017/0362253 A1 | 12/2017 | Xiao et al. | |
| 2018/0057455 A1 | 3/2018 | Yeung et al. | |
| 2018/0057486 A1 | 3/2018 | Wu et al. | |
| 2018/0065917 A1* | 3/2018 | Webber | C07D 401/14 |
| 2018/0177870 A1 | 6/2018 | Liu et al. | |
| 2018/0305315 A1 | 10/2018 | Aktoudianakis et al. | |
| 2019/0117654 A1 | 4/2019 | Warrell et al. | |
| 2019/0135834 A1 | 5/2019 | Tamura et al. | |
| 2019/0270727 A1 | 9/2019 | Aktoudianakis et al. | |
| 2019/0308957 A1 | 10/2019 | Wang et al. | |
| 2019/0337906 A1 | 11/2019 | Yang et al. | |
| 2020/0017471 A1 | 1/2020 | Aktoudianakis et al. | |
| 2020/0157094 A1 | 5/2020 | Du et al. | |
| 2020/0223833 A1 | 7/2020 | Kang et al. | |
| 2021/0008049 A1 | 1/2021 | Malathong et al. | |

FOREIGN PATENT DOCUMENTS

| | | | |
|---|---|---|---|
| CN | 109096219 A | 12/2018 | |
| CN | 109232498 A | 1/2019 | |
| CN | 109665968 A | 4/2019 | |
| CN | 109721527 A | 5/2019 | |
| CN | 109776377 A | 5/2019 | |
| CN | 109776445 A | 5/2019 | |
| CN | 110092745 A | 8/2019 | |
| CN | 110200959 A | 9/2019 | |
| CN | 110240587 A | 9/2019 | |
| CN | 109045036 B | 10/2020 | |
| NO | 2015034820 A1 | 3/2015 | |
| NO | 2018009505 A1 | 1/2018 | |
| WO | 9745403 A1 | 12/1997 | |
| WO | 9931063 A1 | 6/1999 | |
| WO | 0147867 A1 | 7/2001 | |
| WO | 2006097176 A1 | 9/2006 | |
| WO | 2008053199 A1 | 5/2008 | |
| WO | 2008127274 A2 | 10/2008 | |
| WO | 2011051535 A1 | 5/2011 | |
| WO | 2011130478 A1 | 10/2011 | |
| WO | 2012003912 A1 | 1/2012 | |
| WO | 2013006394 A1 | 1/2013 | |
| WO | 2013033228 A1 | 3/2013 | |
| WO | 2013033258 A1 | 3/2013 | |
| WO | 2014165128 A2 | 10/2014 | |
| WO | 2015069693 A1 | 5/2015 | |
| WO | 2015160641 A2 | 10/2015 | |
| WO | 2016025932 A1 | 2/2016 | |
| WO | 2016025933 A2 | 2/2016 | |
| WO | 2016039937 A1 | 3/2016 | |
| WO | 2016039938 A1 | 3/2016 | |
| WO | 2016039939 A1 | 3/2016 | |
| WO | 2016109706 A1 | 7/2016 | |
| WO | 2016168524 A1 | 10/2016 | |
| WO | 2017015451 A1 | 1/2017 | |
| WO | 2017042121 A1 | 3/2017 | |
| WO | 2017066227 A1 | 4/2017 | |
| WO | 2017070284 A1 | 4/2017 | |
| WO | 2017087777 A1 | 5/2017 | |
| WO | 2017106634 A1 | 6/2017 | |
| WO | 2017140728 A1 | 8/2017 | |
| WO | 2017192961 A1 | 11/2017 | |
| WO | 2017205464 A1 | 11/2017 | |
| WO | WO 2017202275 | * 11/2017 | |
| WO | 2018005192 A1 | 1/2018 | |
| WO | 2018005193 A1 | 1/2018 | |
| WO | 2018005374 A1 | 1/2018 | |
| WO | 2018006795 A1 | 1/2018 | |
| WO | 2018013789 A1 | 1/2018 | |
| WO | 2018026971 A1 | 2/2018 | |
| WO | 2018044963 A1 | 3/2018 | |
| WO | 2018045142 A1 | 3/2018 | |
| WO | 2018047109 A1 | 3/2018 | |
| WO | 2018118848 A1 | 6/2018 | |
| WO | 2018119221 A1 | 6/2018 | |
| WO | 2018119224 A1 | 6/2018 | |
| WO | 2018119236 A1 | 6/2018 | |
| WO | 2018119263 A1 | 6/2018 | |
| WO | 2018119266 A1 | 6/2018 | |
| WO | 2018119286 A1 | 6/2018 | |
| WO | 2018121560 A1 | 7/2018 | |
| WO | 2018183171 A1 | 10/2018 | |
| WO | 2018195321 A1 | 10/2018 | |
| WO | 2018196768 A1 | 11/2018 | |
| WO | 2018237153 A1 | 12/2018 | |
| WO | 2019076343 A1 | 4/2019 | |
| WO | 2019087214 A1 | 5/2019 | |
| WO | 2019149183 A1 | 8/2019 | |
| WO | 2019160882 A1 | 8/2019 | |
| WO | 2019169123 A1 | 9/2019 | |
| WO | 2019174533 A1 | 9/2019 | |
| WO | 2019175897 A1 | 9/2019 | |
| WO | 2019191624 A1 | 10/2019 | |
| WO | 2019192506 A1 | 10/2019 | |
| WO | 2019204609 A1 | 10/2019 | |
| WO | 2019217821 A1 | 11/2019 | |
| WO | 2020011209 A1 | 1/2020 | |
| WO | 2020011243 A1 | 1/2020 | |
| WO | 2020011246 A1 | 1/2020 | |
| WO | 2020014643 A1 | 1/2020 | |
| WO | 2020047035 A1 | 3/2020 | |
| WO | 2020206000 A1 | 10/2020 | |
| WO | 2021147940 A1 | 7/2021 | |
| WO | 2022208269 A2 | 10/2022 | |
| WO | 2023108108 A1 | 6/2023 | |

OTHER PUBLICATIONS

Chen, et al., "Toward Supramolecular Ion Channels Formed by Oligonucleotide Analogs: Hydrophobic Guanine Dimers", Tetrahedron Letters, vol. 39, 1998, pp. 3627-3630.

Gao, et al., "A high-yield synthesis of [m]biphenyl-extended pillar[n]arenes for an efficient selective inclusion of toluene and m-xylene in the solid state", Chem Comm, vol. 52, 2016, pp. 5804-5807.

Guzik, et al., "Small-Molecule Inhibitors of the Programmed Cell Death-1/Programmed Death-Ligand 1 (PD-1/PD-L1) Interaction via Transiently Induced Protein States and Dimerization of PD-L1", J Med Chem, vol. 60, No. 13, 2017, pp. 5857-5867.

Jaquinod, et al., "Biphenyl-Strapped Diphenylporphyrins: Synthesis and Spectroscopic Characterization of a Series of Porphyrins with Ether-Linked Straps. Preliminary CO Binding Properties of Their Iron(II) Derivatives", Inorg Chem, vol. 37, 1998, pp. 1142-1149.

Kim, et al., "An Effective Antiviral Approach Targeting Hapatitis B Virus with NJK14047, a Novel and Selective Biphenyl Amide p38 Mitogen-Activated Protein Kinase Inhibitor", Antimicrobial Agents and Chemotherapy, vol. 61, No. 8, 10 pages, 2017, e00214-17.

Leoni, et al., "HIV, HCV and HBV: A Review of Parallels and Differences", Infect Dis Ther, vol. 7, 2018, pp. 407-419.

Liu, "Structural basis of anti-PD-L1 monoclonal antibody avelumab for tumor therapy", Cell Res, vol. 27, 2017, pp. 151-153.

Ohaegbulam, et al., "Human cancer immunotherapy with antibodies to the PD-1 and PD-L1 pathway", Trends in Mol Med, vol. 21, No. 1, Jan. 2015, pp. 24-33.

Shaabani , et al., "A patent review on PD-1/PD-L1 antagonists: small molecules, peptides and macrocycles (2015-2018)", Expert

(56) References Cited

OTHER PUBLICATIONS

Opinion on Therapeutic Patents, DOI: 10.1080/13543776.2018. 1512706, 2018, pp. 1-22.
Teranishi, "Regioselective 2A,2D-disulfonyl capping of beta-cyclodextrin for practical bifunctionalization on the secondary hydroxyl face", Tetrahedron Lett, vol. 42, 2001, pp. 5477-5480.
Zak, et al., "Structural basis for small molecule targeting of the programmed death ligand 1 (PD-L1)", ImpactJournals.com/Oncotarget, Advance Publications, Apr. 13, 2016, pp. 1-13.
Zak, et al., "Structure of the Complex of Human Programmed Death 1, PD-1, and Its Ligand PD-L1", Structure, vol. 23, 2015, pp. 2341-2348.
Koniarczyk, et al., "A Pyridine-Pyridine Cross-Coupling Reaction via Dearomatized Radical Intermediates", Angew Chem Int Ed, vol. 58, 2019, pp. 14882-14886.

\* cited by examiner

SUBSTITUTED 1,1'-BIPHENYL COMPOUNDS, ANALOGUES THEREOF, AND METHODS USING SAME

CROSS-REFERENCE TO RELATED APPLICATIONS

The present application is a 35 U.S.C. § 371 national phase application of, and claims priority to, International Application No. PCT/US2019/024896, filed Mar. 29, 2019, which claims priority under 35 U.S.C. § 119(e) to U.S. Provisional Patent Applications No. 62/650,054, filed Mar. 29, 2018, and No. 62/662,032, filed Apr. 24, 2018, all of which are incorporated herein by reference in their entireties.

BACKGROUND OF THE INVENTION

Hepatitis B virus is a noncytopathic, liver tropic DNA virus belonging to Hepadnaviridae family. Hepatitis B viral infection is one of the world's most prevalent diseases, being listed by National Institute of Allergy and Infectious Diseases (NIAID) as a High Priority Area of Interest. Although most individuals resolve the infection following acute symptoms, approximately 30% of cases become chronic. 350-400 million people worldwide are estimated to have chronic hepatitis B, leading to 0.5-1 million deaths per year, due largely to the development of hepatocellular carcinoma, cirrhosis and/or other complications.

A limited number of drugs are currently approved for the management of chronic hepatitis B, including two formulations of alpha-interferon (standard and pegylated) and five nucleoside/nucleotide analogues (lamivudine, adefovir, entecavir, telbivudine, and tenofovir) that inhibit hepatitis B virus (HBV) DNA polymerase. At present, the first-line treatment choices are entecavir, tenofovir and/or peg-interferon alfa-2a. However, peg-interferon alfa-2a achieves desirable serological milestones in only one third of treated patients, and is frequently associated with severe side effects. Entecavir and tenofovir are potent HBV inhibitors, but require long-term or possibly lifetime administration to continuously suppress HBV replication, and may eventually fail due to emergence of drug-resistant viruses. There is thus a pressing need for the introduction of novel, safe and effective therapies for chronic hepatitis B.

Hepatitis D virus (HDV) is a small circular enveloped RNA virus that can propagate only in the presence of HBV. In particular, HDV requires the HBV surface antigen protein to propagate itself. Infection with both HBV and HDV results in more severe complications compared to infection with HBV alone. These complications include a greater likelihood of experiencing liver failure in acute infections and a rapid progression to liver cirrhosis, with an increased chance of developing liver cancer in chronic infections. In combination with hepatitis B virus, hepatitis D has the highest mortality rate of all the hepatitis infections. The routes of transmission of HDV are similar to those for HBV. Infection is largely restricted to persons at high risk of HBV infection, particularly injecting drug users and persons receiving clotting factor concentrates.

Currently, there is no effective antiviral therapy available for the treatment of acute or chronic type D hepatitis. Interferon-alfa, given weekly for 12 to 18 months, is the only licensed treatment for hepatitis D. Response to this therapy is limited-in only about one-quarter of patients is serum HDV RNA undetectable 6 months post therapy.

There is a need in the art for the identification of novel compounds that can be used to treat and/or prevent HBV infection in a subject. In certain embodiments, the novel compounds can be used in patients that are HBV infected, patients who are at risk of becoming HBV infected, and/or patients that are infected with drug-resistant HBV. In other embodiments, the HBV-infected subject is further HDV-infected. The present invention addresses this need.

BRIEF SUMMARY OF THE INVENTION

The invention provides certain compounds of formula (I), or a salt, solvate, geometric isomer, stereoisomer, tautomer and any mixtures thereof, wherein the substituents in (I) are defined elsewhere herein:

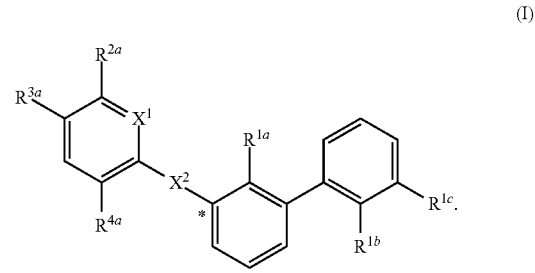

(I)

The invention further provides pharmaceutical compositions comprising at least one compound of the invention. In certain embodiments, the pharmaceutical compositions further comprise at least one pharmaceutically acceptable carrier. In other embodiments, the pharmaceutical compositions further comprise at least one additional agent that treats or prevents hepatitis virus infection. In yet other embodiments, the hepatitis virus is hepatitis B virus (HBV). In yet other embodiments, the hepatitis virus is hepatitis D virus (HDV).

The invention further provides a method of treating or preventing hepatitis virus infection in a subject. In certain embodiments, the method comprises administering to the subject a therapeutically effective amount of a compound of the invention, or a salt, solvate, prodrug, stereoisomer, tautomer, or any mixtures thereof. In other embodiments, the subject is infected with HBV. In yet other embodiments, the subject is infected with HDV. In yet other embodiments, the subject is infected with HBV and HDV. In yet other embodiments, the subject is further administered at least one additional agent useful for treating the hepatitis virus infection. In yet other embodiments, the subject is in need of the treatment or prevention.

DETAILED DESCRIPTION OF THE INVENTION

The invention relates, in certain aspects, to the discovery that certain substituted 3,3'-bis(phenoxymethyl)-1,1'-biphenyl compounds are useful to treat and/or prevent hepatitis B virus (HBV) infection and/or hepatitis B virus-hepatitis D virus (HBV-HDV) infection and related conditions in a subject. In certain embodiments, these compounds are administered along with at least one additional agent useful for treating and/or preventing the viral infection. In other embodiments, the subject is infected with HBV. In yet other embodiments, the HBV-infected subject is further infected with HDV.

Definitions

As used herein, each of the following terms has the meaning associated with it in this section. Unless defined otherwise, all technical and scientific terms used herein generally have the same meaning as commonly understood by one of ordinary skill in the art to which this invention belongs. Generally, the nomenclature used herein and the laboratory procedures in animal pharmacology, pharmaceutical science, separation science and organic chemistry are those well-known and commonly employed in the art. It should be understood that the order of steps or order for performing certain actions is immaterial, so long as the present teachings remain operable. Moreover, two or more steps or actions can be conducted simultaneously or not.

As used herein, the articles "a" and "an" refer to one or to more than one (i.e., to at least one) of the grammatical object of the article. By way of example, "an element" means one element or more than one element.

As used herein, the term "alkenyl," employed alone or in combination with other terms, means, unless otherwise stated, a stable monounsaturated or diunsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—CH=$CH_2$.

As used herein, the term "alkoxy" employed alone or in combination with other terms means, unless otherwise stated, an alkyl group having the designated number of carbon atoms, as defined elsewhere herein, connected to the rest of the molecule via an oxygen atom, such as, for example, methoxy, ethoxy, 1-propoxy, 2-propoxy (or isopropoxy) and the higher homologs and isomers. A specific example is ($C_1$-$C_3$)alkoxy, such as, but not limited to, ethoxy and methoxy.

As used herein, the term "alkyl" by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. A specific embodiment is ($C_1$-$C_6$) alkyl, such as, but not limited to, ethyl, methyl, isopropyl, isobutyl, n-pentyl, n-hexyl and cyclopropylmethyl.

As used herein, the term "alkynyl" employed alone or in combination with other terms means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —$CH_2$—C≡CH. The term "homopropargylic" refers to a group exemplified by —$CH_2CH_2$—C≡CH.

As used herein, the term "aromatic" refers to a carbocycle or heterocycle with one or more polyunsaturated rings and having aromatic character, i.e., having (4n+2) delocalized π (pi) electrons, where 'n' is an integer.

As used herein, the term "aryl" employed alone or in combination with other terms means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl and naphthyl. Aryl groups also include, for example, phenyl or naphthyl rings fused with one or more saturated or partially saturated carbon rings (e.g., bicyclo[4.2.0]octa-1,3,5-trienyl, or indanyl), which can be substituted at one or more carbon atoms of the aromatic and/or saturated or partially saturated rings.

As used herein, the term "aryl-($C_1$-$C_6$)alkyl" refers to a functional group wherein a one to six carbon alkylene chain is attached to an aryl group, e.g., —$CH_2CH_2$-phenyl or —$CH_2$-phenyl (or benzyl). Specific examples are aryl-$CH_2$— and aryl-CH($CH_3$)—. The term "substituted aryl-($C_1$-$C_6$)alkyl" refers to an aryl-($C_1$-$C_6$)alkyl functional group in which the aryl group is substituted. A specific example is substituted aryl($CH_2$)—. Similarly, the term "heteroaryl-($C_1$-$C_6$)alkyl" refers to a functional group wherein a one to three carbon alkylene chain is attached to a heteroaryl group, e.g., —$CH_2CH_2$-pyridyl. A specific example is heteroaryl-($CH_2$)—. The term "substituted heteroaryl-($C_1$-$C_6$)alkyl" refers to a heteroaryl-($C_1$-$C_6$)alkyl functional group in which the heteroaryl group is substituted. A specific example is substituted heteroaryl-($CH_2$)—.

In one aspect, the terms "co-administered" and "co-administration" as relating to a subject refer to administering to the subject a compound and/or composition of the invention along with a compound and/or composition that may also treat or prevent a disease or disorder contemplated herein. In certain embodiments, the co-administered compounds and/or compositions are administered separately, or in any kind of combination as part of a single therapeutic approach. The co-administered compound and/or composition may be formulated in any kind of combinations as mixtures of solids and liquids under a variety of solid, gel, and liquid formulations, and as a solution.

As used herein, the term "cycloalkyl" by itself or as part of another substituent refers to, unless otherwise stated, a cyclic chain hydrocarbon having the number of carbon atoms designated (i.e., $C_3$-$C_6$ refers to a cyclic group comprising a ring group consisting of three to six carbon atoms) and includes straight, branched chain or cyclic substituent groups. Examples of ($C_3$-$C_6$)cycloalkyl groups are cyclopropyl, cyclobutyl, cyclopentyl and cyclohexyl. Cycloalkyl rings can be optionally substituted. Non-limiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

As used herein, a "disease" is a state of health of a subject wherein the subject cannot maintain homeostasis, and wherein if the disease is not ameliorated then the subject's health continues to deteriorate.

As used herein, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, the term "halide" refers to a halogen atom bearing a negative charge. The halide anions are fluoride (F), chloride (CF), bromide (BC), and iodide (1).

As used herein, the term "halo" or "halogen" alone or as part of another substituent refers to, unless otherwise stated, a fluorine, chlorine, bromine, or iodine atom.

As used herein, the term "Hepatitis B virus" (or HBV) refers to a virus species of the genus Orthohepadnavirus, which is a part of the Hepadnaviridae family of viruses, and that is capable of causing liver inflammation in humans.

As used herein, the term "Hepatitis D virus" (or HDV) refers to a virus species of the genus Deltaviridae, which is capable of causing liver inflammation in humans. The HDV particle comprises an envelope, which is provided by HBV and surrounds the RNA genome and the HDV antigen. The HDV genome is a single, negative stranded, circular RNA molecule nearly 1.7 kb in length. The genome contains several sense and antisense open reading frames (ORFs), only one of which is functional and conserved. The RNA genome is replicated through an RNA intermediate, the antigenome. The genomic RNA and its complement, the antigenome, can function as ribozymes to carry out self-cleavage and self-ligation reactions. A third RNA present in the infected cell, also complementary to the genome, but 800 bp long and polyadenylated, is the mRNA for the synthesis of the delta antigen (HDAg).

As used herein, the term "heteroalkenyl" by itself or in combination with another term refers to, unless otherwise stated, a stable straight or branched chain monounsaturated or diunsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—CH$_3$, —CH=CH—CH$_2$—OH, —CH$_2$—CH=N—OCH$_3$, —CH=CH—N(CH$_3$)—CH$_3$, and —CH$_2$—CH=CH—CH$_2$—SH.

As used herein, the term "heteroalkyl" by itself or in combination with another term refers to, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —OCH$_2$CH$_2$CH$_3$, —CH$_2$CH$_2$CH$_2$OH, —CH$_2$CH$_2$NHCH$_3$, —CH$_2$SCH$_2$CH$_3$, and —CH$_2$CH$_2$S(=O)CH$_3$. Up to two heteroatoms may be consecutive, such as, for example, —CH$_2$NH—OCH$_3$, or —CH$_2$CH$_2$SSCH$_3$.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

As used herein, the term "heterocycle" or "heterocyclyl" or "heterocyclic" by itself or as part of another substituent refers to, unless otherwise stated, an unsubstituted or substituted, stable, mono- or multi-cyclic heterocyclic ring system that comprises carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "pharmaceutical composition" or "composition" refers to a mixture of at least one compound useful within the invention with a pharmaceutically acceptable carrier. The pharmaceutical composition facilitates administration of the compound to a subject.

As used herein, the term "pharmaceutically acceptable" refers to a material, such as a carrier or diluent, which does not abrogate the biological activity or properties of the compound useful within the invention, and is relatively non-toxic, i.e., the material may be administered to a subject without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" refers to a salt of the administered compound prepared from pharmaceutically acceptable non-toxic acids and/or bases, including inorganic acids, inorganic bases, organic acids, inorganic bases, solvates (including hydrates) and clathrates thereof.

As used herein, a "pharmaceutically effective amount," "therapeutically effective amount" or "effective amount" of a compound is that amount of compound that is sufficient to provide a beneficial effect to the subject to which the compound is administered.

The term "prevent," "preventing" or "prevention" as used herein means avoiding or delaying the onset of symptoms associated with a disease or condition in a subject that has not developed such symptoms at the time the administering of an agent or compound commences. Disease, condition and disorder are used interchangeably herein.

By the term "specifically bind" or "specifically binds" as used herein is meant that a first molecule preferentially binds to a second molecule (e.g., a particular receptor or enzyme), but does not necessarily bind only to that second molecule.

As used herein, the terms "subject" and "individual" and "patient" can be used interchangeably and may refer to a human or non-human mammal or a bird. Non-human mammals include, for example, livestock and pets, such as ovine, bovine, porcine, canine, feline and murine mammals. In certain embodiments, the subject is human.

As used herein, the term "substituted" refers to that an atom or group of atoms has replaced hydrogen as the substituent attached to another group.

As used herein, the term "substituted alkyl," "substituted cycloalkyl," "substituted alkenyl" or "substituted alkynyl" refers to alkyl, cycloalkyl, alkenyl or alkynyl, as defined elsewhere herein, substituted by one, two or three substituents independently selected from the group consisting of halogen, —OH, alkoxy, tetrahydro-2-H-pyranyl, —NH$_2$, —NH(C$_1$-C$_6$ alkyl), —N(C$_1$-C$_6$ alkyl)$_2$, 1-methyl-imidazol-2-yl, pyridin-2-yl, pyridin-3-yl, pyridin-4-yl, —C(=O)OH, —C(=O)O(C$_1$-C$_6$)alkyl, trifluoromethyl, —C(=O)NH$_2$, —C(=O)NH(C$_1$-C$_6$)alkyl, —C(=O)N((C$_1$-C$_6$)alkyl)$_2$, —SO$_2$NH$_2$, —SO$_2$NH(C$_1$-C$_6$ alkyl), —SO$_2$N(C$_1$-C$_6$ alkyl)$_2$, —C(=NH)NH$_2$, and —NO$_2$, in certain embodiments containing one or two substituents independently selected from halogen, —OH, alkoxy, —NH$_2$, trifluoromethyl, —N(CH$_3$)$_2$, and —C(=O)OH, in certain embodiments independently selected from halogen, alkoxy and —OH. Examples of substituted alkyls include, but are not limited to, 2,2-difluoropropyl, 2-carboxycyclopentyl and 3-chloropropyl.

For aryl, aryl-(C$_1$-C$_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet another embodiments, the substituents vary in number between one and two. In yet other embodiments, the substituents are independently selected from the group consisting of C$_1$-C$_6$ alkyl, —OH, C$_1$-C$_6$ alkoxy, halo, amino, acetamido and nitro. As used herein, where a substituent is an alkyl or alkoxy group, the carbon chain may be branched, straight or cyclic.

In certain embodiments, each occurrence of alkyl or cycloalkyl is independently optionally substituted with at least one substituent selected from the group consisting of C$_1$-C$_6$ alkyl, halo, —OR, phenyl (thus yielding, in non-limiting examples, optionally substituted phenyl-(C$_1$-C$_3$ alkyl), such as, but not limited to, benzyl or substituted benzyl) and —N(R)(R), wherein each occurrence of R is independently H, C$_1$-C$_6$ alkyl or C$_3$-C$_8$ cycloalkyl. In other embodiments, each occurrence of aryl or heteroaryl is independently optionally substituted with at least one substituent selected from the group consisting of C$_1$-C$_6$ alkyl, C$_1$-C$_6$ haloalkyl, C$_1$-C$_6$ haloalkoxy, halo, —CN, —OR, —N(R)(R), —NO$_2$, —S(=O)$_2$N(R)(R), acyl, and C$_1$-C$_6$ alkoxycarbonyl, wherein each occurrence of R is independently H, C$_1$-C$_6$ alkyl or C$_3$-C$_8$ cycloalkyl. In yet other embodiments, each occurrence of aryl or heteroaryl is independently optionally substituted with at least one substituent selected from the group consisting of C$_1$-C$_6$ alkyl, C$_1$-C$_6$ haloalkyl, C$_1$-C$_6$ haloalkoxy, halo, —CN, —OR, —N(R)(R), and C$_1$-C$_6$ alkoxycarbonyl, wherein each occurrence of R is independently H, C$_1$-C$_6$ alkyl or C$_3$-C$_8$ cycloalkyl.

Unless otherwise noted, when two substituents are taken together to form a ring having a specified number of ring atoms (e.g., R$^2$ and R$^3$ taken together with the nitrogen to which they are attached to form a ring having from 3 to 7 ring members), the ring can have carbon atoms and optionally one or more (e.g., 1 to 3) additional heteroatoms independently selected from nitrogen, oxygen, or sulfur. The ring can be saturated or partially saturated, and can be optionally substituted.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given elsewhere herein for "alkyl" and "aryl" respectively.

In certain embodiments, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_4$, $C_1$-$C_3$, $C_2$-$C_6$, $C_2$-$C_5$, $C_3$-$C_5$, $C_4$-$C_5$, and $C_5$-$C_6$ alkyl.

The terms "treat," "treating" and "treatment," as used herein, means reducing the frequency or severity with which symptoms of a disease or condition are experienced by a subject by virtue of administering an agent or compound to the subject.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual and partial numbers within that range, for example, 1, 2, 2.7, 3, 4, 5, 5.3, and 6. This applies regardless of the breadth of the range.

Compounds

Programmed death-ligand 1 (PD-L1), which is also known as cluster of differentiation 274 (CD274) or B7 homolog 1 (B7-H1), is a human transmembrane protein that plays a major role in suppressing the immune system as needed. Generally, the presence of a foreign antigen in the body triggers proliferation of antigen-specific CD8+ T cells in the lymph nodes. However, binding of PD-L1 to the receptor programmed cell death protein 1 (PD-1) or B7.1 membrane protein (both of which are found on activated T cells, B cells, and myeloid cells), transmits an inhibitory signal, which reduces proliferation of the CD8+ T cells in the lymph nodes. Such interaction effectively suppresses the immune response and avoids detection and destruction of the antigens.

In certain embodiments, small-molecule immunomodulators targeting the PD-1/PD-L1 signaling pathway are used to treat and/or prevent hepatitis B virus (HBV) infection and related conditions in a subject. In other embodiments, inhibition of PDL-1 enhances the immune response to at least one HBV antigen.

The invention include a compound of formula (I), or a salt, solvate, prodrug, stereoisomer (such as, in a non-limiting example, an enantiomer or diastereoisomer, and any mixtures thereof, such as, in a non-limiting example, mixtures in any proportion of enantiomers and/or diastereoisomers thereof), tautomer, and/or geometric isomer, and any mixtures thereof. It should be noted that the absolute stereochemistry of the chiral center(s) represented in any structure depicted herein and/or compound named herein is merely illustrative and non-limiting.

In certain embodiments, the compound of formula (I) is:

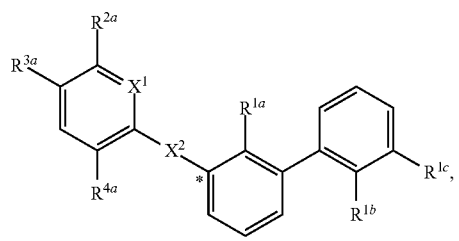

(I)

wherein in (I):

$X^1$ is selected from the group consisting of CH and N;

$X^2$ is selected from the group consisting of —$OCH_2$—, —$CH_2O$—, —$C(=O)NH$—, and —$NHC(=O)$—, wherein the bond marked with *** is to the phenyl ring carbon marked with *;

$R^{1a}$ is selected from the group consisting of H, $C_1$-$C_3$ alkyl, $C_1$-$C_3$ alkoxy, cyano, halogen, and $C_1$-$C_3$ haloalkyl;

$R^{1b}$ is selected from the group consisting of H, $C_1$-$C_3$ alkyl, $C_1$-$C_3$ alkoxy, cyano, halogen, and $C_1$-$C_3$ haloalkyl;

$R^{1c}$ is selected from the group consisting of H, $C_1$-$C_6$ alkyl, —OH, $C_1$-$C_6$ alkoxy optionally substituted with at least one selected from the group consisting of OH, $C_1$-$C_6$ alkoxy, phenyl, and optionally substituted heterocyclyl (such as but not limited to piperidinyl, pipyrolidinyl, or morpholinyl, and hydroxylated derivatives thereof),

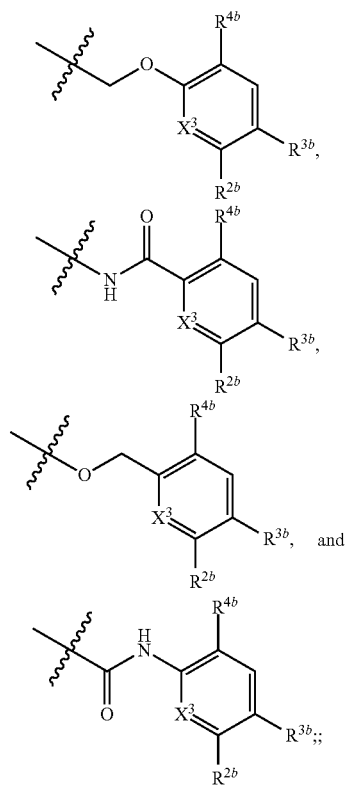

$X^3$ is selected from the group consisting of CH and N;

$R^{2a}$ is selected from the group consisting of $C_1$-$C_6$ alkyl, $C_1$-$C_6$ alkoxy, —$(CH_2)_{1-3}$ (optionally substituted phenyl), —$(CH_2)_{1-3}$ (optionally substituted heteroaryl), —$O(CH_2)_{1-3}$ (optionally substituted phenyl), —$O(CH_2)_{1-3}$ (optionally substituted heteroaryl), —$(CH_2)_{1-3}C(=O)OR^I$, —$(CH_2)_{1-3}C(=O)NR^IR^I$, —$O(CH_2)_{1-3}C(=O)OR^I$, and —$O(CH_2)_{1-3}C(=O)NR^IR^I$, wherein each occurrence of $R^I$ is independently H or $C_1$-$C_6$ alkyl optionally substituted with halogen, —OH, $C_1$-$C_6$ alkoxy, —$NH_2$, —$NH(C_1$-$C_6$ alkyl), and —$N(C_1$-$C_6$ alkyl)($C_1$-$C_6$ alkyl, or two $R^I$ can combine with the N atom to which they are bound to form 3-8 membered optionally substituted heterocyclyl;

$R^{2b}$ is selected from the group consisting of $C_1$-$C_6$ alkyl, $C_1$-$C_6$ alkoxy, —$(CH_2)_{1-3}$ (optionally substituted phenyl), —$(CH_2)_{1-3}$ (optionally substituted heteroaryl), —$O(CH_2)_{1-3}$ (optionally substituted phenyl), —$O(CH_2)_{1-3}$ (optionally substituted heteroaryl), —$(CH_2)_{1-3}C(=O)OR^{II}$, —$(CH_2)_{1-3}C(=O)NR^{II}R^{II}$, —$O(CH_2)_{1-3}C(=O)OR^{II}$, and —$O(CH_2)_{1-3}C(=O)NR^{II}R^{II}$, wherein each occurrence of $R^{II}$ is independently H or $C_1$-$C_6$ alkyl optionally substituted with halogen, —OH, $C_1$-$C_6$ alkoxy, —$NH_2$, —$NH(C_1$-$C_6$ alkyl), and —$N(C_1$-$C_6$ alkyl)($C_1$-$C_6$ alkyl), or two $R^{II}$ can combine with the N atom to which they are bound to form 3-8 membered optionally substituted heterocyclyl, $R^{3a}$ is selected from the group consisting of —CHO, —C(O)OR$^{III}$, —C(=O)NR$^{III}$R$^{III}$, —C(=NR$^5$)NR$^{III}$R$^{III}$, optionally substituted heterocyclyl, —$(CH_2)_{1-3}$ (optionally substituted heterocyclyl), optionally substituted $C_1$-$C_6$ alkoxy, optionally substituted $C_1$-$C_6$ aminoalkyl, and optionally substituted $C_1$-$C_6$ hydroxyalkyl, wherein each occurrence of $R^{III}$ is independently H or $C_1$-$C_6$ alkyl optionally substituted with halogen, —OH, $C_1$-$C_6$ alkoxy, —$NH_2$, —$NH(C_1$-$C_6$ alkyl), and —$N(C_1$-$C_6$ alkyl)($C_1$-$C_6$ alkyl), wherein each occurrence of $R^5$ is independently H or $C_1$-$C_6$ alkyl optionally substituted with halogen, —OH, $C_1$-$C_6$ alkoxy, —$NH_2$, —$NH(C_1$-$C_6$ alkyl), and —$N(C_1$-$C_6$ alkyl)($C_1$-$C_6$ alkyl), or two $R^{III}$ can combine with the N atom to which they are bound to form 3-8 membered optionally substituted heterocyclyl, or, if $R^{3a}$ is —C(=NR$^5$)NR$^{III}$R$^{III}$, then $R^5$ and one $R^{III}$ can combine to form 4-8 membered optionally substituted heterocyclyl;

$R^{3b}$ is selected from the group consisting of —CHO, —C(O)OR$^{IV}$, —C(=O)NR$^{IV}$R$^{IV}$, —C(=NR$^5$)NR$^{IV}$R$^{IV}$, optionally substituted heterocyclyl, —$(CH_2)_{1-3}$ (optionally substituted heterocyclyl), optionally substituted $C_1$-$C_6$ alkoxy, optionally substituted $C_1$-$C_6$ aminoalkyl, and optionally substituted $C_1$-$C_6$ hydroxyalkyl, wherein each occurrence of $R^{IV}$ is independently H or $C_1$-$C_6$ alkyl optionally substituted with halogen, —OH, $C_1$-$C_6$ alkoxy, —$NH_2$, —$NH(C_1$-$C_6$ alkyl), and —$N(C_1$-$C_6$ alkyl)($C_1$-$C_6$ alkyl), wherein each occurrence of $R^5$ is independently H or $C_1$-$C_6$ alkyl optionally substituted with halogen, —OH, $C_1$-$C_6$ alkoxy, —$NH_2$, —$NH(C_1$-$C_6$ alkyl), and —$N(C_1$-$C_6$ alkyl)($C_1$-$C_6$ alkyl), or two $R^{IV}$ can combine with the N atom to which they are bound to form 3-8 membered optionally substituted heterocyclyl, or, if $R^{3b}$ is —C(=NR$^5$)NR$^{IV}$R$^{IV}$, then $R^5$ and one $R^{IV}$ can combine to form 4-8 membered optionally substituted heterocyclyl;

$R^{4a}$ is selected from the group consisting of halogen, cyano, and $C_1$-$C_3$ alkyl; and $R^{4b}$ is selected from the group consisting of halogen, cyano, and $C_1$-$C_3$ alkyl;

or a salt, solvate, geometric isomer, stereoisomer, tautomer and any mixtures thereof.

In certain embodiments, the compound of formula (I) is:

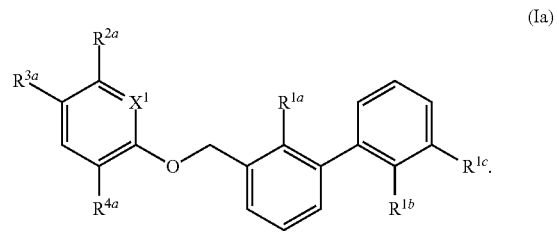

(Ia)

In certain embodiments, the compound of formula (I) is:

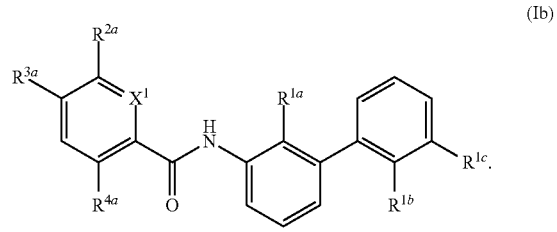

(Ib)

In certain embodiments, the compound of formula (I) is:

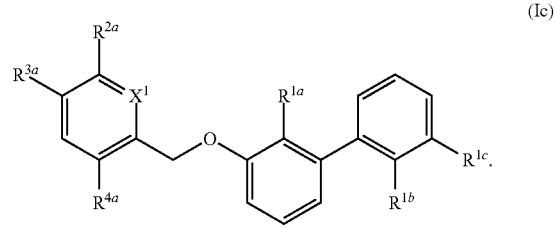

(Ic)

In certain embodiments, the compound of formula (I) is:

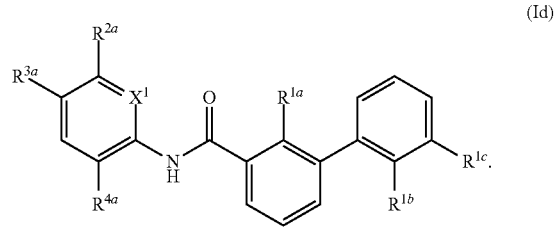

(Id)

In certain embodiments, $R^{1a}$ is identical to $R^{1b}$. In other embodiments, $R^{1a}$ is not identical to $R^{1b}$. In yet other embodiments, $R^{1a}$ is methyl. In yet other embodiments, $R^{1b}$ is methyl. In yet other embodiments, $R^{1a}$ is H. In yet other embodiments, $R^{1b}$ is H. In yet other embodiments, $R^{1a}$ is Cl. In yet other embodiments, $R^{1b}$ is Cl.

In certain embodiments, $R^{1c}$ is H. In other embodiments, $R^{1c}$ is —$O(CH_2)_{1-6}$-(hydroxypiperidinyl).

In certain embodiments, $R^{2a}$ is identical to $R^{2b}$. In other embodiments, $R^{2a}$ is not identical to $R^{2b}$. In yet other embodiments, $R^{2a}$ is selected from the group consisting of $C_1$-$C_6$ alkoxy, —$CH_2$ (optionally substituted pyridinyl), —$O(CH_2)_{1-3}C(=O)OH$, and —$O(CH_2)_{1-3}C(=O)O(C_1$-$C_6$ alkyl). In yet other embodiments, $R^{2b}$ is selected from the group consisting of $C_1$-$C_6$ alkoxy, —$CH_2$ (optionally substituted pyridinyl), —$O(CH_2)_{1-3}C(=O)OH$, and —$O(CH_2)_{1-3}C(=O)O(C_1$-$C_6$ alkyl).

In certain embodiments, $R^{3a}$ is identical to $R^{3b}$. In other embodiments, $R^{3a}$ is not identical to $R^{3b}$.

In certain embodiments, $R^{3a}$ is selected from the group consisting of —CHO, —$CH_2OH$, —$C(=NH)NH_2$, —$(CH_2)_{0-1}$ (optionally substituted piperidinyl), —$(CH_2)_{0-1}$ (optionally substituted tetrahydropyrimidinyl), —$(CH_2)_{0-1}$ (optionally substituted imidazolyl), —$(CH_2)_{0-1}$ (optionally substituted dihydroimidazolyl), —$C(=O)NH(C_1$-$C_6$ hydroxyalkyl), $CH_2NH(C_1$-$C_6$ haloalkyl), $CH_2NH(C_1$-$C_6$ hydroxyalkyl), —$CH_2N(C_1$-$C_6$ hydroalkyl)($C_1$-$C_6$ hydroalkyl), —$CH_2NH(C_1$-$C_6$ aminoalkyl), —$CH_2NH(C_1$-$C_6$ acetamidoalkyl), —$CH_2NH$—$CH[C(=O)OH](CH_2)_{1-6}OH$, and —$CH_2NH$—$CH[C(=O)OC_1$-$C_6$alkyl]$(CH_2)_{1-6}OH$.

In certain embodiments, $R^{3a}$ is selected from the group consisting of —$C(=NH)NH_2$, —$(CH_2)_{0-1}$ (optionally substituted piperidinyl), —$(CH_2)_{0-1}$ (optionally substituted tetrahydropyrimidinyl), —$(CH_2)_{0-1}$ (optionally substituted imidazolyl), and —$(CH_2)_{0-1}$ (optionally substituted dihydroimidazolyl).

In certain embodiments, in $R^{3a}$ the —$C(=NH)NH_2$, piperidinyl, tetrahydropyrimidinyl, imidazolyl, or dihydroimidazolyl is optionally substituted with at least one selected from the group consisting of $C_1$-$C_6$ alkyl, $C_1$-$C_6$ hydroxyalkyl, $C_1$-$C_6$ aminoalkyl, $C_1$-$C_6$N-acylaminoalkyl, —$(CH_2)_{0-3}C(=O)OH$, —$(CH_2)_{0-3}C(=O)O(C_1$-$C_6$ alkyl), —OH, $C_1$-$C_6$ alkoxy, —$O(CH_2)_{0-3}C(=O)OH$, or —$O(CH_2)_{0-3}C(=O)O(C_1$-$C_6$ alkyl).

In certain embodiments, $R^{3b}$ is selected from the group consisting of —CHO, —$CH_2OH$, —$C(=NH)NH_2$, —$(CH_2)_{0-1}$ (optionally substituted piperidinyl), —$(CH_2)_{0-1}$ (optionally substituted tetrahydropyrimidinyl), —$(CH_2)_{0-1}$ (optionally substituted imidazolyl), —$(CH_2)_{0-1}$ (optionally substituted dihydroimidazolyl), —$C(=O)NH(C_1$-$C_6$ hydroxyalkyl), —$CH_2NH(C_1$-$C_6$ haloalkyl), —$CH_2NH(C_1$-$C_6$ hydroxyalkyl), —$CH_2N(C_1$-$C_6$ hydroxyalkyl)($C_1$-$C_6$ hydroxyalkyl), —$CH_2NH(C_1$-$C_6$ aminoalkyl), —$CH_2NH(C_1$-$C_6$ acetamidoalkyl), —$CH_2NH$—$CH[C(=O)OH](CH_2)_{1-6}OH$, and —$CH_2NH$—$CH[C(=O)OC_1$-$C_6$alkyl]$(CH_2)_{1-6}OH$.

In certain embodiments, $R^{3b}$ is selected from the group consisting of —$C(=NH)NH_2$, —$(CH_2)_{0-1}$ (optionally substituted piperidinyl), —$(CH_2)_{0-1}$ (optionally substituted tetrahydropyrimidinyl), —$(CH_2)_{0-1}$ (optionally substituted imidazolyl), and —$(CH_2)_{0-1}$ (optionally substituted dihydroimidazolyl).

In certain embodiments, in $R^{3b}$ the —$C(=NH)NH_2$, piperidinyl, tetrahydropyrimidinyl, imidazolyl, or dihydroimidazolyl is optionally substituted with at least one selected from the group consisting of $C_1$-$C_6$ alkyl, $C_1$-$C_6$ hydroxyalkyl, $C_1$-$C_6$ aminoalkyl, $C_1$-$C_6$N-acylaminoalkyl, —$(CH_2)_{0-3}C(=O)OH$, —$(CH_2)_{0-3}C(=O)O(C_1$-$C_6$ alkyl), —OH, $C_1$-$C_6$ alkoxy, —$O(CH_2)_{0-3}C(=O)OH$, or —$O(CH_2)_{0-3}C(=O)O(C_1$-$C_6$ alkyl).

In certain embodiments, $R^{4a}$ is identical to $R^{4b}$. In other embodiments, $R^{4a}$ is not identical to $R^{4b}$. In other embodiments, $R^{4a}$ is chloro. In yet other embodiments, $R^{4b}$ is chloro.

In certain embodiments, the heterocyclyl is selected from the group consisting of imidazolyl, dihydroimidazolyl, piperidinyl, piperazinyl, morpholinyl, pyrrolidinyl, and tetrahydropyrimidinyl.

In certain embodiments, the heteroaryl is selected from the group consisting of pyridinyl, pyrimidinyl, pyrrolyl, oxazolyl, isoxazolyl, oxadiazolyl, imidazolyl, pyrazolyl, and triazolyl.

In certain embodiments, each occurrence of alkyl or cycloalkyl is independently optionally substituted with at least one substituent selected from the group consisting of $C_1$-$C_6$ alkyl, halo, —CN, —OR, phenyl (thus yielding, in non-limiting examples, optionally substituted phenyl-($C_1$-$C_3$ alkyl), such as, but not limited to, benzyl or substituted benzyl), and —N(R)(R), wherein each occurrence of R is independently H, $C_1$-$C_6$ alkyl, or $C_3$-$C_8$ cycloalkyl.

In certain embodiments, each occurrence of phenyl, heterocyclyl, or heteroaryl is independently optionally substituted with at least one substituent selected from the group consisting of $C_1$-$C_6$ alkyl, $C_1$-$C_6$ haloalkyl, $C_1$-$C_6$ alkoxy, $C_1$-$C_6$ haloalkoxy, halo, —CN, —C(=O)OR, —OR, —N(R)(R), —$NO_2$, —$S(=O)_2N(R)(R)$, acyl, and $C_1$-$C_6$ alkoxycarbonyl, wherein each occurrence of R is independently H, $C_1$-$C_6$ alkyl, or $C_3$-$C_8$ cycloalkyl.

In certain embodiments, the compound of formula (I) is selected from the group consisting of:

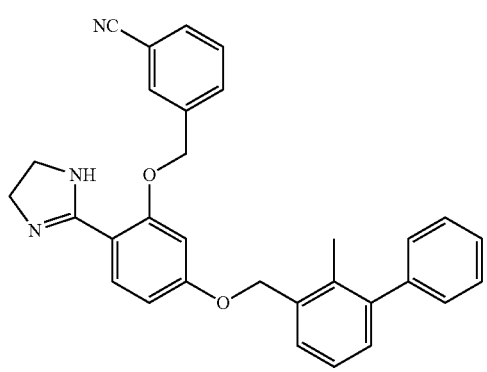 [SMILES: Cc1c(COc2ccc(C3=NCCN3)c(OCc3cccc(C#N)c3)c2)cccc1-c1ccccc1]

1

3-((2-(4,5-dihydro-1H-imidazol-2-yl)-5-((2-methyl-[1,1'-biphenyl]-3-yl)methoxy)phenoxy)methyl)benzonitrile;

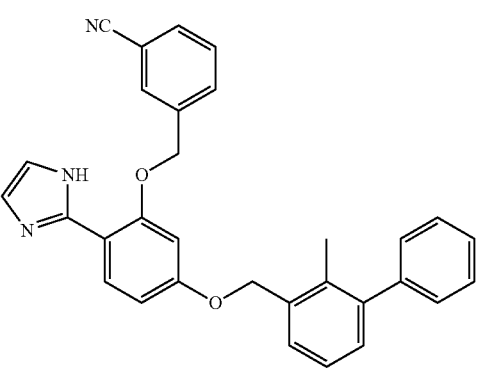

2

3-((2-(1H-imidazol-2-yl)-5-((2-methyl-[1,1'-biphenyl]-3-yl)methoxy)phenoxy)methyl)benzonitrile;

-continued

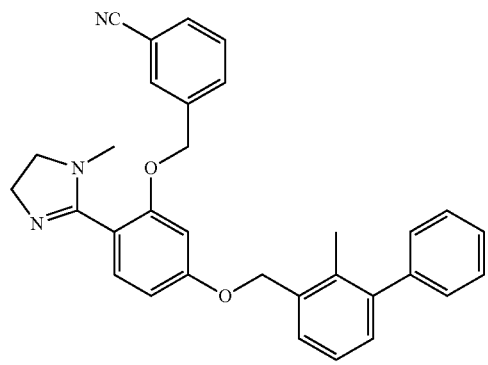

3-((2-(1-methyl-4,5-dihydro-1H-imidazol-2-yl)-5-((2-methyl-[1,1'-biphenyl]-3-yl)methoxy)phenoxy)methyl)benzonitrile;

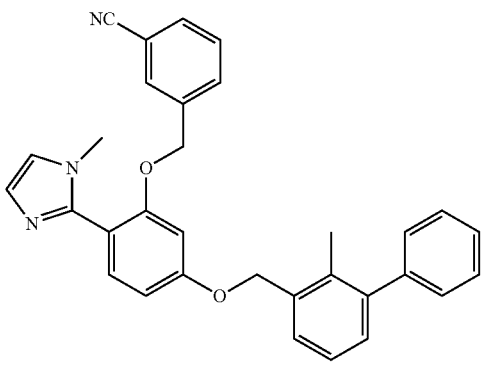

3-((2-(1-methyl-1H-imidazol-2-yl)-5-((2-methyl-[1,1'-biphenyl]-3-yl)methoxy)phenoxy)methyl)benzonitrile;

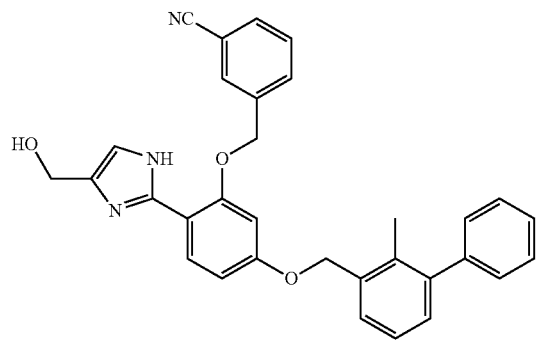

3-((2-(4-(hydroxymethyl)-1H-imidazol-2-yl)-5-((2-methyl-[1,1'-biphenyl]-3-yl)methoxy)phenoxy)methyl)benzonitrile;

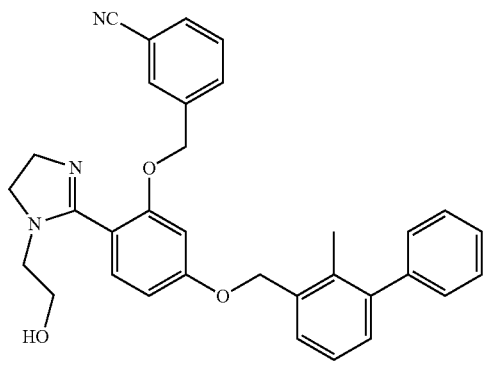

3-((2-(1-(2-hydroxyethyl)-4,5-dihydro-1H-imidazol-2-yl)-5-((2-methyl-[1,1'-biphenyl]-3-yl)methoxy)phenoxy)methyl)benzonitrile;

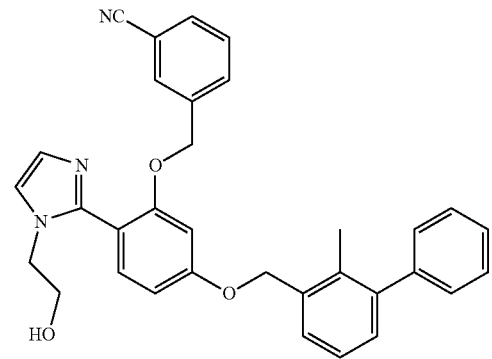

3-((2-(1-(2-hydroxyethyl)-1H-imidazol-2-yl)-5-((2-methyl-[1,1'-biphenyl]-3-yl)methoxy)phenoxy)methyl)benzonitrile;

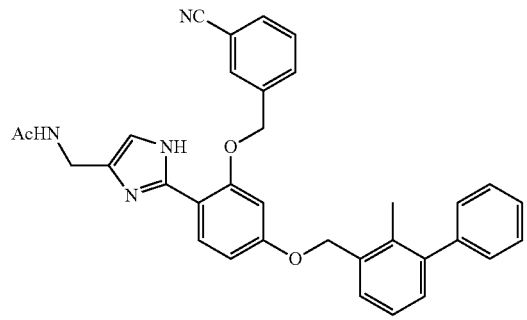

N-((2-(2-((3-cyanobenzyl)oxy)-4-((2-methyl-[1,1'-biphenyl]-3-yl)methoxy)phenyl)-1H-imidazol-4-yl)methyl)acetamide;

-continued

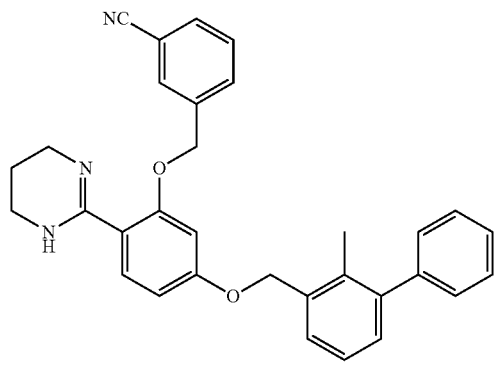 [SMILES: Cc1c(COc2ccc(C3=NCCCN3)c(OCc3cccc(C#N)c3)c2)cccc1-c1ccccc1]

3-((5-((2-methyl-[1,1'-biphenyl]-3-yl)methoxy)-2-(1,4,5,6-tetrahydropyrimidin-2-yl)phenoxy)methyl)benzonitrile;

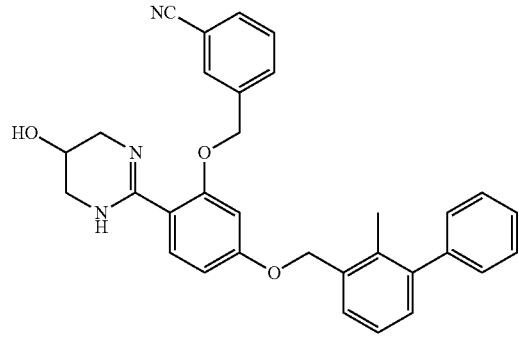 [SMILES: Cc1c(COc2ccc(C3=NCC(O)CN3)c(OCc3cccc(C#N)c3)c2)cccc1-c1ccccc1]

3-((2-(5-hydroxy-1,4,5,6-tetrahydropyrimidin-2-yl)-5-((2-methyl-[1,1'-biphenyl]-3-yl)methoxy)phenoxy)methyl)benzonitrile;

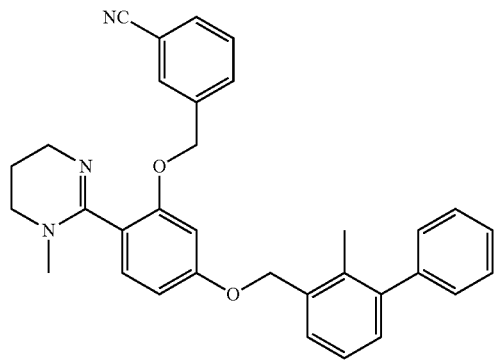 [SMILES: Cc1c(COc2ccc(C3=NCCCN3C)c(OCc3cccc(C#N)c3)c2)cccc1-c1ccccc1]

3-((2-(1-methyl-1,4,5,6-tetrahydropyrimidin-2-yl)-5-((2-methyl-[1,1'-biphenyl]-3-yl)methoxy)phenoxy)methyl)benzonitrile;

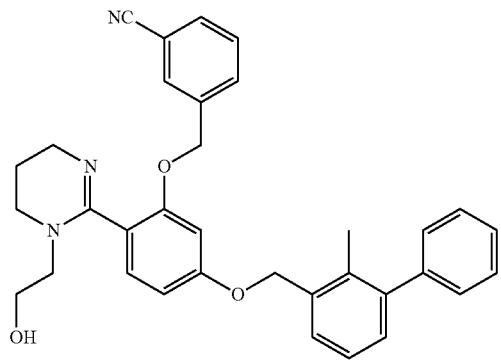 [SMILES: Cc1c(COc2ccc(C3=NCCCN3CCO)c(OCc3cccc(C#N)c3)c2)cccc1-c1ccccc1]

3-((2-(1-(2-hydroxyethyl)-1,4,5,6-tetrahydropyrimidin-2-yl)-5-((2-methyl-[1,1'-biphenyl]-3-yl)methoxy)phenoxy)methyl)benzonitrile;

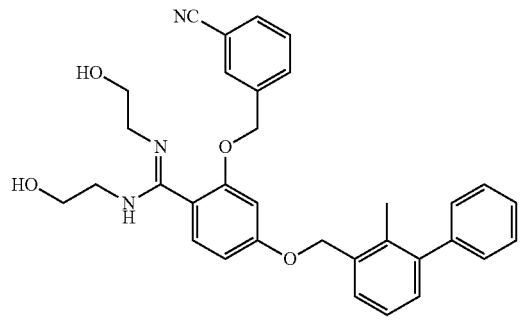 [SMILES: Cc1c(COc2ccc(/C(=N/CCO)NCCO)c(OCc3cccc(C#N)c3)c2)cccc1-c1ccccc1]

2-((3-cyanobenzyl)oxy)-N,N'-bis(2-hydroxyethyl)-4-((2-methyl-[1,1'-biphenyl]-3-yl)methoxy)benzimidamide;

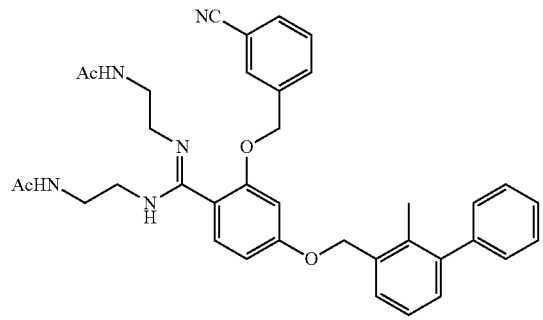

N-(2-N'-(2-acetamidoethyl)-2-((3-cyanobenzyl)oxy)-4-((2-methyl-[1,1'-biphenyl]-3-yl)methoxy)benzimidamido)ethyl)acetamide;

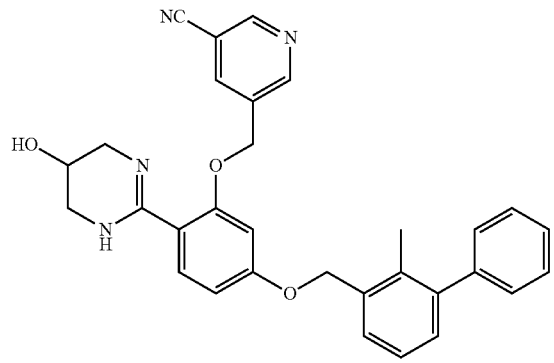

5-((2-(5-hydroxy-1,4,5,6-tetrahydropyrimidin-2-yl)-5-((2-methyl-[1,1'-biphenyl]-3-yl)methoxy)phenoxy)methyl)nicotinonitrile;

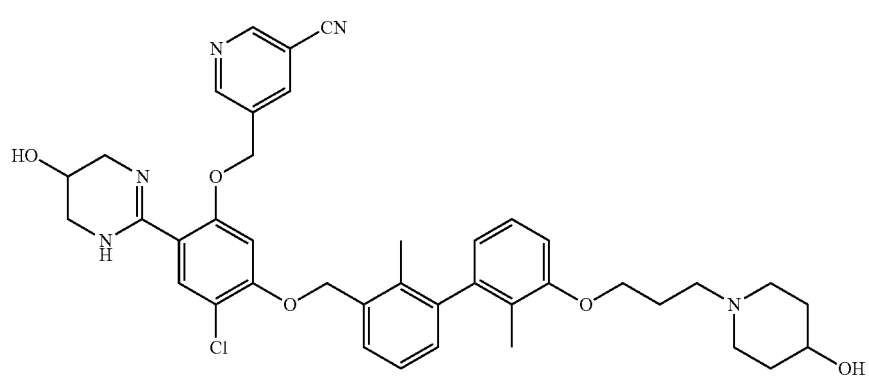 [SMILES: Cc1c(COc2cc(OCc3cncc(C#N)c3)c(C3=NCC(O)CN3)cc2Cl)cccc1-c1cccc(OCCCN2CCC(O)CC2)c1C]

5-((4-chloro-2-(5-hydroxy-1,4,5,6-tetrahydropyrimidin-2-yl)-5-((3'-(3-(4-hydroxypiperidin-1-yl)propoxy)-2,2'-dimethyl-[1,1'-biphenyl]-3-yl)methoxy)phenoxy)methyl)nicotinonitrile;

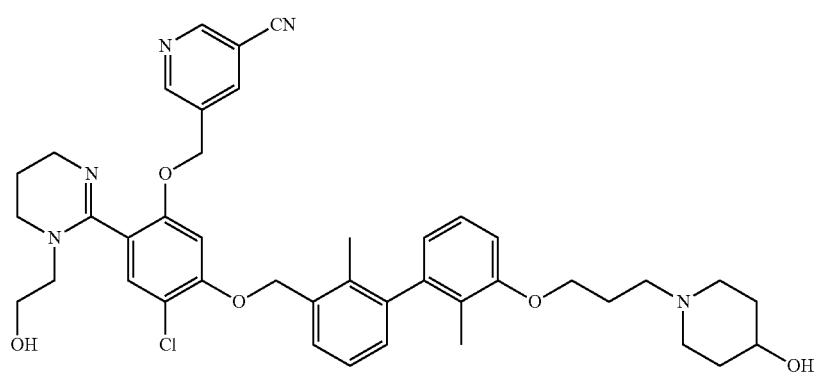 [SMILES: Cc1c(COc2cc(OCc3cncc(C#N)c3)c(C3=NCCCN3CCO)cc2Cl)cccc1-c1cccc(OCCCN2CCC(O)CC2)c1C]

5-((4-chloro-2-(1-(2-hydroxyethyl)-1,4,5,6-tetrahydropyrimidin-2-yl)-5-((3'-(3-(4-hydroxypiperidin-1-yl)propoxy)-2,2'-dimethyl-[1,1'-biphenyl]-3-yl)methoxy)phenoxy)methyl)nicotinonitrile;

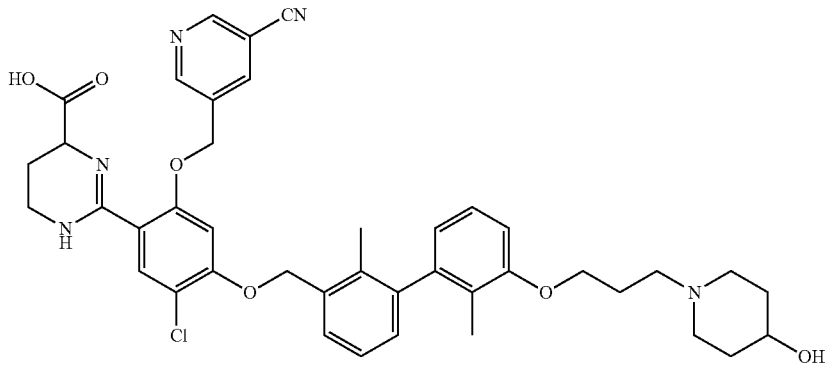 [SMILES: Cc1c(COc2cc(OCc3cncc(C#N)c3)c(C3=NC(C(=O)O)CCN3)cc2Cl)cccc1-c1cccc(OCCCN2CCC(O)CC2)c1C]

2-(5-chloro-2-((5-cyanopyridin-3-yl)methoxy)-4-((3'-(3-(4-hydroxypiperidin-1-yl)propoxy)-2,2'-dimethyl-[1,1'-biphenyl]-3-yl)methoxy)phenyl)-1,4,5,6-tetrahydropyrimidine-4-carboxylic acid;

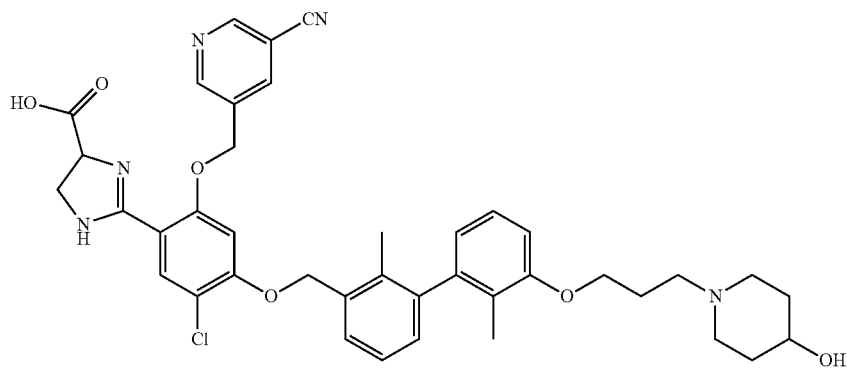

2-(5-chloro-2-((5-cyanopyridin-3-yl)methoxy)-4-((3'-(3-(4-hydroxypiperidin-1yl)propoxy)-2,2'-dimethyl-[1,1'-biphenyl]-3-yl)methoxy)phenyl)-4,5-dihydro-1H-imidazole-4-carboxylic acid;

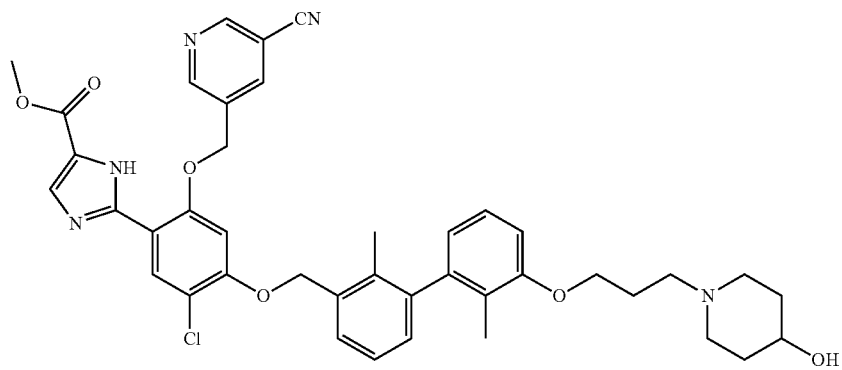

methyl 2-(5-chloro-2-((5-cyanopyridin-3-yl)methoxy)-4-((3'-(3-(4-hydroxypiperidin-1-yl)propoxy)-2,2'-dimethyl-[1,1'-biphenyl]-3-yl)methoxy)pehnyl)-1H-imidazole-5-carboxylate;

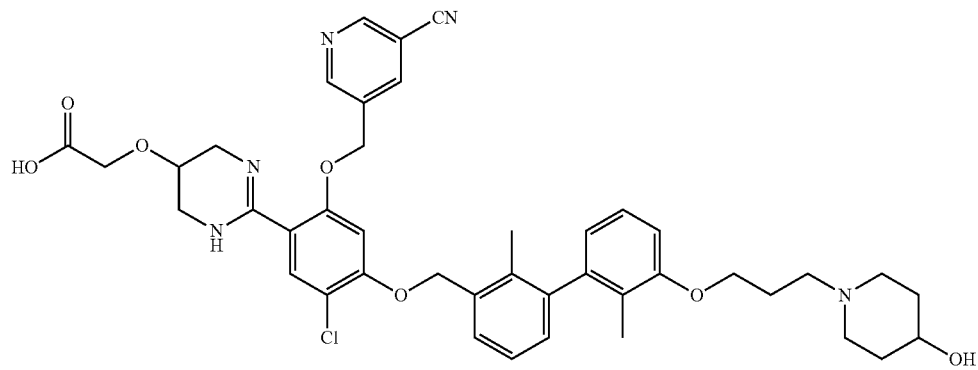 [SMILES: Cc1c(COc2cc(OCc3cncc(C#N)c3)c(C3=NCC(OCC(=O)O)CN3)cc2Cl)cccc1-c1cccc(OCCCN2CCC(O)CC2)c1C]

2-((2-(5-chloro-2-((5-cyanopyridin-3-yl)methoxy)-4-((3'-(3-(4-hydroxypiperidin-1-yl)propoxy)-2,2'-dimethyl-
[1,1'-biphenyl]-3-yl)methoxy)phenyl-1,4,5,6-tetrahydropyrimidin-5-yl)oxy)acetic acid;

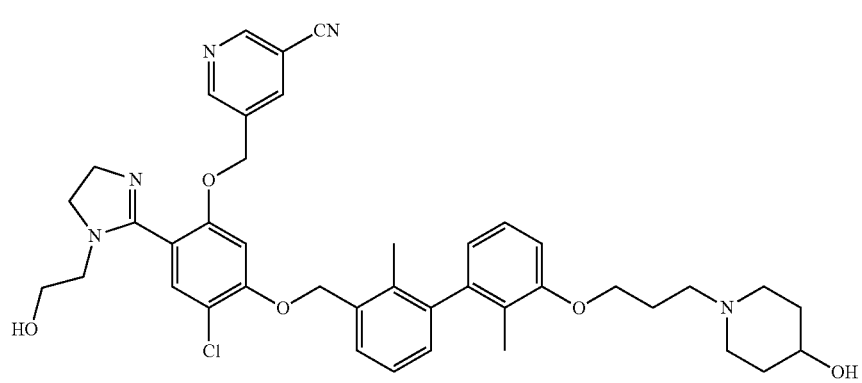

5-((4-chloro-2-(1-(2-hydroxyethyl)-4,5-dihydro-1H-imidazol-2-yl)-5-((3'-(3-(4-hydroxypiperidin-1-yl)
propoxy)-2,2'-dimethyl-[1,1'-biphenyl]-3-yl)methoxy)phenoxy)methyl)nicotinonitrile

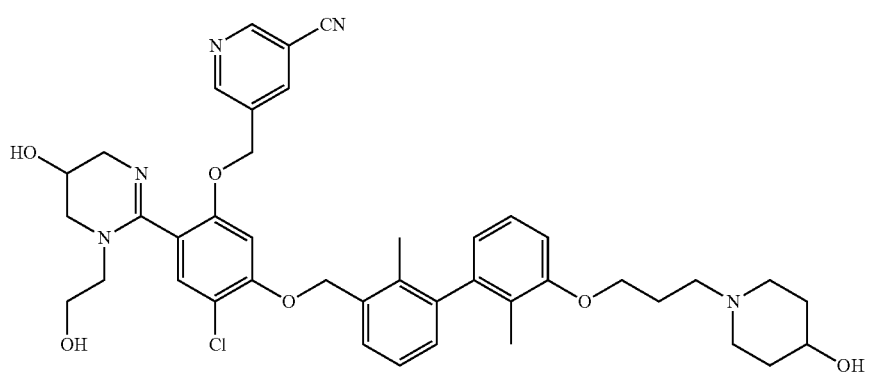 [SMILES: Cc1c(COc2cc(OCc3cncc(C#N)c3)c(C3=NCC(O)CN3CCO)cc2Cl)cccc1-c1cccc(OCCCN2CCC(O)CC2)c1C]

5-((4-chloro-2-(5-hydroxy-1-(2-hydroxyethyl)-1,4,5,6-tetrahydropyrimidin-2-yl)-5-((3'-(3-(4-hydroxypiperidin-1-yl)
propoxy)-2,2'-dimethyl-[1,1'-biphenyl]-3-yl)methoxy)phenoxy)methyl)nicotinonitrile;

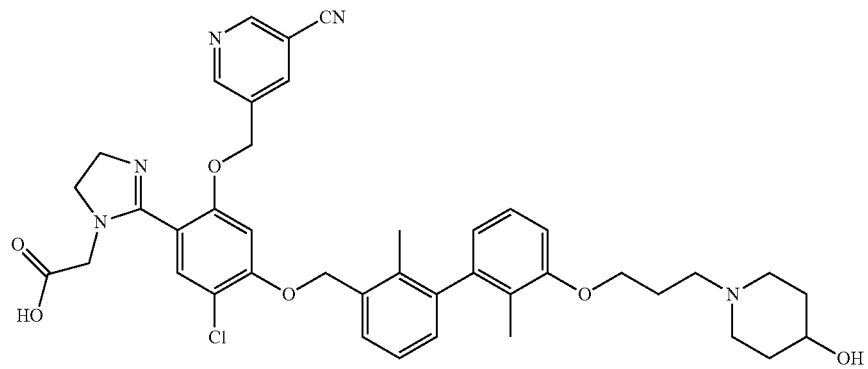 [SMILES: Cc1c(COc2cc(OCc3cncc(C#N)c3)c(C3=NCCN3CC(=O)O)cc2Cl)cccc1-c1cccc(OCCCN2CCC(O)CC2)c1C]

2-(2-(5-chloro-2-((5-cyanopyridin-3-yl)methoxy)-4-((3'-(3-(4-hydroxypiperidin-1-yl)propoxy)-2,2'-dimethyl-[1,1'-biphenyl]-3-yl)methoxy)phenyl)-4,5-dihydro-1H-imidazol-1-yl)acetic acid;

24

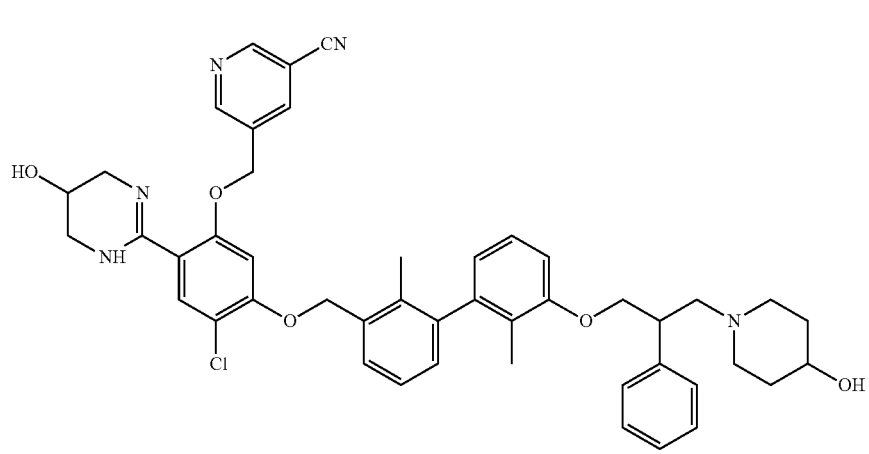 [SMILES: Cc1c(COc2cc(OCc3cncc(C#N)c3)c(C3=NCC(O)CN3)cc2Cl)cccc1-c1cccc(OCC(CN2CCC(O)CC2)c2ccccc2)c1C]

5-((4-chloro-2-(5-hydroxy-1,4,5,6-tetrahydropyrimidin-2-yl)-5-((3'-(3-(4-hydroxypiperidin-1-yl)-2-phenylpropoxy)-2,2'-dimethyl-[1,1'-biphenyl]-3-yl)methoxy)phenoxy)methyl)nicotinonitrile;

25

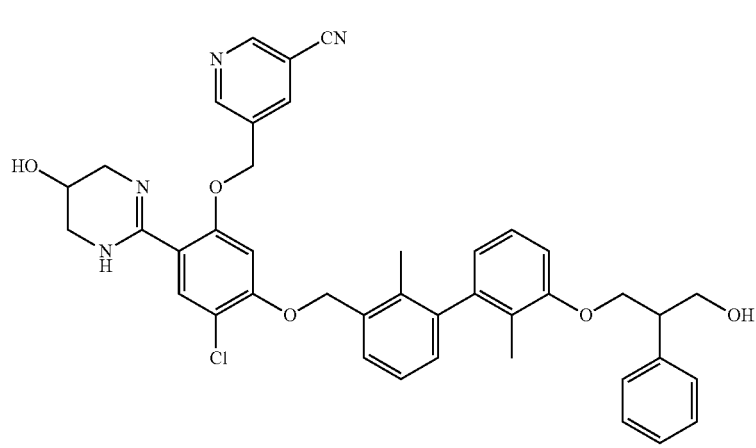 [SMILES: Cc1c(COc2cc(OCc3cncc(C#N)c3)c(C3=NCC(O)CN3)cc2Cl)cccc1-c1cccc(OCC(CO)c2ccccc2)c1C]

5-((4-chloro-2-(5-hydroxy-1,4,5,6-tetrahydropyrimidin-2-yl)-5-((3'-(3-hydroxy-2-phenylpropoxy)-2,2'-dimethyl-[1,1'-biphenyl]-3-yl)methoxy)phenoxy)methyl)nicotinonitrile;

26

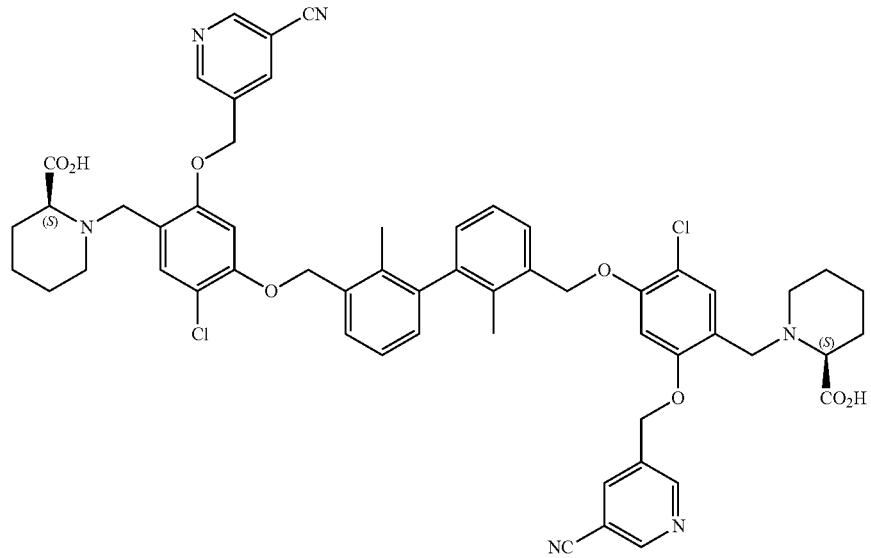

(2S,2′S)-1,1′-(((((2,2′-dimethyl-[1,1′-biphenyl]-3,3′-diyl)bis(methylene))bis(oxy))bis(5-chloro-2-((5-cyanopyridin-3-yl)methoxy)-4,1-phenylene))bis(methylene))bis(piperidine-2-carboxylic acid);

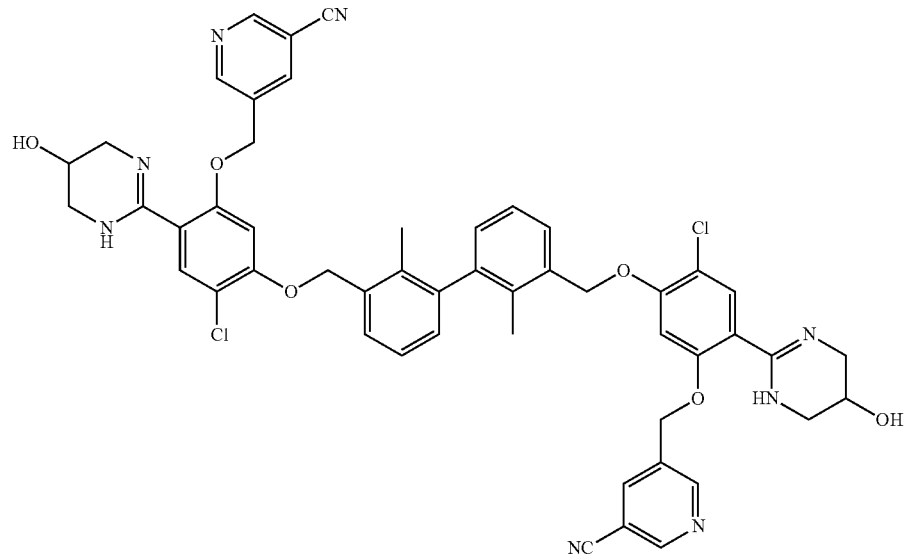 [SMILES: Cc1c(COc2cc(OCc3cncc(C#N)c3)c(C3=NCC(O)CN3)cc2Cl)cccc1-c1cccc(COc2cc(OCc3cncc(C#N)c3)c(C3=NCC(O)CN3)cc2Cl)c1C]

5,5′-(((((2,2′-dimethyl-[1,1′-biphenyl]-3,3′-diyl)bis(methylene))bix(oxy))bis(4-chloro-6-(5-hydroxy-1,4,5,6-tetrahydropyrimidin-2-yl)-3,1-phenylene))bis(oxy))bis(methylene))dinicotinonitrile;

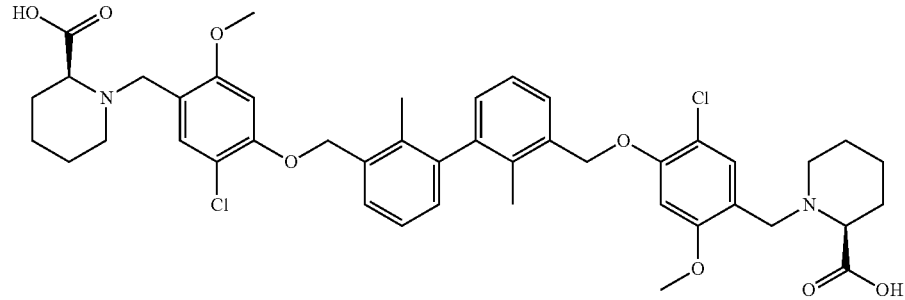 [SMILES: COc1cc(OCc2cccc(-c3cccc(COc4cc(OC)c(CN5CCCC[C@H]5C(=O)O)cc4Cl)c3C)c2C)c(Cl)cc1CN1CCCC[C@H]1C(=O)O]

(2S,2′S)-1,1′-(((((2,2′-dimethyl-[1,1′-biphenyl]-3,3′-diyl)bis(methylene))bis(oxy))bis(5-chloro-2-methoxy-4,1-phenylene))bis(methylene))bis(piperidine-2-carboxylic acid;

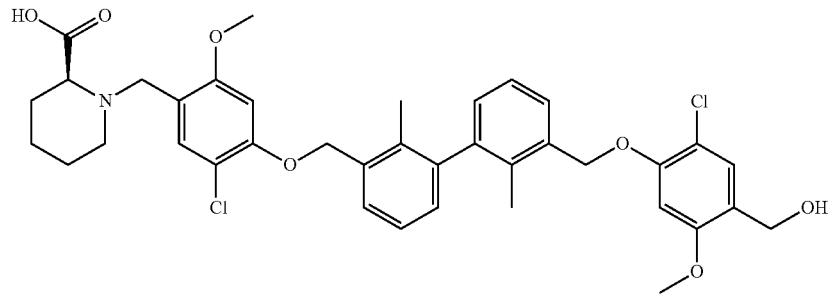 [SMILES: COc1cc(OCc2cccc(-c3cccc(COc4cc(OC)c(CN5CCCC[C@H]5C(=O)O)cc4Cl)c3C)c2C)c(Cl)cc1CO]

(S)-1-(5-chloro-4-((3'-((2-chloro-4-(hydroxymethyl)-5-methoxyphenoxy)methyl)-2,2'-dimethyl-[1,1'-biphenyl]-3-yl)methoxy)-2-methoxybenzyl)piperidine-2-carboxylic acid;

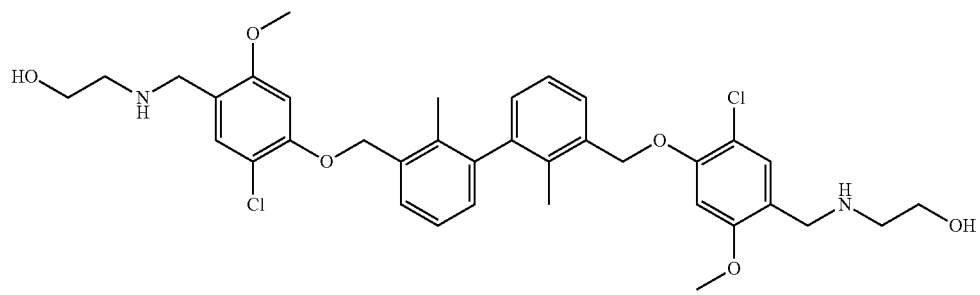 [SMILES: COc1cc(OCc2cccc(-c3cccc(COc4cc(OC)c(CNCCO)cc4Cl)c3C)c2C)c(Cl)cc1CNCCO]

2,2'-((((((2,2'-dimethyl-[1,1'-biphenyl]-3,3'-diyl)bis(methylene))bis(oxy))bis(5-chloro-2-methoxy-4,1-phenylene))bis(methylene))bis(azanediyl))bis(ethan-1-ol);

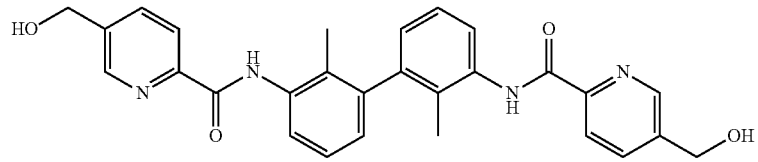 [SMILES: Cc1c(NC(=O)c2ccc(CO)cn2)cccc1-c1cccc(NC(=O)c2ccc(CO)cn2)c1C]

N,N'-(2,2'-dimethyl-[1,1'-biphenyl]-3,3'-diyl)bis(5-hydroxymethyl)picolinamide);

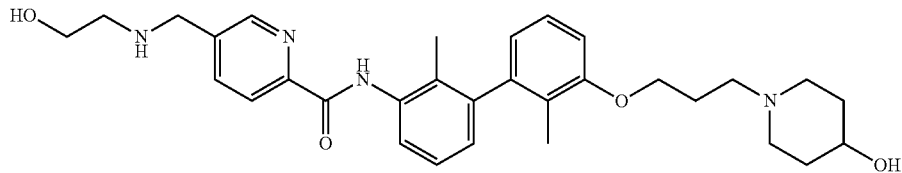 [SMILES: Cc1c(NC(=O)c2ccc(CNCCO)cn2)cccc1-c1cccc(OCCCN2CCC(O)CC2)c1C]

5-(((2-hydroxyethyl)amino)methyl)-N-(3'-(3-(4-hydroxypiperidin-1-yl)propoxy)-2,2'-dimethyl-[1,1'-biphenyl]-3-yl)picolinamide;

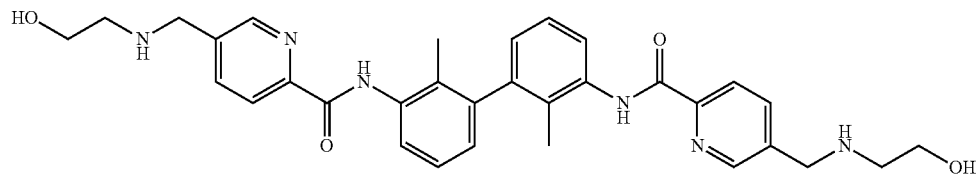 [SMILES: Cc1c(NC(=O)c2ccc(CNCCO)cn2)cccc1-c1cccc(NC(=O)c2ccc(CNCCO)cn2)c1C]

N,N'-(2,2'-dimethyl-[1,1'-biphenyl]-3,3'-diyl)bis(5-(((2-hydroxyethyl)amino)methyl)picolinamide);

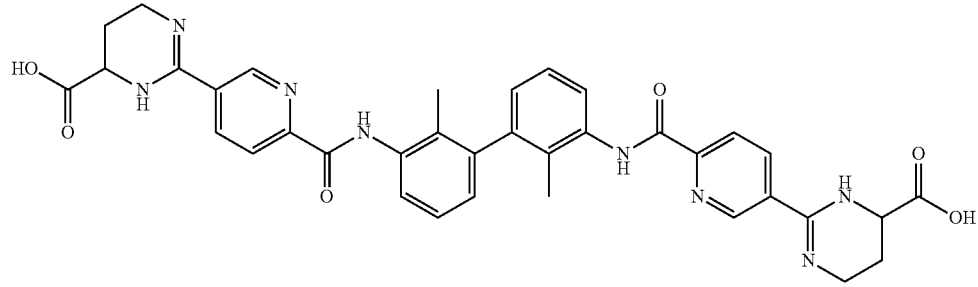 [SMILES: Cc1c(NC(=O)c2ccc(C3=NCCC(C(=O)O)N3)cn2)cccc1-c1cccc(NC(=O)c2ccc(C3=NCCC(C(=O)O)N3)cn2)c1C]

2,2'-((((2,2'-dimethyl-[1,1'-biphenyl]-3,3'-diyl)bis(azanediyl))bis(carbonyl))bis(pyridine-6,3-diyl))
bis(3,4,5,6-tetrahydropyrimidine-4-carboxylic acid);

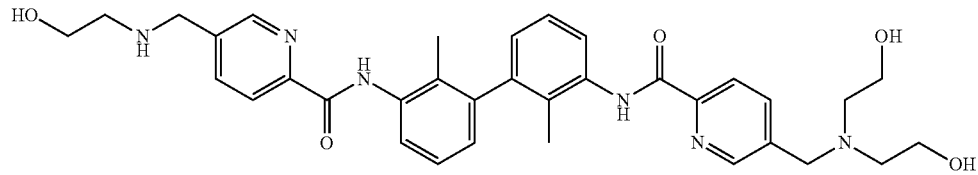 [SMILES: Cc1c(NC(=O)c2ccc(CNCCO)cn2)cccc1-c1cccc(NC(=O)c2ccc(CN(CCO)CCO)cn2)c1C]

5-((bis(2-hydroxyethyl)amino)methyl)-N-(3'-(5-(((2-hydroxyethyl)amino)methyl)
picolinamido)-2,2'-dimethyl-[1,1'-biphenyl]-3-yl)picolinamide;

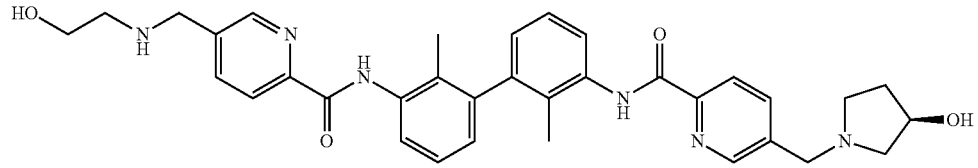

(R)-5-(((2-hydroxyethyl)amino)methyl)-N-(3'-(5-((3-hydroxypyrrolidin-1-yl)methyl)picolinamido)-
2,2'-dimethyl-[1,1'-biphenyl]-3-yl)picolinamide;

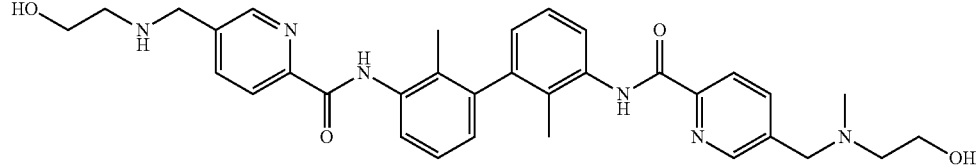 [SMILES: Cc1c(NC(=O)c2ccc(CNCCO)cn2)cccc1-c1cccc(NC(=O)c2ccc(CN(C)CCO)cn2)c1C]

5-(((2-hydroxyethyl)-(methyl)amino)methyl)-N-(3'-(5-(((2-hydroxyethyl)amino)methyl)picolinamido)-2,2'-dimethyl-
[1,1'-biphenyl]-3-yl)picolinamide;

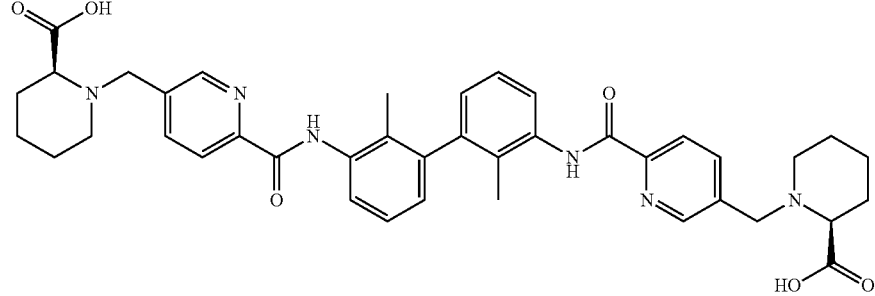 [SMILES: Cc1c(NC(=O)c2ccc(CN3CCCC[C@H]3C(=O)O)cn2)cccc1-c1cccc(NC(=O)c2ccc(CN3CCCC[C@H]3C(=O)O)cn2)c1C]

(2S,2'S)-1,1'-(((((2,2'-dimethyl-[1,1'-biphenyl]-3,3'-diyl)bis(azanediyl))bis(carbonyl))bis
(pyridine-6,3-diyl)bis(methylene))bis(piperidine-2-carboxylic acid);

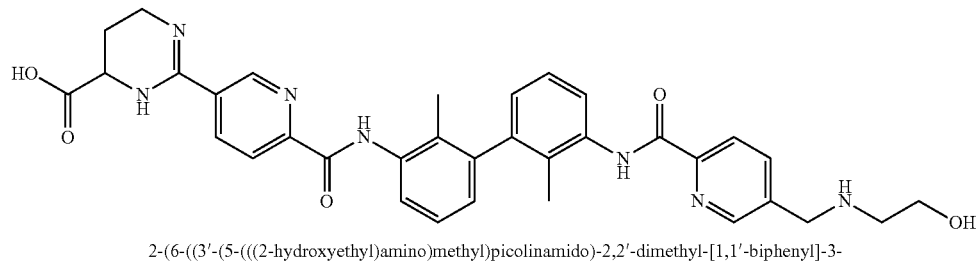

2-(6-((3'-(5-(((2-hydroxyethyl)amino)methyl)picolinamido)-2,2'-dimethyl-[1,1'-biphenyl]-3-yl)carbamoyl)pyridin-3-yl)3,4,5,6-tetrahydropyrimidine-4-carboxylic acid;

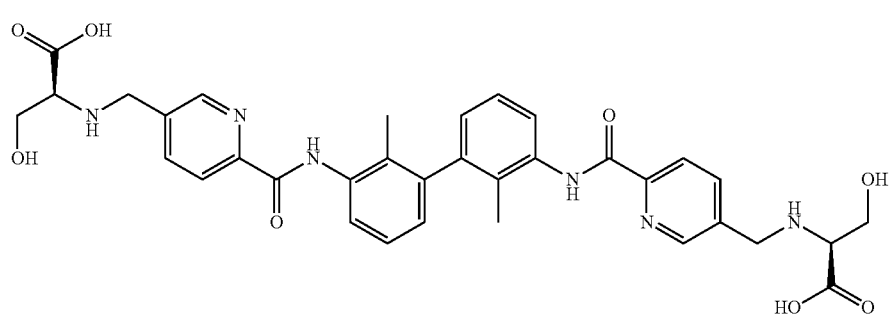 [SMILES: Cc1c(NC(=O)c2ccc(CN[C@@H](CO)C(=O)O)cn2)cccc1-c1cccc(NC(=O)c2ccc(CN[C@@H](CO)C(=O)O)cn2)c1C]

(2S,2'S)-2,2'-((((((2,2'-dimethyl-[1,1'-biphenyl]-3,3'-diyl)bis(azanediyl))bis(carbonyl))bis(pyridine-6,3-diyl))bis(methylene))bis(azanediyl))bis(3-hydroxypropanoic acid);

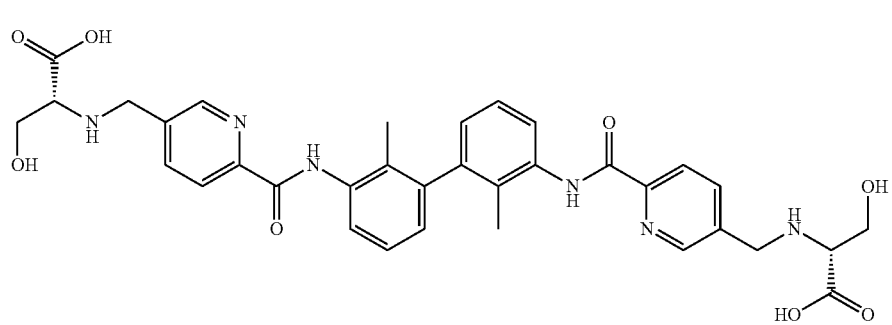 [SMILES: Cc1c(NC(=O)c2ccc(CN[C@H](CO)C(=O)O)cn2)cccc1-c1cccc(NC(=O)c2ccc(CN[C@H](CO)C(=O)O)cn2)c1C]

(2R,2'R)-2,2'-((((((2,2'-dimethyl-[1,1'-biphenyl]-3,3'-diyl)bis(azanediyl))bis(carbonyl))bis(pyridine-6,3-diyl))bis(methylene))bis(azanediyl))bis(3-hydroxypropanoic acid);

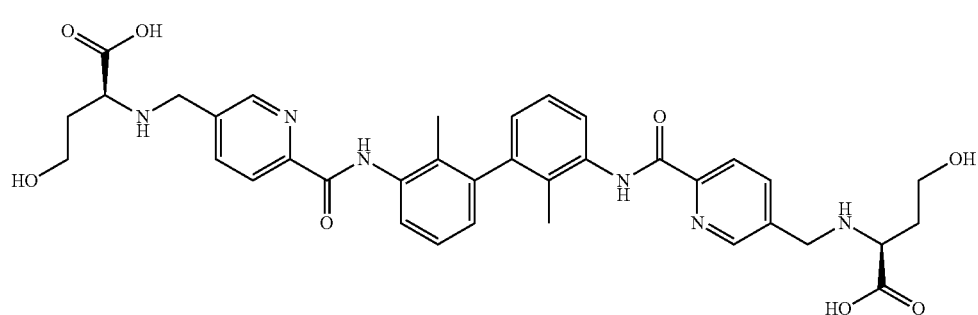 [SMILES: Cc1c(NC(=O)c2ccc(CN[C@@H](CCO)C(=O)O)cn2)cccc1-c1cccc(NC(=O)c2ccc(CN[C@@H](CCO)C(=O)O)cn2)c1C]

(2S,2'S)-2,2'-((((((2,2'-dimethyl-[1,1'-biphenyl]-3,3'-diyl)bis(azanediyl))bis(carbonyl))bis(pyridine-6,3-diyl))bis(methylene))bis(azanediyl))bis(4-hydroxybutanoic acid);

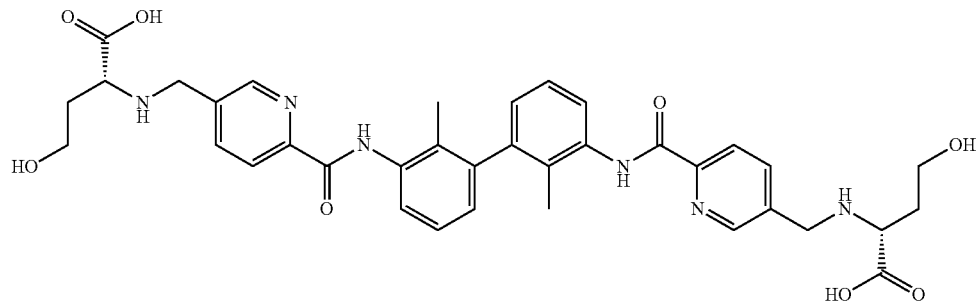 [SMILES: Cc1c(NC(=O)c2ccc(CN[C@H](CCO)C(=O)O)cn2)cccc1-c1cccc(NC(=O)c2ccc(CN[C@H](CCO)C(=O)O)cn2)c1C]

(2R,2′R)-2,2′-((((((2,2′-dimethyl-diyl))bis(methylene))bis(azanediyl))bis(carbonyl))bis(pyridine-6,3-diyl))bis(methylene))bis(azanediyl))bis(4-hydroxybutanoic acid;

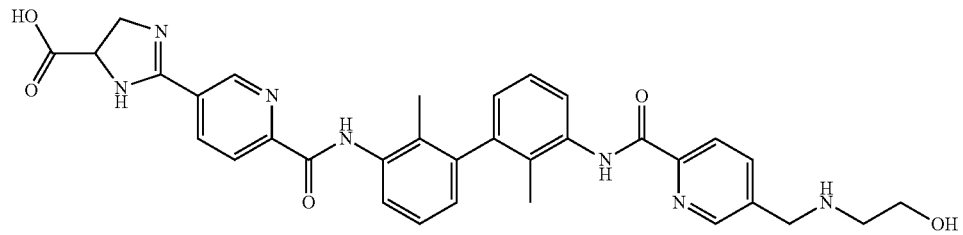

2-(6-((3′-(5-(((2-hydroxyethyl)amino)methyl)picolinamido)-2,2′-dimethyl-[1,1′-biphenyl]-3-yl)carbamoyl)pyridin-3-yl)-4,5-dihydro-1H-imidazole-5-carboxylic acid;

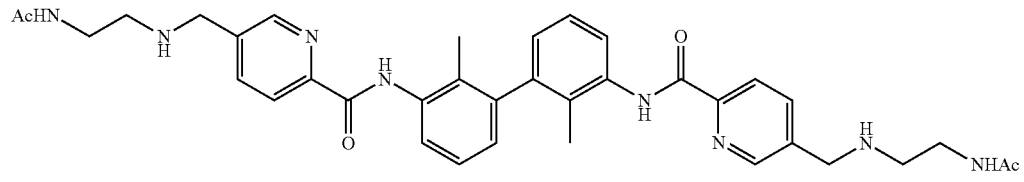 [SMILES: CC(=O)NCCNCc1ccc(C(=O)Nc2cccc(-c3cccc(NC(=O)c4ccc(CNCCNC(C)=O)cn4)c3C)c2C)nc1]

N,N′-(2,2′-dimethyl-[1,1′-biphenyl]-3,3′-diyl)bis(5-(((2-acetamidoethyl)amino)methyl)picolinamide);

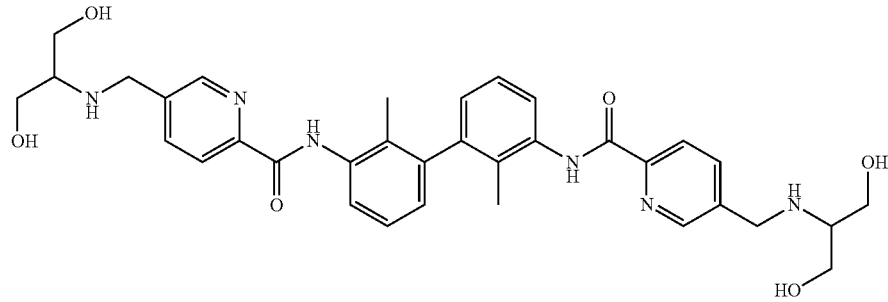

N,N′-(2,2′-dimethyl-[1,1′-biphenyl]-3,3′-diyl)bis(5-(((1,3-dihydroxypropan-2-yl)amino)methyl)picolinamide);

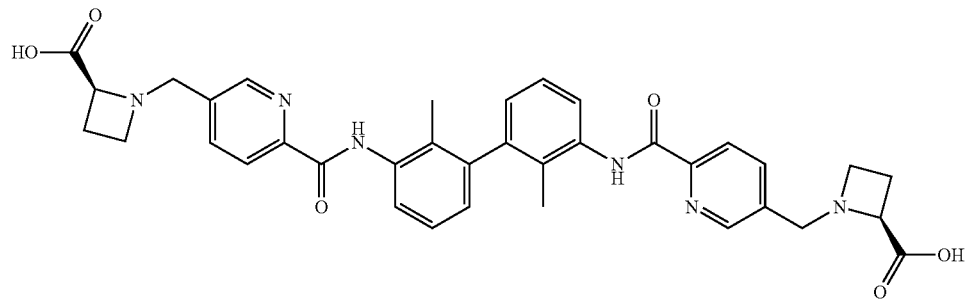

(2S,2′S)-1,1′-(((((2,2′-dimethyl-[1,1′-biphenyl]3,3′-diyl)bis(azanediyl))bis(carbonyl))bis(pyridine-6,3-diyl))bis(methylene)bis(azetidine-2-carboxylic acid);

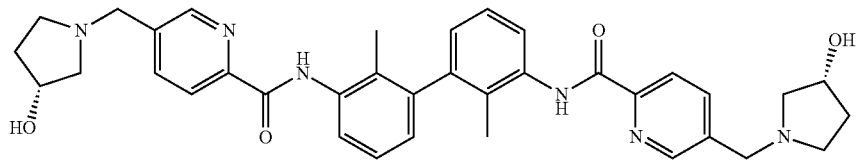

N,N'-(2,2'-dimethyl-[1,1'-biphenyl]-3,3'-diyl)bis(5-(((R)-3-hydroxypyrrolidin-1-yl)methyl)picolinamide);

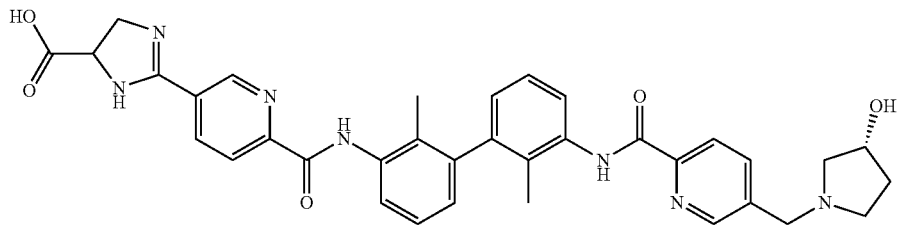

2-(6-((3'-(5-(((R)-3-hydroxypyrrolidin-1-yl)methyl)picolinamido)-2,2'-dimethyl-[1,1'-biphenyl]-3-yl)carbamoyl)pyridin-3-yl)-4,5-dihydro-1H-imidazole-5-carboxylic acid;

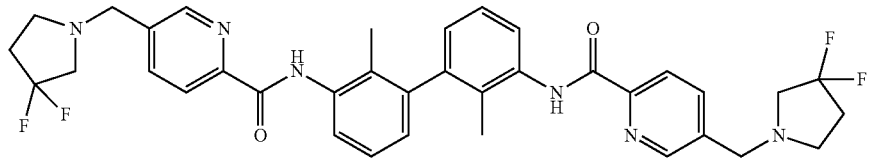

N,N'-(2,2'-dimethyl-[1,1'-biphenyl]-3,3'-diyl)bis(5-((3,3-difluoropyrrolidin-1-yl)methyl)picolinamide);

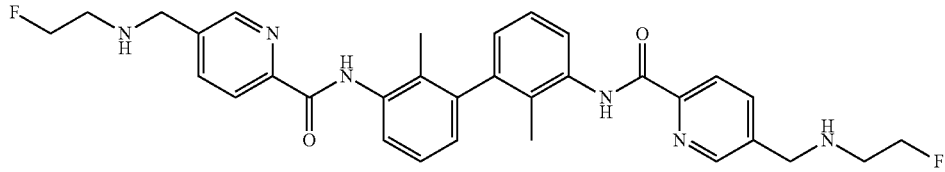 [SMILES: Cc1c(NC(=O)c2ccc(CNCCF)cn2)cccc1-c1cccc(NC(=O)c2ccc(CNCCF)cn2)c1C]

N,N'-(2,2'-dimethyl-[1,1'-biphenyl]-3,3'-diyl)bis(5-(((2-fluoroethyl)amino)methyl)picolinamide);

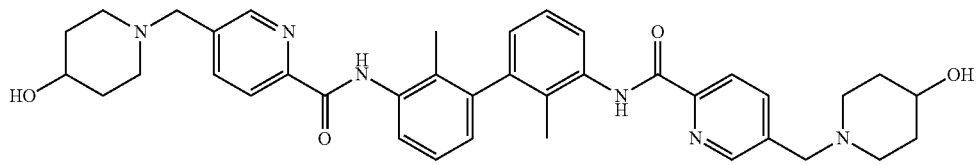 [SMILES: Cc1c(NC(=O)c2ccc(CN3CCC(O)CC3)cn2)cccc1-c1cccc(NC(=O)c2ccc(CN3CCC(O)CC3)cn2)c1C]

N,N'-(2,2'-dimethyl-[1,1'-biphenyl]-3,3'-diyl)bis(5-((4-hydroxypiperidin-1-yl)methyl)picolinamide);

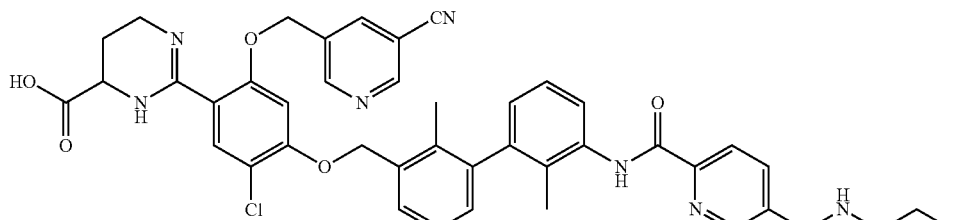

2-(5-chloro-2-((5-cyanopyridin-3-yl)methoxy)-4-((3'-(5-(((2-hydroxyethyl)amino)methyl)picolinamido)-2,2'-dimethyl-[1,1'-biphenyl]-3-yl)methoxy)phenyl)-3,4,5,6-tetrahydropyrimidine-4-carboxylic acid;

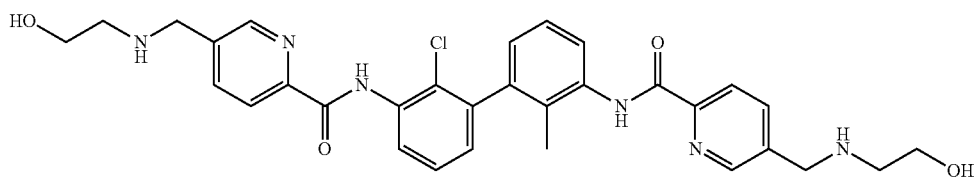

N,N'-(2-chloro-2'-methyl-[1,1'-biphenyl]-3,3'-diyl)bis(5-(((2-hydroxyethyl)amino)methyl)picolinamide)

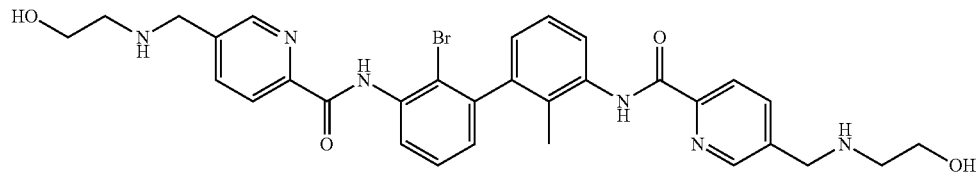 [SMILES: Cc1c(NC(=O)c2ccc(CNCCO)cn2)cccc1-c1cccc(NC(=O)c2ccc(CNCCO)cn2)c1Cl]

N,N'-(2-bromo-2'-methyl-[1,1'-biphenyl]3,3'-diyl)bis(5-(((2-hydroxyethyl)amino)methyl)picolinamide);

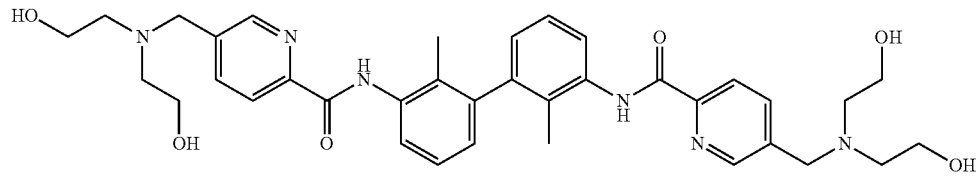 [SMILES: Cc1c(NC(=O)c2ccc(CN(CCO)CCO)cn2)cccc1-c1cccc(NC(=O)c2ccc(CN(CCO)CCO)cn2)c1C]

N,N'-(2,2'-dimethyl-[1,1'-biphenyl]-3,3'-diyl)bis(5-((bis(2-hydroxyethyl)amino)methyl)picolinamide);

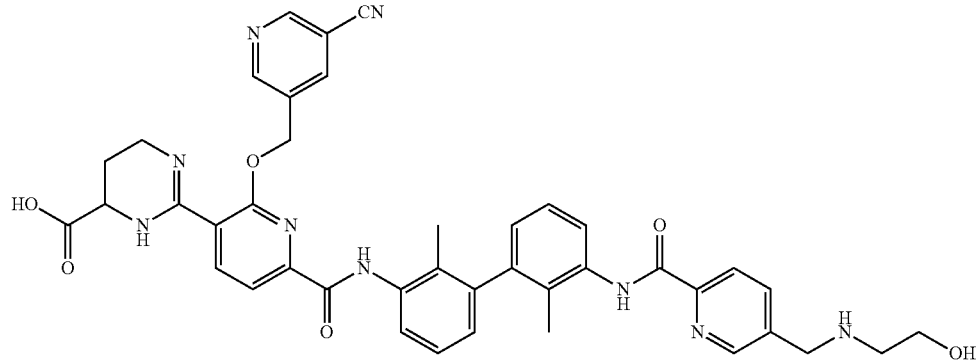 [SMILES: Cc1c(NC(=O)c2ccc(CNCCO)cn2)cccc1-c1cccc(NC(=O)c2ccc(C3=NCCC(C(=O)O)N3)c(OCc3cncc(C#N)c3)n2)c1C]

2-(2-((5-cyanopyridin-3-yl)methoxy)-6-((3'-(5-(((2-hydroxyethyl)amino)methyl)picolinamido)-2,2'-dimethyl-[1,1'-biphenyl]-3-yl)carbamoyl)pyridin-3-yl)-3,4,5,6-tetrahydropyrimidine-4-carboxylic acid;

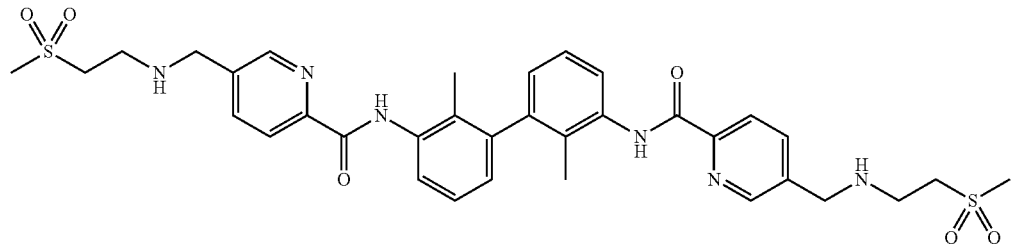

N,N'-(2,2'-dimethyl-[1,1'-biphenyl]-3,3'-diyl)bis(5-(((2-(methylsulfonyl)ethyl)amino)methyl)picolinamide);

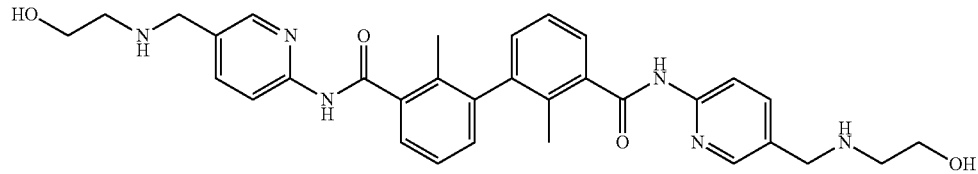 [SMILES: Cc1c(C(=O)Nc2ccc(CNCCO)cn2)cccc1-c1cccc(C(=O)Nc2ccc(CNCCO)cn2)c1C]

N³, N³'-bis(5-(((2-hydlroxyethyl)amino)methyl)pyridin-2-yl)-2,2'-dimethyl-[1,1'-biphenyl]-3,3'-dicarboxamide;

61

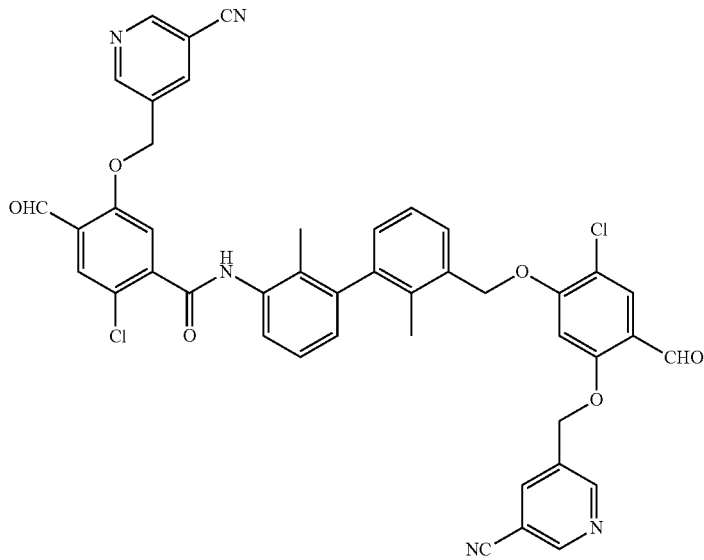 [SMILES: Cc1c(COc2cc(OCc3cncc(C#N)c3)c(C=O)cc2Cl)cccc1-c1cccc(COc2cc(OCc3cncc(C#N)c3)c(C=O)cc2Cl)c1C]

5,5′-((((((2,2′-dimethyl-[1,1′-biphenyl]-3,3′-diyl)bis(methylene))bis(oxy))bis(4-chloro-6-formyl-3,1-phenylene))bis
(oxy))bis(methylene))dinicotinonitrile;

62

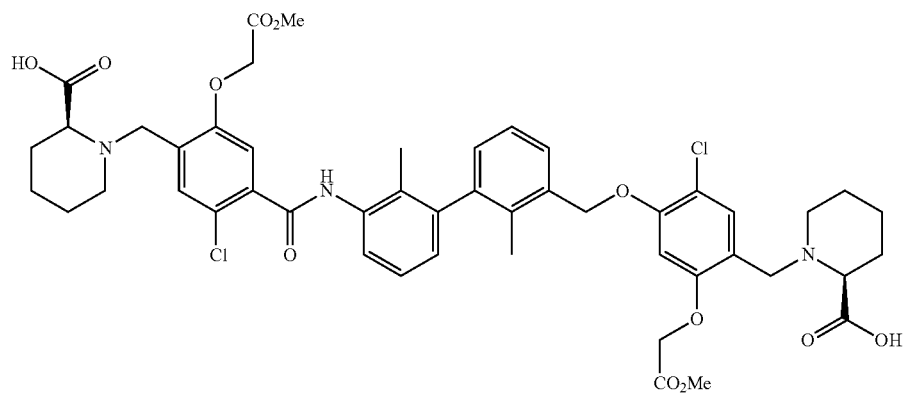

(2S,2′S)-1,1′-(((((2,2′-dimethyl-[1,1′-biphenyl]-3,3′-diyl)bis(methylene))bis(oxy))bis
(5-chloro-2-(2-methoxy-2-oxoethoxy)-4,1-phenylene))bis(methylene))bis(piperidine-2-carboxylic acid);

63

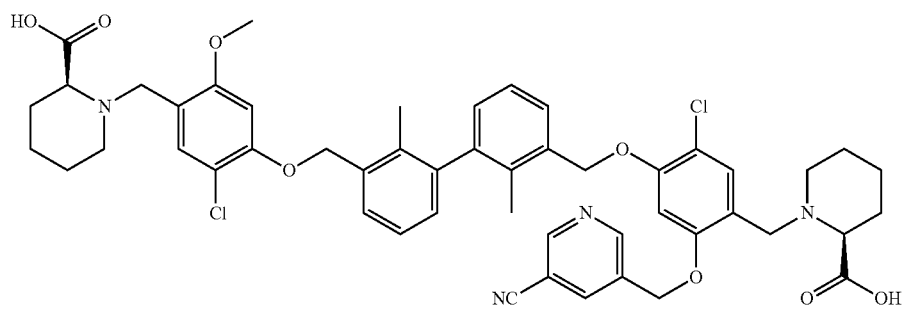

5-chloro-4-((3′-((2-chloro-5-((5-cyanopyridin-3-yl)methoxy)-4-(((2-hydroxyethyl)amino)methyl)
phenoxy)methyl)-2,2′-dimethyl-[1,1′-biphenyl]-3-yl)methoxy)-2-((5-cyanopyridin-3-yl)methoxy)-N-(2-hydroxyethyl)benzamide;

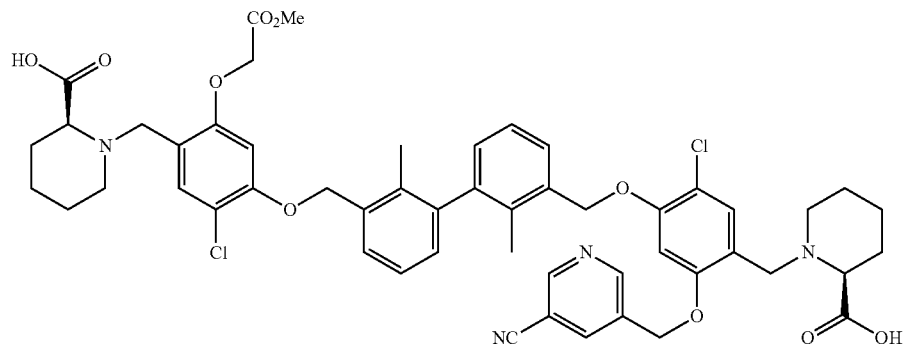

(S)-1-(4-((3'-((4-(((S)-2-carboxypiperidin-1-yl)methyl)-2-chloro-5-((5-cyanopyridin-3-yl)methoxy)phenoxy)methyl)-
2,2'-dimethyl-[1,1'-biphenyl]-3-yl)methoxy)-5-chloro-2-(2-methoxy-2-oxoethoxy)benzyl)piperidine-2-carboxylic acid;

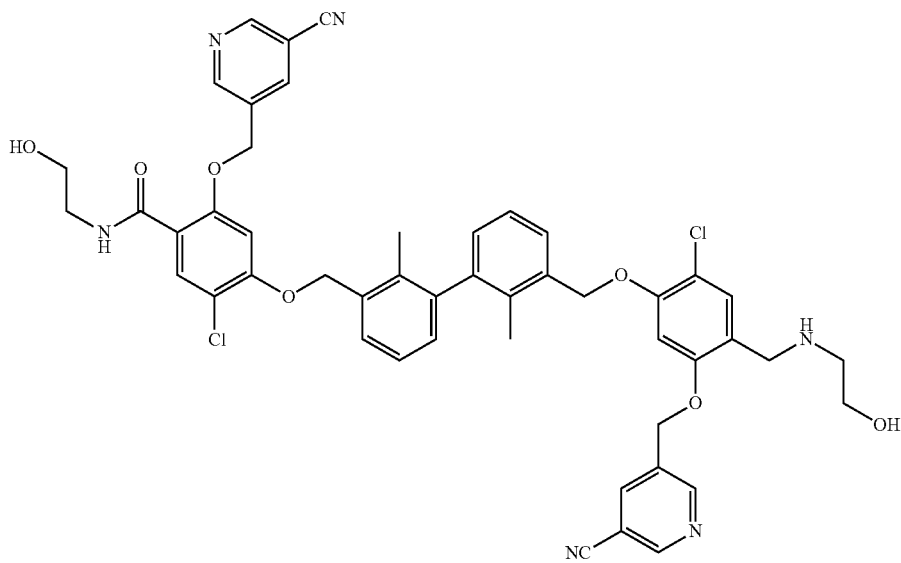

5-chloro-4-((3'-((2-chloro-5-((5-cyanopyridin-3-yl)methoxy)-4-(((2-hydroxyethyl)amino)methyl)phenoxy)methyl-2,2'-dimethyl-
[1,1'-biphenyl]-3-yl)methoxy)-2-((5-cyanopyridin-3-yl)methoxy)-N-(2-hydroxyethyl)benzamide;

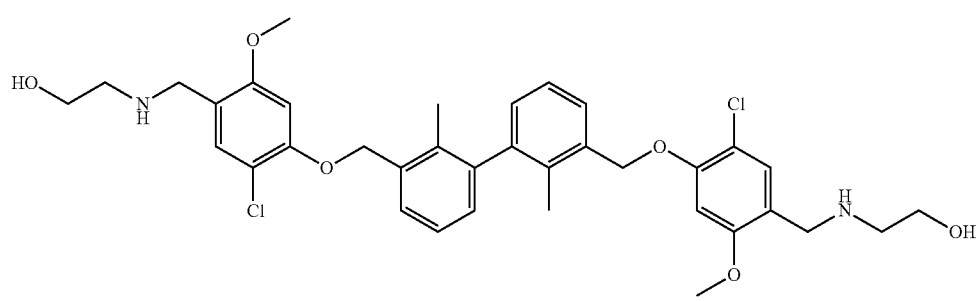

2,2'-((((((2,2'-dimethyl-[1,1'-biphenyl]-3,3'-diyl)bis(methylene))bis(oxy))bis(5-chloro-2-methoxy-4,
1-phenylene))bis(methylene))bis(azanediyl))bis(ethan-1-ol).

The compounds of the invention may possess one or more stereocenters, and each stereocenter may exist independently in either the (R) or (S) configuration. In certain embodiments, compounds described herein are present in optically active or racemic forms. The compounds described herein encompass racemic, optically active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically active starting materials, chiral synthesis, or chromatographic separation using a chiral stationary phase. A compound illustrated herein by the racemic formula further represents either of the two enantiomers or mixtures thereof, or in the case where two or more chiral center are present, all diastereomers or mixtures thereof.

In certain embodiments, the compounds of the invention exist as tautomers. All tautomers are included within the scope of the compounds recited herein.

Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In certain embodiments, substitution with heavier isotopes such as deuterium affords greater chemical stability. Isotopically labeled compounds are prepared by any suitable method or by processes using an appropriate isotopically labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

In all of the embodiments provided herein, examples of suitable optional substituents are not intended to limit the scope of the claimed invention. The compounds of the invention may contain any of the substituents, or combinations of substituents, provided herein.

Salts

The compounds described herein may form salts with acids or bases, and such salts are included in the present invention. The term "salts" embraces addition salts of free acids or bases that are useful within the methods of the invention. The term "pharmaceutically acceptable salt" refers to salts that possess toxicity profiles within a range that affords utility in pharmaceutical applications. In certain embodiments, the salts are pharmaceutically acceptable salts. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (or pamoic), methanesulfonic, ethanesulfonic, benzenesulfonic, pantothenic, sulfanilic, 2-hydroxyethanesulfonic, trifluoromethanesulfonic, p-toluenesulfonic, cyclohexylaminosulfonic, stearic, alginic, β-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound of the invention.

Suitable pharmaceutically acceptable base addition salts of compounds of the invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (or N-methylglucamine) and procaine. All of these salts may be prepared from the corresponding compound by reacting, for example, the appropriate acid or base with the compound.

Combination Therapies

In one aspect, the compounds of the invention are useful within the methods of the invention in combination with one or more additional agents useful for treating HBV and/or HDV infections. These additional agents may comprise compounds or compositions identified herein, or compounds (e.g., commercially available compounds) known to treat, prevent, or reduce the symptoms of HBV and/or HDV infections.

Non-limiting examples of one or more additional agents useful for treating HBV and/or HDV infections include: (a) reverse transcriptase inhibitors; (b) capsid inhibitors; (c) cccDNA formation inhibitors; (d) sAg secretion inhibitors; (e) oligomeric nucleotides targeted to the Hepatitis B genome; (f) immunostimulators; and (g) RNA destabilizer.

(a) Reverse Transcriptase Inhibitors

In certain embodiments, the reverse transcriptase inhibitor is a reverse-transcriptase inhibitor (NARTI or NRTI). In other embodiments, the reverse transcriptase inhibitor is a nucleotide analog reverse-transcriptase inhibitor (NtARTI or NtRTI).

Reported reverse transcriptase inhibitors include, but are not limited to, entecavir, clevudine, telbivudine, lamivudine, adefovir, and tenofovir, tenofovir disoproxil, tenofovir alafenamide, adefovir dipovoxil, (1R,2R,3R,5R)-3-(6-amino-9H-9-purinyl)-2-fluoro-5-(hydroxymethyl)-4-methylenecyclopentan-1-ol (described in U.S. Pat. No. 8,816,074, incorporated herein in its entirety by reference), emtricitabine, abacavir, elvucitabine, ganciclovir, lobucavir, famciclovir, penciclovir, and amdoxovir.

Reported reverse transcriptase inhibitors further include, but are not limited to, entecavir, lamivudine, and (1R,2R,3R,5R)-3-(6-amino-9H-9-purinyl)-2-fluoro-5-(hydroxymethyl)-4-methylenecyclopentan-1-ol.

Reported reverse transcriptase inhibitors further include, but are not limited to, a covalently bound phosphoramidate or phosphonamidate moiety of the above-mentioned reverse transcriptase inhibitors, or as described in for example U.S. Pat. No. 8,816,074, US Patent Application Publications No. US 2011/0245484 A1, and US 2008/0286230A1, all of which incorporated herein in their entireties by reference.

Reported reverse transcriptase inhibitors further include, but are not limited to, nucleotide analogs that comprise a phosphoramidate moiety, such as, for example, methyl ((((1R,3R,4R,5R)-3-(6-amino-9H-purin-9-yl)-4-fluoro-5-hydroxy-2-methylenecyclopentyl) methoxy)(phenoxy) phosphoryl)-(D or L)-alaninate and methyl ((((1R,2R,3R,4R)-3-fluoro-2-hydroxy-5-methylene-4-(6-oxo-1,6-dihydro-9H-purin-9-yl)cyclopentyl)methoxy)(phenoxy) phosphoryl)-(D or L)-alaninate. Also included are the individual diastereomers thereof, which include, for example, methyl ((R)-(((1R,3R,4R,5R)-3-(6-amino-9H-purin-9-yl)-4-fluoro-5-hydroxy-2-methylenecyclopentyl)methoxy)(phenoxy) phosphoryl)-(D or L)-alaninate and methyl ((S)-(((1R,3R,4R,5R)-3-(6-amino-9H-purin-9-yl)-4-fluoro-5-hydroxy-2-methylenecyclopentyl) methoxy)(phenoxy)phosphoryl)-(D or L)-alaninate.

Reported reverse transcriptase inhibitors further include, but are not limited to, compounds comprising a phosphonamidate moiety, such as, for example, tenofovir alafenamide, as well as those described in U.S. Patent Application Publication No. US 2008/0286230 A1, incorporated herein in its entirety by reference. Methods for preparing stereoselective phosphoramidate or phosphonamidate containing actives are described in, for example, U.S. Pat. No. 8,816,074, as well as U.S. Patent Application Publications No. US 2011/0245484 A1 and US 2008/0286230 A1, all of which incorporated herein in their entireties by reference.

(b) Capsid Inhibitors

As described herein, the term "capsid inhibitor" includes compounds that are capable of inhibiting the expression and/or function of a capsid protein either directly or indirectly. For example, a capsid inhibitor may include, but is not limited to, any compound that inhibits capsid assembly, induces formation of non-capsid polymers, promotes excess capsid assembly or misdirected capsid assembly, affects capsid stabilization, and/or inhibits encapsidation of RNA (pgRNA). Capsid inhibitors also include any compound that inhibits capsid function in a downstream event(s) within the replication process (e.g., viral DNA synthesis, transport of relaxed circular DNA (rcDNA) into the nucleus, covalently closed circular DNA (cccDNA) formation, virus maturation, budding and/or release, and the like). For example, in certain embodiments, the inhibitor detectably inhibits the expression level or biological activity of the capsid protein as measured, e.g., using an assay described herein. In certain embodiments, the inhibitor inhibits the level of rcDNA and downstream products of viral life cycle by at least 5%, at least 10%, at least 20%, at least 50%, at least 75%, or at least 90%.

Reported capsid inhibitors include, but are not limited to, compounds described in International Patent Applications Publication Nos WO 2013006394, WO 2014106019, and WO2014089296, all of which incorporated herein in their entireties by reference.

Reported capsid inhibitors also include, but are not limited to, the following compounds and pharmaceutically acceptable salts and/or solvates thereof: Bay-41-4109 (see Int'l Patent Application Publication No. WO 2013144129), AT-61 (see Int'l Patent Application Publication No. WO 1998033501; and King, et al., 1998, Antimicrob. Agents Chemother. 42(12):3179-3186), DVR-01 and DVR-23 (see Int'l Patent Application Publication No. WO 2013006394; and Campagna, et al., 2013, J. Virol. 87(12):6931, all of which incorporated herein in their entireties by reference.

In addition, reported capsid inhibitors include, but are not limited to, those generally and specifically described in U.S. Patent Application Publication Nos. US 2015/0225355, US 2015/0132258, US 2016/0083383, US 2016/0052921 and Int'l Patent Application Publication Nos. WO 2013096744, WO 2014165128, WO 2014033170, WO 2014033167, WO 2014033176, WO 2014131847, WO 2014161888, WO 2014184350, WO 2014184365, WO 2015059212, WO 2015011281, WO 2015118057, WO 2015109130, WO 2015073774, WO 2015180631, WO 2015138895, WO 2016089990, WO 2017015451, WO 2016183266, WO 2017011552, WO 2017048950, WO2017048954, WO 2017048962, WO 2017064156 and are incorporated herein in their entirety by reference.

(c) cccDNA Formation Inhibitors

Covalently closed circular DNA (cccDNA) is generated in the cell nucleus from viral rcDNA and serves as the transcription template for viral mRNAs. As described herein, the term "cccDNA formation inhibitor" includes compounds that are capable of inhibiting the formation and/or stability of cccDNA either directly or indirectly. For example, a cccDNA formation inhibitor may include, but is not limited to, any compound that inhibits capsid disassembly, rcDNA entry into the nucleus, and/or the conversion of rcDNA into cccDNA. For example, in certain embodiments, the inhibitor detectably inhibits the formation and/or stability of the cccDNA as measured, e.g., using an assay described herein. In certain embodiments, the inhibitor inhibits the formation and/or stability of cccDNA by at least 5%, at least 10%, at least 20%, at least 50%, at least 75%, or at least 90%.

Reported cccDNA formation inhibitors include, but are not limited to, compounds described in Int'l Patent Application Publication No. WO 2013130703, and are incorporated herein in their entirety by reference.

In addition, reported cccDNA formation inhibitors include, but are not limited to, those generally and specifically described in U.S. Patent Application Publication No. US 2015/0038515 A1, and are incorporated herein in their entirety by reference.

(d) sAg Secretion Inhibitors

As described herein, the term "sAg secretion inhibitor" includes compounds that are capable of inhibiting, either directly or indirectly, the secretion of sAg (S, M and/or L surface antigens) bearing subviral particles and/or DNA containing viral particles from HBV-infected cells. For example, in certain embodiments, the inhibitor detectably inhibits the secretion of sAg as measured, e.g., using assays known in the art or described herein, e.g., ELISA assay or by Western Blot. In certain embodiments, the inhibitor inhibits the secretion of sAg by at least 5%, at least 10%, at least 20%, at least 50%, at least 75%, or at least 90%. In certain embodiments, the inhibitor reduces serum levels of sAg in a patient by at least 5%, at least 10%, at least 20%, at least 50%, at least 75%, or at least 90%.

Reported sAg secretion inhibitors include compounds described in U.S. Pat. No. 8,921,381, as well as compounds described in U.S. Patent Application Publication Nos. US 2015/0087659 and US 2013/0303552, all of which are incorporated herein in their entireties by reference.

In addition, reported sAg secretion inhibitors include, but are not limited to, those generally and specifically described in Int'l Patent Application Publication Nos. WO 2015113990, WO 2015173164, US 2016/0122344, WO 2016107832, WO 2016023877, WO 2016128335, WO 2016177655, WO 2016071215, WO 2017013046, WO 2017016921, WO 2017016960, WO 2017017042, WO 2017017043, WO 2017102648, WO 2017108630, WO 2017114812, WO 2017140821 and are incorporated herein in their entirety by reference.

(e) Immunostimulators

The term "immunostimulator" includes compounds that are capable of modulating an immune response (e.g., stimulate an immune response (e.g., an adjuvant)). Immunostimulators include, but are not limited to, polyinosinic:polycytidylic acid (poly I:C) and interferons.

Reported immunostimulators include, but are not limited to, agonists of stimulator of IFN genes (STING) and interleukins. Reported immunostimulators further include, but are not limited to, HBsAg release inhibitors, TLR-7 agonists (such as, but not limited to, GS-9620, RG-7795), T-cell stimulators (such as, but not limited to, GS-4774), RIG-1 inhibitors (such as, but not limited to, SB-9200), and SMAC-mimetics (such as, but not limited to, Birinapant).

(f) Oligomeric Nucleotides

Reported oligomeric nucleotides targeted to the Hepatitis B genome include, but are not limited to, Arrowhead-ARC-520 (see U.S. Pat. No. 8,809,293; and Wooddell et al., 2013, Molecular Therapy 21(5):973-985, all of which incorporated herein in their entireties by reference).

In certain embodiments, the oligomeric nucleotides can be designed to target one or more genes and/or transcripts of the HBV genome. Oligomeric nucleotide targeted to the Hepatitis B genome also include, but are not limited to, isolated, double stranded, siRNA molecules, that each include a sense strand and an antisense strand that is hybridized to the sense strand. In certain embodiments, the siRNA target one or more genes and/or transcripts of the HBV genome.

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to elsewhere herein may be applied to experimental data to generate a corresponding graph to aid in assessing the effects of the drug combination. The corresponding graphs associated with the equations referred to elsewhere herein are the concentration-effect curve, isobologram curve and combination index curve, respectively.

Synthesis

The present invention further provides methods of preparing the compounds of the present invention. Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field.

It is appreciated that where typical or preferred process conditions (i.e., reaction temperatures, times, mole ratios of reactants, solvents, pressures, and so forth) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene, et al., Protective Groups in Organic Synthesis, 2d. Ed. (Wiley & Sons, 1991), the entire disclosure of which is incorporated by reference herein for all purposes.

The reactions or the processes described herein can be carried out in suitable solvents that can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

A compound of formula I can be prepared, for example, according to the synthetic methods outlined in Schemes 1-3. It should be noted that any absolute stereochemistry of the chiral center(s) represented in Schemes 1-3 is merely illustrative, and these Schemes may be used to prepare any of the stereoisomers (or any mixtures thereof) of any of the compounds of the invention

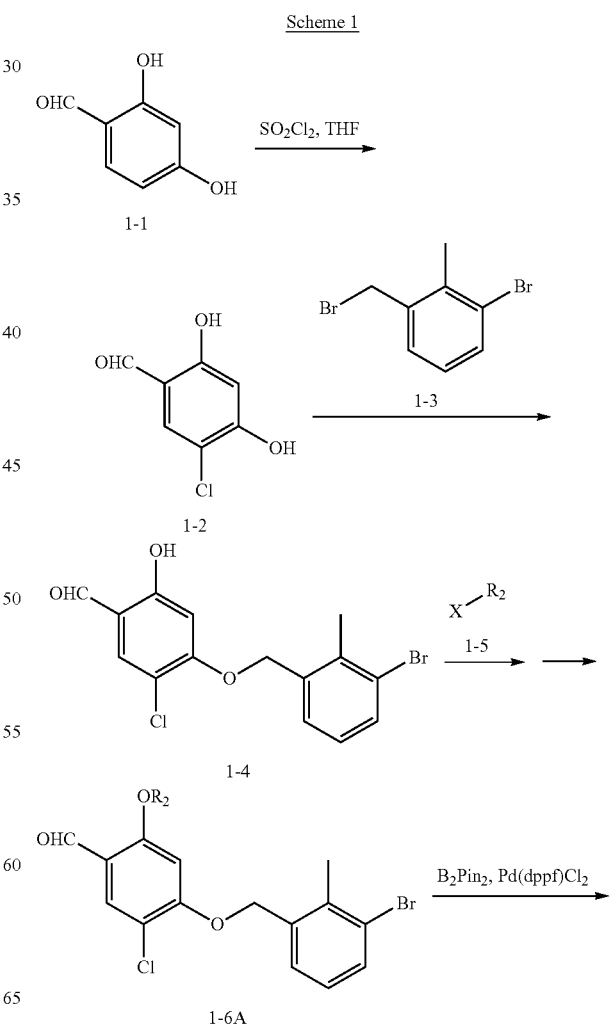

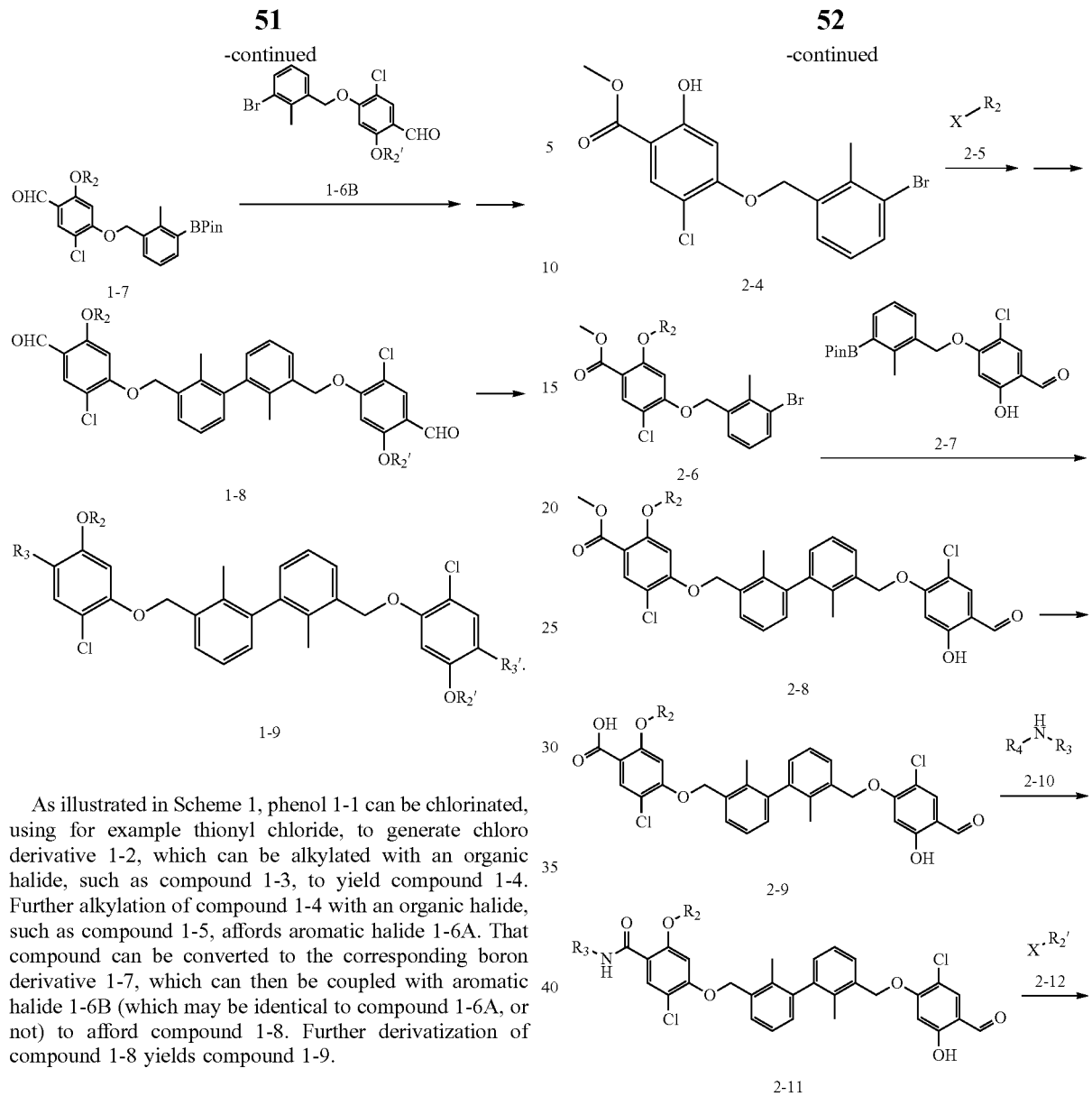

As illustrated in Scheme 1, phenol 1-1 can be chlorinated, using for example thionyl chloride, to generate chloro derivative 1-2, which can be alkylated with an organic halide, such as compound 1-3, to yield compound 1-4. Further alkylation of compound 1-4 with an organic halide, such as compound 1-5, affords aromatic halide 1-6A. That compound can be converted to the corresponding boron derivative 1-7, which can then be coupled with aromatic halide 1-6B (which may be identical to compound 1-6A, or not) to afford compound 1-8. Further derivatization of compound 1-8 yields compound 1-9.

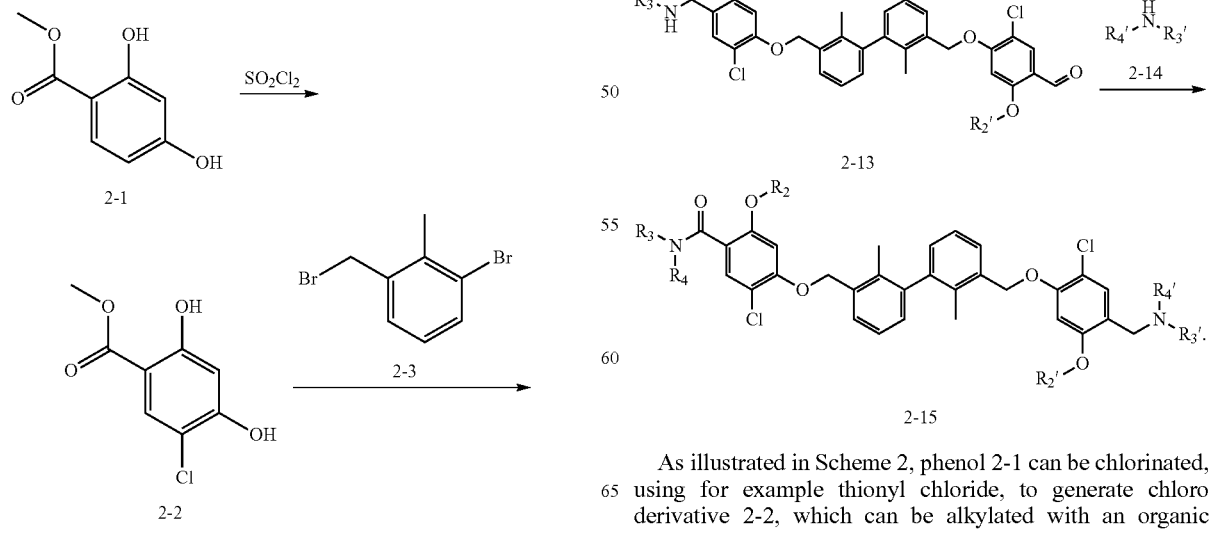

As illustrated in Scheme 2, phenol 2-1 can be chlorinated, using for example thionyl chloride, to generate chloro derivative 2-2, which can be alkylated with an organic halide, such as compound 2-3, to yield compound 2-4.

Further alkylation of compound 2-4 with an organic halide, such as compound 2-5, affords aromatic halide 2-6. That compound can be coupled with boron derivative 2-7 to afford monoester 2-8. Compound 2-8 can be converted to the corresponding carboxylic acid 2-9, and amidated with amine 2-10 under reductive conditions to generate compound 2-11, which can then be alkylated to yield 2-13 and then subjected to reductive amination with 2-14 to yield compound 2-15.

Scheme 3.

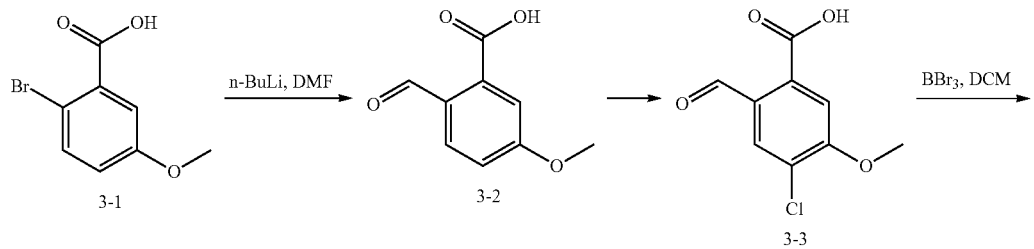

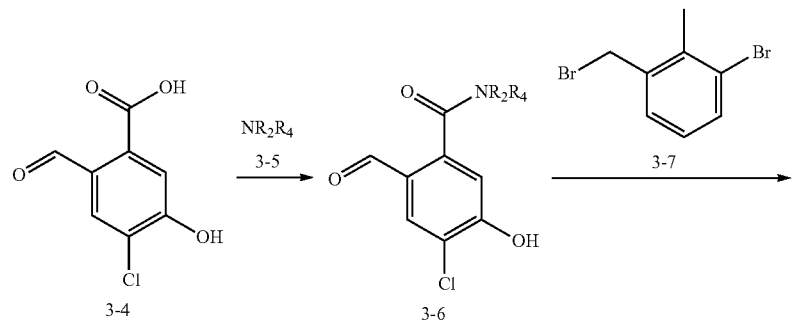

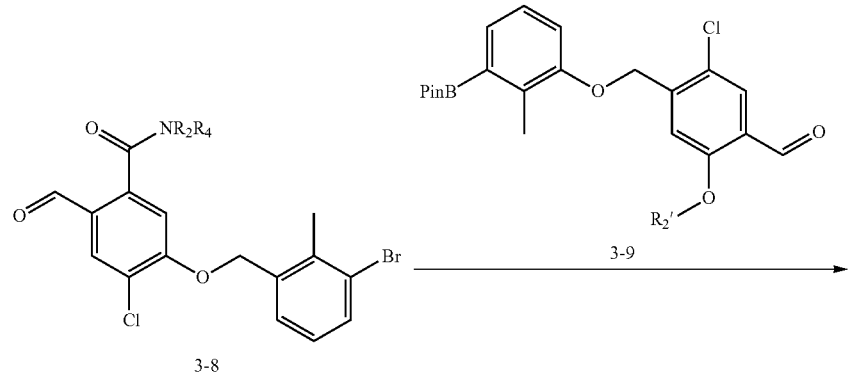

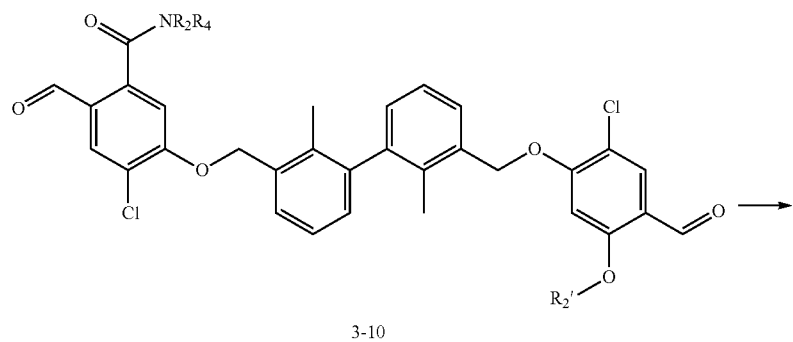

-continued

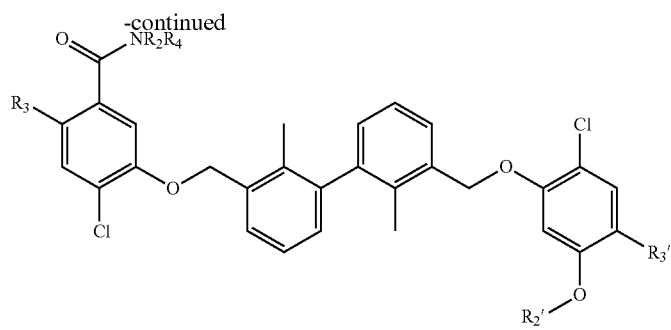

3-11

As illustrated in Scheme 3, bromide 3-1 can be formylated, using for example n-butyl lithium and DMF, to yield aldehyde 3-2, which can be chlorinated using for example thionyl chloride to yield compound 3-3. Deprotection of the methyl ether in 3-3 yields phenol 3-4, which can be converted to amide 3-6, and subsequently alkylated to compound 3-8. That compound can be coupled with boron derivative 3-9 to afford compound 3-10, which may be further derivatized to compound 3-11.

Further illustrations of method useful for preparing compounds of the invention are shown in Schemes 4-9.

Scheme 4.
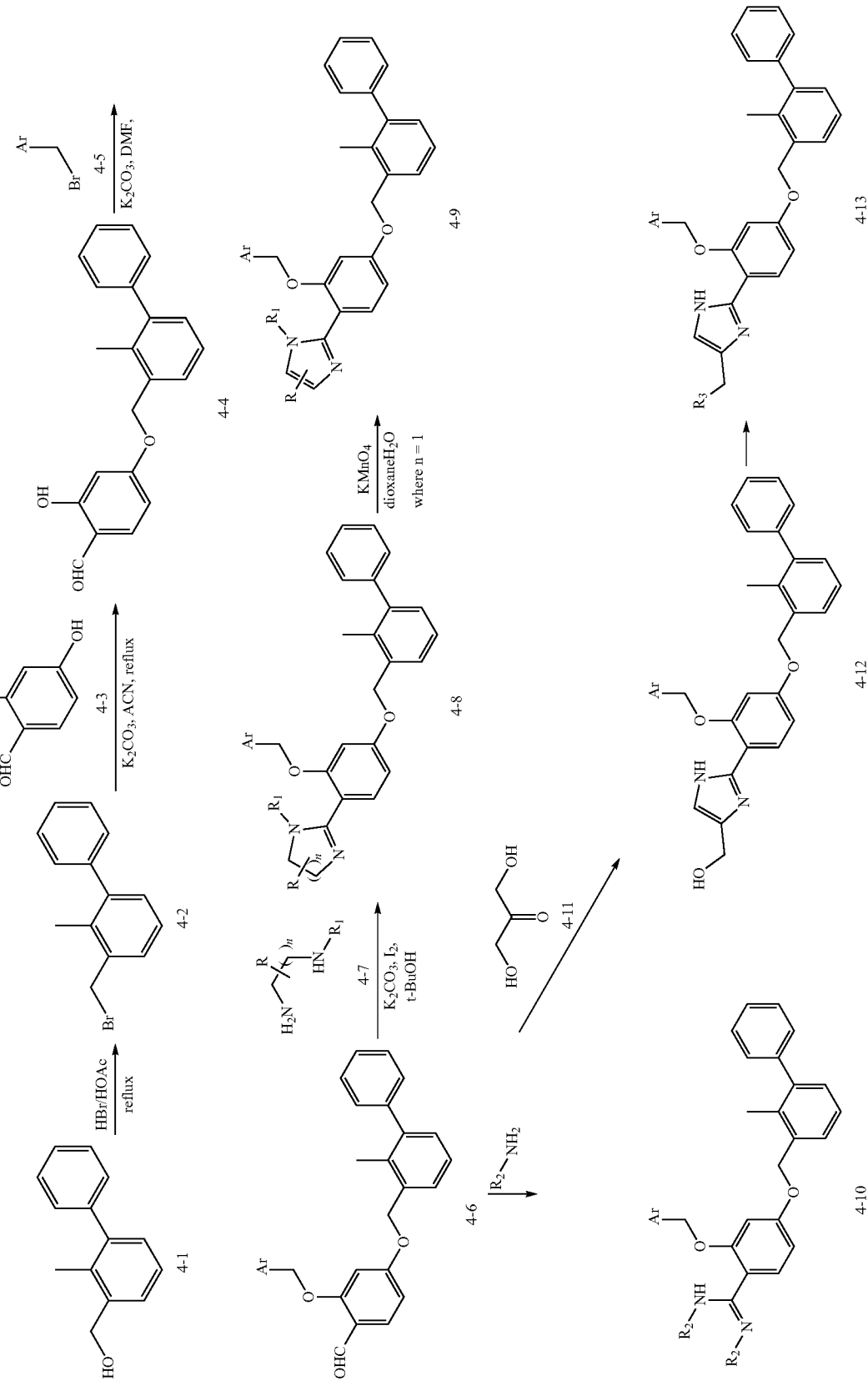

Scheme 5.
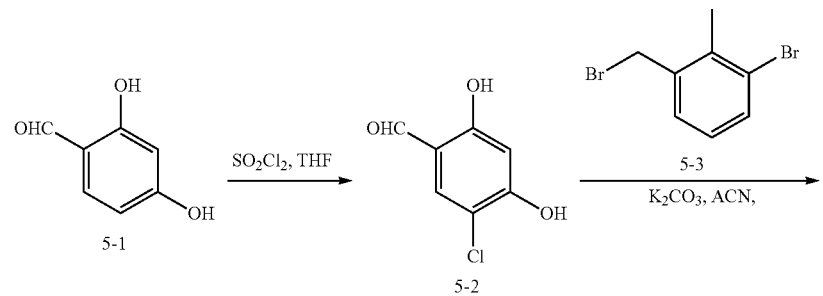
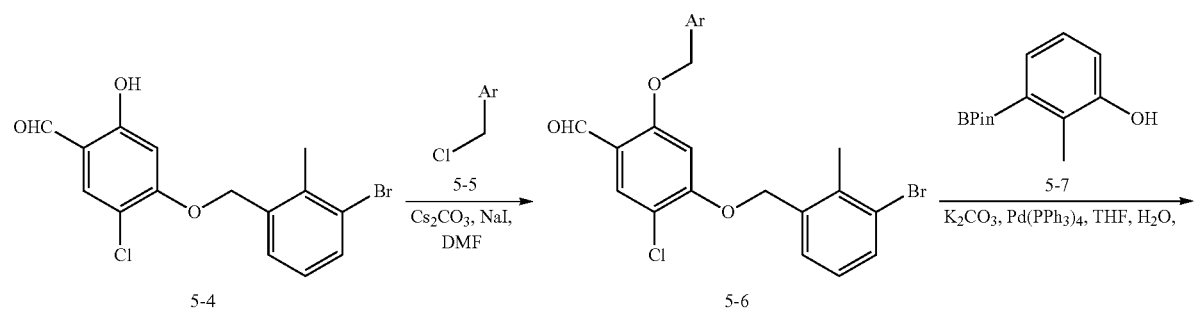
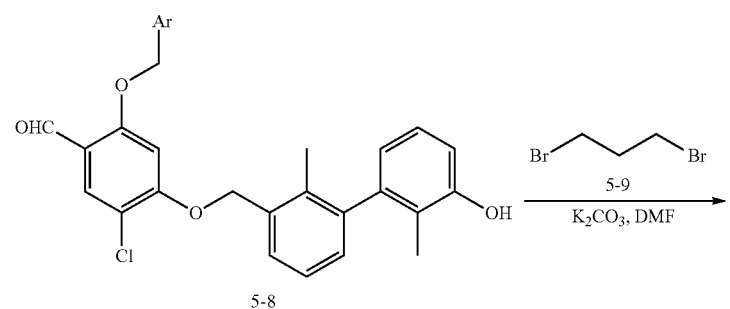
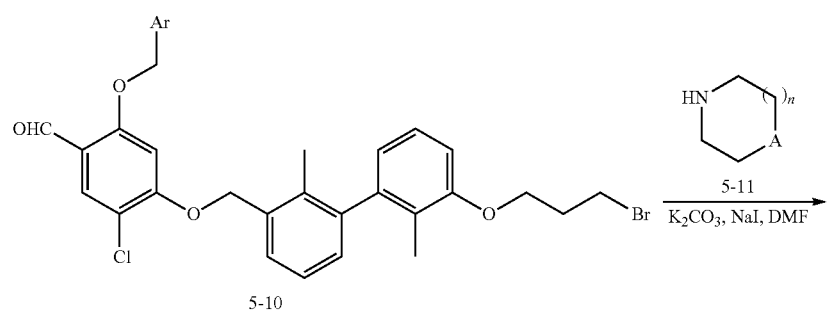

-continued
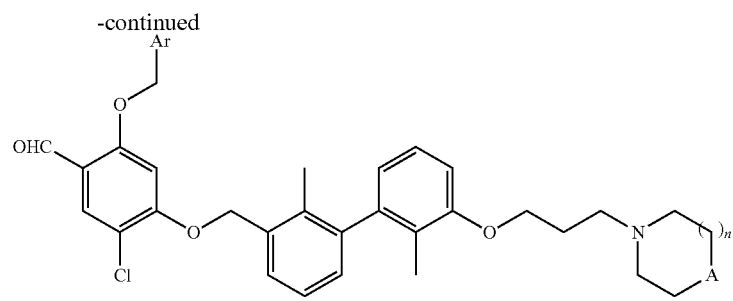
5-12
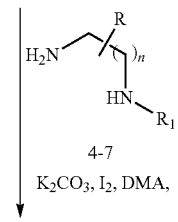
4-7
K₂CO₃, I₂, DMA,
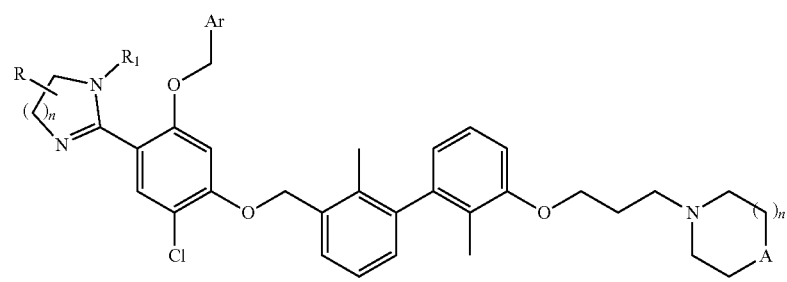
5-13
Scheme 6.
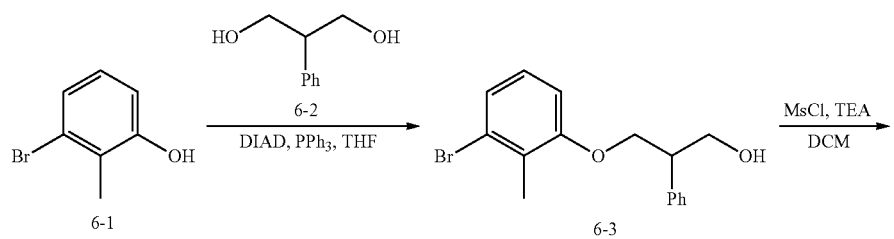
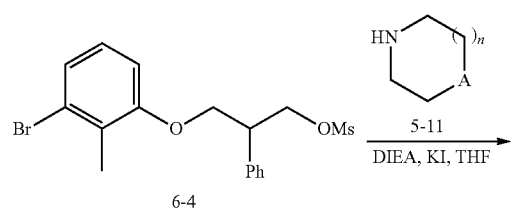

-continued
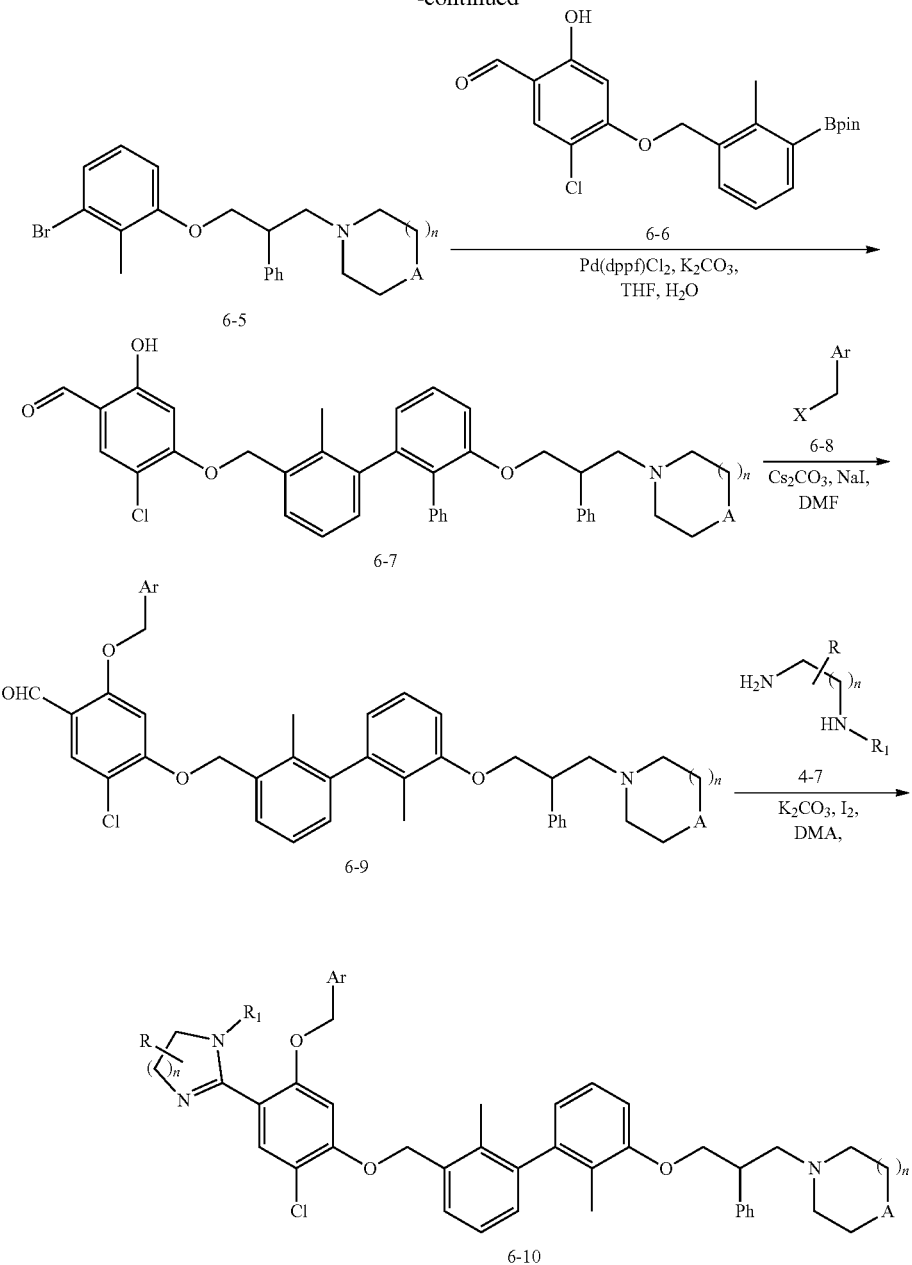
Scheme 7.
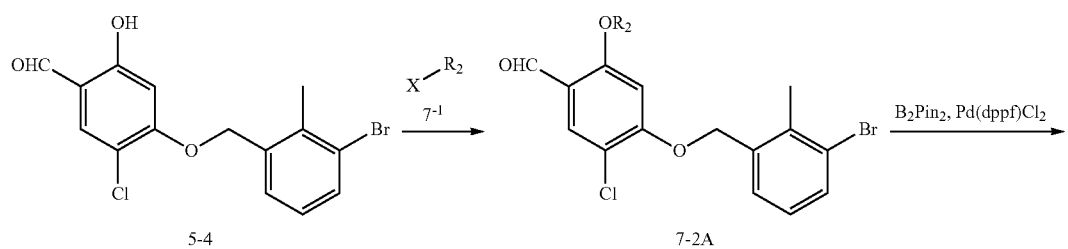

-continued
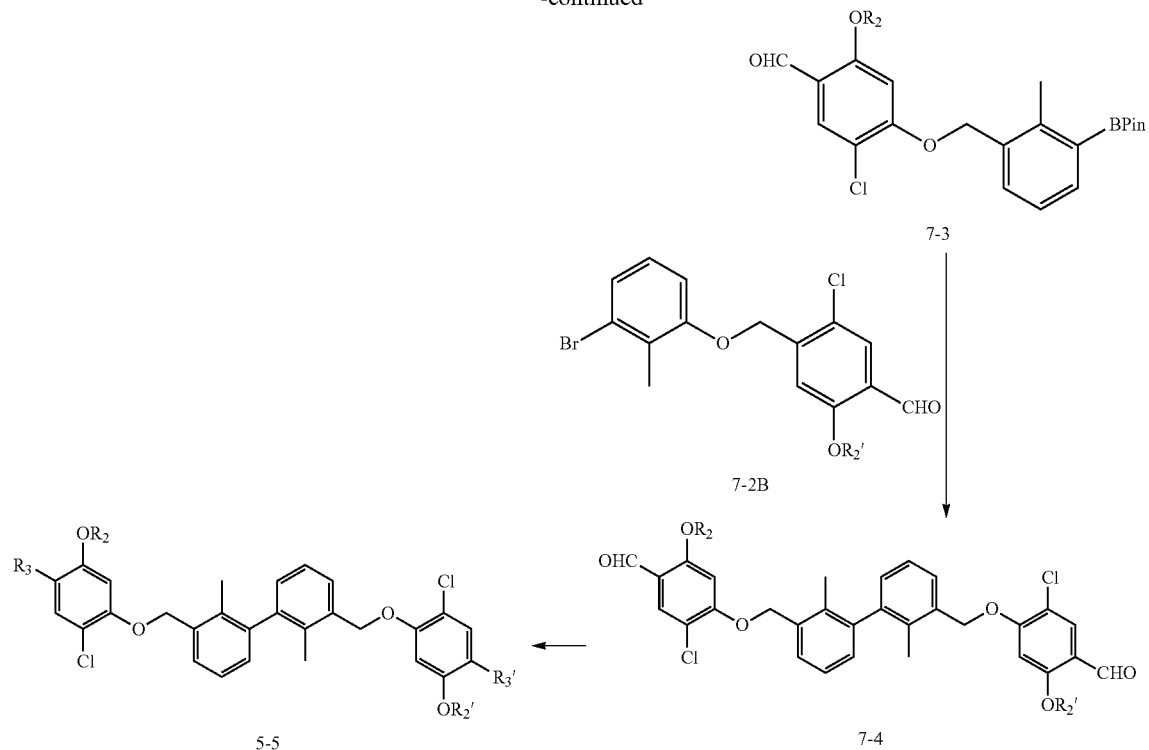
Scheme 8.
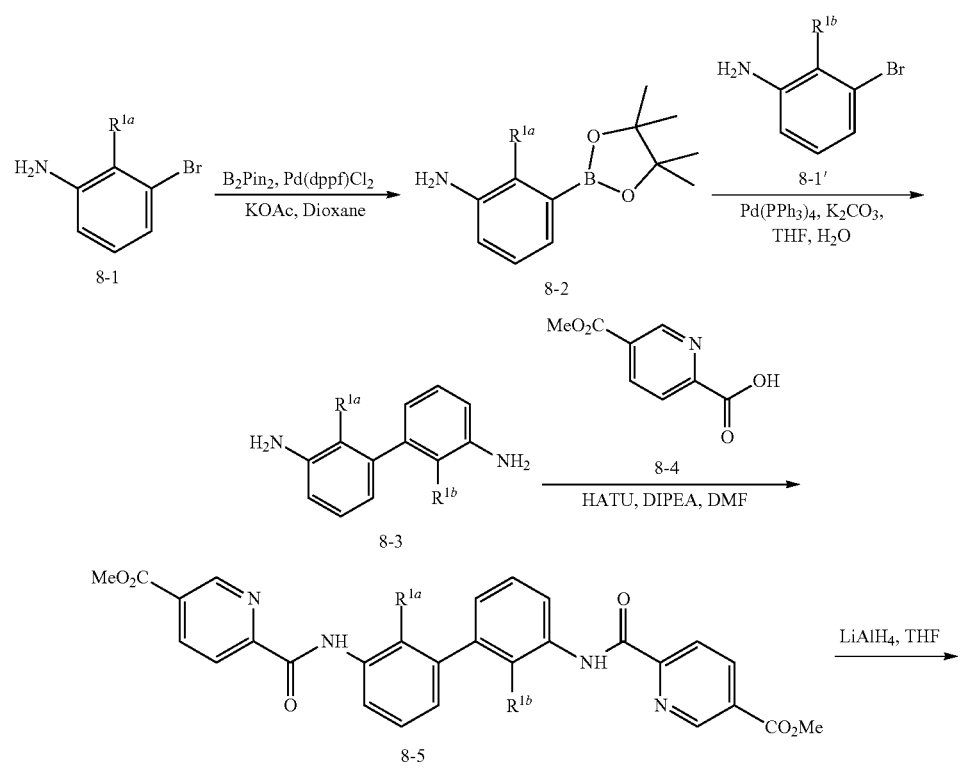

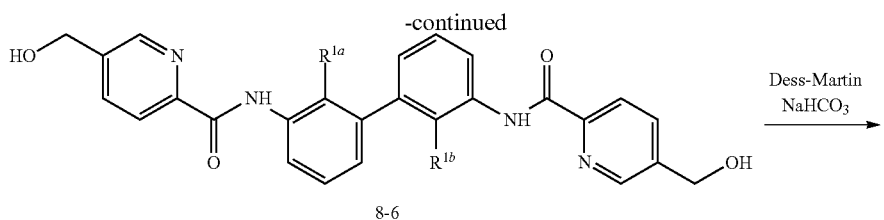
8-6
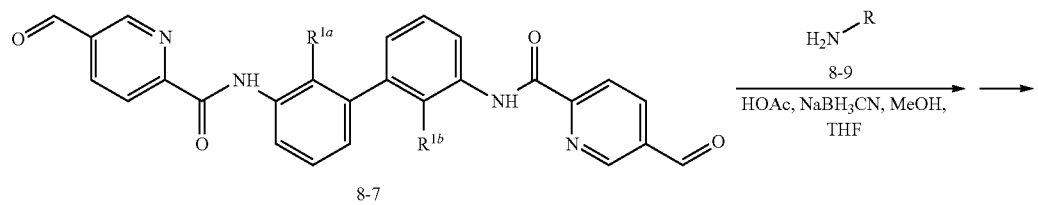
8-7
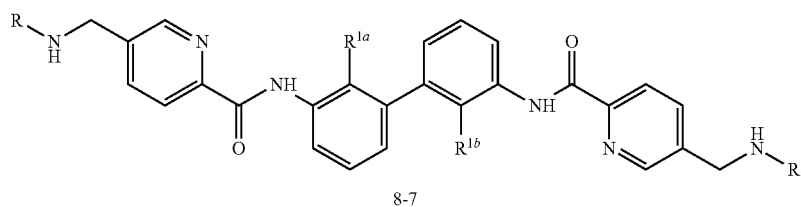
8-7
Scheme 9.
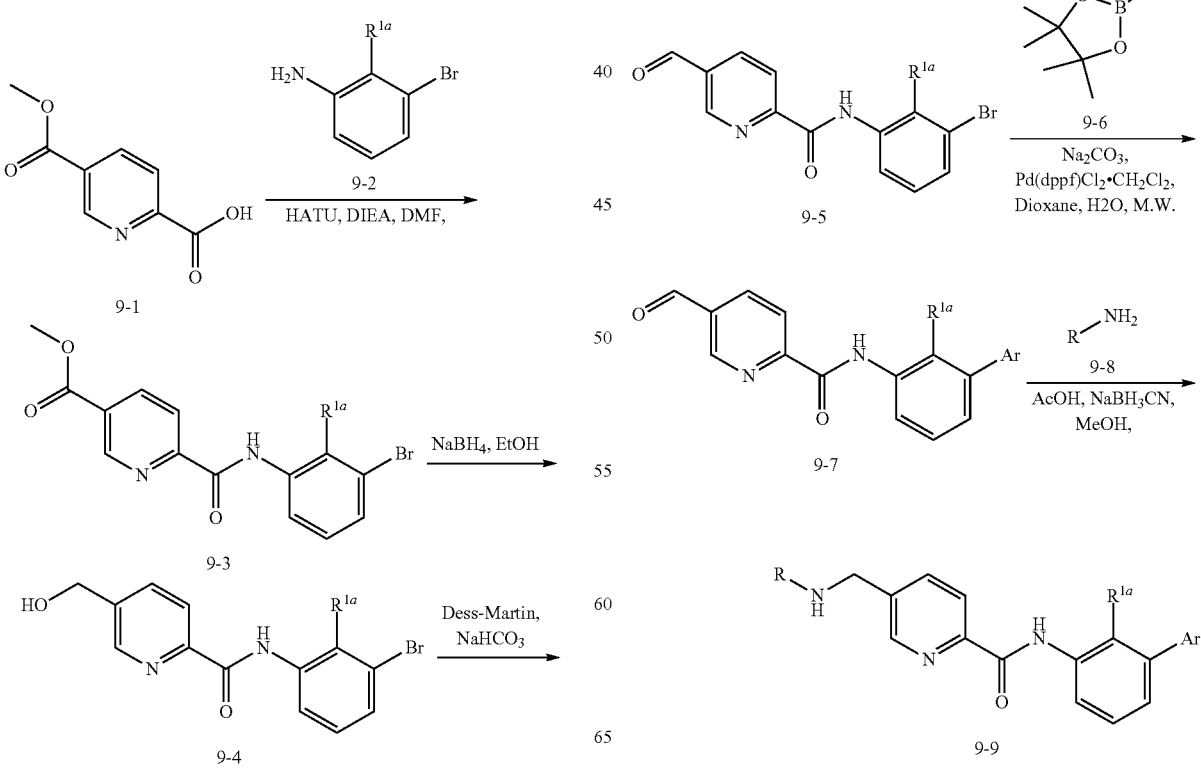

Scheme 10.

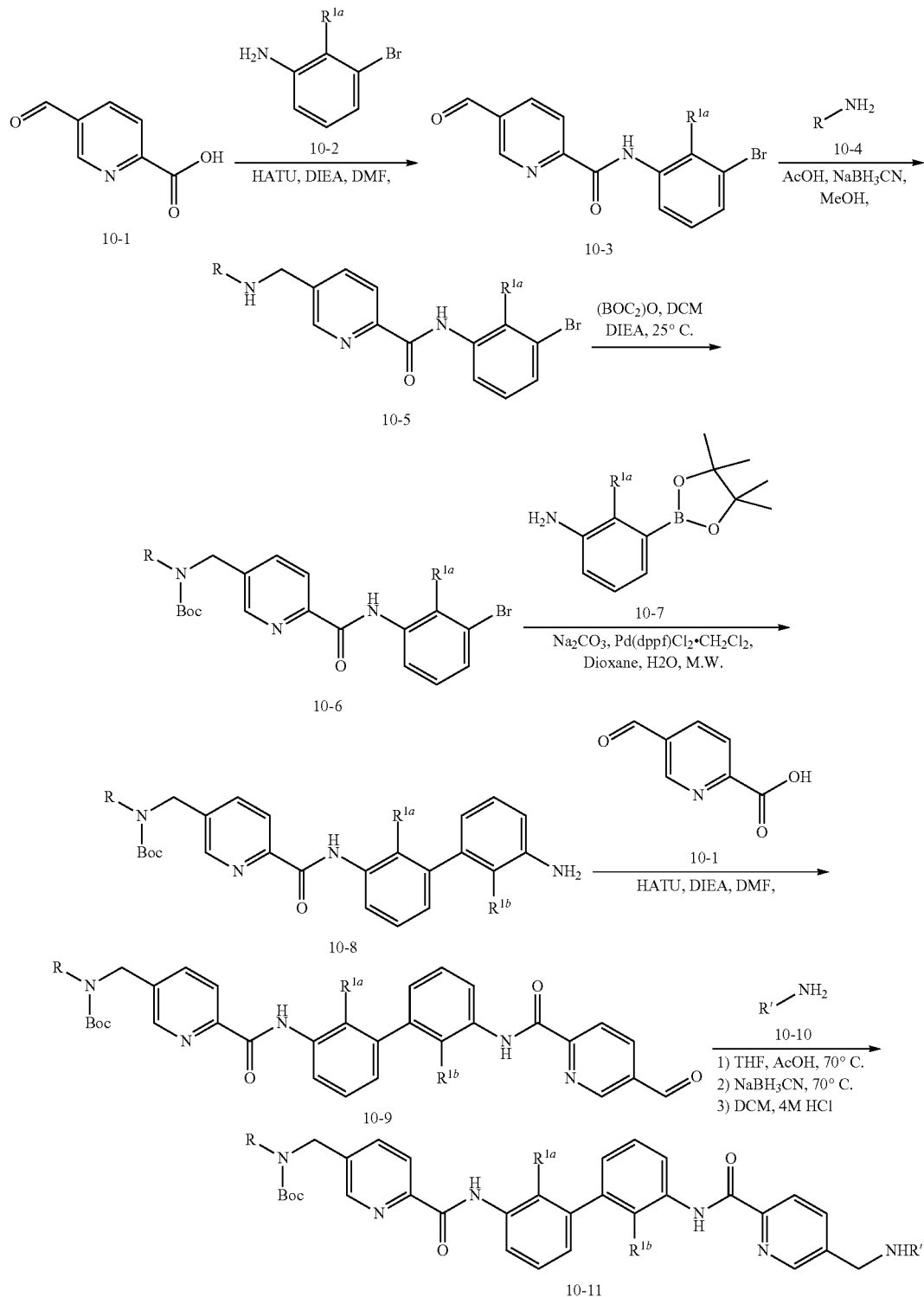

Methods

The invention provides a method of treating or preventing hepatitis virus infection in a subject. In certain embodiments, the infection comprises hepatitis B virus (HBV) and/or hepatitis D virus (HDV) infection. In other embodiments, the infection comprises hepatitis B virus (HBV) infection. In yet other embodiments, the infection comprises hepatitis D virus (HDV) infection. In yet other embodiments, the method comprises administering to the subject in need thereof a therapeutically effective amount of at least one compound of the invention. In yet other embodiments, the compound of the invention is the only antiviral agent administered to the subject. In yet other embodiments, the at least one compound is administered to the subject in a pharmaceutically acceptable composition. In yet other embodiments, the subject is further administered at least one additional agent useful for treating the hepatitis virus infection. In yet other embodiments, the at least one additional agent comprises at least one selected from the group consisting of reverse transcriptase inhibitor; capsid inhibitor; cccDNA formation inhibitor; sAg secretion inhibitor; oligomeric nucleotide targeted to the Hepatitis B genome; immunostimulator; and RNA destabilizer. In yet other embodiments, the subject is co-administered the at least one compound and the at least one additional agent. In yet other embodiments, the at least one compound and the at least one additional agent are coformulated.

In certain embodiments, the subject is a mammal. In other embodiments, the mammal is a human.

Pharmaceutical Compositions and Formulations

The invention provides pharmaceutical compositions comprising at least one compound of the invention or a salt or solvate thereof, which are useful to practice methods of the invention. Such a pharmaceutical composition may consist of at least one compound of the invention or a salt or solvate thereof, in a form suitable for administration to a subject, or the pharmaceutical composition may comprise at least one compound of the invention or a salt or solvate thereof, and one or more pharmaceutically acceptable carriers, one or more additional ingredients, or some combination of these. At least one compound of the invention may be present in the pharmaceutical composition in the form of a physiologically acceptable salt, such as in combination with a physiologically acceptable cation or anion, as is well known in the art.

In certain embodiments, the pharmaceutical compositions useful for practicing the method of the invention may be administered to deliver a dose of between 1 ng/kg/day and 100 mg/kg/day. In other embodiments, the pharmaceutical compositions useful for practicing the invention may be administered to deliver a dose of between 1 ng/kg/day and 1,000 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for nasal, inhalational, oral, rectal, vaginal, pleural, peritoneal, parenteral, topical, transdermal, pulmonary, intranasal, buccal, ophthalmic, epidural, intrathecal, intravenous or another route of administration. A composition useful within the methods of the invention may be directly administered to the brain, the brainstem, or any other part of the central nervous system of a mammal or bird. Other contemplated formulations include projected nanoparticles, microspheres, liposomal preparations, coated particles, polymer conjugates, resealed erythrocytes containing the active ingredient, and immunologically-based formulations.

In certain embodiments, the compositions of the invention are part of a pharmaceutical matrix, which allows for manipulation of insoluble materials and improvement of the bioavailability thereof, development of controlled or sustained release products, and generation of homogeneous compositions. By way of example, a pharmaceutical matrix may be prepared using hot melt extrusion, solid solutions, solid dispersions, size reduction technologies, molecular complexes (e.g., cyclodextrins, and others), microparticulate, and particle and formulation coating processes. Amorphous or crystalline phases may be used in such processes.

The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology and pharmaceutics. In general, such preparatory methods include the step of bringing the active ingredient into association with a carrier or one or more other accessory ingredients, and then, if necessary or desirable, shaping or packaging the product into a desired single-dose or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In certain embodiments, the compositions of the invention are formulated using one or more pharmaceutically acceptable excipients or carriers. In certain embodiments, the pharmaceutical compositions of the invention comprise a therapeutically effective amount of at least one compound of the invention and a pharmaceutically acceptable carrier. Pharmaceutically acceptable carriers, which are useful, include, but are not limited to, glycerol, water, saline, ethanol, recombinant human albumin (e.g., RECOMBUMIN®), solubilized gelatins (e.g., GELOFUSINE®), and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), recombinant human albumin, solubilized gelatins, suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, isotonic agents, for example, sugars, sodium chloride, or polyalcohols such as mannitol and sorbitol, are included in the composition. Prolonged absorption of the injectable compositions may be brought about by including in the composition an agent that delays absorption, for example, aluminum monostearate or gelatin.

Formulations may be employed in admixtures with conventional excipients, i.e., pharmaceutically acceptable organic or inorganic carrier substances suitable for oral, parenteral, nasal, inhalational, intravenous, subcutaneous, transdermal enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or fragrance-conferring substances and the like. They may also be combined where desired with other active agents, e.g., other analgesic, anxiolytics or hypnotic agents. As used herein, "additional ingredients" include, but are not limited to, one or more ingredients that may be used as a pharmaceutical carrier.

The composition of the invention may comprise a preservative from about 0.005% to 2.0% by total weight of the composition. The preservative is used to prevent spoilage in the case of exposure to contaminants in the environment. Examples of preservatives useful in accordance with the invention include but are not limited to those selected from the group consisting of benzyl alcohol, sorbic acid, parabens, imidurea and combinations thereof. One such preservative is a combination of about 0.5% to 2.0% benzyl alcohol and 0.05% to 0.5% sorbic acid.

The composition may include an antioxidant and a chelating agent which inhibit the degradation of the compound. Antioxidants for some compounds are BHT, BHA, alpha-tocopherol and ascorbic acid in the exemplary range of about 0.01% to 0.3%, or BHT in the range of 0.03% to 0.1% by weight by total weight of the composition. The chelating agent may be present in an amount of from 0.01% to 0.5% by weight by total weight of the composition. Exemplary chelating agents include edetate salts (e.g. disodium edetate) and citric acid in the weight range of about 0.01% to 0.20%, or in the range of 0.02% to 0.10% by weight by total weight of the composition. The chelating agent is useful for chelating metal ions in the composition that may be detrimental to the shelf life of the formulation. While BHT and disodium edetate are exemplary antioxidant and chelating agent, respectively, for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethyl cellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, acacia, and ionic or non ionic surfactants. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, ionic and non-ionic surfactants, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying. Methods for mixing components include physical milling, the use of pellets in solid and suspension formulations and mixing in a transdermal patch, as known to those skilled in the art.

Administration/Dosing

The regimen of administration may affect what constitutes an effective amount. The therapeutic formulations may be administered to the patient either prior to or after the onset of a disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, such as a mammal, such as a human, may be carried out using known procedures, at dosages and for periods of time effective to treat a disease or disorder contemplated herein. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 mg/kg to 100 mg/kg of body weight/per day. One of ordinary skill in the art would be able to study the relevant factors and make the determination regarding the effective amount of the therapeutic compound without undue experimentation.

The compound may be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon a number of factors, such as, but not limited to, type and severity of the disease being treated, and type and age of the animal.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder in a patient.

In certain embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physician taking all other factors about the patient into account.

Compounds of the invention for administration may be in the range of from about 1 µg to about 7,500 mg, about 20 µg to about 7,000 mg, about 40 µg to about 6,500 mg, about 80 µg to about 6,000 mg, about 100 µg to about 5,500 mg, about 200 µg to about 5,000 mg, about 400 µg to about 4,000 mg, about 800 µg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments there-in-between.

In some embodiments, the dose of a compound of the invention is from about 0.5 µg and about 5,000 mg. In some embodiments, a dose of a compound of the invention used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder in a patient.

The term "container" includes any receptacle for holding the pharmaceutical composition or for managing stability or water uptake. For example, in certain embodiments, the container is the packaging that contains the pharmaceutical composition, such as liquid (solution and suspension), semisolid, lyophilized solid, solution and powder or lyophilized formulation present in dual chambers. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease or disorder in a patient.

Administration

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, epidural, intrapleural, intraperitoneal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, emulsions, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic, generally recognized as safe (GRAS) pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation. Hard capsules comprising the active ingredient may be made using a physiologically degradable composition, such as gelatin. The capsules comprise the active ingredient, and may further comprise additional ingredients including, for example, an inert solid diluent such as calcium carbonate, calcium phosphate, or kaolin.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin from animal-derived collagen or from a hypromellose, a modified form of cellulose, and manufactured using optional mixtures of gelatin, water and plasticizers such as sorbitol or glycerol. Such soft capsules comprise the active ingredient, which may be mixed with water or an oil medium such as peanut oil, liquid paraffin, or olive oil.

For oral administration, the compounds of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY® film coating systems available from Colorcon, West Point, Pa. (e.g., OPADRY® OY Type, OYC Type, Organic Enteric OY-P Type, Aqueous Enteric OY-A Type, OY-PM Type and OPADRY® White, 32K18400). It is understood that similar type of film coating or polymeric products from other companies may be used.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e., having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds useful within the methods of the invention, and a further layer providing for the immediate release of one or more compounds useful within the methods of the invention. Using a wax/pH-sensitive polymer mix, a gastric insoluble composition may be obtained in which the active ingredient is entrapped, ensuring its delayed release.

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl para-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Injectable formulations may also be prepared, packaged, or sold in devices such as patient-controlled analgesia (PCA) devices. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form in a recombinant human albumin, a fluidized gelatin, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (i.e., U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In other embodiments, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. For example, it should be present in an amount from about 0.0005% to about 5% of the composition; for example, it should be present in an amount of from about 0.001% to about 1% of the composition. Such compounds may be synthetically- or naturally derived.

Buccal Administration

A pharmaceutical composition of the invention may be prepared, packaged, or sold in a formulation suitable for buccal administration. Such formulations may, for example, be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, may have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems:

In certain embodiments, the compositions and/or formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In certain embodiments of the invention, the compounds useful within the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that may, although not necessarily, include a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Example 1: 3-((2-(4,5-Dihydro-1H-imidazol-2-yl)-5-((2-methyl-[1,1'-biphenyl]-3-yl)methoxy)phenoxy)methyl)benzonitrile

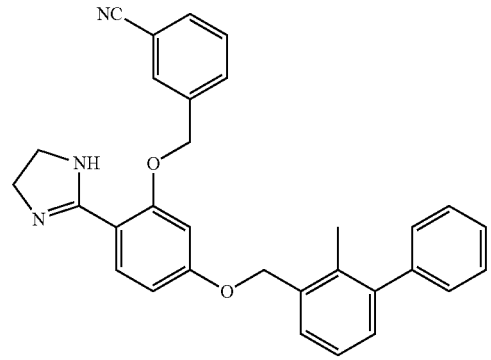

(a) 1-(bromomethyl)-2-methyl-3-phenyl-benzene

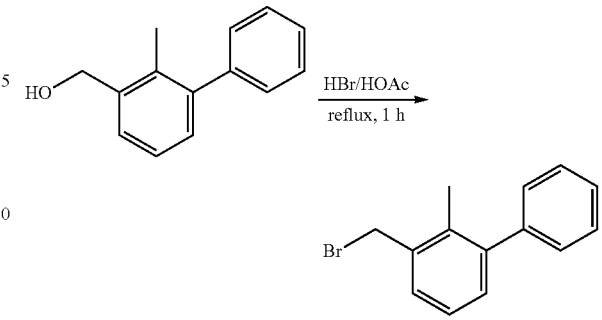

A mixture of (2-methyl-3-phenyl-phenyl)methanol (10 g, 50.44 mmol) in HBr/AcOH (100 mL) was stirred at 80° C.

for 1 hr. The solvent was removed under vacuum to give 1-(bromomethyl)-2-methyl-3-phenyl-benzene (14 g, crude) as a yellow solid, which was used for the next step without further purification.

(b) 2-hydroxy-4-[(2-methyl-3-phenyl-phenyl)methoxy]benzaldehyde

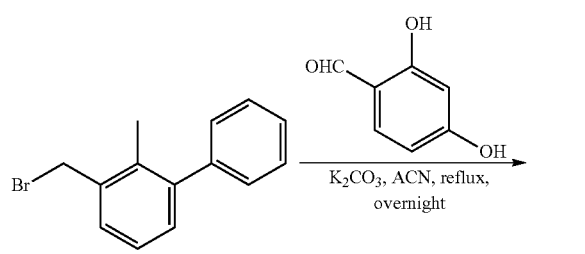

To a mixture of 1-(bromomethyl)-2-methyl-3-phenyl-benzene (14 g, 53.61 mmol) and 2,4-dihydroxybenzaldehyde (6.66 g, 48.25 mmol) in MeCN (150 mL) was added K$_2$CO$_3$ (14.82 g, 107.2 mmol). The reaction was stirred for 12 hr at 80° C. After cooling to the room temperature, the reaction mixture was filtered and washed with 60 mL of MeCN. The filter-cake was added 100 mL of water and stirred at 15° C. for 1 hr. Then the mixture was filtered to give (10.4 g, 60.9% yield) of 2-hydroxy-4-[(2-methyl-3-phenyl-phenyl)methoxy]benzaldehyde as a yellow solid. $^1$H NMR (400 MHz, DMSO-d$_6$): δ 10.09 (s, 1H), 7.55-7.26 (m, 10H), 6.51 (d, J=2.4 Hz, 1H), 6.44 (d, J=8.4 Hz, 1H), 5.13 (s, 2H), 2.15 (s, 3H).

(c) 3-[[2-formyl-5-[(2-methyl-3-phenyl-phenyl)methoxy]phenoxy]methyl] benzonitrile

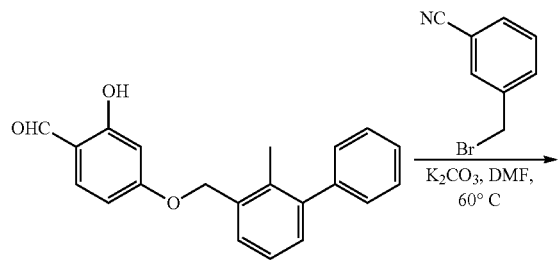

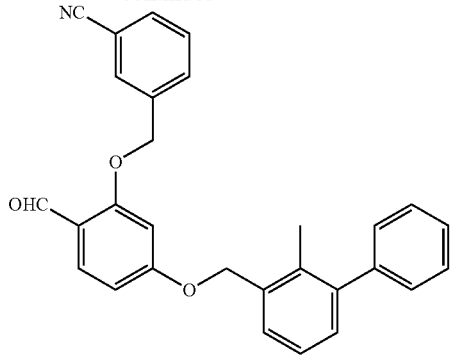

To a solution of 2-hydroxy-4-[(2-methyl-3-phenyl-phenyl)methoxy] benzaldehyde (10.4 g, 32.67 mmol) and 3-(bromomethyl)benzonitrile (7.68 g, 39.2 mmol) in DMF (200 mL) was added K$_2$CO$_3$ (10.38 g, 75.13 mmol). The reaction was stirred for 4 hr at 60° C. After cooling, water (200 mL) and EtOAc (200 mL) were added and stirred for 1 hr. Then the mixture was filtered and washed with water 100 mL. The solvent was removed under vacuum to afford 3-[[2-formyl-5-[(2-methyl-3-phenyl-phenyl)methoxy]phenoxy]methyl]benzonitrile (10 g, 70.62% yield), as a yellow solid, which was used for the next step without further purification. $^1$H NMR (400 MHz, DMSO-d$_6$): δ 10.23 (s, 1H), 7.99 (s, 1H), 7.83-7.72 (m, 2H), 7.70-7.61 (m, 1H), 7.45-7.44 (m, 1H), 7.42-7.30 (m, 3H), 7.29 (m, 1H), 7.27 (m, 3H), 7.20 (m, 1H), 6.94 (s, 1H), 6.83 (m, 1H), 5.34 (s, 2H), 5.26 (s, 2H), 2.18 (s, 3H).

(d) 3-((2-(4,5-dihydro-1H-imidazol-2-yl)-5-((2-methyl-[1,1'-biphenyl]-3-yl)methoxy) phenoxy)methyl)benzonitrile

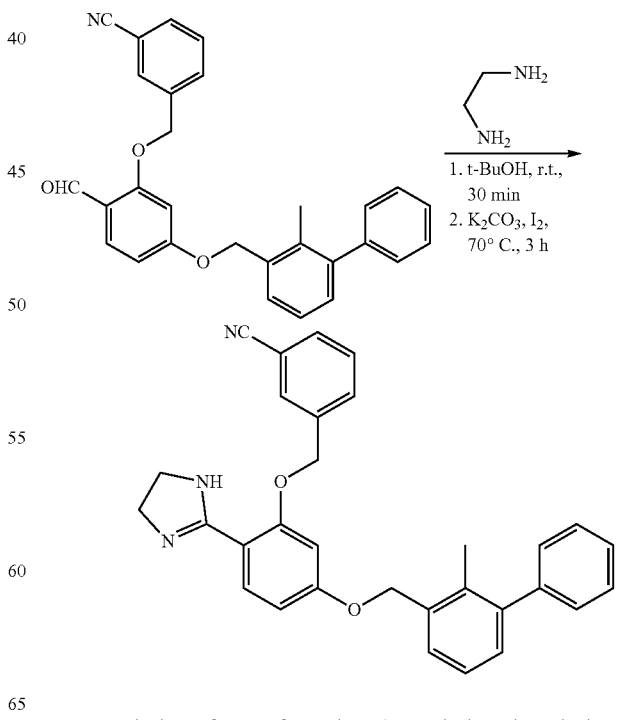

To a solution of 3-[[2-formyl-5-[(2-methyl-3-phenyl-phenyl)methoxy]phenoxy]methyl] benzonitrile (2.5 g, 5.77 mmol) in t-BuOH (50 mL) was added ethane-1,2-diamine (381 mg, 6.3 mmol, 424 µL). The mixture was stirred at 15° C. for 0.5 h. Then K₂CO₃ (996 mg, 7.2 mmol) and I₂ (4.39 g, 17.30 mmol, 3.49 mL) were added and the mixture was stirred at 70° C. for 3 h. The reaction mixture was poured into water (100 mL) and treated with Na₂S₂O₃ (saturated aqueous solution, 20 mL). The precipitate was collected by filtration. 3-[[2-(4, 5-dihydro-1H-imidazol-2-yl)-5-[(2-methyl-3-phenyl-phenyl)methoxy] phenoxy]methyl]benzonitrile (2.0 g) was obtained as red solid. MS: m/z found 474 [M+H]⁺. ¹H NMR (400 MHz, CD₃OD) δ 7.85 (s, 1H), 7.78 (d, J=7.89 Hz, 1H), 7.75 (d, J=8.77 Hz, 1H), 7.71 (d, J=7.89 Hz, 1H), 7.60 (s, 1H), 7.58 (s, 1H), 7.56 (s, 1H), 7.55-7.61 (m, 1H), 7.55-7.61 (m, 1H), 7.40-7.45 (m, 2H), 7.33-7.37 (m, 2H), 7.19-7.28 (m, 4H), 6.86-6.90 (m, 2H), 5.47 (s, 2H), 5.24 (s, 2H), 4.88 (s, 9H), 4.04 (s, 4H), 3.30 (dt, J=3.18, 1.70 Hz, 5H), 2.19 (s, 3H).

Example 2: 3-[[2-(1H-Imidazol-2-yl)-5-[(2-methyl-3-phenyl-phenyl)methoxy]phenoxy] methyl] benzonitrile

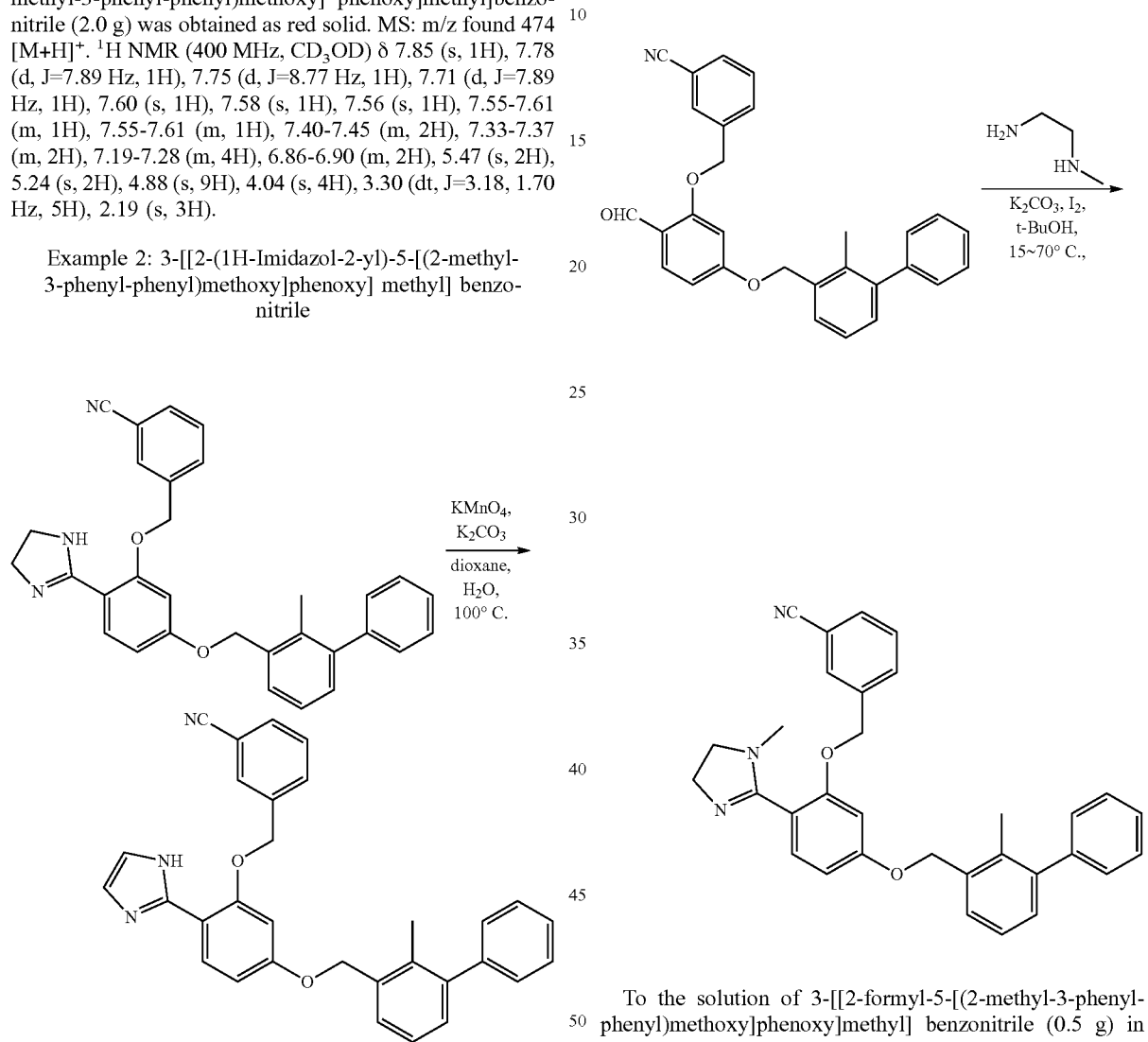

To a solution of 3-[[2-(4,5-dihydro-1H-imidazol-2-yl)-5-[(2-methyl-3-phenyl-phenyl)methoxy] phenoxy]methyl] benzonitrile (0.3 g, 0.633 mmol) in dioxane (20 mL) and H₂O (10 mL) was added K₂CO₃ (262 mg, 1.9 mmol) and KMnO₄ (200 mg, 1.2 mmol). The mixture was stirred at 100° C. for 16 hr. The reaction mixture was filtered, the filtrate was concentrated, and the residue was purified by prep-HPLC (column: Agela Durashell C18 150*25 5µ; mobile phase: [water (10 mM NH₄HCO₃)-ACN]; B %: 45%-70%, 12 min) to give 3-[[2-(1H-imidazol-2-yl)-5-[(2-methyl-3-phenyl-phenyl)methoxy] phenoxy]methyl]benzonitrile (34.1 mg, 10.96% yield, 96% purity) as a white solid. MS: m/z found 472 [M+H]⁺; ¹H NMR (400 MHz, DMSO-d₆) δ ppm 11.70 (br s, 1H), 7.97 (s, 1H), 7.93 (d, J=8.61 Hz, 1H), 7.79 (br d, J=7.94 Hz, 1H), 7.75 (br d, J=7.50 Hz, 1H), 7.56 (t, J=7.44 Hz, 1H), 7.34-7.47 (m, 4H), 7.14-7.31 (m, 5H), 6.97 (s, 1H), 6.73-6.80 (m, 2H), 5.42 (s, 2H), 5.12 (s, 2H), 3.25-3.29 (m, 1H), 2.50-2.53 (m, 3H), 2.15 (s, 3H).

Example 3: 3-[[2-(1-Methyl-4,5-dihydroimidazol-2-yl)-5-[(2-methyl-3-phenyl-phenyl)methoxy]phenoxy] methyl]benzonitrile To the solution of 3-[[2-formyl-5-[(2-methyl-3-phenyl-phenyl)methoxy]phenoxy]methyl] benzonitrile (0.5 g) in t-BuOH (6 ml) was added N'-methylethane-1,2-diamine (93.8 mg). The mixture was stirred at 15° C. for 0.5 hr. Then K₂CO₃ (198.68 mg) and I₂ (875.64 mg) were added to the reaction mixture followed by stirring at 70° C. for 3 hr. The reaction was quenched with saturated Na₂SO₃ solution (10 mL) and extracted with CHCl₃ (3×10 ml). The organic layer was washed with brine (2×30 mL), dried over Na₂SO₄, filtered and concentrated to give 3-[[2-(1-methyl-4,5-dihydroimidazol-2-yl)-5-[(2-methyl-3-phenyl-phenyl)methoxy] phenoxy]methyl] benzonitrile (0.6 g), as a yellow solid. MS: m/z found 488.3 [M+H]⁺; ¹H NMR (400 MHz, DMSO-d₆): δ 7.92 (s, 2H), 7.86-7.79 (m, 2H), 7.67-7.63 (m, 1H), 7.48-7.44 (m, 4H), 7.40-7.36 (m, 1H), 7.32-7.29 (m, 3H), 7.23-7.21 (d, J=6.4 Hz, 1H), 7.07 (d, J=2.0 Hz, 1H), 6.97-6.94 (m, 1H), 5.33 (s, 2H), 5.27 (s, 2H), 4.04-3.99 (m, 2H), 3.93-3.89 (m, 2H), 2.90 (s, 3H), 2.20 (s, 3H).

Example 4: Ethyl (7R)-2-cyclopropyl-7-isopropyl-3-(3-methoxypropoxy)-11-oxo-6,7-dihydropyrido[1,2-d][1,4]benzoxazepine-10-carboxylate

Example 5: 3-[[2-[4-(Hydroxymethyl)-1H-imidazol-2-yl]-5-[(2-methyl-3-phenyl-phenyl)methoxy]phenoxy]methyl]benzonitrile

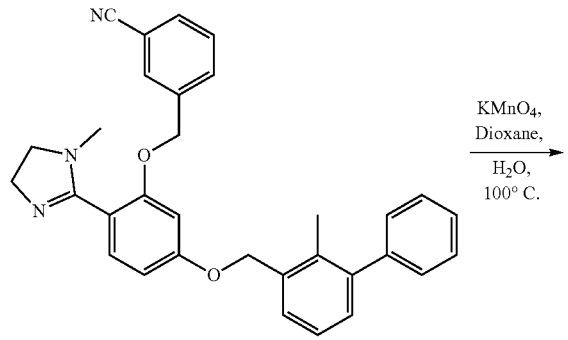
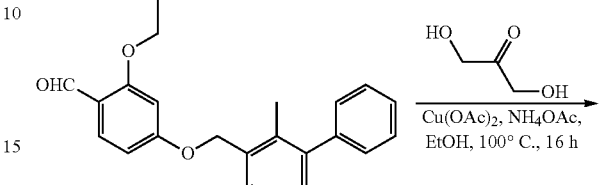
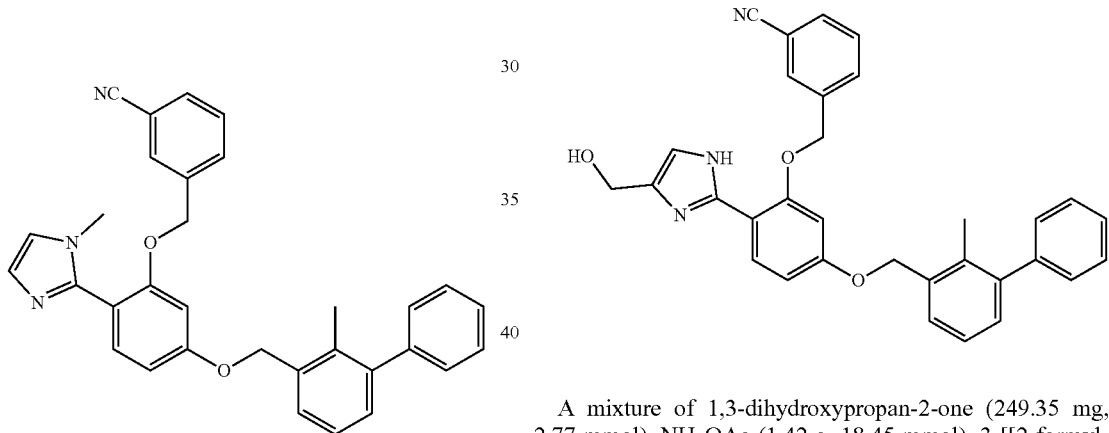

To a mixture of 3-[[2-(1-methyl-4,5-dihydroimidazol-2-yl)-5-[(2-methyl-3-phenyl-phenyl)methoxy]phenoxy]methyl]benzonitrile (200 mg, 410.18 μmol) in dioxane (4 mL) and H₂O (1 mL) was added KMnO₄ (71.30 mg, 451.20 μmol) under N₂. The mixture was heated to 100° C. and stirred for 16 hours. The reaction mixture was filtered. The filtrate was concentrated under reduced pressure. The residue combined with that from another 100 mg scale batch was purified by prep-HPLC (column: YMC-Actus Triart C18 100*30 mm*5 μm; mobile phase: [water (10 mM NH₄HCO₃)-MeCN]; B %: 50%-70%, 12 min) to give 3-[[2-(1-methyl imidazol-2-yl)-5-[(2-methyl-3-phenyl-phenyl)methoxy]phenoxy]methyl]benzonitrile (21.4 mg) as white solid. MS: m/z found 486.2 [M+H]⁺; ¹H NMR (400 MHz, DMSO-d₆): δ 7.80-7.78 (d, J=7.6 Hz, 1H), 7.75 (s, 1H), 7.66-7.64 (d, J=7.6 Hz, 1H), 7.60-7.56 (m, 1H), 7.50-7.46 (m, 3H), 7.41-7.38 (m, 1H), 7.35-7.29 (m, 4H), 7.23-7.19 (m, 2H), 6.94-6.94 (m, 2H), 6.83-6.81 (dd, J=2 Hz, J=8 Hz, 1H), 5.22 (d, 4H), 3.43 (s, 3H), 2.23 (s, 3H).

A mixture of 1,3-dihydroxypropan-2-one (249.35 mg, 2.77 mmol), NH₄OAc (1.42 g, 18.45 mmol), 3-[[2-formyl-5-[(2-methyl-3-phenyl-phenyl)methoxy]phenoxy]methyl]benzonitrile (0.4 g, 0.923 mmol) and Cu(OAc)₂ (502.78 mg, 2.77 mmol) in EtOH (50 mL) was heated to 100° C. for 16 hr. The reaction was filtered and washed with EtOH (50 mL). The filtrate was concentrated. The residue was purified by column chromatography (SiO₂, Petroleum ether/Ethyl acetate=1/1 to 0:1) to give a solid (150 mg). That solid was purified by prep-HPLC (neutral condition; column: Agela Durashell C18 150*25 5μ; mobile phase: [water (10 mM NH₄HCO₃)-ACN]; B %: 55%-75%, 10 min) to give 3-[[2-[4-(hydroxymethyl)-1H-imidazol-2-yl]-5-[(2-methyl-3-phenyl-phenyl)methoxy]phenoxy]methyl]benzonitrile (30.64 mg) as white solid. MS: m/z found 502.2 [M+H]⁺; ¹H NMR (400 MHz, DMSO-d₆): δ 11.55 (s, 1H), 8.00 (s, 1H), 7.94-7.80 (m, 1H), 7.77-7.60 (m, 2H), 7.58 (m, 1H), 7.48-7.41 (m, 4H), 7.38-7.30 (m, 3H), 7.26-7.00 (m, 1H), 6.80 (s, 1H), 6.78-6.76 (m, 2H), 5.43 (s, 2H), 5.14 (m, 2H) 4.82 (m, 1H), 4.42 (s, 2H), 2.17 (s, 3H); ¹H NMR (400 MHz, CD₃OD): δ 7.90-7.88 (m, 1H), 7.81 (s, 1H), 7.74-7.65 (m, 2H), 7.55-7.51 (m, 1H), 7.45-7.35 (m, 4H), 7.29-7.18 (m, 4H), 7.06 (m, 1H), 6.80-6.76 (m, 2H), 5.38 (s, 2H), 5.15 (m, 2H), 4.61 (s, 2H), 2.20 (m, 3H).

Example 6: 3-[[2-[1-(2-Hydroxyethyl)-4,5-dihydro-imidazol-2-yl]-5-[(2-methyl-3-phenyl-phenyl)methoxy] phenoxy]methyl]benzonitrile Example 7: 3-[[2-[1-(2-Hydroxyethyl)imidazo]-2-yl]-5-[(2-methyl-3-phenyl-phenyl)methoxy]phenoxy] methyl]benzonitrile

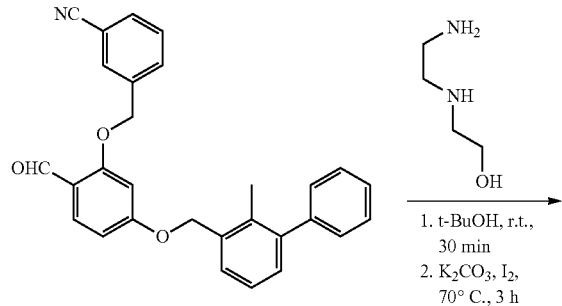

To a solution 3-[[2-formyl-5-[(2-methyl-3-phenyl-phenyl)methoxy]phenoxy]methyl]benzonitrile (1 g, 2.31 mmol) in t-BuOH (20 mL) was added 2-(2-aminoethylamino)ethanol (264.65 mg, 2.54 mmol). The mixture was stirred at 25° C. for 0.5 hr. Then $K_2CO_3$ (415.04 mg, 3.00 mmol) and $I_2$ (1.76 g, 6.93 mmol) was added to the mixture. The mixture was stirred at 70° C. for 3 hr. The reaction mixture was poured into water (20 mL) and treated with aq. $Na_2S_2O_3$ (saturated, 20 mL). The precipitate was collected by filtration. 100 mg of the residue was purified by prep-HPLC (column: Boston Green ODS 150*30 5μ; mobile phase: [water (0.05% HCl)-ACN]; B %: 30%-65%, 11 min) to give 3-[[2-[1-(2-hydroxyethyl)-4,5-dihydroimidazol-2-yl]-5-[(2-methyl-3-phenyl-phenyl)methoxy] phenoxy]methyl]benzonitrile (51.55 mg, 47.9%) as a yellow solid as hydrochloride salt. MS: m/z found 518.3 [M+Na]$^+$; $^1$H NMR (400 MHz, DMSO-d$_6$): δ 10.26 (s, 1H), 7.90 (s, 1H), 7.79-7.84 (m, 2H), 7.62-7.65 (m, 1H), 7.43-7.51 (m, 4H), 7.30-7.37 (m, 1H), 7.27-7.30 (m, 3H), 7.21-7.22 (m, 1H), 7.02-7.03 (m, 1H), 6.91-6.94 (m, 1H), 5.30 (s, 2H), 5.23 (s, 2H), 5.05-5.08 (m, 1H), 4.03-4.08 (m, 2H), 3.90-3.95 (m, 2H) 3.49-3.53 (m, 2H), 3.28-3.32 (m, 2H), 2.18 (s, 3H). $^1$H NMR (400 MHz, CD$_3$OD): δ 7.84 (s, 1H), 7.72-7.77 (m, 2H), 7.58-7.62 (m, 1H), 7.50-7.52 (d, J=8.4 Hz, 1H), 7.33-7.44 (m, 4H), 7.20-7.29 (m, 4H), 6.95-6.96 (m, 1H), 6.88-6.91 (m, 1H), 5.29 (s, 2H), 5.24 (s, 2H), 4.13-4.19 (m, 2H), 3.99-4.05 (m, 2H), 3.66-3.69 (m, 2H), 3.43-3.47 (m, 2H), 2.22 (s, 3H).

To a solution of 3-[[2-[1-(2-hydroxyethyl)-4,5-dihydro-imidazol-2-yl]-5-[(2-methyl-3-phenyl-phenyl)methoxy] phenoxy]methyl]benzonitrile (300 mg, 0.58 mmol) in dioxane (10 mL) and water (5 mL) was added $KMnO_4$ (183.2 mg, 1.16 mmol) and $K_2CO_3$ (240.3 mg, 1.74 mmol). The mixture was stirred at 90° C. for 12 hr. The reaction mixture was filtered. The filtrate was concentrated. The residue was purified by prep-HPLC (column: Boston Green ODS 150*30 5μ; mobile phase: [water (0.05% HCl)-ACN]; B %: 35%-65%, 11 min) to give 3-[[2-[1-(2-hydroxyethyl)imidazol-2-yl]-5-[(2-methyl-3-phenyl-phenyl)methoxy] phenoxy]methyl] benzonitrile HCl salt (55.22 mg, 17.2%) as a white solid. MS: m/z found 516.3 [M+Na]$^+$; $^1$H NMR (400 MHz, DMSO-d$_6$): δ 14.50 (br, 1H), 7.85 (s, 1H), 7.76-7.85 (m, 3H), 7.60-7.70 (m, 1H), 7.55-7.58 (m, 2H), 7.42-7.45 (m, 3H), 7.31-7.40 (m, 1H), 7.28-7.31 (m, 3H), 7.15-7.20 (m, 1H), 7.05 (s, 1H), 6.85-6.95 (m, 1H), 5.25-5.26 (m, 4H) 5.09 (br, 1H), 3.99-4.01 (m, 2H), 3.62-3.64 (m, 2H), 2.19 (s, 3H).

Example 8: N-[[2-[2-[(3-Cyanophenyl)methoxy]-4-[(2-methyl-3-phenyl-phenyl)methoxy]phenyl]-1H-imidazol-4-yl]methyl]acetamide

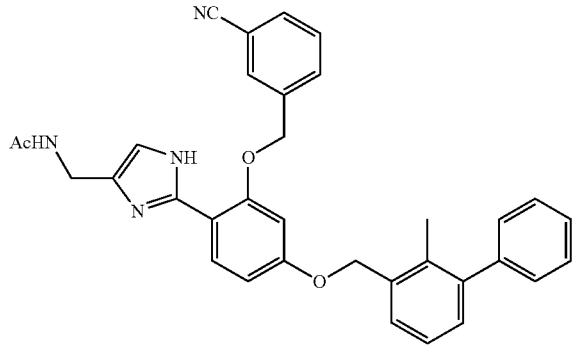

(a) 3-[[2-[4-(azidomethyl)-1H-imidazol-2-yl]-5-[(2-methyl-3-phenyl-phenyl)methoxy]phenoxy]methyl]benzonitrile

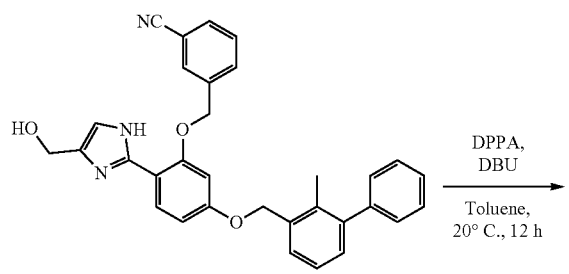

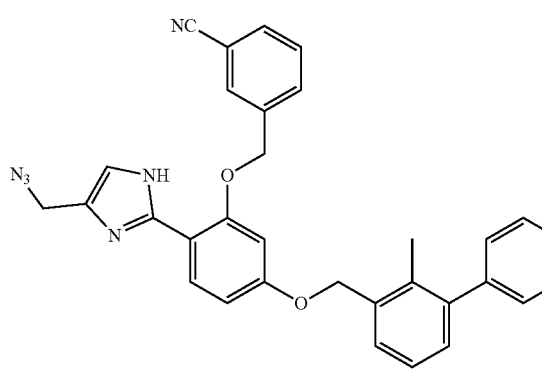

To a solution of 3-[[2-[4-(hydroxymethyl)-1H-imidazol-2-yl]-5-[(2-methyl-3-phenyl-phenyl)methoxy]phenoxy]methyl]benzonitrile (320 mg, 0.64 mmol) in toluene (10 mL) was added DPPA (210.69 mg, 0.77 mmol) and DBU (116.55 mg, 0.77 mmol). The mixture was stirred at 20° C. for 12 hr. The reaction mixture was concentrated. The residue was purified by prep-TLC (SiO$_2$, PE:EtOAc=1:1) to give 3-[[2-[4-(azidomethyl)-1H-imidazol-2-yl]-5-[(2-methyl-3-phenyl-phenyl)methoxy]phenoxy]methyl]benzonitrile (150 mg, 44.65%) as a white solid. LCMS: m/z found 527 [M+H]$^+$.

(b) 3-[[2-[4-(aminomethyl)-1H-imidazol-2-yl]-5-[(2-methyl-3-phenyl-phenyl)methoxy]phenoxy] methyl] benzonitrile

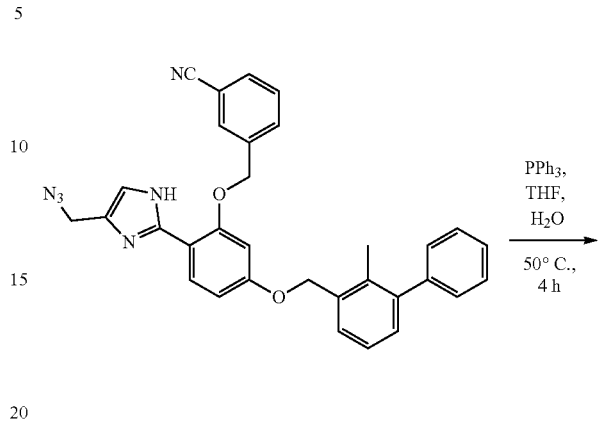

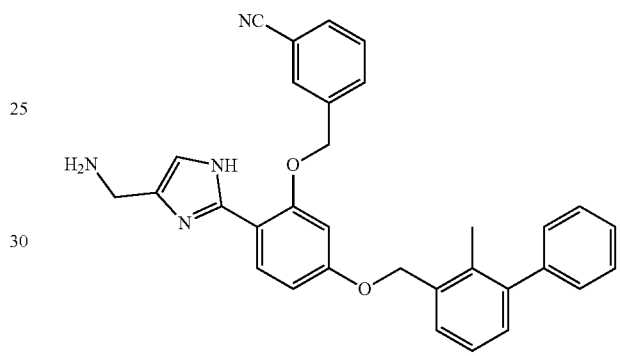

To a solution of 3-[[2-[4-(azidomethyl)-1H-imidazol-2-yl]-5-[(2-methyl-3-phenyl-phenyl)methoxy]phenoxy]methyl]benzonitrile (150 mg, 0.28 mmol) in THF (2 mL) and H$_2$O (0.2 mL) was added PPh$_3$ (224.14 mg, 0.85 mmol). The mixture was stirred at 50° C. for 4 hr. The reaction mixture was concentrated. The residue was purified by prep-TLC (silica gel, Petroleum ether/Ethyl acetate=1:1) to give 3-[[2-[4-(aminomethyl)-1H-imidazol-2-yl]-5-[(2-methyl-3-phenyl-phenyl)methoxy]phenoxy]methyl] benzonitrile (60 mg, 42.08%) as a white solid. LCMS: m/z found 501 [M+H]$^+$.

(c) N-[[2-[2-[(3-cyanophenyl)methoxy]-4-[(2-methyl-3-phenyl-phenyl)methoxy]phenyl]-1H-imidazol-4-yl]methyl]acetamide

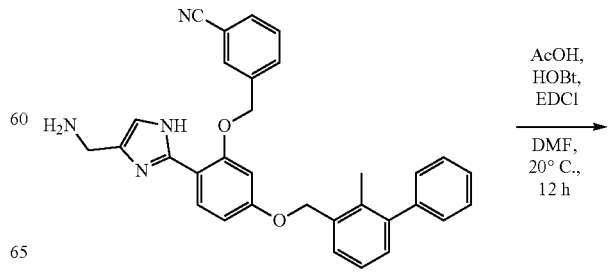

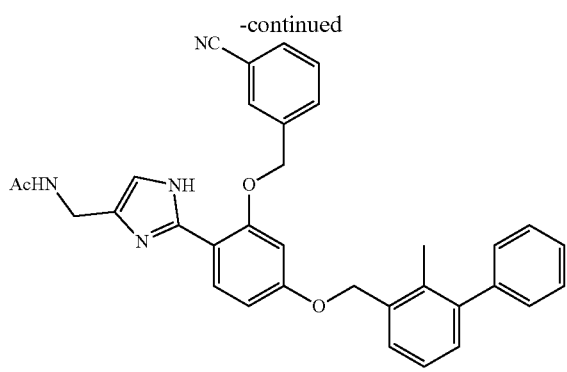

To a solution of 3-[[2-[4-(aminomethyl)-1H-imidazol-2-yl]-5-[(2-methyl-3-phenyl-phenyl)methoxy]phenoxy]methyl]benzonitrile (55 mg, 0.11 mmol) and acetic acid (7.92 mg, 131.84 μmol) in DMF (1 mL) was added HOBt (17.81 mg, 0.13 mmol) and EDCI (25.27 mg, 0.13 mmol). The mixture was stirred at 20° C. for 12 hr. The reaction mixture was concentrated. The residue was purified with other batch by prep-HPLC (column: Boston Green ODS 150*30 5μ; mobile phase: [water (0.05% HCl)-ACN]; B %: 35%-65%, 11 min) to give N-[[2-[2-[(3-cyanophenyl)methoxy]-4-[(2-methyl-3-phenyl-phenyl)methoxy]phenyl]-1H-imidazol-4-yl]methyl]acetamide (49.75 mg, 77.6%, HCl salt) as a white solid. MS: m/z found 543.3 [M+H]$^+$; $^1$H NMR (400 MHz, DMSO-d$_6$): δ 14.00 (br, 2H), 8.45-8.46 (m, 1H), 7.95 (s, 1H), 7.78-7.79 (m, 1H), 7.76-7.77 (m, 2H), 7.50-7.57 (m, 1H), 7.50 (s, 1H), 7.42-7.44 (m, 4H), 7.18-7.29 (m, 4H), 6.95 (m, 2H), 5.46 (s, 2H), 5.22 (s, 2H) 4.32-4.34 (d, J=5.2 Hz, 2H), 2.15 (s, 3H), 1.87 (s, 3H).

Example 9: 3-[[5-[(2-Methyl-3-phenyl-phenyl)methoxy]-2-(1,4,5,6-tetrahydropyrimidin-2-yl)phenoxy]methyl]benzonitrile

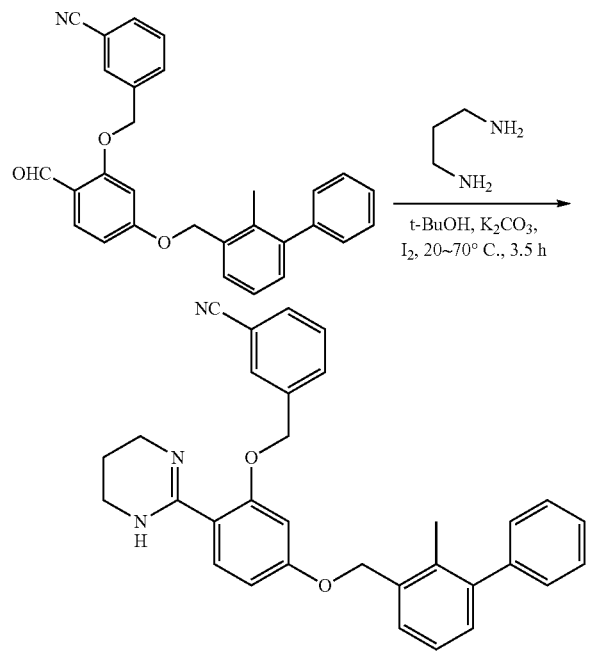

To a solution of 3-[[2-formyl-5-[(2-methyl-3-phenylphenyl)methoxy]phenoxy]methyl] benzonitrile (0.2 g, 0.46 mmol) in t-BuOH (3 mL) and 37.62 mg (507.50 μmol, 42.36 μL, 1.1 eq) of propane-1,3-diamine at 20° C. for 0.5 hr. To the mixture was added 79.71 mg (576.70 μmol, 1.25 eq) of K$_2$CO$_3$ and 351.30 mg (1.38 mmol, 3 eq) of I$_2$. The mixture was stirred at 70° C. for 3 hr. The reaction mixture was quenched by addition of 100 mL of water, and then diluted with 20 mL of saturated aq.Na$_2$SO$_3$ and extracted with 30 mL×3 of EtOAc. The combined organic layers were washed with 20 mL of brine, dried over Na$_2$SO$_4$, filtered and concentrated under reduced pressure to give a residue. The residue was purified by prep-HPLC (column: Phenomenex luna C18 250*50 mm*10 μm; mobile phase: [water (0.05% HCl)-ACN]; B %: 25%-55%, 20 min). 110.13 mg (209.58 μmol, 45.43%) of 3-[[5-[(2-methyl-3-phenyl-phenyl)methoxy]-2-(1,4,5,6-tetrahydropyrimidin-2-yl) phenoxy]methyl]benzonitrile as hydrochloride salt was obtained as a white solid. MS: m/z found 488.3 [M+H]$^+$; $^1$H NMR (400 MHz, DMSO-d$_6$): δ 9.74 (s, 2H), 7.92 (s, 1H), 7.85-7.79 (m, 2H), 7.67-7.65 (m, 1H), 7.49-7.41 (m, 4H), 7.39-7.32 (m, 1H), 7.30-7.21 (m, 4H), 6.99-6.98 (m, 1H), 6.91-6.88 (m, 1H), 5.29-5.26 (m, 4H), 3.46 (m, 4H), 2.19 (s, 3H), 1.95 (m, 2H); $^1$H NMR (400 MHz, CD$_3$OD): δ 7.85 (s, 1H), 7.78-7.72 (m, 2H), 7.62-7.58 (m, 1H), 7.50-7.36 (m, 5H), 7.34-7.20 (m, 4H), 6.93-6.92 (m, 1H), 6.87-6.84 (m, 1H), 5.29-5.25 (m, 4H), 3.58-3.55 (m, 4H), 2.22 (s, 3H), 2.13-2.07 (m, 2H).

Example 10: 3-[[2-(5-Hydroxy-1,4,5,6-tetrahydropyrimidin-2-yl)-5-[(2-methyl-3-phenyl-phenyl)methoxy]phenoxy]methyl]benzonitrile

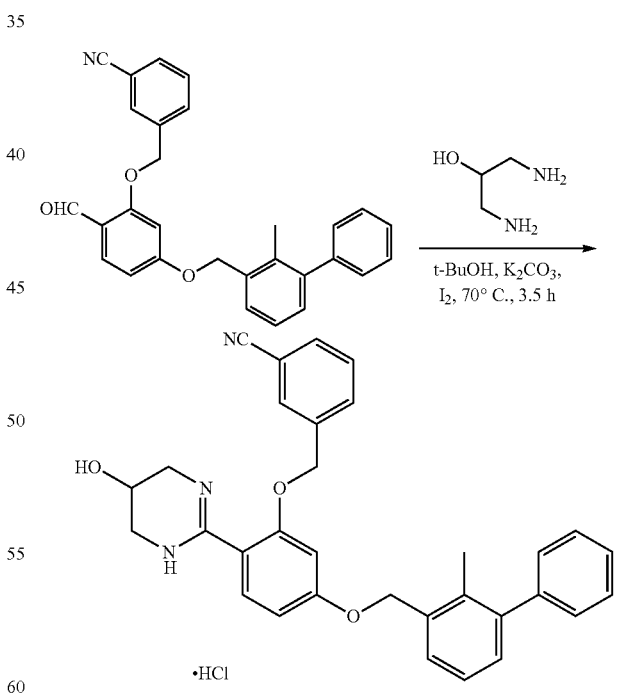

To a solution of 3-[[2-formyl-5-[(2-methyl-3-phenyl-phenyl)methoxy]phenoxy]methyl] benzonitrile (0.2 g, 0.46 mmol) in t-BuOH (2 mL) was added 1,3-diaminopropan-2-ol (41.58 mg, 0.46 mmol) and the mixture was stirred at 20° C. for 0.5 hr. Then K$_2$CO$_3$ (79.71 mg, 0.58 mmol) and I$_2$ (351.30 mg, 1.38 mmol) was added. The mixture was stirred at 70° C. for 3 hr. The reaction mixture was quenched with water (100 mL), and then treated with aq. Na₂SO₃ (sat. 20 mL) and extracted with EtOAc (30 mL×3). The combined organic layers were washed with brine (20 mL), dried over Na₂SO₄, filtered and concentrated under reduced pressure. The residue was purified by prep-HPLC (column: Phenomenex luna C18 150*25 10μ; mobile phase: [water (0.05% HCl)-ACN]; B %: 25%-55%, 20 min). 3-[[2-(5-hydroxy-1,4,5,6-tetrahydropyrimidin-2-yl)-5-[(2-methyl-3-phenyl-phenyl)methoxy]phenoxy]methyl]benzonitrile (99.42 mg, 39.6%, HCl salt) was obtained as a white solid. MS: m/z found 504.0 [M+H]⁺; ¹H NMR (400 MHz, DMSO-d₆): δ 9.72 (s, 2H), 7.96 (s, 1H), 7.86-7.81 (m, 2H), 7.65-7.63 (m, 1H), 7.46-7.39 (m, 5H), 7.32-7.23 (m, 4H), 7.01-7.00 (m, 1H), 6.92-6.89 (m, 1H), 5.63-5.62 (m, 1H), 5.30-5.27 (m, 4H), 4.24-4.23 (s, 1H), 3.54-3.51 (m, 2H), 3.35-3.33 (m, 3H) 2.20 (s, 3H); ¹H NMR (400 MHz, CD₃OD): δ 7.90 (s, 1H), δ 7.82-7.79 (m, 1H), δ 7.71-7.69 (m, 1H), 7.60-7.56 (m, 1H), δ 7.51-7.49 (m, 1H), δ 7.44-7.35 (m, 4H), δ 7.28-7.19 (m, 4H), 6.93-6.92 (m, 1H), δ 6.87-6.84 (m, 1H), 5.28-5.24 (m, 4H), 4.38-4.37 (m, 1H), 3.65-3.61 (m, 2H), 3.49-3.45 (m, 2H), 2.22 (s, 3H).

Example 11: 3-[[2-(1-Methyl-5,6-dihydro-4H-pyrimidin-2-yl)-5-[(2-methyl-3-phenyl-phenyl)methoxy]phenoxy]methyl]benzonitrile

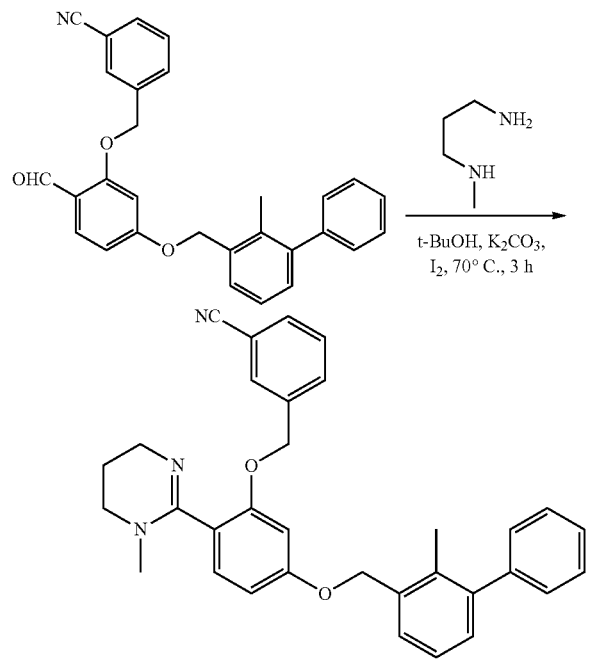

To a solution of 3-[[2-formyl-5-[(2-methyl-3-phenyl-phenyl)methoxy]phenoxy]methyl] benzonitrile (0.2 g, 0.46 mmol) in t-BuOH (6 mL), N'-methylpropane-1,3-diamine (61.00 mg, 0.69 mmol), I₂ (351.30 mg, 1.38 mmol) and K₂CO₃ (79.71 mg, 0.58 mol) was added. The mixture was stirred at 70° C. for 3 hr. The reaction mixture was filtered and concentrated under reduced pressure. The residue was purified by prep-HPLC (column: Phenomenex luna C18 250*50 mm*10 μm; mobile phase: [water (0.05% HCl)-ACN]; B %: 25%-55%, 20 min). 3-[[2-(1-methyl-5,6-dihydro-4H-pyrimidin-2-yl)-5-[(2-methyl-3-phenyl-phenyl)methoxy]phenoxy] methyl]benzonitrile as hydrochloride salt (241.98 mg, 97%) was obtained as a white solid. MS: m/z found 502.3 [M+H]⁺; ¹H NMR (400 MHz, DMSO-d₆): δ 9.75 (s, 1H), 7.85-7.82 (m, 2H), 7.75-7.73 (m, 1H), 7.66-7.64 (m, 4H), 7.47-7.38 (m, 5H), 7.31-7.29 (m, 3H), 7.27-7.22 (m, 1H), 7.03-7.02 (m, 1H), 6.93-6.90 (m, 1H), 5.31 (s, 2H), 5.23 (s, 2H), 3.27-3.54 (m, 2H), 3.38 (s, 2H), 2.89 (s, 3H), 2.18 (s, 3H), 2.10-1.93 (m, 2H); ¹H NMR (400 MHz, CD₃OD): δ 7.81 (s, 1H), 7.76-7.73 (m, 2H), 7.64-7.60 (m, 1H), 7.45-7.34 (m, 5H), 7.29-7.20 (m, 4H), 6.96-6.96 (m, 1H), 6.91-6.88 (m, 1H), 5.31 (s, 2H), 5.25 (s, 2H), 3.63-3.62 (m, 2H), 3.53-3.50 (m, 2H), 3.01 (s, 3H), 2.23-2.11 (m, 5H).

Example 12: 3-[[2-[1-(2-Hydroxyethyl)-5,6-dihydro-4H-pyrimidin-2-yl]-5-[(2-methyl-3-phenyl-phenyl)methoxy]phenoxy]methyl]benzonitrile

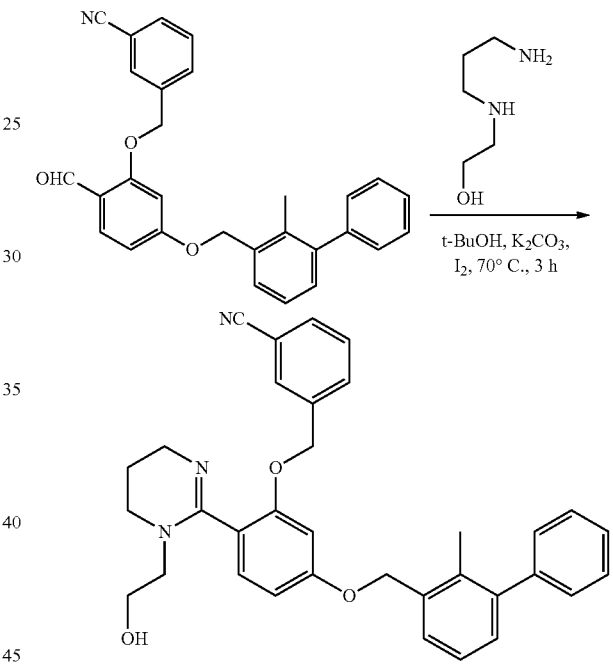

To a solution of 3-[[2-formyl-5-[(2-methyl-3-phenyl-phenyl)methoxy]phenoxy]methyl] benzonitrile (0.2 g, 0.46 mmol) in t-BuOH (2 mL) was added 2-(3-aminopropylamino)ethanol (81.78 mg, 0.69 mmol), I₂ (351.30 mg, 1.38 mmol) and K₂CO₃ (79.71 mg, 0.58 mmol). The mixture was stirred at 70° C. for 3 hr. The reaction mixture was filtered and concentrated under reduced pressure. The residue was purified by prep-HPLC (column: Phenomenex luna(2) C18 250*50 10μ; mobile phase: [water (0.05% HCl)-ACN]; B %: 25%-55%, 20 min) to give 3-[[2-[1-(2-hydroxyethyl)-5,6-dihydro-4H-pyrimidin-2-yl]-5-[(2-methyl-3-phenyl-phenyl)methoxy] phenoxy]methyl]benzonitrile hydrochloride salt (174.93 mg, 67% yield) as a white solid. MS: m/z found 532.3 [M+H]⁺; ¹H NMR (400 MHz, DMSO-d₆): δ 9.81 (s, 1H), 7.86-7.83 (m, 2H), 7.77-7.75 (m, 1H), 7.65-7.48 (m, 1H), 7.47-7.39 (m, 5H), 7.32-7.24 (m, 4H), 7.02-7.01 (m, 1H), 6.93-6.90 (m, 1H), 5.30-5.23 (m, 4H), 4.98 (m, 1H), 3.69-3.41 (m, 9H), 3.30-3.22 (m, 2H), 2.20-2.04 (m, 4H), 1.91-1.90 (m, 1H); ¹H NMR (400 MHz, CD₃OD): δ 7.82 (s, 1H), 7.76-7.15 (m, 2H), 7.62-7.58 (m, 1H), 7.44-7.35 (m, 5H), 7.28-7.19 (m, 4H), 6.93-6.86 (m, 2H), 5.31-5.23 (m, 4H), 3.79-3.50 (m, 7H), 3.48-3.30 (m, 1H), 2.26-2.22 (m, 4H), 2.10-2.07 (m, 1H).

Example 13: 2-[(3-Cyanophenyl)methoxy]-N,N'-bis(2-hydroxyethyl)-4-[(2-methyl-3-phenyl-phenyl)methoxy]benzamidine

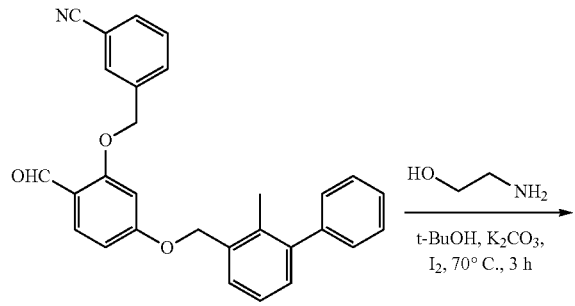

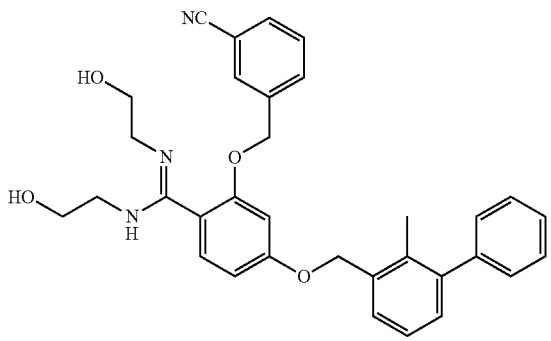

To a solution of 3-[[2-formyl-5-[(2-methyl-3-phenyl-phenyl)methoxy]phenoxy]methyl] benzonitrile (400 mg, 0.92 mmol) in t-BuOH (5 mL) was added 2-aminoethanol (169.09 mg, 2.77 mmol), $K_2CO_3$ (159.41 mg, 1.15 mmol) and $I_2$ (702.59 mg, 2.77 mmol). The mixture was stirred at 70° C. for 3 hr. The reaction mixture was filtered and concentrated under reduced pressure. The residue was purified by prep-HPLC (column: Phenomenex luna(2) C18 250*50 10u; mobile phase: [water (0.05% HCl)-ACN]; B %: 25%-55%, 20 min). The residue was purified by prep-HPLC (column: UniSil 120*30*10 um; mobile phase [water (0.05% HCl)-ACN]; B %: 30%-60%, 11 min). 2-[(3-cyanophenyl)methoxy]-N,N'-bis(2-hydroxyethyl)-4-[(2-methyl-3-phenyl-phenyl)methoxy]benzamidine hydrochloride salt (15.28 mg, 2.89%) was obtained as a yellow solid. MS: m/z found 536.3 $[M+H]^+$; $^1H$ NMR (400 MHz, DMSO-$d_6$): δ 9.64-9.62 (m, 1H), 9.30-9.23 (m, 1H), 7.89-7.63 (m, 3H), 7.48-7.46 (m, 1H), 7.43-7.40 (m, 5H), 7.33-7.24 (m, 4H), 7.03-7.02 (m, 1H), 6.93-6.91 (m, 1H), 5.31-5.25 (m, 4H), 5.14-5.11 (m, 1H), 4.93-4.90 (m, 1H), 3.64-3.62 (m, 2H), 3.50-3.41 (m, 4H), 3.14-3.13 (m, 2H), 2.23-2.21 (m, 3H)$^1H$ NMR (400 MHz, CD$_3$OD): δ 7.85-7.73 (m, 3H), 7.63-7.59 (m, 1H), 7.46-7.22 (m, 9H), 6.98-6.90 (m, 2H), 5.31-5.27 (m, 4H), 3.85-3.75 (m, 2H), 3.60-3.58 (m, 4H), 3.33-3.22 (m, 2H), 2.28-2.23 (m, 3H).

Example 14: N-[2-[[(Z)—N-(2-Acetamidoethyl)-C-[2-[(3-cyanophenyl)methoxy]-4-[(2-methyl-3-phenyl-phenyl)methoxy]phenyl]carbonimidoyl]amino]ethyl]acetamide

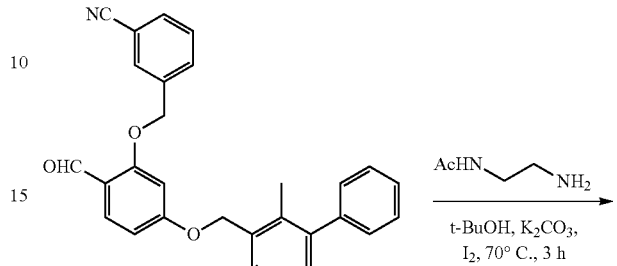

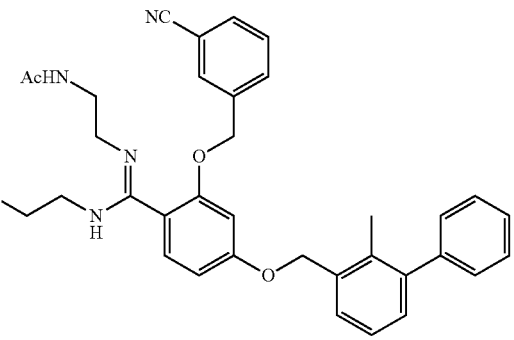

To a solution of 3-[[2-formyl-5-[(2-methyl-3-phenyl-phenyl)methoxy]phenoxy]methyl] benzonitrile (400 mg, 0.92 mmol) in t-BuOH (6 mL) was added N-(2-aminoethyl)acetamide (282.73 mg, 2.77 mmol), $K_2CO_3$ (159.41 mg, 1.15 mmol) and $I_2$ (702.59 mg, 2.77 mmol). The mixture was stirred at 70° C. for 3 hr. The reaction mixture was filtered and concentrated under reduced pressure. The residue was purified by prep-HPLC (column: Phenomenex luna(2) C18 250*50 10μ; mobile phase: [water (0.05% HCl)-ACN]; B %: 25%-55%, 20 min). The residue was purified by prep-HPLC (column: UniSil 120*30*10 μm; mobile phase: [water (0.05% HCl)-ACN]; B %: 30%-60%, 11 min). N-[2-[[(Z)—N-(2-acetamidoethyl)-C-[2-[(3-cyanophenyl)methoxy]-4-[(2-methyl-3-phenyl-phenyl)methoxy]phenyl]carbonimidoyl]amino]ethyl]acetamide hydrochloride salt (37.81 mg, 6.16%) was obtained as a yellow solid. MS: m/z found 618.0 $[M+H]^+$; $^1H$ NMR (400 MHz, DMSO-$d_6$): δ 9.66-9.65 (m, 1H), 7.46 (s, 1H), 8.27-8.24 (m, 1H), 8.09-8.02 (m, 1H), 7.88-7.64 (m, 3H), 7.48-7.46 (m, 1H), 7.46-7.24 (m, 5H), 7.01-6.92 (m, 2H), 5.37-5.25 (m, 4H), 3.29-3.13 (m, 8H), 2.20 (s, 3H), 1.88-1.73 (m, 6H); $^1H$ NMR (400 MHz, CD$_3$OD): δ 7.80-7.58 (m, 4H), 7.40-7.21 (m, 10H), 6.94-6.89 (m, 2H), 5.27-5.23 (m, 4H), 3.50-3.30 (m, 8H), 2.22-2.22 (m, 3H), 1.98-1.89 (m, 6H).

Example 15: 5-((2-(5-Hydroxy-1,4,5,6-tetrahydro-pyrimidin-2-yl)-5-((2-methyl-[1,1'-biphenyl]-3-yl)methoxy)phenoxy)methyl)nicotinonitrile

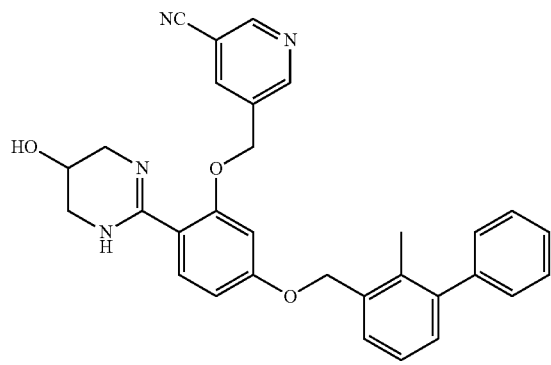

(a) 5-(hydroxymethyl)pyridine-3-carbonitrile

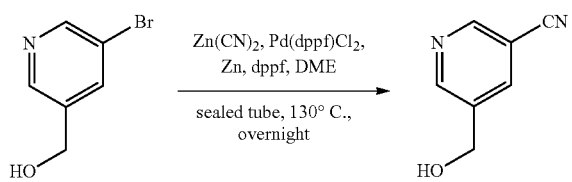

A solution of (5-bromo-3-pyridyl)methanol (3 g, 15.96 mmol), Zn(CN)$_2$ (2.06 g, 17.55 mmol), DPPF (0.88 g, 1.60 mmol), Zn (0.1 g, 1.60 mmol) and Pd(dppf)Cl$_2$ (1.17 g, 1.60 mmol) in DME (40 mL) was degassed and purged with N$_2$ for 3 times. The mixture was stirred at 130° C. for 15 hr under N$_2$ atmosphere. The reaction mixture was filtered and concentrated. The residue was purified by column chromatography (silica gel, Petroleum ether:Ethyl acetate=40:1 to 0:1) to give 5-(hydroxymethyl)pyridine-3-carbonitrile (1 g, 13.86% yield, 89% purity) as a black solid that can be used directly for next step. MS: m/z found 135.1[M+H]$^+$; $^1$H NMR (400 MHz, CDCl$_3$): δ 8.72 (s, 2H), 7.95 (s, 1H), 4.75 (s, 2H).

(b) 5-(chloromethyl)pyridine-3-carbonitrile

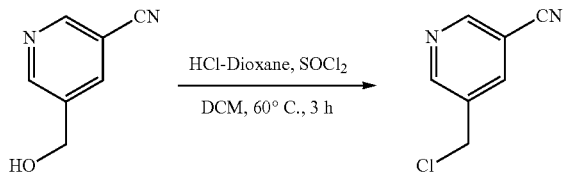

To a solution of 5-(hydroxymethyl)pyridine-3-carbonitrile (2 g, 14.91 mmol) in DCM (10 mL) was added hydrogen chloride in dioxane (4M, 5 mL) and concentrated. To the residue was added SOCl$_2$ (6.50 mL, 89.61 mmol) and stirred for 3 hr at 60° C. After cooling, toluene (200 mL) was added and the mixture was filtered. The filtrate was adjusted to pH=7 with sat. NaHCO$_3$ and extracted with DCM (3×50 mL). The organic phase was combined and dried over Na$_2$SO$_4$ and then concentrated under reduced pressure to give 5-(chloromethyl)pyridine-3-carbonitrile (1.7 g, 74.72% yield) as a black solid.

(c) 5-[[2-formyl-5-[(2-methyl-3-phenyl-phenyl)methoxy]phenoxy]methyl]pyridine-3-carbonitrile

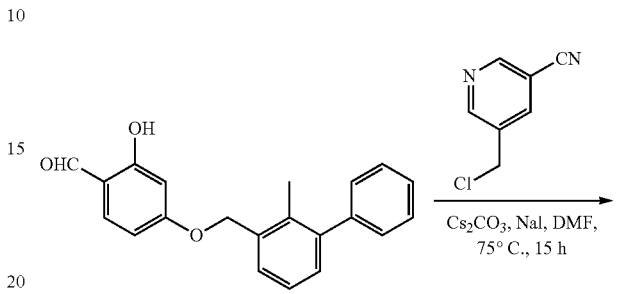

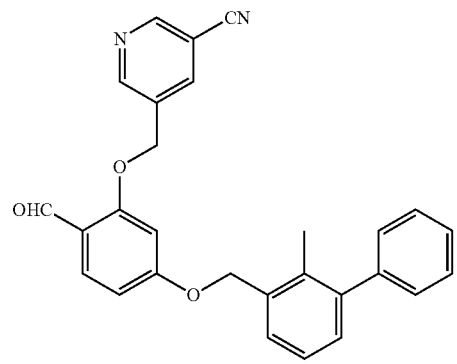

To a solution of 2-hydroxy-4-[(2-methyl-3-phenyl-phenyl) methoxy]benzaldehyde (1.65 g, 3.89 mmol) in DMF (2 mL) was added 5-(chloromethyl)pyridine-3-carbonitrile (711.71 mg, 4.66 mmol), Cs$_2$CO$_3$ (1.52 g, 4.66 mmol) and NaI (58.26 mg, 0.39 mol). The mixture was stirred at 75° C. for 15 hr. The reaction mixture was extracted with 3×30 mL of DCM. The combined organic layers were washed with 3×30 mL of brine, dried with anhydrous Na$_2$SO$_4$, filtered and concentrated under reduced pressure. The residue was purified by column chromatography (silica gel, Petroleum ether/Ethyl acetate=20/1-2/1). 5-[[2-formyl-5-[(2-methyl-3-phenyl-phenyl) methoxy]phenoxy]methyl]pyridine-3-carbonitrile (1.18 g, 66.83% yield) was obtained as a white solid. MS: m/z found 449.0 [M+H]$^+$; $^1$H NMR (400 MHz, DMSO-d$_6$): δ 10.27 (s, 1H), 9.02-9.01 (m, 2H), 8.53 (m, 1H), 7.75-7.73 (m, 1H), 7.48-7.23 (m, 8H), 7.00 (m, 1H), 6.88-6.85 (m, 1H), 5.41 (s, 2H), 5.29 (m, 2H), 2.20 (m, 3H).

(d) 5-((2-(5-hydroxy-1,4,5,6-tetrahydropyrimidin-2-yl)-5-((2-methyl-[1,1'-biphenyl]-3-yl)methoxy)phenoxy)methyl)nicotinonitrile

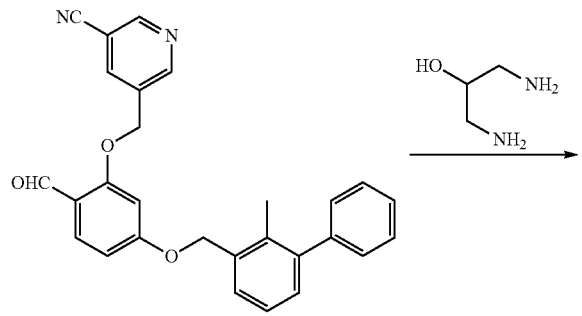

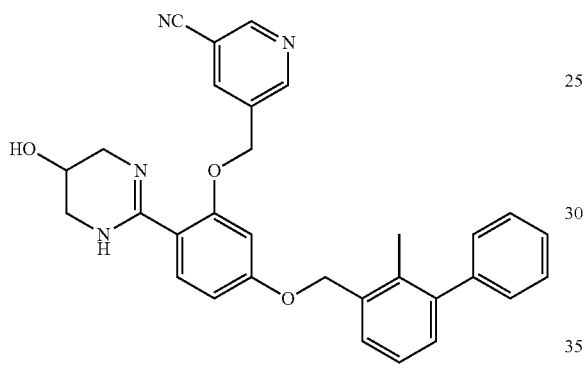

To a solution of 5-[2-formyl-5-({2-methyl-[1,1'-biphenyl]-3-yl}methoxy)phenoxymethyl] pyridine-3-carbonitrile (88 mg, 0.2 mmol) in t-BuOH (1 ml) and DMA (1.5 ml) was added 1,3-diaminopropan-2-ol (27 mg, 0.3 mmol), $K_2CO_3$ (35 mg, 0.25 mmol) and iodine (153 mg, 0.6 mmol). The reaction mixture was stirred at 30° C. for overnight. The reaction mixture was diluted with MeOH to 6 ml and filtrated. The filtrate was subjected to prep HPLC. The pure fractions were combined and the MeCN was evaporated and the remaining was freeze dried to give 5-((2-(5-hydroxy-1,4,5,6-tetrahydropyrimidin-2-yl)-5-((2-methyl-[1,1'-biphenyl]-3-yl)methoxy) phenoxy)methyl)nicotinonitrile TFA salt (58.8 mg). MS: m/z found 505.4 [M+H]$^+$; $^1$H NMR (400 MHz, $CD_3OD$) δ 8.91 (dd, J=15.2, 2.1 Hz, 2H), 8.37 (ddt, J=2.1, 1.5, 0.7 Hz, 1H), 7.51 (d, J=8.6 Hz, 1H), 7.47-7.38 (m, 3H), 7.40-7.31 (m, 1H), 7.36-7.20 (m, 3H), 7.21 (dd, J=7.7, 1.7 Hz, 1H), 6.97 (d, J=2.2 Hz, 1H), 6.89 (dd, J=8.6, 2.2 Hz, 1H), 5.34 (d, J=0.8 Hz, 2H), 5.26 (s, 2H), 4.38 (dd, J=3.5, 2.3 Hz, 1H), 3.63 (dd, J=12.7, 2.7 Hz, 2H), 3.47 (dd, J=12.8, 3.0 Hz, 2H), 2.23 (s, 3H).

Example 16: 5-[[4-Chloro-5-[[3-[3-[3-(4-hydroxy-1-piperidyl)propoxy]-2-methyl-phenyl]-2-methyl-phenyl]methoxy]-2-(5-hydroxy-1,4,5,6-tetrahydropyrimidin-2-yl)phenoxy] methyl]pyridine-3-carbonitrile

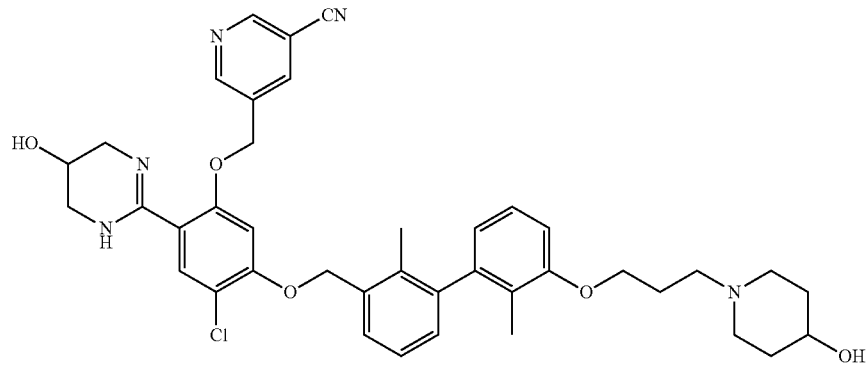

(a) 5-chloro-2,4-dihydroxy-benzaldehyde

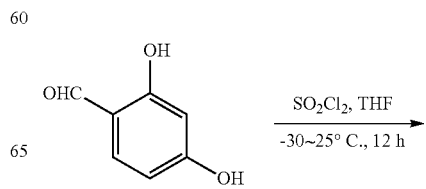

-continued

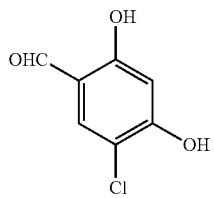

To a mixture of 2,4-dihydroxybenzaldehyde (20 g, 145 mmol) in tetrahydrofuran (THF) (300 mL) was added dropwise sulfuryl chloride (19.54 g, 145 mmol, 14.48 mL) at −30° C., and then the solution was stirred at 25° C. for 12 hr. The reaction was quenched with saturated sodium bicarbonate (NaHCO₃) to pH=7, and concentrated. The residue was purified by column chromatography (silica gel, petroleum ether:ethyl acetate=8:1 to 3:1) to yield the semi-purified product. Portion of this product (10 g, 58.0 mmol, 1 eq) was dissolved in 200 mL of 1N NaOH, and the solution was stirred at 25° C. for 1 hr. The mixture was extracted with 2×200 mL of ethyl acetate (EtOAc), and the aqueous solution was acidified with aqueous 3 N HCl solution to pH=1. Then the mixture was filtered, and the solid was washed with 100 mL of water to give 5-chloro-2,4-dihydroxy-benzaldehyde (9 g, 52.2 mmol, 90.0% yield) as a gray solid. ¹H NMR (400 MHz, CDCl₃): δ 11.25 (s, 1H), 9.69 (s, 1H), 7.52 (s, 1H), 6.61 (s, 1H).

(b) 1-bromo-3-(bromomethyl)-2-methyl-benzene

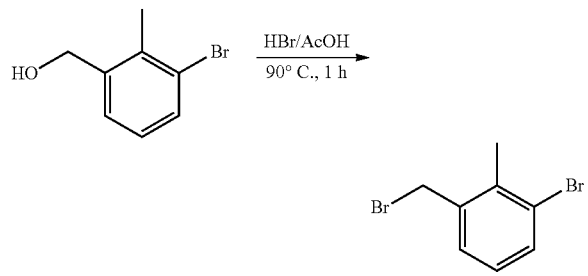

A solution of (3-bromo-2-methyl-phenyl)methanol (5 g, 24.9 mmol) in 50 mL hydrobromic acid in acetic acid (AcOH) (1 M) was degassed and purged with N₂ for 3 times. The mixture was stirred under N₂ gas at 90° C. for 1 hr. The reaction mixture was filtered and concentrated under reduced pressure to give 1-bromo-3-(bromomethyl)-2-methyl-benzene (6 g, 22.7 mmol, 91.4% yield) as a yellow solid that was used directly for next step.

(c) 4-[(3-bromo-2-methyl-phenyl)methoxy]-5-chloro-2-hydroxy-benzaldehyde

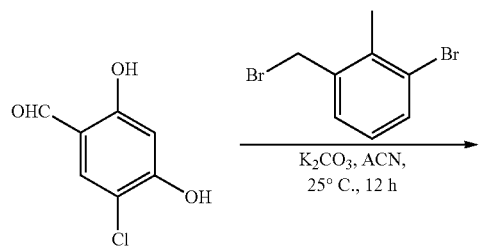

-continued

To a mixture of 5-chloro-2,4-dihydroxy-benzaldehyde (9 g, 52.15 mmol) and K₂CO₃ (14.42 g, 104 mmol) in MeCN (80 mL) was added dropwise a solution of 1-bromo-3-(bromomethyl)-2-methyl-benzene (8.67 g, 32.9 mmol) in acetonitrile (20 mL). The reaction mixture was stirred at 25° C. for 12 hr. To the mixture was added water until all K₂CO₃ was dissolved, and the system was then filtered to give a light yellow solid. To the residue were added 100 mL of ethyl acetate and 100 mL of water. The resultant mixture was stirred at 25° C. for 0.5 hr. Then the mixture was filtered, and the filtrate was washed with 20 mL of EtOAc. The filter cake was concentrated under vacuum to give crude 4-[(3-bromo-2-methyl-phenyl)methoxy]-5-chloro-2-hydroxy-benzaldehyde (13 g) as a gray solid. ¹H NMR (400 MHz, CDCl₃) δ 11.43 (s, 1H), 9.72 (s, 1H), 7.62-7.56 (m, 1H), 7.44-7.42 (m, 2H), 7.28 (s, 1H), 7.14-7.12 (t, 1H, J=8 Hz), 6.60 (s, 1H), 5.18 (s, 2H), 2.47 (s, 3H).

(d) 5-[[5-[(3-bromo-2-methyl-phenyl)methoxy]-4-chloro-2-formyl-phenoxy]methyl] pyridine-3-carbonitrile

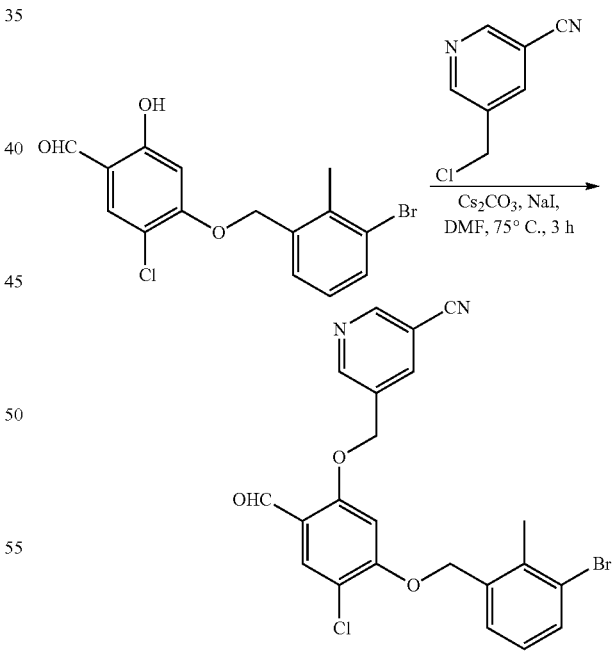

A solution of 4-[(3-bromo-2-methyl-phenyl)methoxy]-5-chloro-2-hydroxy-benzaldehyde (12.5 g, 35.2 mmol), 5-(chloromethyl)pyridine-3-carbonitrile (4.02 g, 26.4 mmol), Cs₂CO₃ (13.74 g, 42.2 mmol), and NaI (526.88 mg, 3.52 mmol) in dimethylformamide (DMF) (150 mL) was stirred for 3 hr at 75° C. The mixture was poured into ice-water (500 mL) and stirred for 20 min. The precipitate was collected, washed with cold ethyl acetate (EtOAc, 100 mL), and dried under vacuum. The residue was treated with 150 mL of EtOAc and stirred for 1 hr at 25° C. Then the mixture was filtered and washed with 100 mL of EtOAc. The residue was concentrated to give 9.5 g (crude) of 5-[[5-[(3-bromo-2-methyl-phenyl)methoxy]-4-chloro-2-formyl-phenoxy]methyl]pyridine-3-carbonitrile as a grey solid. LC-MS: m/z found 472.9[M+H]$^+$.

(e) 2-methyl-3-(4,4,5,5-tetramethyl-1,3,2-dioxaborolan-2-yl)phenol

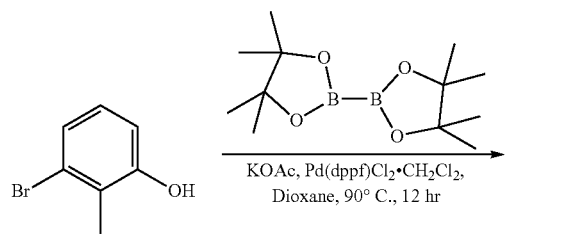

A solution of 3-bromo-2-methyl-phenol (10 g, 53.47 mmol) and 4,4,5,5-tetramethyl-2-(4,4,5,5-tetramethyl-1,3,2-dioxaborolan-2-yl)-1,3,2-dioxaborolane (21.72 g, 85.55 mmol) in dioxane (100 mL) was added KOAc (15.74 g, 160.40 mmol) and Pd(dppf)Cl$_2$·CH$_2$Cl$_2$ (4.37 g, 5.35 mmol). The mixture was stirred at 90° C. for 12 hr. The reaction mixture was filtered. The filtrate was concentrated. The residue was purified by column chromatography (silica gel, Petroleum ether: Ethyl acetate=20:1 to 5:1) to give 2-methyl-3-(4,4,5,5-tetramethyl-1,3,2-dioxaborolan-2-yl) phenol (10 g, 42.72 mmol, 79.90% yield) as a yellow solid.

(f) 5-[[4-chloro-2-formyl-5-[[3-(3-hydroxy-2-methyl-phenyl)-2-methyl-phenyl]methoxy] phenoxy]methyl]pyridine-3-carbonitrile

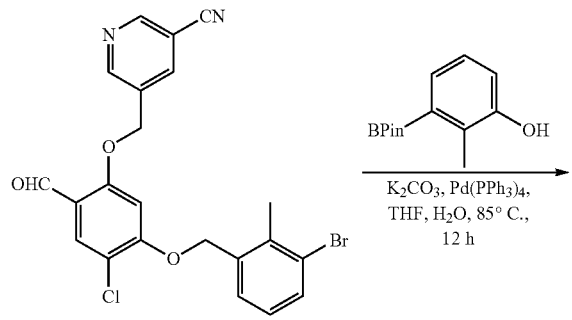

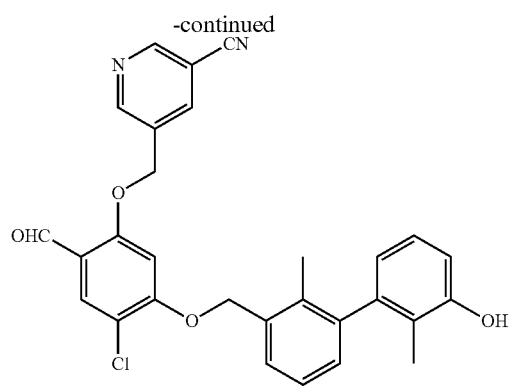

A solution of 5-[[5-[(3-bromo-2-methyl-phenyl) methoxy]-4-chloro-2-formyl-phenoxy]methyl] pyridine-3-carbonitrile (8 g, 16.96 mmol), 2-methyl-3-(4,4,5,5-tetramethyl-1,3,2-dioxaborolan-2-yl)phenol (5.96 g, 25.44 mmol), K$_2$CO$_3$ (7.03 g, 50.88 mmol) and Pd(PPh$_3$)$_4$ (1.96 g, 1.70 mmol) in THF (100 mL) and H$_2$O (50 mL) was degassed and purged with N$_2$ for 3 times. Then the mixture was stirred at 85° C. for 12 hr under N$_2$ atmosphere. After cooling, H$_2$O (30 mL) was added and the mixture was filtered. The filtrate was extracted with EtOAc (3×50 mL). The organic phase was dried over Na$_2$SO$_4$ and then concentrated. The residue was purified by column chromatography (silica gel, Petroleum ether/Ethyl acetate=50:1 to 1:1) to give 5-[[4-chloro-2-formyl-5-[[3-(3-hydroxy-2-methyl-phenyl)-2-methyl-phenyl]methoxy]phenoxy] methyl]pyridine-3-carbonitrile (5 g, 10.02 mmol, 59.09% yield) as a white solid. MS: m/z found 499.1[M+H]$^+$

(g) 5-[[5-[[3-[3-(3-bromopropoxy)-2-methyl-phenyl]-2-methyl-phenyl]methoxy]-4-chloro-2-formyl-phenoxy]methyl]pyridine-3-carbonitrile

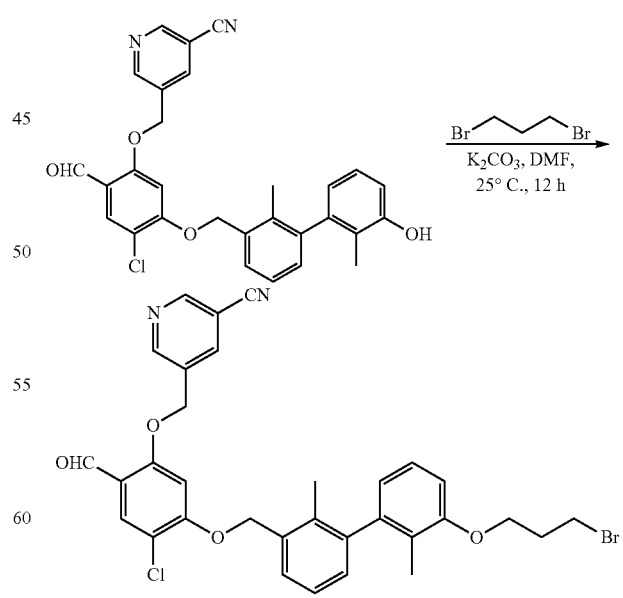

A solution of 5-[[4-chloro-2-formyl-5-[[3-(3-hydroxy-2-methyl-phenyl)-2-methyl-phenyl]methoxy]phenoxy] methyl]pyridine-3-carbonitrile (5 g, 10.02 mmol) and K₂CO₃ (1.38 g, 10.02 mmol) in DMF (50 mL) was stirred at 25° C. for 2 hr. Then 1,3-dibromopropane (6.07 g, 30.06 mmol, 3.07 mL) was added to the reaction mixture and the mixture was stirred at 25° C. for 10 hr. The reaction mixture was quenched with H₂O (15 mL) and extracted with EtOAc (3×10 mL). The combined organic layers were dried over Na₂SO₄, filtered and concentrated. The residue was purified by column chromatography (silica gel, Petroleum ether: Ethyl acetate=50:1 to 0:1) to give 5-[[5-[[3-[3-(3-bromopropoxy)-2-methyl-phenyl]-2-methyl-phenyl]methoxy]-4-chloro-2-formyl-phenoxy]methyl]pyridine-3-carbonitrile (3.5 g, 5.65 mmol, 56.34% yield) as a yellow solid. LC-MS: m/z found 621.0 [M+H]⁺

(h) 5-[[4-chloro-2-formyl-5-[[3-[3-[3-(4-hydroxy-1-piperidyl)propoxy]-2-methyl-phenyl]-2-methyl-phenyl]methoxy]phenoxy]methyl]pyridine-3-carbonitrile

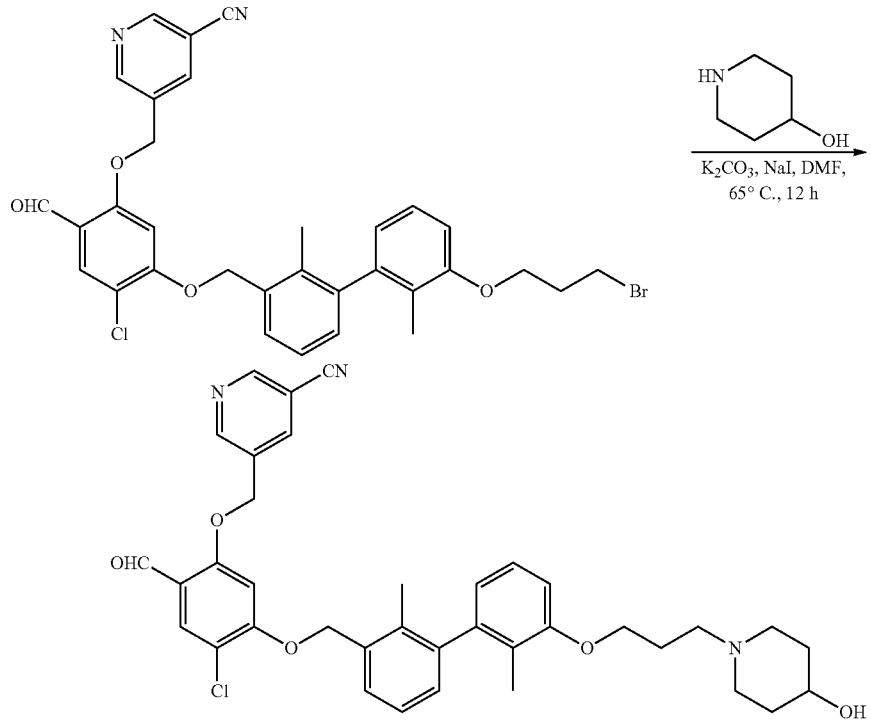

To a solution of 5-[[5-[[3-[3-(3-bromopropoxy)-2-methyl-phenyl]-2-methyl-phenyl]methoxy]-4-chloro-2-formyl-phenoxy]methyl]pyridine-3-carbonitrile (2 g, 3.23 mmol) in DMF (12 mL) was added piperidin-4-ol (326.32 mg, 3.23 mmol), K₂CO₃ (668.81 mg, 4.84 mmol), and NaI (96.72 mg, 0.65 mmol). The reaction mixture was stirred at 65° C. for 12 hr. The mixture was separated between 3×40 mL of EtOAc and 30 mL of H₂O. The combined organic layer was washed with brine (2×10 mL), dried over Na₂SO₄, filtered and concentrated. The residue was purified by prep-HPLC (column: Phenomenex luna C18 250×50 mm×10 μm; mobile phase: [water (0.05% HCl)-ACN]; B %: 30%-60%, 20 min) to give 5-[[4-chloro-2-formyl-5-[[3-[3-[3-(4-hydroxy-1-piperidyl)propoxy]-2-methyl-phenyl]-2-methyl-phenyl] methoxy]phenoxy]methyl]pyridine-3-carbonitrile (0.7 g, 1.07 mmol, 33.2% yield) as a light yellow solid. LC-MS: m/z found 640.3 [M+H]⁺; ¹H NMR (400 MHz, DMSO-d₆): δ 10.22 (s, 1H), 9.95 (br, 1H), 9.01-9.00 (t, 2H, J=2.4 Hz), 8.54-8.53 (t, 1H, J=2.0 Hz), 7.70 (s, 1H), 7.50-7.48 (d, 1H, J=6.8 Hz), 7.28-7.24 (m, 2H), 7.22-7.18 (m, 1H), 7.07-7.05 (d, 1H, J=7.6 Hz), 6.95-6.93 (d, 1H, J=8.4 Hz), 6.69-6.67 (d, 1H, J=7.2 Hz), 5.47 (s, 2H), 5.40 (s, 2H), 4.11-4.01 (m, 2H), 3.42-3.10 (m, 6H), 2.97-2.85 (m, 1H), 2.21-2.15 (m, 2H), 2.00 (s, 3H), 1.92-1.89 (m, 2H), 1.82-1.81 (m, 2H), 1.73-1.59 (m, 2H).

(i) 5-[[4-chloro-5-[[3-[3-[3-(4-hydroxy-1-piperidyl)propoxy]-2-methyl-phenyl]-2-methyl-phenyl]methoxy]-2-(5-hydroxy-1,4,5,6-tetrahydropyrimidin-2-yl)phenoxy] methyl]pyridine-3-carbonitrile

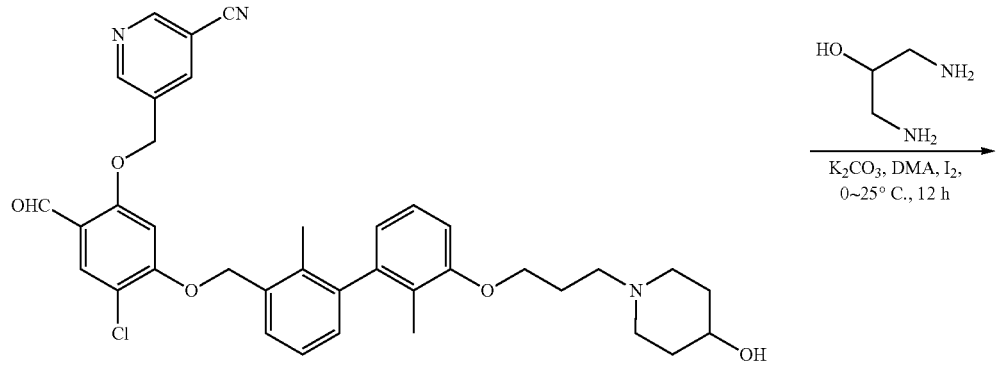

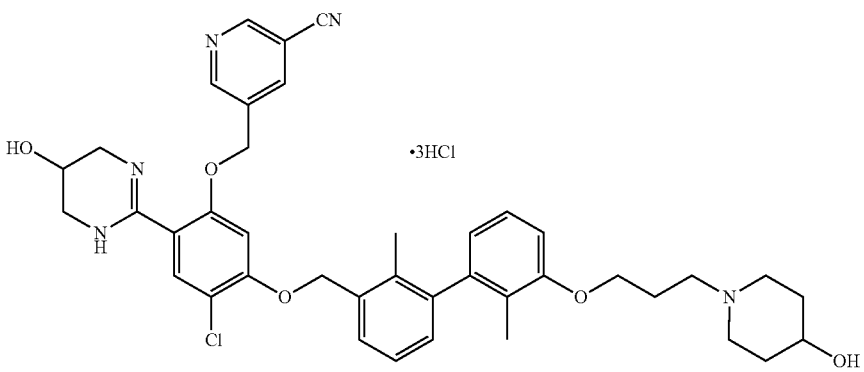

To a solution of 5-[[4-chloro-2-formyl-5-[[3-[3-[3-(4-hydroxy-1-piperidyl)propoxy]-2-methyl-phenyl]-2-methyl-phenyl]methoxy]phenoxy]methyl]pyridine-3-carbonitrile (700 mg, 1.09 mmol) and 1,3-diaminopropan-2-ol (197.09 mg, 2.19 mmol) in DMA (10 mL) was added $K_2CO_3$ (226.69 mg, 1.64 mmol) and $I_2$ (832.60 mg, 3.28 mmol) at 0° C. The mixture was stirred at 25° C. for 12 hr. The reaction mixture was filtered to give a solution. The solution was purified by prep-HPLC (column: Phenomenex luna(2) C18 250*50 10μ; mobile phase: [water (0.05% HCl)-ACN]; B %: 10%-40%, 20 min) to give a solution. The solution was concentrated at 30° C. to remove MeCN, and lyophilized to give 5-[[4-chloro-5-[[3-[3-[3-(4-hydroxy-1-piperidyl)propoxy]-2-methyl-phenyl]-2-methyl-phenyl]methoxy]-2-(5-hydroxy-1,4,5,6-tetrahydropyrimidin-2-yl)phenoxy]methyl]pyridine-3-carbonitrile HCl salt (408.25 mg, 49.5% yield) as a yellow solid. MS: m/z found 710.3 [M+H]⁺; ¹H NMR (400 MHz, DMSO-$d_6$): δ 10.48 (m, 1H), 9.87-9.83 (m, 2H), 9.03-8.99 (m, 2H), 8.45 (s, 1H), 7.62 (s, 1H), 7.52-7.50 (m, 1H), 7.35-7.33 (m, 1H), 7.33-7.30 (m, 1H), 7.28-7.19 (m, 1H), 7.09-7.07 (m, 1H), 6.98-6.92 (m, 1H), 6.70-6.68 (d, 1H, J=7.6 Hz), 5.43-5.41 (m, 4H), 4.21 (s, 1H), 4.09-4.07 (m, 3H), 3.66-3.60 (m, 1H), 3.50-3.47 (m, 3H), 3.31-3.28 (m, 3H), 3.20-3.08 (m, 3H), 2.98-2.90 (m, 1H), 2.22 (m, 2H), 2.03 (s, 3H), 1.99-1.90 (m, 2H), 1.83 (s, 3H), 1.74-1.70 (m, 2H). ¹H NMR (400 MHz, $CD_3OD$): δ 9.63 (s, 1H), 8.96-8.94 (d, 2H, J=9.2 Hz), 8.42 (s, 2H), 7.63 (s, 1H), 7.50-7.48 (d, 1H, J=9.2 Hz), 7.28-7.23 (m, 1H), 7.21-7.19 (m, 2H), 7.10-7.07 (d, 1H, J=7.6 Hz), 6.97-6.94 (d, 1H, J=8.4 Hz), 6.73-6.71 (d, 1H, J=8.4 Hz), 5.43 (s, 2H), 5.39 (s, 2H), 4.39-4.38 (m, 1H), 4.18-4.15 (m, 2H), 4.10 (m, 1H), 3.86-3.83 (m, 1H), 3.68-3.60 (m, 3H), 3.49-3.44 (m, 3H), 3.40-3.36 (m, 2H), 3.12-3.06 (m, 1H), 2.35-2.28 (m, 2H), 2.18-2.10 (m, 1H), 2.09 (s, 3H), 2.01-1.96 (m, 2H), 1.91 (s, 3H), 1.78-1.71 (m, 1H).

Example 17: 5-[[4-Chloro-2-[1-(2-hydroxyethyl)-5,6-dihydro-4H-pyrimidin-2-yl]-5-[[3-[3-[3-(4-hydroxy-1-piperidyl)propoxy]-2-methyl-phenyl]-2-methyl-phenyl]methoxy]phenoxy] methyl] pyridine-3-carbonitrile

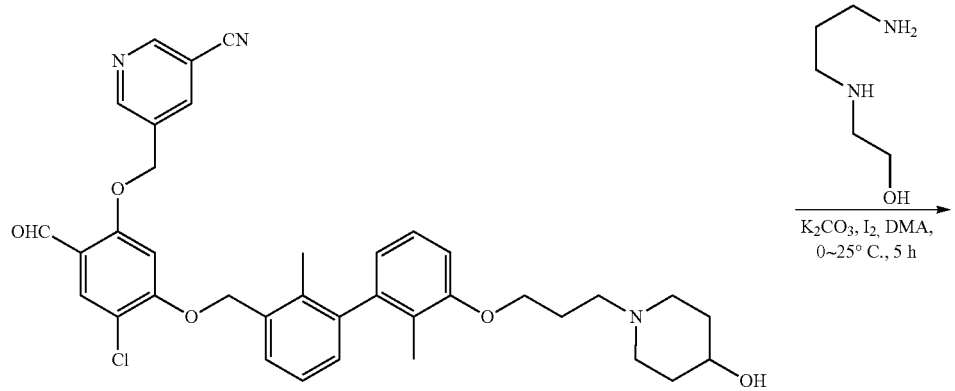

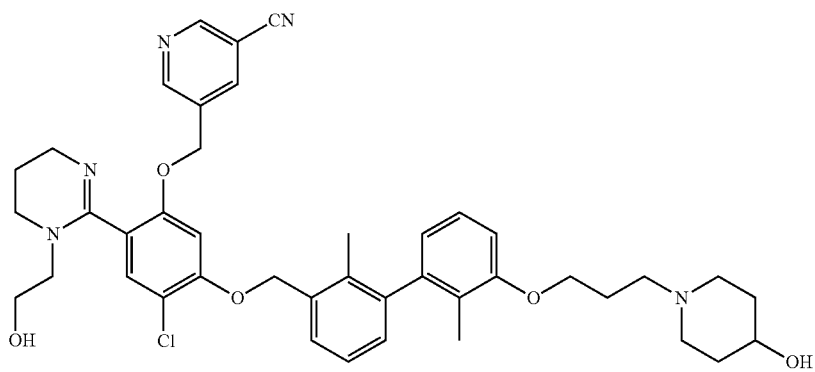

To a solution of 5-[[4-chloro-2-formyl-5-[[3-[3-[3-(4-hydroxy-1-piperidyl)propoxy]-2-methyl-phenyl]-2-methyl-phenyl]methoxy]phenoxy]methyl]pyridine-3-carbonitrile (300 mg, 468.63 μmol) in DMA (2 mL) was added 2-(3-aminopropylamino)ethanol (110.76 mg, 937.26 μmol), $K_2CO_3$ (80.96 mg, 585.79 μmol) and $I_2$ (356.83 mg, 1.41 mmol) at 0° C. and the mixture was stirred at 0° C. for 1 hr. The mixture was stirred at 25° C. for 4 hr. The reaction mixture was filtered and concentrated under reduced pressure. The residue was purified by prep-HPLC (column: Luna C18 100*30 5μ; mobile phase: [water (0.05% HCl)-ACN]; B %: 15%-45%, 10 min). The residue was purified by prep-HPLC (column: Waters Xbridge Prep OBD C18 150*30 10μ; mobile phase: [water (10 mM $NH_4HCO_3$)-ACN]; B %: 20%-45%, 10 min). 5-[[4-chloro-2-[1-(2-hydroxyethyl)-5,6-dihydro-4H-pyrimidin-2-yl]-5-[[3-[3-[3-(4-hydroxy-1-piperidyl)propoxy]-2-methyl-phenyl]-2-methyl-phenyl]methoxy]phenoxy]methyl]pyridine-3-carbonitrile (16.21 mg, 4.50% yield) was obtained as a yellow solid. MS: m/z found 738.3 [M+H]$^+$; $^1$H NMR (400 MHz, DMSO-d$_6$): δ 9.01 (s, 1H), 8.91 (s, 1H), 8.31 (s, 1H), 7.52-7.51 (m, 1H), 7.30-7.16 (m, 4H), 7.09-7.07 (m, 1H), 6.97-6.94 (m, 1H), 6.69-6.67 (m, 1H), 5.35-5.30 (m, 4H), 4.53 (m, 2H), 4.04-4.02 (m, 2H), 3.33 (m, 2H), 3.05 (m, 1H), 2.67 (m, 4H), 2.44-2.33 (m, 5H), 2.04-1.82 (m, 12H), 1.71-1.68 (m, 3H), 1.40-1.35 (m, 2H); $^1$H NMR (400 MHz, CD$_3$OD): δ 8.91-8.89 (m, 2H), 8.26 (s, 1H), 7.47-7.42 (m, 2H), 7.26-7.08 (m, 4H), 6.93-6.91 (m, 1H), 6.69-6.62 (m, 1H), 5.39-5.32 (m, 4H), 4.12-4.07 (m, 2H), 3.62-3.30 (m, 7H), 3.18-3.14 (m, 1H), 2.85 (m, 2H), 2.62-2.58 (m, 2H), 2.21-1.87 (m, 15H), 1.62-1.55 (m, 2H).

Example 18: 2-[5-Chloro-2-[(5-cyano-3-pyridyl)methoxy]-4-[[3-[3-[3-(4-hydroxy-1-piperidyl)propoxy]-2-methyl-phenyl]-2-methyl-phenyl]methoxy]phenyl]-1,4,5,6-tetrahydropyrimidine-4-carboxylic acid

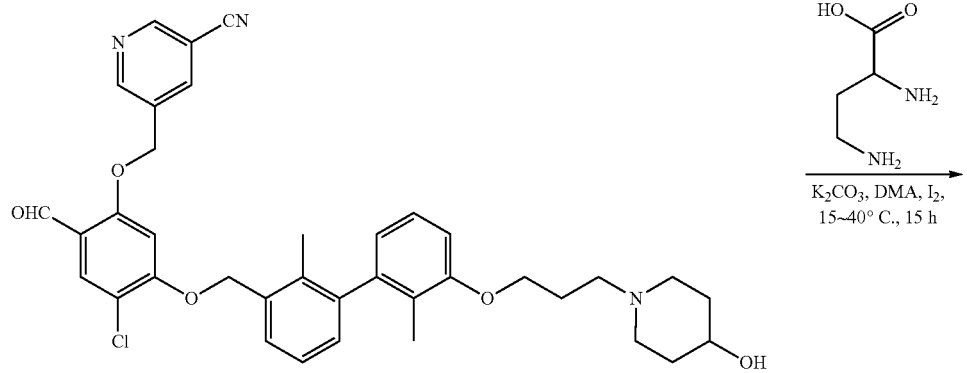

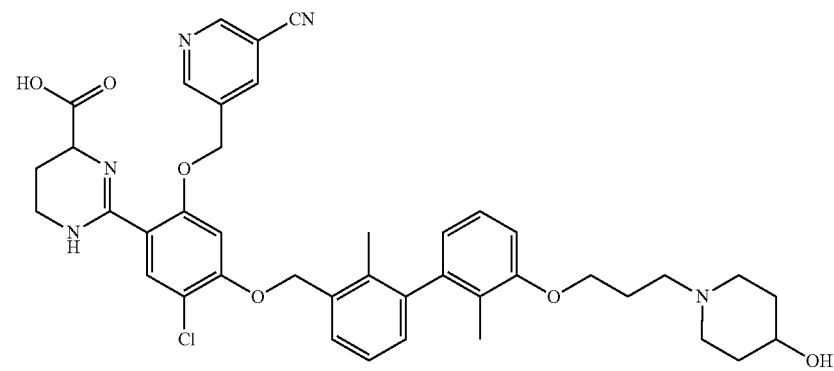

To a mixture of 5-[[4-chloro-2-formyl-5-[[3-[3-[3-(4-hydroxy-1-piperidyl)propoxy]-2-methyl-phenyl]-2-methylphenyl]methoxy]phenoxy]methyl]pyridine-3-carbonitrile (100 mg, 156.21 μmol) and 2,4-diaminobutanoic acid di-HCl salt (59.69 mg, 312.42 μmol) in DMA (2 mL) was added $K_2CO_3$ (107.95 mg, 781.05 μmol) and $I_2$ (118.94 mg, 468.63 μmol) in one portion at 15° C. under $N_2$. The mixture was heated to 40° C. and stirred for 15 hours. Three batches of same scale were combined and the mixture was filtered. The filtrate was purified directly with prep-HPLC (column: Phenomenex Luna C18 200*40 mm*10 um; mobile phase: [water (0.1% TFA)-ACN]; B %: 20%-40%, 10 min.) to give a solution. To the solution was added 20 mL of sat. $NaHCO_3$ to pH=9. The solution was extracted with 2×15 mL of ethyl acetate to give a combined organic phase. The organic phase was dried with anhydrous $Na_2SO_4$, filtered and concentrated to give 2-[5-chloro-2-[(5-cyano-3-pyridyl)methoxy]-4-[[3-[3-[3-(4-hydroxy-1-piperidyl)propoxy]-2-methyl-phenyl]-2-methyl-phenyl]methoxy]phenyl]-1,4,5,6-tetrahydropyrimidine-4-carboxylic acid (47.20 mg) as a white solid. MS: m/z found 738.1 [M+H]$^+$; $^1$H NMR (400 MHz, DMSO-$d_6$): δ 9.63 (s, 1H), 9.02-8.95 (m, 2H), 8.46 (s, 1H), 7.64 (s, 1H), 7.51-7.49 (d, J=8 Hz, 1H), 7.30-7.19 (m, 3H), 7.09-7.07 (d, J=7.2 Hz, 1H) 6.96-6.94 (d, J=7.6 Hz, 1H) 6.69-6.67 (d, J=6.8 Hz, 1H) 5.41 (s, 4H), 4.05 (m, 2H), 2.82 (m, 1H), 2.02-1.91 (m, 9H), 1.84-1.73 (m, 7H), 1.43 (m, 3H), 1.24 (s, 3H), 0.85 (m, 2H). $^1$H NMR (400 MHz, $CD_3OD$): δ 8.91-8.90 (m, 2H), 8.32 (s, 2H), 7.74 (s, 1H), 7.46-7.44 (d, J=7.2 Hz, 1H), 7.26-7.16 (m, 2H), 7.12-7.07 (m, 2H), 6.94-6.92 (d, J=7.2 Hz, 1H) 6.70-6.68 (d, J=7.6 Hz, 1H) 5.39-5.26 (m, 4H) 4.09-4.08 (m, 2H), 3.74 (m, 1H), 3.56-3.47 (m, 2H), 3.05 (m, 2H), 2.85 (m, 2H), 2.56 (m, 1H), 2.22-2.20 (m, 2H), 2.14-2.10 (m, 2H), 2.07 (s, 3H), 1.91-1.86 (m, 5H), 1.68-1.65 (m, 2H), 1.28 (s, 1H), 0.89-0.87 (m, 1H).

Example 19: 2-[5-Chloro-2-[(5-cyano-3-pyridyl) methoxy]-4-[[3-[3-[3-(4-hydroxy-1-piperidyl) propoxy]-2-methyl-phenyl]-2-methyl-phenyl] methoxy]phenyl]-4,5-dihydro-1H-imidazole-4-carboxylic acid

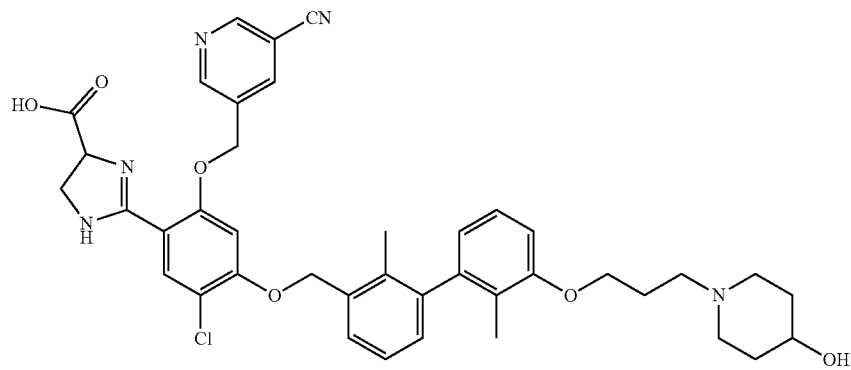

(a) methyl 2,3-diaminopropanoate

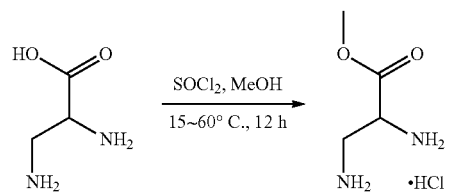

To a solution of 2,3-diaminopropanoic acid (900 mg, 8.64 mmol) in MeOH (10 mL) was added $SOCl_2$ (5.14 g, 43.22 mmol) at 15° C. The mixture was stirred at 60° C. for 12 hr. The mixture was concentrated to give methyl 2,3-diaminopropanoate hydrogen chloride salt (900 mg, 67.34% yield) as a white solid.

(b) methyl 2-[5-chloro-2-[(5-cyano-3-pyridyl) methoxy]-4-[[3-[3-[3-(4-hydroxy-1-piperidyl) propoxy]-2-methyl-phenyl]-2-methyl-phenyl] methoxy]phenyl]-4,5-dihydro-1H-imidazole-4-carboxylate

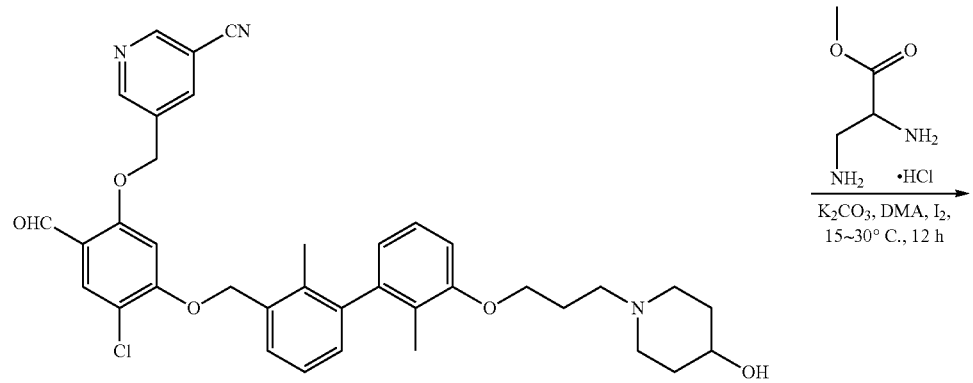

-continued

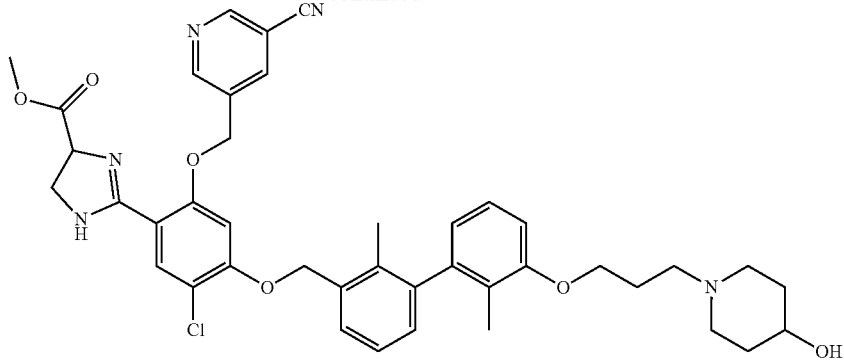

To a solution of 5-[[4-chloro-2-formyl-5-[[3-[3-[3-(4-hydroxy-1-piperidyl)propoxy]-2-methyl-phenyl]-2-methyl-phenyl]methoxy]phenoxy]methyl]pyridine-3-carbonitrile (150 mg, 234.31 µmol) and methyl 2,3-diaminopropanoate di-HCl salt (134.30 mg, 702.94 µmol) in DMA (3 mL) was added $K_2CO_3$ (323.85 mg, 2.34 mmol) and $I_2$ (237.89 mg, 937.26 µmol) at 15° C. The mixture was stirred at 30° C. for 12 hr. The reaction mixture (combined with other two batches of same scale) was filtered. The filtrate was purified directly with prep-HPLC (column: Phenomenex luna(2) C18 250*50 10µ; mobile phase: [water (0.1% TFA)-ACN]; B %: 60%-90%, 20 min) to give methyl 2-[5-chloro-2-[(5-cyano-3-pyridyl)methoxy]-4-[[3-[3-[3-(4-hydroxy-1-piperidyl)propoxy]-2-methyl-phenyl]-2-methyl-phenyl]methoxy]phenyl]-4,5-dihydro-1H-imidazole-4-carboxylate (120 mg, 23.12% yield) as a yellow solid. LCMS: m/z found 738.4 $[M+H]^+$ (c) 2-[5-chloro-2-[(5-cyano-3-pyridyl)methoxy]-4-[[3-[3-[3-(4-hydroxy-1-piperidyl) propoxy]-2-methyl-phenyl]-2-methyl-phenyl]methoxy]phenyl]-4,5-dihydro-1H-imidazole-4-carboxylic acid

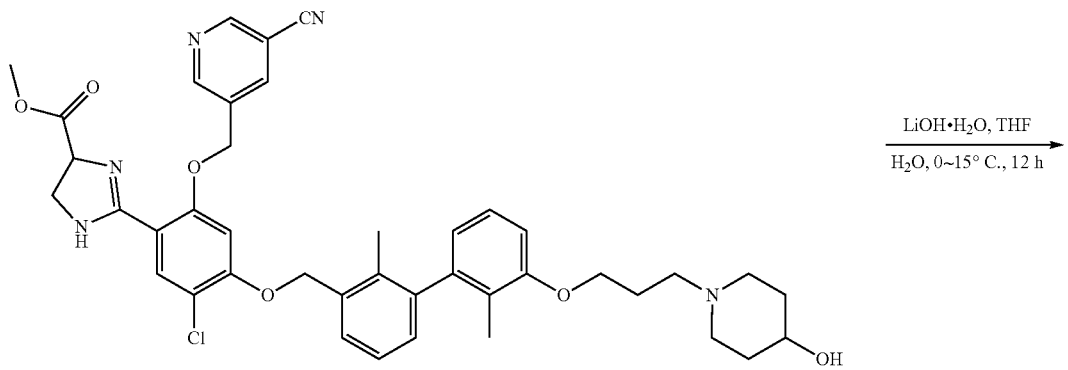

LiOH·H$_2$O, THF
H$_2$O, 0~15° C., 12 h

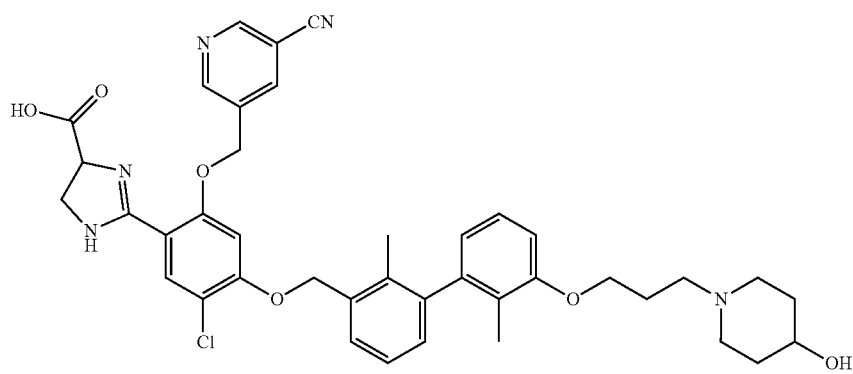

To a solution of methyl 2-[5-chloro-2-[(5-cyano-3-pyridyl)methoxy]-4-[[3-[3-[3-(4-hydroxy-1-piperidyl)propoxy]-2-methyl-phenyl]-2-methyl-phenyl]methoxy]phenyl]-4,5-dihydro-1H-imidazole-4-carboxylate (120 mg, 162.54 µmol) in THF (2 mL) and H$_2$O (1 mL) was added LiOH·H$_2$O (6.82 mg, 162.54 µmol) at 0° C. The mixture was stirred at 15° C. for 12 hr. The mixture was concentrated. The residue was purified by prep-HPLC (column: Agela Durashell C18 150*25 5µ; mobile phase: [water (10 mM NH$_4$HCO$_3$)-ACN]; B %: 30%-60%, 10 min) to give 2-[5-chloro-2-[(5-cyano-3-pyridyl)methoxy]-4-[[3-[3-[3-(4-hydroxy-1-piperidyl)propoxy]-2-methyl-phenyl]-2-methyl-phenyl]methoxy]phenyl]-4,5-dihydro-1H-imidazole-4-carboxylic acid (45.14 mg, 38.35% yield), as a white solid. MS: m/z found 724.1 [M+H]$^+$; $^1$H NMR (400 MHz, DMSO-d$_6$): δ 9.01 (s, 2H), 8.52 (s, 1H), 7.99 (s, 1H), 7.45-7.43 (d, J=7.2 Hz, 1H), 7.27-7.17 (m, 3H), 7.08-7.06 (d, J=7.6 Hz, 1H), 6.95-6.93 (d, J=8.4 Hz, 1H), 6.67-6.65 (d, J=7.6 Hz, 1H), 5.52 (s, 2H), 5.36 (s, 2H), 4.28-4.23 (m, 1H), 4.04-3.94 (m, 4H), 2.69 (m, 2H), 1.99 (m, 5H), 1.92-1.86 (m, 5H), 1.79-1.78 (m, 3H), 1.70-1.67 (m, 2H), 1.39-1.32 (m, 2H); $^1$H NMR (400 MHz, CD$_3$OD): δ 8.95-8.94 (d, J=2 Hz, 1H), 8.91-8.90 (d, J=1.6 Hz, 1H), 8.36 (s, 1H), 7.97 (s, 1H), 7.41-7.39 (d, J=7.2 Hz, 1H), 7.25-7.16 (m, 2H), 7.10-7.08 (m, 2H), 6.93-6.91 (d, J=8.4 Hz, 1H), 6.69-6.67 (d, J=7.2 Hz, 1H), 5.54 (s, 2H), 5.35 (s, 2H), 4.65-4.60 (m, 1H), 4.23-4.17 (m, 1H), 4.09-4.03 (m, 3H), 3.65 (m, 1H), 2.91-2.88 (m, 2H), 2.65-2.61 (m, 2H), 2.27 (m, 2H), 2.08-2.01 (m, 5H), 1.89-1.85 (m, 5H), 1.64-1.55 (m, 2H).

Example 20: Methyl 2-(5-chloro-2-((5-cyanopyridin-3-yl)methoxy)-4-((3'-(3-(4-hydroxypiperidin-1-yl)propoxy)-2,2'-dimethyl-[1,1'-biphenyl]-3-yl)methoxy)phenyl)-1H-imidazole-5-carboxylate

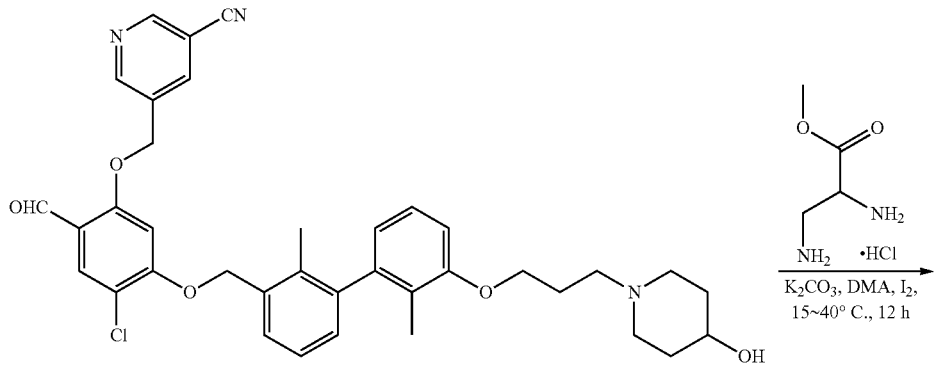

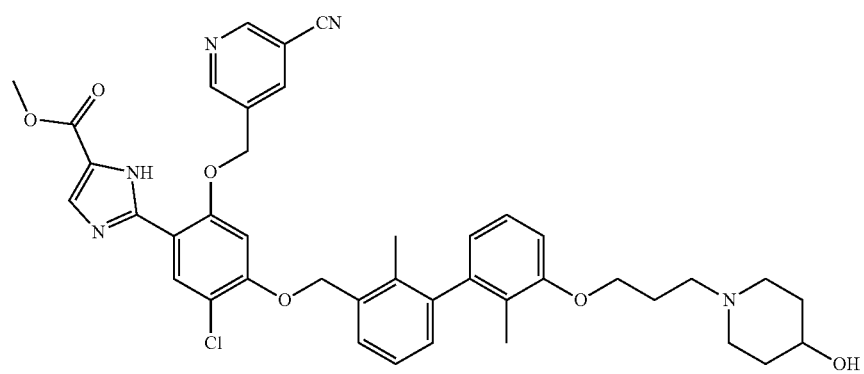

To a mixture of 5-[[4-chloro-2-formyl-5-[[3-[3-[3-(4-hydroxy-1-piperidyl)propoxy]-2-methyl-phenyl]-2-methyl-phenyl]methoxy]phenoxy]methyl]pyridine-3-carbonitrile (300 mg, 468.63 μmol) and methyl 2,3-diaminopropanoate as hydrogen chloride salt (181.12 mg, 1.17 mmol) in DMA (4 mL) was added $K_2CO_3$ (129.54 mg, 937.26 μmol) and $I_2$ (356.83 mg, 1.41 mmol) in one portion at 15° C. under $N_2$. The mixture was heated to 30° C. and stirred for 6 hours. The reaction was partly complete. To the mixture was added additional $K_2CO_3$ (300 mg) and $I_2$ (360 mg) at 15° C., and then was heated to 40° C. and stirred for 6 hours. The mixture was filtered. The filtrate was purified by prep-HPLC (column: Nano-micro Kromasil C18 100*30 mm 5 μm; mobile phase: [water (0.1% TFA)-ACN]; B %: 25%-51%, 10 min) to give a semi-purified product. This product was further purified by p-TLC (EtOAc:MeOH=2:1) to give methyl 2-(5-chloro-2-((5-cyanopyridin-3-yl)methoxy)-4-((3'-(3-(4-hydroxypiperidin-1-yl)propoxy)-2,2'-dimethyl-[1,1'-biphenyl]-3-yl)methoxy)phenyl)-1H-imidazole-5-carboxylate (15.21 mg) as a yellow solid. MS: m/z found 736.4 [M+H]$^+$; $^1$H NMR (400 MHz, CD$_3$OD): δ 8.84-8.83 (d, J=1.6 Hz, 1H), 8.81-8.80 (d, J=2 Hz, 1H), 8.20 (s, 1H), 7.94 (s, 1H), 7.75 (s, 1H), 7.44-7.42 (d, J=7.2 Hz, 1H), 7.21-7.14 (m, 2H), 7.06-7.04 (d, J=7.2 Hz, 1H), 6.95-6.89 (m, 2H), 6.68-6.66 (d, J=7.2 Hz, 1H), 5.32 (s, 2H), 5.24 (s, 2H), 4.07-4.02 (m, 2H), 3.86 (s, 3H), 4.67-3.62 (m, 1H), 2.87-2.84 (m, 2H), 2.61-2.57 (m, 2H), 2.23-2.17 (m, 2H), 2.05-1.99 (m, 6H), 1.89-1.85 (m, 6H), 1.62-1.53 (m, 2H).

Example 21: 2-[[2-[5-Chloro-2-[(5-cyano-3-pyridyl)methoxy]-4-[[3-[3-[3-(4-hydroxy-1-piperidyl)propoxy]-2-methyl-phenyl]-2-methyl-phenyl]methoxy]phenyl]-1,4,5,6-tetrahydropyrimidin-5-yl]oxy] acetic acid

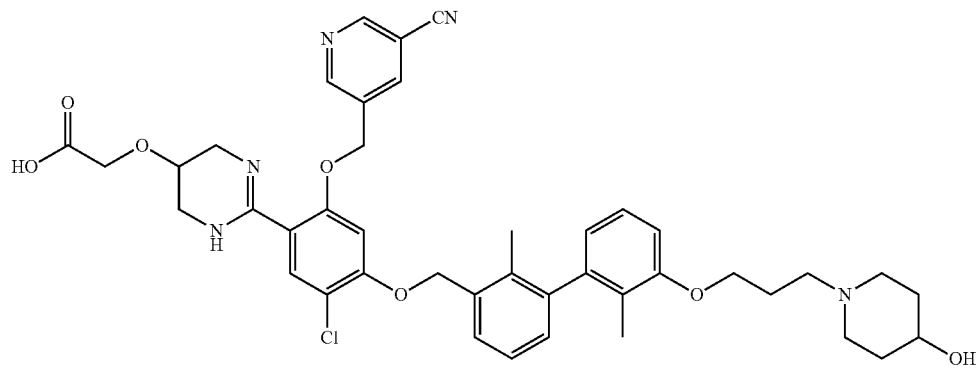

(a) tert-butyl N-[3-(tert-butoxycarbonylamino)-2-hydroxy-propyl]carbamate

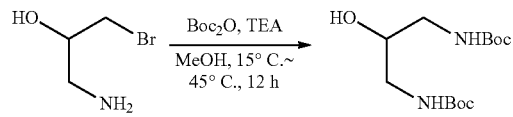

To a solution of 1,3-diaminopropan-2-ol (5 g, 55.48 mmol) in MeOH (50 mL) was added TEA (16.84 g, 166.44 mmol, 23.17 mL) and Boc$_2$O (31.48 g, 144.25 mmol, 33.14 mL) at 15° C. The mixture was stirred at 45° C. for 12 h under $N_2$ atmosphere. The reaction mixture was concentrated under reduced pressure. The residue was purified by column chromatography (silica gel, Petroleum ether/Ethyl acetate=20/1 to 0:1) to give tert-butyl N-[3-(tert-butoxycarbonylamino)-2-hydroxy-propyl]carbamate (15.47 g, 96.04% yield) as a white solid. $^1$H NMR (400 MHz, CDCl$_3$): δ 5.03 (brs, 2H), 4.08-4.02 (m, 2H), 4.27 (s, 2H), 3.22-3.06 (m, 4H), 1.37 (s, 18H).

(b) tert-butyl 2-[2-(tert-butoxycarbonylamino)-1-[(tert-butoxycarbonylamino)methyl] ethoxy] acetate

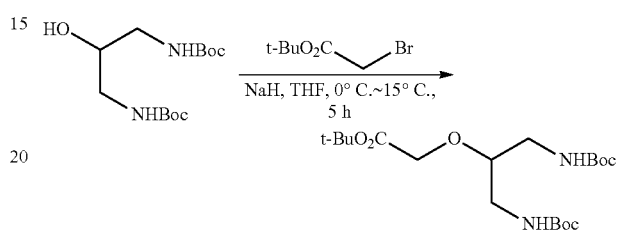

To a solution of tert-butyl 2-bromoacetate (17.36 g, 89.00 mmol, 13.15 mL) in THF (160 mL) was added NaH (11.75 g, 293.71 mmol, 60% purity) at 0° C. and tert-butyl N-[3-(tert-butoxycarbonylamino)-2-hydroxy-propyl] carbamate (25.84 g, 89.00 mmol). The mixture was stirred at 15° C. for 4.5 h. The reaction was quenched with H$_2$O (100 mL) and extracted with EtOAc (50 mL×4). The combined organic layers were washed with brine (50 mL), dried over Na$_2$SO$_4$, filtered and concentrated under reduced pressure. The residue was purified by column chromatography (silica gel, Petroleum ether/Ethyl acetate=1:0 to 20:1) to give tert-butyl 2-[2-(tert-butoxycarbonylamino)-1-[(tert-butoxycarbonylamino)methyl]ethoxy] acetate (11.87 g, 33.0% yield) as a white solid. LCMS: m/z found 405.3 [M+H]$^+$.

(c) 2-[2-amino-1-(aminomethyl)ethoxy]acetic acid; dihydrochloride

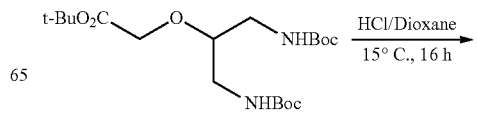

-continued

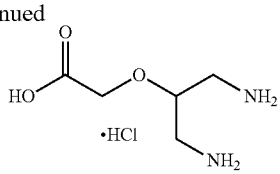

A mixture of tert-butyl 2-[2-(tert-butoxycarbonylamino)-1-[(tert-butoxycarbonylamino) methyl]ethoxy]acetate (11.87 g, 29.35 mmol) and HCl/dioxane (6 M, 48.91 mL) in DCM (120 mL) was stirred at 15° C. for 16 h. The reaction mixture was concentrated under reduced pressure to give 2-[2-amino-1-(aminomethyl)ethoxy]acetic acid dihydrochloride (7.36 g) as a white solid. $^1$H NMR (400 MHz, DMSO-d$_6$): δ 8.33 (brs, 6H), 4.27 (s, 2H), 3.99 (m, 1H), 3.11-3.02 (m, 4H).

(d) 2-[[2-[5-chloro-2-[(5-cyano-3-pyridyl)methoxy]-4-[[3-[3-[3-(4-hydroxy-1-piperidyl)propoxy]-2-methyl-phenyl]-2-methyl-phenyl] methoxy] phenyl]-1,4,5,6-tetrahydropyrimidin-5-yl]oxy] acetic acid To a mixture of 5-[[4-chloro-2-formyl-5-[[3-[3-[3-(4-hydroxy-1-piperidyl)propoxy]-2-methyl-phenyl]-2-methyl-phenyl]methoxy]phenoxy]methyl]pyridine-3-carbonitrile (100 mg, 156.21 μmol) and 2-[2-amino-1-(aminomethyl)ethoxy] acetic acid di-HCl salt (86.34 mg, 390.52 μmol) in DMA (2.5 mL) was added K$_2$CO$_3$ (172.72 mg, 1.25 mmol) and I$_2$ (118.94 mg, 468.63 μmol) under N$_2$. The mixture was stirred at 40° C. for 12 h. The mixture was purified directly without work-up. The residue was purified by prep-HPLC (column: Phenomenex Luna C18 200*40 mm*10 μum; mobile phase: [water (0.1% TFA)-ACN]; B %: 20%-40%, 10 min) to give a semi-purified product that was further purified by prep-HPLC (column: Waters Xbridge 150*25 5μ; mobile phase: [water (10 mM NH$_4$HCO$_3$)-ACN]; B %: 27%-47%, 12 min) to give 2-[[2-[5-chloro-2-[(5-cyano-3-pyridyl)methoxy]-4-[[3-[3-[3-(4-hydroxy-1-piperidyl)propoxy]-2-methyl-phenyl]-2-methyl-phenyl]methoxy]phenyl]-1,4,5,6-tetrahydropyrimidin-5-yl]oxy]acetic acid (14.3 mg) as a white solid. LCMS: m/z found 768.2 [M+H]$^+$; $^1$H NMR (400 MHz, DMSO-d$_6$): δ 9.02-9.01 (d, J=2 Hz, 1H), 8.99-8.98 (d, J=2 Hz, 1H), 8.43 (s, 1H), 7.65 (s, 1H), 7.49-7.47 (d, J=7.2 Hz, 1H), 7.29-7.25 (m, 2H), 7.21-7.17 (t, J=8.2 Hz, 1H), 7.09-7.07 (d, J=7.2 Hz, 1H), 6.95-6.93 (d, J=8 Hz, 1H), 6.67-6.65 (d, J=7.6 Hz, 1H), 5.40-5.37 (m, 4H), 4.12 (brs, 1H), 4.04-3.99 (m, 2H), 3.63 (s, 2H), 3.57-3.53 (m, 2H), 3.46-3.42 (m, 4H), 2.71-2.68 (m, 2H), 2.43-2.39 (m, 3H), 2.02 (s, 3H), 1.98-1.95 (m, 2H), 1.89-1.84 (m, 2H), 1.81 (s, 3H), 1.70-1.67 (m, 2H), 1.39-1.31 (m,

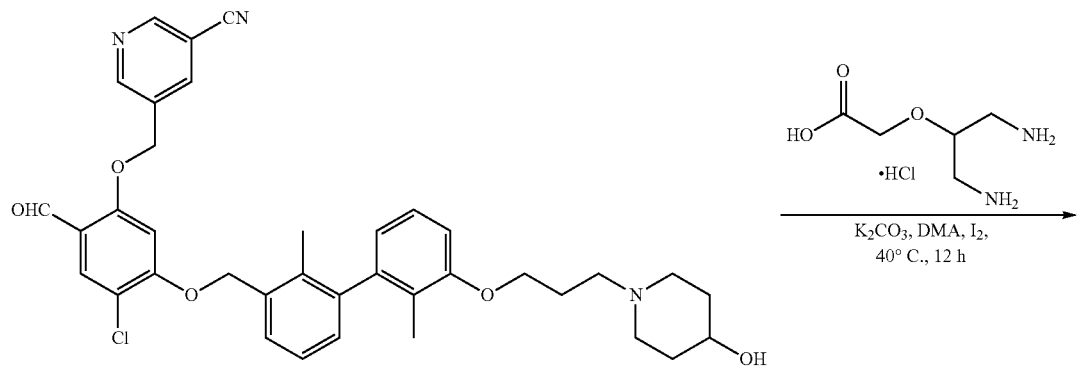

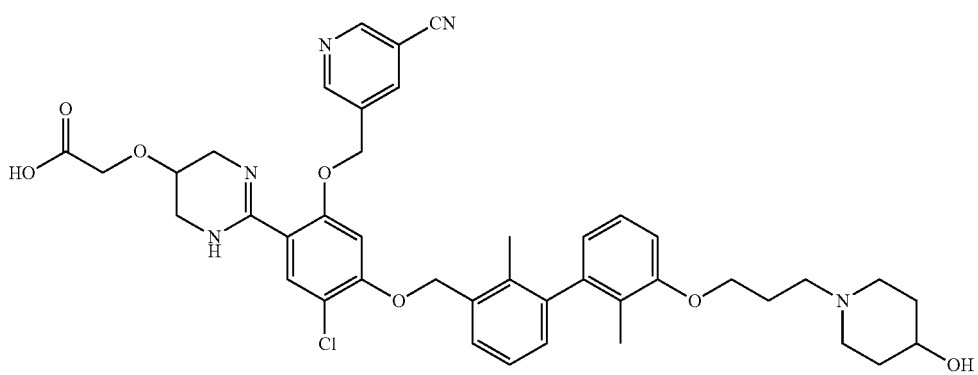

2H). ¹H NMR (400 MHz, CD₃OD): δ 8.93-8.92 (d, J=2 Hz, 1H), 8.91-8.90 (d, J=2 Hz, 1H), 8.32 (s, 1H), 7.67 (s, 1H), 7.46-7.44 (d, J=7.6 Hz, 1H), 7.26-7.22 (t, J=7.6 Hz, 1H), 7.20-7.16 (t, J=8 Hz, 1H), 7.14 (s, 1H), 7.10-7.08 (d, J=7.2 Hz, 1H), 6.93-6.91 (d, J=8 Hz, 1H), 6.69-6.67 (d, J=7.6 Hz, 1H), 5.39 (s, 2H), 5.37 (s, 2H), 4.19-4.17 (m, 1H), 4.09-4.06 (m, 2H), 3.99 (s, 2H), 3.76-3.75 (d, J=2.4 Hz, 1H), 3.73-3.72 (d, J=2 Hz, 1H), 3.64 (m, 1H), 3.58-3.57 (d, J=2.4 Hz, 1H), 3.55-3.54 (d, J=2.4 Hz, 1H), 2.89-2.86 (m, 2H), 2.64-2.59 (m, 2H), 2.24 (m, 2H), 2.08-2.00 (m, 5H), 1.89-1.86 (m, 5H), 1.63-1.54 (m, 2H).

Example 22: 5-[[4-Chloro-2-[1-(2-hydroxyethyl)-4,5-dihydroimidazol-2-yl]-5-[[3-[3-[3-(4-hydroxy-1-piperidyl)propoxy]-2-methyl-phenyl]-2-methyl-phenyl]methoxy]phenoxy] methyl]pyridine-3-carbonitrile

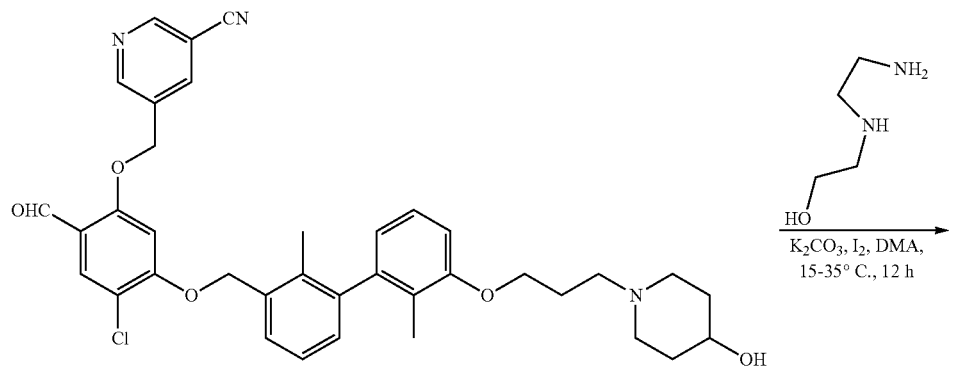

To a mixture of 5-[[4-chloro-2-formyl-5-[[3-[3-[3-(4-hydroxy-1-piperidyl)propoxy]-2-methyl-phenyl]-2-methyl-phenyl]methoxy]phenoxy]methyl]pyridine-3-carbonitrile (200 mg, 312.42 μmol) in DMA (5 mL) was added 2-(2-aminoethylamino)ethanol (97.62 mg, 937.26 μmol, 94.77 μL), K₂CO₃ (215.89 mg, 1.56 mmol) and I₂ (317.18 mg, 1.25 mmol) at 15° C. The mixture was heated to 35° C. and stirred for 12 h. The mixture was filtered, and the filtrate was purified by prep-HPLC (TFA condition; column: Nano-micro Kromasil C18 100*30 mm 5 μm; mobile phase: [water (0.1% TFA)-ACN]; B %: 23%-43%, 10 min). The combined fractions was basified with sat.NaHCO₃ solution and extracted with a mixture of EtOAc/THF (1/1, 3×50 mL). The organic layer was dried over Na₂SO₄, filtered and concentrated to afford 5-[[4-chloro-2-[1-(2-hydroxyethyl)-4,5-dihydroimidazol-2-yl]-5-[[3-[3-[3-(4-hydroxy-1-piperidyl)propoxy]-2-methyl-phenyl]-2-methyl-phenyl]methoxy]phenoxy]methyl]pyridine-3-carbonitrile (59.69 mg, 26.10% yield) as a yellow solid. MS: m/z found 724.2 [M+H]⁺; ¹H NMR (400 MHz, DMSO-d₆): δ 9.07 (d, J=1.8 Hz, 1H), 8.99 (d, J=2.0 Hz, 1H), 8.42 (s, 1H), 7.70 (s, 1H), 7.51 (d, J=7.5 Hz, 1H), 7.37 (s, 1H), 7.30 (t, J=7.5 Hz, 1H), 7.22 (t, J=8 Hz, 1H), 7.11 (d, J=7.1 Hz, 1H), 6.97 (d, J=8.2 Hz, 1H), 6.69 (d, J=7.5 Hz, 1H), 5.46 (s, 2H), 5.41 (s, 2H), 5.03 (br t, J=5.3 Hz, 1H), 4.67 (br s, 1H), 4.09-4.01 (m, 4H), 3.95-3.90 (m, 2H), 3.46-3.61 (m, 3H), 2.88 (br s, 1H), 2.05 (s, 3H), 1.99 (br s, 2H), 1.84 (s, 3H), 1.76 (br s, 2H), 1.48 (br s, 3H), 1.36 (s, 2H), 1.24 (s, 2H).

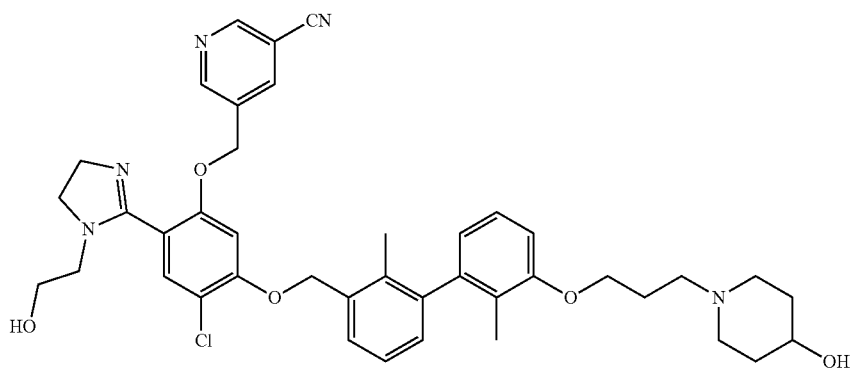

Example 23: (5-[[4-chloro-2-[6-hydroxy-1-(2-hydroxyethyl)-5,6-dihydro-4H-pyrimidin-2-yl]-5-[[3-[3-[3-(4-hydroxy-1-piperidyl)propoxy]-2-methyl-phenyl]-2-methyl-phenyl]methoxy]phenoxy]methyl]pyridine-3-carbonitrile

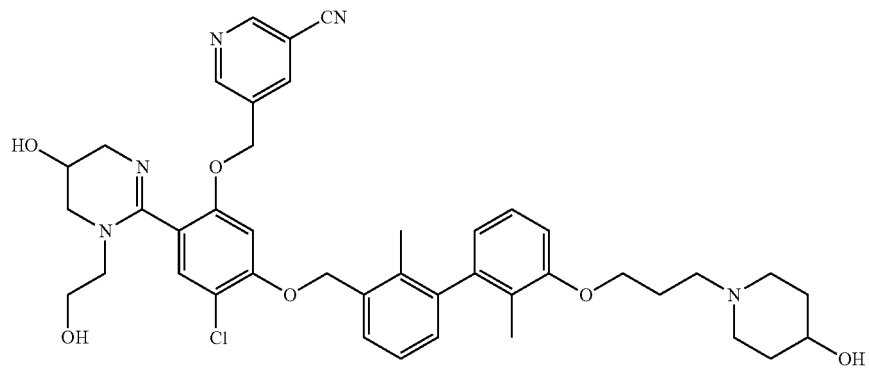

(a) 2-(oxiran-2-ylmethyl)isoindoline-1,3-dione (b) 2-[3-[benzyl(2-hydroxyethyl)amino]-2-hydroxy-propyl]isoindoline-1,3-dione

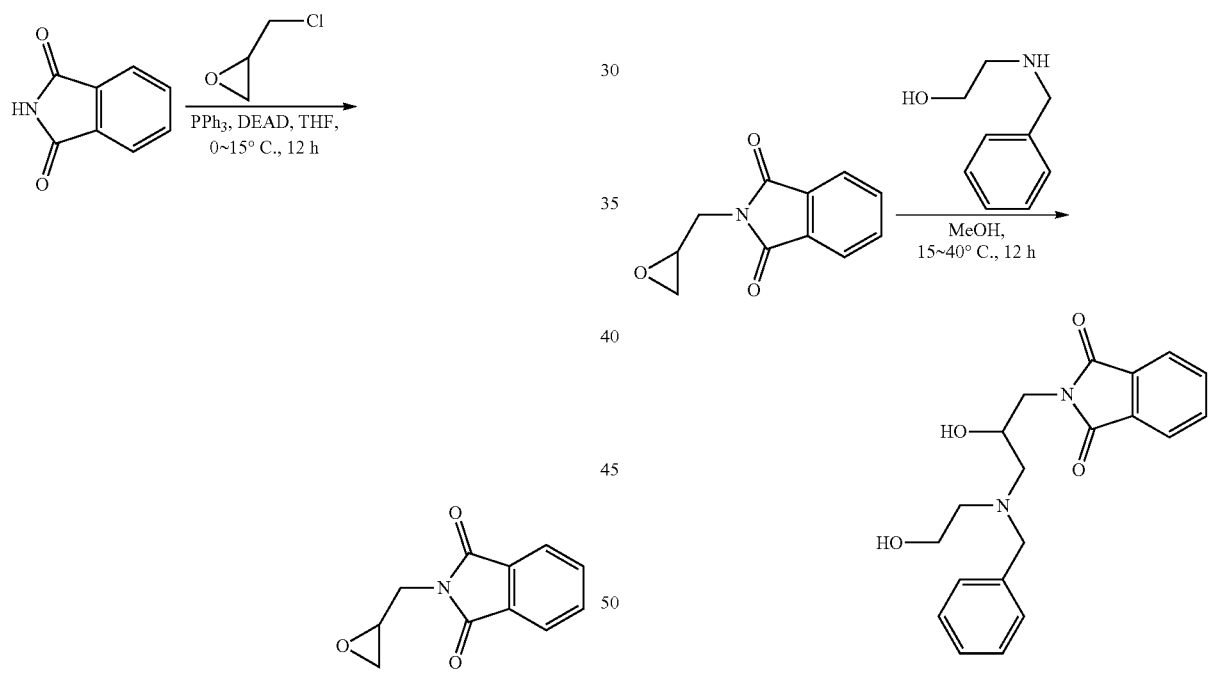

To a mixture of isoindoline-1,3-dione (20 g, 135.93 mmol) and 2-(chloromethyl)oxirane (15.09 g, 163.12 mmol, 12.79 mL) in THF (100 mL) was added PPh$_3$ (53.48 g, 203.90 mmol) at 0° C. Then DEAD (35.51 g, 203.90 mmol, 37.07 mL) was added dropwise at 0° C. under N$_2$. The mixture was stirred at 15° C. for 12 hr. The mixture was filtered and the filtrate was concentrated. The residue was purified by column chromatography (silica gel, Petroleum ether:Ethyl acetate=20:1 to 3:1) to give 2-(oxiran-2-ylmethyl)isoindoline-1,3-dione (11 g, 49.80 mmol, 36.6% yield) as a yellow solid. $^1$H NMR (400 MHz, CDCl$_3$): δ 7.82-7.79 (m, 2H), 7.68-7.65 (m, 2H), 3.90-3.87 (m, 1H), 3.74 (dd, J=14 Hz, 4.8 Hz, 1H), 3.173-3.170 (m, 1H), 2.75-2.72 (m, 1H), 2.63-2.61 (m, 1H).

To a mixture of 2-(oxiran-2-ylmethyl)isoindoline-1,3-dione (3 g, 14.76 mmol) in MeOH (40 mL) was added 2-(benzylamino)ethanol (4.46 g, 29.53 mmol, 4.17 mL) at 15° C. under N$_2$. The mixture was then heated to 40° C. and stirred for 12 hr. The mixture was concentrated. The residue was purified by column chromatography (silica gel, Petroleum ether: Ethyl acetate=5:1 to 1:1) to give 2-[3-[benzyl(2-hydroxyethyl)amino]-2-hydroxy-propyl]isoindoline-1,3-dione (3 g, 5.33 mmol, 36.12% yield) as a yellow oil. $^1$H NMR (400 MHz, CD$_3$OD): δ 7.85-7.80 (m, 4H), 7.32 (d, J=7.2 Hz, 2H), 7.22-7.21 (m, 2H), 7.19-7.15 (m, 1H), 4.05-4.04 (m, 1H), 3.72-3.67 (m, 2H), 3.64-3.60 (m, 4H), 2.69-2.68 (m, 2H), 2.60-2.58 (m, 2H).

(c) 2-[2-hydroxy-3-(2-hydroxyethylamino)propyl]isoindoline-1,3-dione (d) Amino-3-(2-hydroxyethylamino)propan-2-ol

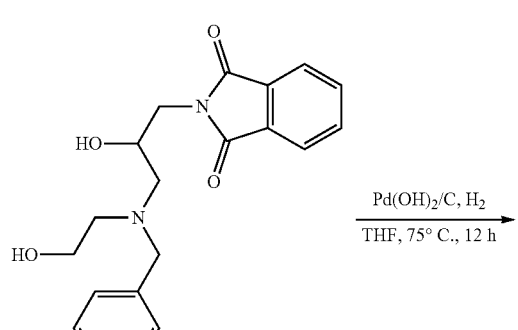

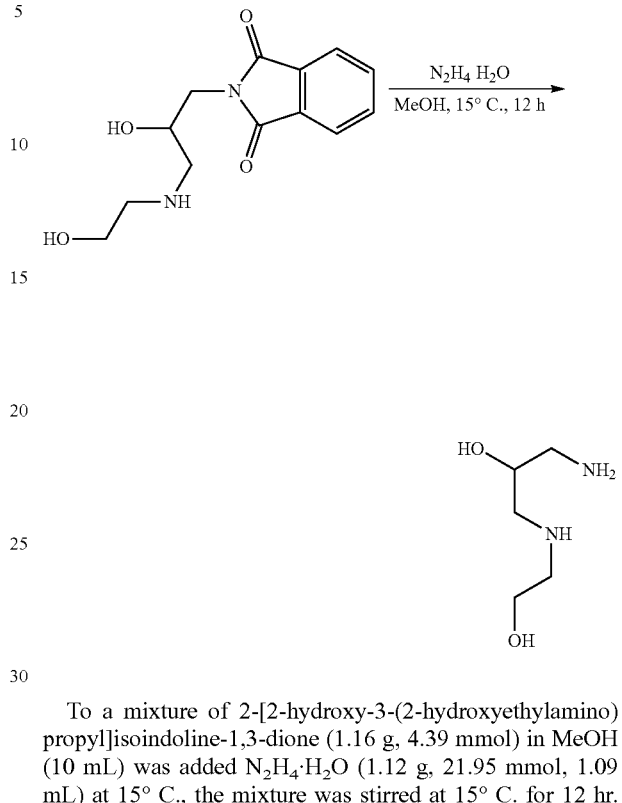

To a solution of 2-[3-[benzyl(2-hydroxyethyl)amino]-2-hydroxy-propyl]isoindoline-1,3-dionein (1.1 g, 3.10 mmol) in THF (20 mL) was added Pd(OH)$_2$/C (0.5 g, 20%) under N$_2$. The suspension was degassed under vacuum and purged with H$_2$ several times. The mixture was heated to 75° C. and stirred under H$_2$ (15 psi) for 12 hr. The mixture was filtered and the filtrate was concentrated to give 2-[2-hydroxy-3-(2-hydroxyethylamino)propyl]isoindoline-1,3-dione (0.7 g, crude, 79% LCMS purity) as a white solid which was used directly without purification. LCMS: m/z found 265.0 [M+H]$^+$.

To a mixture of 2-[2-hydroxy-3-(2-hydroxyethylamino)propyl]isoindoline-1,3-dione (1.16 g, 4.39 mmol) in MeOH (10 mL) was added N$_2$H$_4$·H$_2$O (1.12 g, 21.95 mmol, 1.09 mL) at 15° C., the mixture was stirred at 15° C. for 12 hr. The mixture was filtered and the filtrate was concentrated to give 1-amino-3-(2-hydroxyethylamino)propan-2-ol (0.8 g, crude, 57% LCMS purity) as a white solid, which was used into the next step without further purification. LCMS: m/z found 135.0 [M+H]$^+$ (e) (5-[[4-chloro-2-[6-hydroxy-1-(2-hydroxyethyl)-5,6-dihydro-4H-pyrimidin-2-yl]-5-[[3-[3-[3-(4-hydroxy-1-piperidyl)propoxy]-2-methyl-phenyl]-2-methyl-phenyl]methoxy]phenoxy]methyl]pyridine-3-carbonitrile

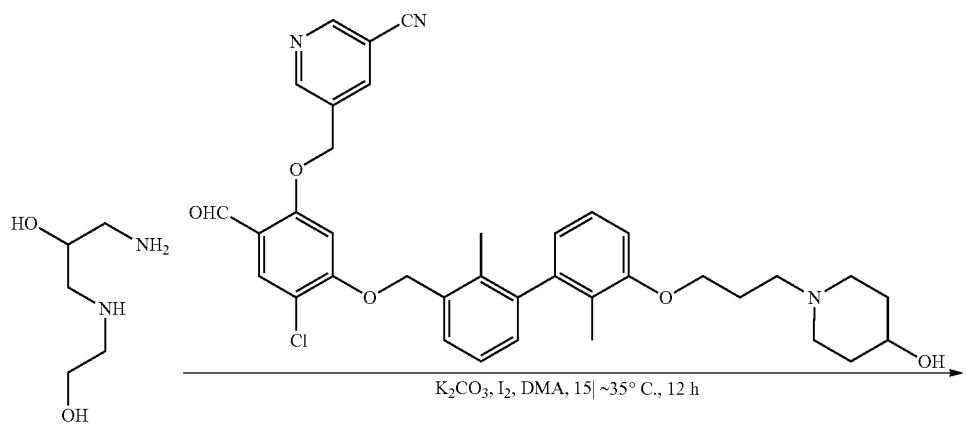

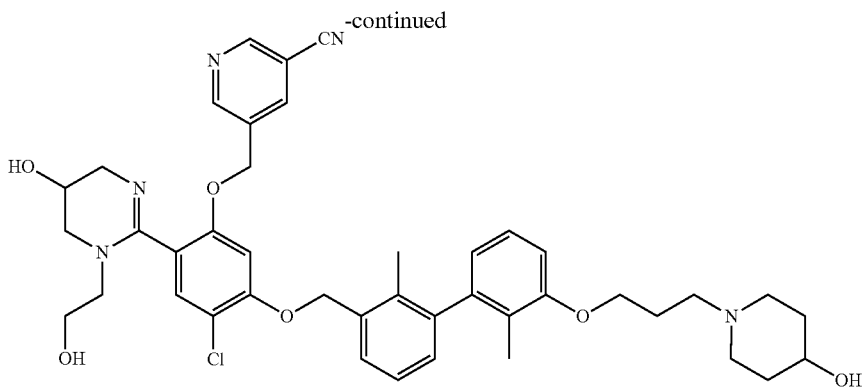

To a mixture of 5-[[4-chloro-2-formyl-5-[[3-[3-[3-(4-hydroxy-1-piperidyl)propoxy]-2-methyl-phenyl]-2-methylphenyl]methoxy]phenoxy]methyl]pyridine-3-carbonitrile (250 mg, 390.52 μmol) in DMA (3 mL) was added 2-amino-1-(2-hydroxyethylamino)ethanol (258.07 mg, 859.15 μmol, 94.77 μL), K$_2$CO$_3$ (269.87 mg, 1.95 mmol) and I$_2$ (396.48 mg, 1.56 mmol, 314.66 μL) at 15° C. The resultant mixture was heated to 35° C. and stirred for 12 hr. The mixture was combined with another 50 mg scaled batch and filtered. The filtrate was purified by prep-HPLC (TFA condition; column: Nano-micro Kromasil C18 100*30 mm 5 μm; mobile phase: [water (0.1% TFA)-ACN]; B %: 20%-40%, 10 min). The desired fractions were combined and adjusted to pH=8 by sat. NaHCO$_3$ solution and extracted with mixture solvent (EtOAc:THF=1:1, 3×50 mL). The organic layer was dried over Na$_2$SO$_4$, filtered and concentrated to give 5-[[4-chloro-2-[6-hydroxy-1-(2-hydroxyethyl)-5,6-dihydro-4H-pyrimidin-2-yl]-5-[[3-[3-[3-(4-hydroxy-1-piperidyl)propoxy]-2-methyl-phenyl]-2-methyl-phenyl]methoxy]phenoxy]methyl]pyridine-3-carbonitrile (9.86 mg) as a yellow solid. MS: m/z found 754.2 [M+H]$^+$; $^1$H NMR (400 MHz, DMSO-d$_6$): δ 9.90-9.69 (m, 1H), 9.06-8.98 (m, 1H), 8.94 (d, J=1.3 Hz, 1H), 8.42-8.32 (m, 1H), 7.56 (s, 1H), 7.52-7.47 (m, 1H), 7.36-7.30 (m, 1H), 7.30-7.24 (m, 1H), 7.08 (br d, J=7.5 Hz, 1H), 6.95 (d, J=8.2 Hz, 1H), 6.68 (br dd, J=7.2, 3.4 Hz, 1H), 5.61 (d, J=2.6 Hz, 1H), 5.48-5.41 (m, 2H), 5.41-5.31 (m, 2H), 5.21 (t, J=5.5 Hz, 1H), 5.09-4.97 (m, 1H), 4.90-4.80 (m, 1H), 4.43-4.28 (m, 2H), 4.10-4.00 (m, 2H), 3.72 (br d, J=13.0 Hz, 1H), 3.58-3.50 (m, 3H), 3.49-3.42 (m, 3H), 3.38 (br d, J=5.3 Hz, 1H), 2.44-2.37 (m, 1H), 2.07-1.97 (m, 5H), 1.96-1.91 (m, 1H), 1.84-1.74 (m, 5H), 1.48 (br s, 2H).

Example 24: 2-[2-[5-Chloro-2-[(5-cyano-3-pyridyl)methoxy]-4-[[3-[3-[3-(4-hydroxy-1-piperidyl)propoxy]-2-methyl-phenyl]-2-methyl-phenyl]methoxy]phenyl]-4,5-dihydroimidazol-1-yl]acetic acid

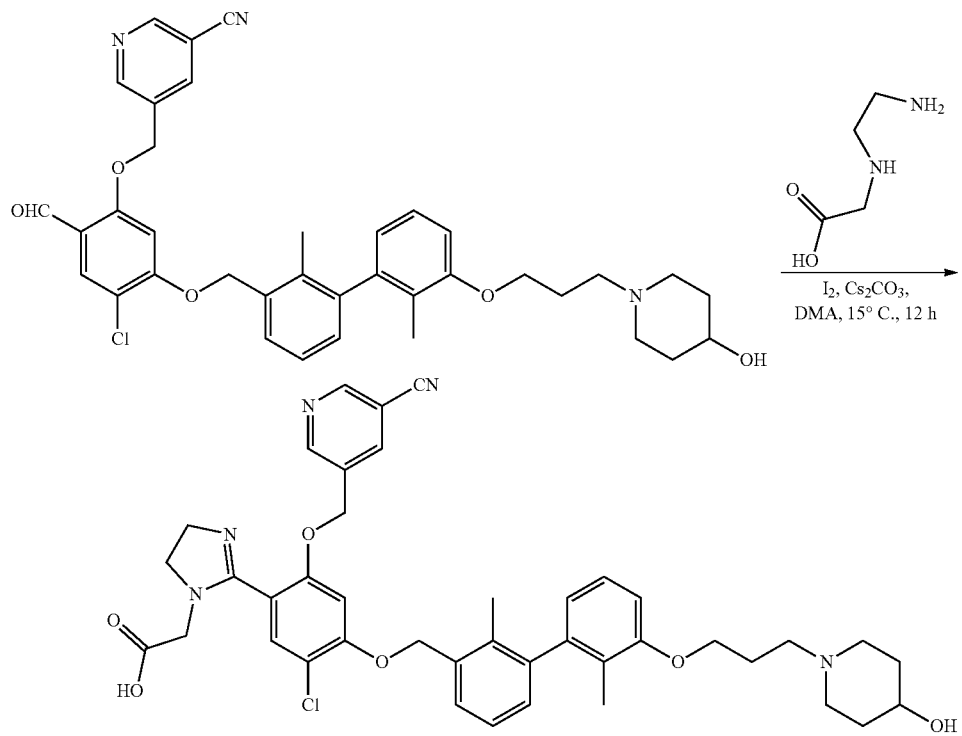

To a mixture of 5-[[4-chloro-2-formyl-5-[[3-[3-[3-(4-hydroxy-1-piperidyl)propoxy]-2-methyl-phenyl]-2-methylphenyl]methoxy]phenoxy]methyl]pyridine-3-carbonitrile (200 mg, 312.42 μmol) in DMA (4 mL) was added 2-(2-aminoethylamino)acetic acid (184.54 mg, 1.56 mmol), Cs$_2$CO$_3$ (814.34 mg, 2.50 mmol) and I$_2$ (317.18 mg, 1.25 mmol, 251.73 μL) at 15° C. The mixture was stirred at 15° C. for 12 hr. The mixture was filtered, and the filtrate was purified directly by prep-HPLC (HCl condition, column: Phenomenex Luna C18 200*40 mm*10 μm; mobile phase: [water (0.05% HCl)-ACN]; B %: 15%-35%, 10 min) to afford 2-[2-[5-chloro-2-[(5-cyano-3-pyridyl)methoxy]-4-[[3-[3-[3-(4-hydroxy-1-piperidyl)propoxy]-2-methyl-phenyl]-2-methyl-phenyl]methoxy]phenyl]-4,5-dihydroimidazol-1-yl]acetic acid hydrogen chloride salt (17.18 mg) as a yellow solid. MS: m/z found 738.2 [M+H]$^+$; $^1$H NMR (400 MHz, DMSO-d$_6$): δ 10.74 (s, 1H), 10.41 (br s, 1H), 9.04 (d, J=1.8 Hz, 1H), 8.95 (d, J=1.8 Hz, 1H), 8.38 (s, 1H), 7.58 (s, 1H), 7.48 (d, J=7.3 Hz, 1H), 7.36 (s, 1H), 7.28 (t, J=7.6 Hz, 1H), 7.24-7.18 (m, 1H), 7.08 (d, J=7.7 Hz, 1H), 6.97 (d, J=8.4 Hz, 1H), 6.69 (d, J=7.3 Hz, 1H), 5.44 (s, 2H), 5.39-5.36 (m, 2H), 4.08-4.03 (m, 6H), 3.98-3.93 (m, 3H), 3.46 (br d, J=11.9 Hz, 1H), 3.30 (br d, J=10.4 Hz, 1H), 3.22-3.16 (m, 3H), 2.98-2.89 (m, 1H), 2.24-2.20 (m, 2H), 2.02 (s, 3H), 1.98-1.89 (m, 2H), 1.83 (s, 3H), 1.73-1.70 (m, 2H).

Example 25: 5-[[4-chloro-5-[[3-[3-[3-(4-hydroxy-1-piperidyl)-2-phenyl-propoxy]-2-methyl-phenyl]-2-methyl-phenyl]methoxy]-2-(5-hydroxy-1,4,5,6-tetrahydropyrimidin-2-yl)phenoxy]methyl]pyridine-3-carbonitrile

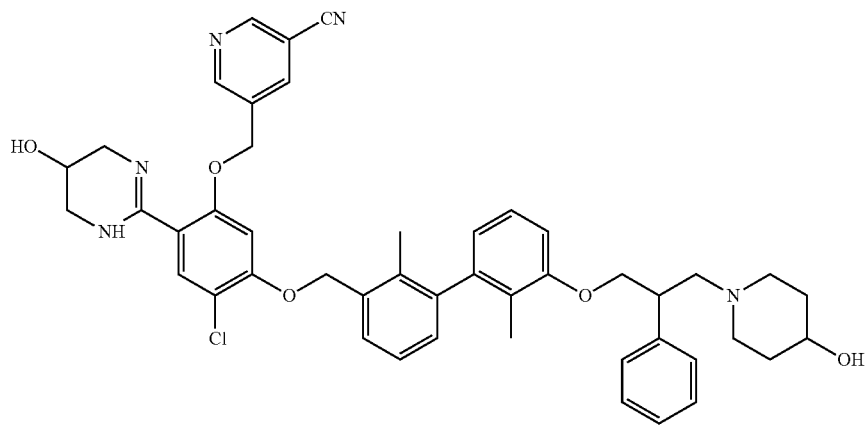

(a) 3-(3-bromo-2-methyl-phenoxy)-2-phenyl-propan-1-ol

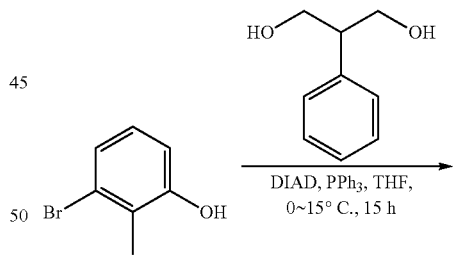

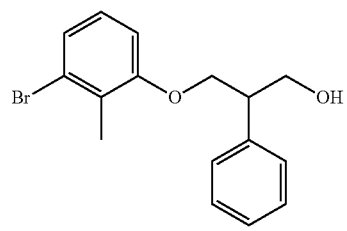

To a solution of 3-bromo-2-methyl-phenol (12.75 g, 68.17 mmol) in THF (50 mL) was added 2-phenylpropane-1,3-diol (12.45 g, 81.80 mmol) and DIAD (20.68 g, 102.25 mmol, 19.88 mL). After that, PPh₃ (35.76 g, 136.34 mmol) was added at 0° C. The mixture was stirred at 15° C. for 15 h. The reaction mixture was diluted with water (40 mL) and extracted with EtOAc (3×30 mL). The combined organic layers were washed with brine (3×30 mL), dried over Na₂SO₄, filtered and concentrated under reduced pressure. The residue was purified by flash silica gel chromatography (ISCO®; 40 g SEPAFLASH® Silica Flash Column, Eluent of 0-100% Ethyl acetate/Petroleum ethergradient @ 50 mL/min) to give 3-(3-bromo-2-methyl-phenoxy)-2-phenyl-propan-1-ol (12 g, 37.36 mmol, 54.80% yield) as a white solid. $^1$H NMR (400 MHz, CDCl₃) δ 7.36-7.28 (m, 5H), 7.16-7.14 (m, 1H), 6.98 (m, 1H), 6.79-6.77 (m, 1H), 5.01-4.95 (m, 1H), 4.26-4.21 (m, 2H), 4.20 (m, 2H), 4.11-4.02 (s, 1H), 3.77-3.35 (m, 1H), 2.27 (m, 3H).

(b) [3-(3-bromo-2-methyl-phenoxy)-2-phenyl-propyl] methanesulfonate

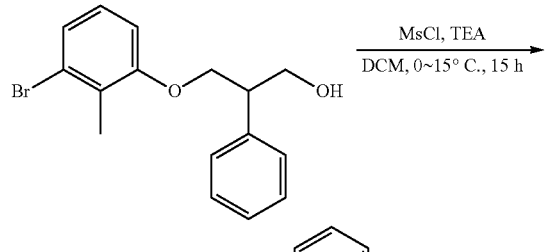

To a solution of 3-(3-bromo-2-methyl-phenoxy)-2-phenyl-propan-1-ol (12 g, 37.36 mmol) in DCM (50 mL) was added TEA (11.34 g, 112.08 mmol, 15.60 mL) and MsCl (6.42 g, 56.04 mmol, 4.34 mL) at 0° C. The mixture was stirred at 15° C. for 15 h. The reaction mixture was concentrated under reduced pressure to give a residue. The residue was purified by flash silica gel chromatography (ISCO®; 80 g SEPAFLASH® Silica Flash Column, Eluent of 0-100% Ethyl acetate/Petroleum ethergradient @ 50 mL/min) to give [3-(3-bromo-2-methyl-phenoxy)-2-phenyl-propyl] methanesulfonate (10 g, 25.04 mmol, 67.04% yield) as a yellow oil. LC-MS: m/z found 422.9[M+Na]⁺.

(c) 1-[3-(3-bromo-2-methyl-phenoxy)-2-phenyl-propyl]piperidin-4-ol

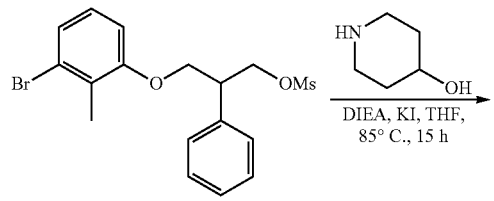

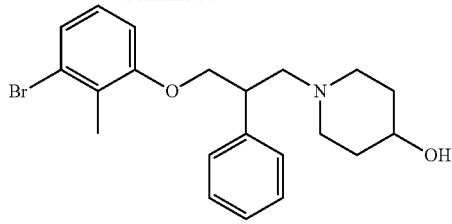

To a solution of [3-(3-bromo-2-methyl-phenoxy)-2-phenyl-propyl] methanesulfonate (10 g, 25.04 mmol) in THF (50 mL) was added piperidin-4-ol (10.13 g, 100.18 mmol), DIEA (9.71 g, 75.13 mmol, 13.09 mL) and KI (2.08 g, 12.52 mmol). The mixture was stirred at 85° C. for 15 h. The reaction mixture was filtered and concentrated under reduced pressure. The residue was purified by prep-HPLC (column: Agela innoval ods-2 250*80 mm; mobile phase: [water (0.1% TFA)-ACN]; B %: 20%-50%, 30 min) to give 1-[3-(3-bromo-2-methyl-phenoxy)-2-phenyl-propyl]piperidin-4-ol (3.5 g, 8.66 mmol, 34.56% yield) as a yellow oil. LC-MS: m/z found 404.2, 406.2[M+H]⁺.

(d) 5-chloro-2-hydroxy-4-[[2-methyl-3-(4,4,5,5-tetramethyl-1,3,2-dioxaborolan-2-yl)phenyl]methoxy]benzaldehyde

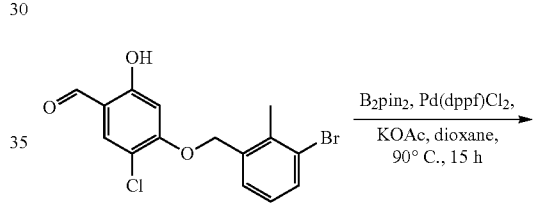

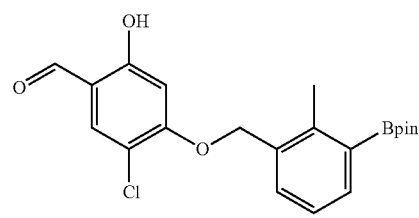

To a solution of 4-[(3-bromo-2-methyl-phenyl)methoxy]-5-chloro-2-hydroxy-benzaldehyde (1 g, 2.81 mmol) in dioxane (10 mL) was added Pd(dppf)Cl₂·CH₂Cl₂ (229.64 mg, 281.21 μmol), 4,4,5,5-tetramethyl-2-(4,4,5,5-tetramethyl-1,3,2-dioxaborolan-2-yl)-1,3,2-dioxaborolane (1.07 g, 4.22 mmol) and KOAc (827.93 mg, 8.44 mmol). The mixture was stirred 90° C. for 15 hr. The reaction mixture was filtered and concentrated under reduced pressure. The residue was purified by flash silica gel chromatography (ISCO®; 20 g SEPAFLASH® Silica Flash Column, Eluent of 0-100% Ethyl acetate/Petroleum ethergradient @ 50 mL/min) to give 5-chloro-2-hydroxy-4-[[2-methyl-3-(4,4,5,5-tetramethyl-1,3,2-dioxaborolan-2-yl)phenyl] methoxy] benzaldehyde (0.5 g, 1.06 mmol, 37.53% yield) as a white solid. LC-MS: m/z found 403 0.2 [M+H]⁺.

(e) 5-chloro-2-hydroxy-4-[[3-[3-[3-(4-hydroxy-1-piperidyl)-2-phenyl-propoxy]-2-methyl-phenyl]-2-methyl-phenyl]methoxy]benzaldehyde

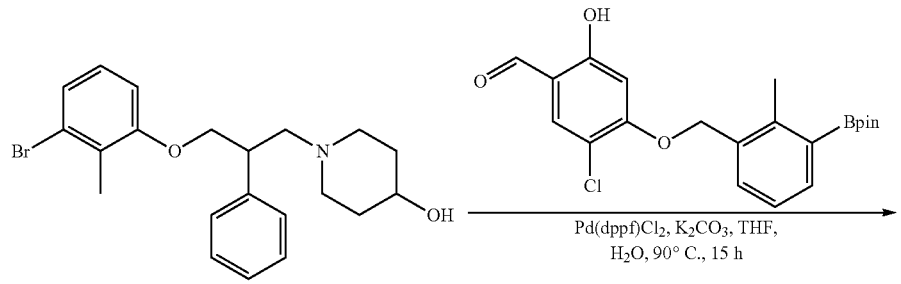

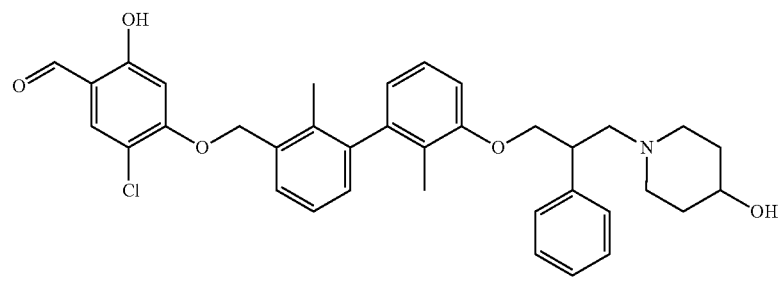

To a solution of 1-[3-(3-bromo-2-methyl-phenoxy)-2-phenyl-propyl]piperidin-4-ol (400 mg, 989.27 µmol) in THF/H₂O (6 mL/6 mL) was added Pd(dppf)Cl₂·CH₂Cl₂ (323.15 mg, 395.71 µmol), 5-chloro-2-hydroxy-4-[[2-methyl-3-(4,4,5,5-tetramethyl-1,3,2-dioxaborolan-2-yl)phenyl]methoxy]benzaldehyde (398.35 mg, 989.27 µmol) and K₂CO₃ (478.54 mg, 3.46 mmol). The mixture was stirred 90° C. for 15 hr. The reaction mixture was concentrated under reduced pressure. The residue was diluted with water (20 mL) and extracted with EtOAc (3×20 mL). The combined organic layers were washed with brine (3×20 mL), dried over Na₂SO₄, filtered and concentrated under reduced pressure. The residue was purified by flash silica gel chromatography (ISCO®; 40 g SEPAFLASH® Silica Flash Column, Eluent of 0-100% Ethyl acetate/Petroleum ether-gradient @ 50 mL/min) to give 5-chloro-2-hydroxy-4-[[3-[3-[3-(4-hydroxy-1-piperidyl)-2-phenyl-propoxy]-2-methyl-phenyl]-2-methyl-phenyl]methoxy] benzaldehyde (0.3 g, 309.93 µmol, 31.33% yield) as a black oil. LC-MS: m/z found 600.4[M+H]⁺.

(f) 5-[[4-chloro-2-formyl-5-[[3-[3-[3-(4-hydroxy-1-piperidyl)-2-phenyl-propoxy]-2-methyl-phenyl]-2-methyl-phenyl]methoxy]phenoxy]methyl]pyridine-3-carbonitrile

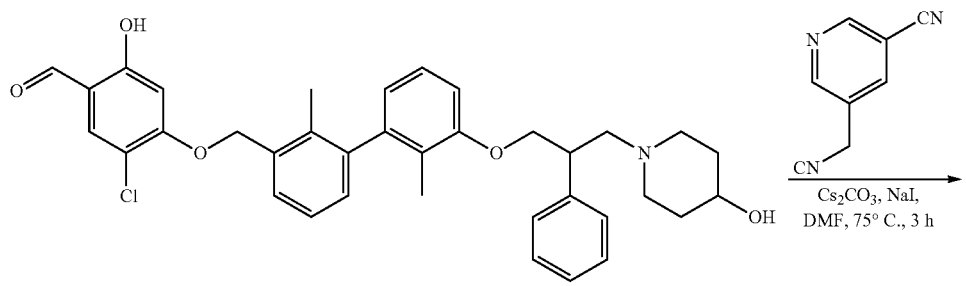

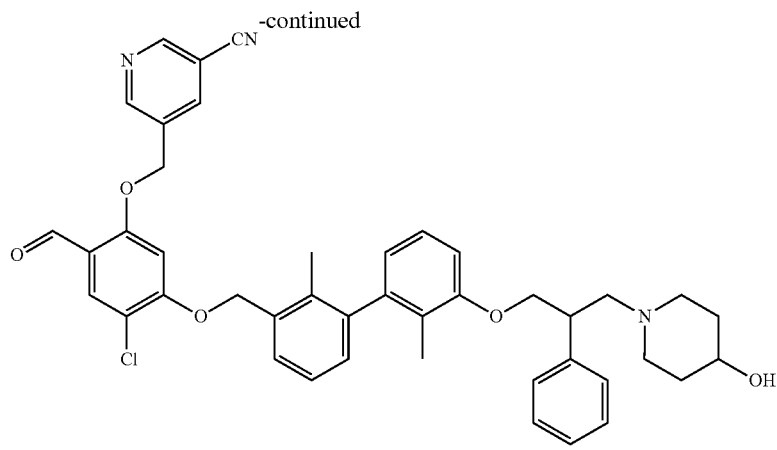

To a solution of 5-chloro-2-hydroxy-4-[[3-[3-[3-(4-hydroxy-1-piperidyl)-2-phenyl-propoxy]-2-methyl-phenyl]-2-methyl-phenyl]methoxy]benzaldehyde (200 mg, 333.25 μmol) in DMF (3 mL) was added Cs$_2$CO$_3$ (542.90 mg, 1.67 mmol), 5-(chloromethyl)pyridine-3-carbonitrile hydrogen chloride salt (75.60 mg, 399.91 μmol) and NaI (24.98 mg, 166.63 μmol). The mixture was stirred 75° C. for 3 hr. The residue was added water (20 mL). The residue was filtered. The filter cake was washed by EtOAc (5 mL) to give 5-[[4-chloro-2-formyl-5-[[3-[3-[3-(4-hydroxy-1-piperidyl)-2-phenyl-propoxy]-2-methyl-phenyl]-2-methyl-phenyl]methoxy] phenoxy]methyl]pyridine-3-carbonitrile (0.2 g, crude) as a black solid. LC-MS: m/z found 716.2 [M+H]$^+$.

(g) 5-[[4-chloro-5-[[3-[3-[3-(4-hydroxy-1-piperidyl)-2-phenyl-propoxy]-2-methyl-phenyl]-2-methyl-phenyl]methoxy]-2-(5-hydroxy-1,4,5,6-tetrahydropyrimidin-2-yl)phenoxy]methyl]pyridine-3-carbonitrile

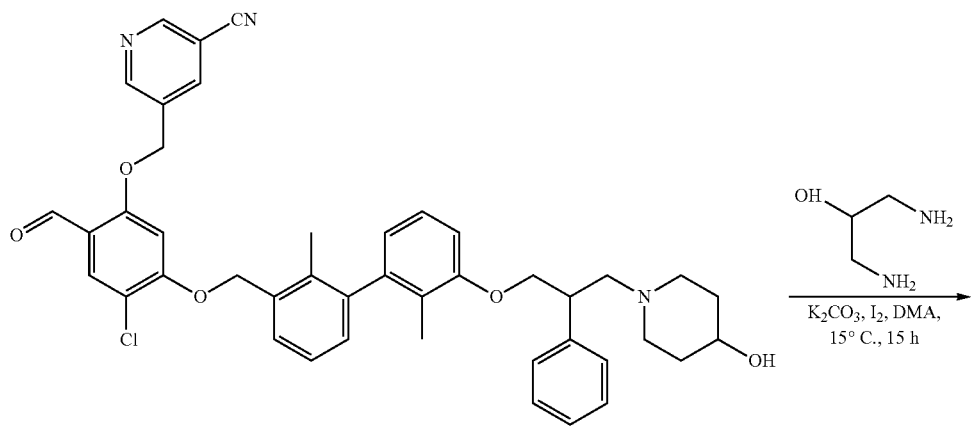

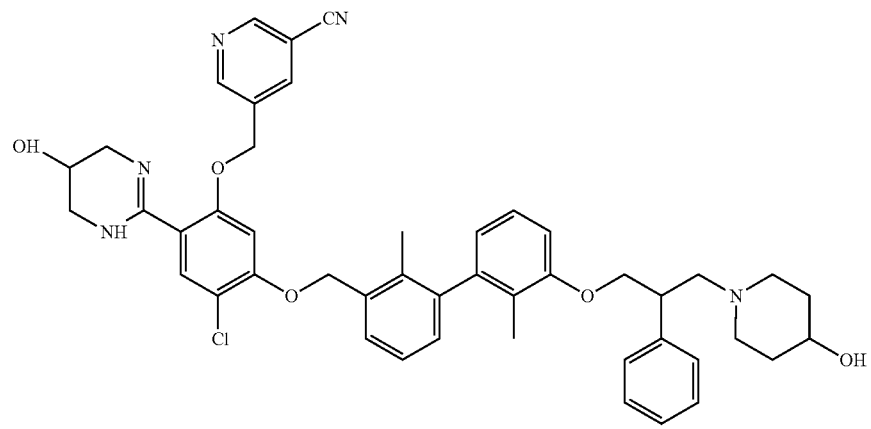

To a solution of 5-[[4-chloro-2-formyl-5-[[3-[3-[3-(4-hydroxy-1-piperidyl)-2-phenyl-propoxy]-2-methyl-phenyl]-2-methyl-phenyl]methoxy]phenoxy]methyl]pyridine-3-carbonitrile (0.2 g, 279.23 μmol) in DMA (4 mL) was added K₂CO₃ (77.18 mg, 558.45 μmol), 1,3-diaminopropan-2-ol (50.33 mg, 558.45 μmol) and I₂ (212.61 mg, 837.68 μmol). The mixture was stirred 15° C. for 15 hr. The reaction mixture was diluted with water (20 mL) and extracted with EtOAc (3×20 mL). The combined organic layers were washed with brine (3×20 mL), dried over Na₂SO₄, filtered and concentrated under reduced pressure to give a residue. The residue was purified by prep-HPLC (column: Phenomenex Synergi C18 100*30 mm*4 μm; mobile phase: [water (0.1% TFA)-ACN]; B %: 25%-55%, 10 min) to get semi-purified product (~40 mg). The product was then further purified by prep-HPLC (column: Luna C18 100*30 5μ; mobile phase: [water (0.1% TFA)-ACN]; B %: 20%-40%, 10 min). The desired fractions were combined and treated with sat. NaHCO₃ to pH=7. The mixture was extracted with 30 mL of EtOAc. The EtOAc solution was concentrated and lyophilized to give 5-[[4-chloro-5-[[3-[3-[3-(4-hydroxy-1-piperidyl)-2-phenyl-propoxy]-2-methyl-phenyl]-2-methyl-phenyl]methoxy]-2-(5-hydroxy-1,4,5,6-tetrahydropyrimidin-2-yl)phenoxy]methyl]pyridine-3-carbonitrile (25.37 mg, 31.70 μmol, 11.35% yield) as a white solid. MS: m/z found 786.3 [M+H]⁺; ¹H NMR (400 MHz, DMSO-d₆): δ 9.77 (br, 2H), 9.02 (s, 1H), 8.96 (s, 1H), 8.400 (s, 1H), 7.61 (s, 1H), 7.48-7.46 (m, 2H), 7.34-7.25 (m, 6H), 7.18-7.15 (m, 2H), 7.06-7.02 (m, 1H), 6.95-6.88 (m, 1H), 6.66-6.62 (m, 1H), 5.58 (br, 1H), 5.40 (s, 4H), 5.28 (m, 1H), 5.10 (m, 1H), 4.5 (br, 1H), 4.37 (br, 1H), 4.26-4.11 (m, 3H), 3.98 (br, 1H), 3.83-3.76 (m, 1H), 3.50-3.47 (m, 1H) 2.80-2.65 (m, 3H), 2.42-2.40 (m, 1H), 2.13-2.11 (m, 1H), 1.99-1.93 (m, 5H), 1.88 (s, 1H), 1.75-1.65 (m, 5H), 1.33-1.31 (m, 2H), 1.18 (s, 1H); ¹H NMR (400 MHz, CD₃OD): δ 8.94-8.91 (m, 2H), 8.38 (s, 1H), 7.64-7.63 (m, 1H), 7.48-7.46 (m, 2H), 7.42-7.35 (m, 4H), 7.30-7.25 (m, 2H), 7.19-7.16 (m, 2H), 7.08-7.06 (m, 1H), 6.93-6.91 (m, 1H), 6.70-6.68 (m, 1H), 5.40-5.38 (m, 4H), 4.58-4.54 (m, 1H), 4.40-4.38 (s, 1H), 4.25-4.22 (m, 2H), 4.20-4.18 (m, 1H), 3.98-3.72 (m, 2H), 3.64-3.58 (m, 4H), 3.49-3.45 (m, 3H), 3.14-3.04 (m, 2H), 2.69-2.55 (m, 2H), 2.14-2.06 (m, 3H) 1.96 (s, 1H), 1.88 (m, 2H), 1.82-1.77 (m, 3H), 1.66 (m, 2H), 1.38-1.27 (m, 1H);

Example 26: 5-[[4-Chloro-5-[[3-[3-(3-hydroxy-2-phenyl-propoxy)-2-methyl-phenyl]-2-methyl-phenyl] methoxy]-2-(5-hydroxy-1,4,5,6-tetrahydropyrimidin-2-yl)phenoxy]methyl]pyridine-3-carbonitrile

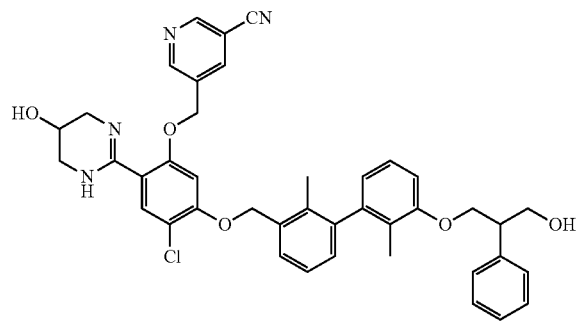

(a) 5-[[4-chloro-2-formyl-5-[[3-[3-(3-hydroxy-2-phenyl-propoxy)-2-methyl-phenyl]-2-methyl-phenyl]methoxy]phenoxy]methyl]pyridine-3-carbonitrile

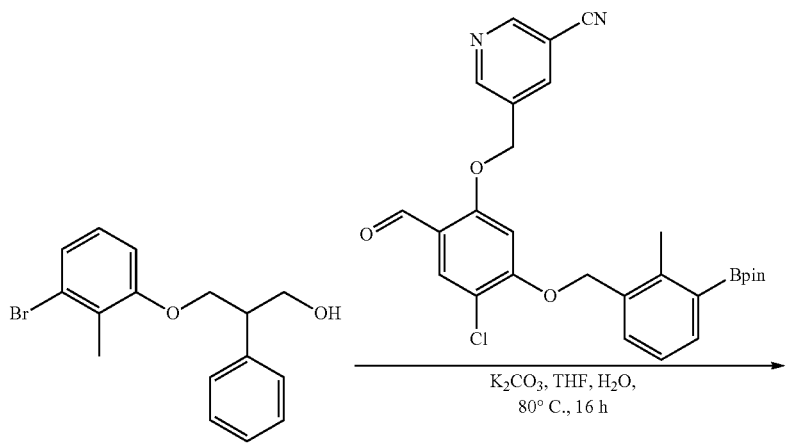

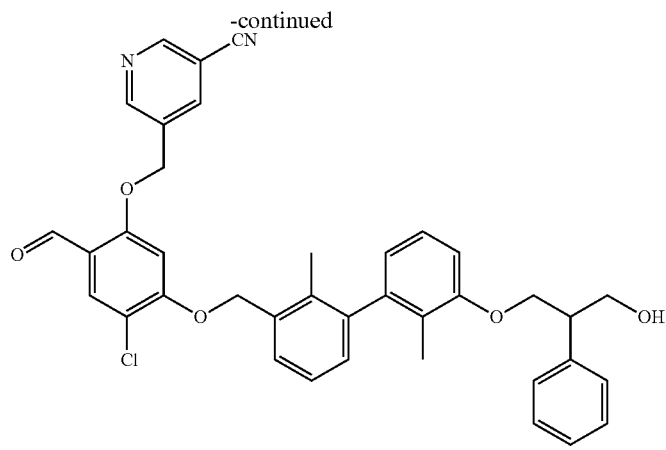

To a mixture of 3-(3-bromo-2-methyl-phenoxy)-2-phenyl-propan-1-ol (100 mg, 311.32 μmol) and 5-[[4-chloro-5-[(2,3-dimethylphenyl)methoxy]-2-formyl-phenoxy]methyl]pyridine-3-carbonitrile (152.00 mg, 373.59 μmol) in THF/H₂O (0.5 mL/0.5 mL) was added Pd(dppf)Cl₂·CH₂Cl₂ (25.42 mg, 31.13 μmol) and K₂CO₃ (107.57 mg, 778.31 μmol) at 15° C. under N₂. The mixture was stirred at 80° C. for 16 hr. The reaction mixture was concentrated under reduced pressure. The residue was purified by prep-TLC (silica gel, DCM:MeOH=10:1) to give 5-[[4-chloro-2-formyl-5-[[3-[3-(3-hydroxy-2-phenyl-propoxy)-2-methyl-phenyl]-2-methyl-phenyl]methoxy]phenoxy]methyl]pyridine-3-carbonitrile (100 mg, 50.73% yield) as a brown solid. LCMS: m/z found 633.2 [M+H]⁺.

(b) 5-[[4-chloro-5-[[3-[3-(3-hydroxy-2-phenyl-propoxy)-2-methyl-phenyl]-2-methyl-phenyl]methoxy]-2-(5-hydroxy-1,4,5,6-tetrahydropyrimidin-2-yl)phenoxy]methyl] pyridine-3-carbonitrile

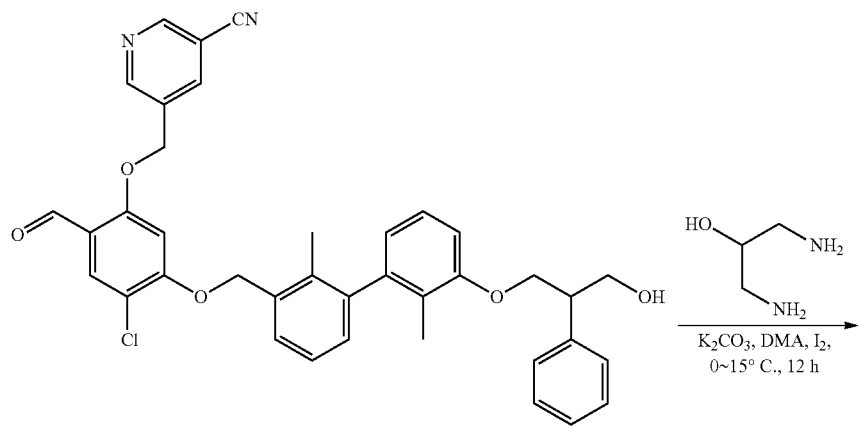

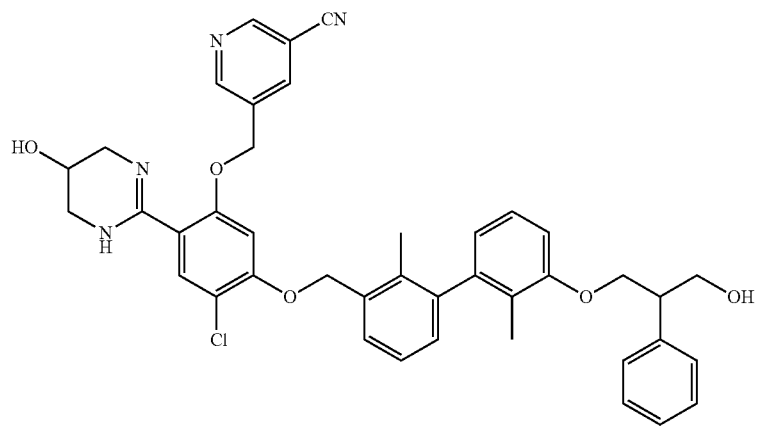

To a mixture of 5-[[4-chloro-2-formyl-5-[[3-[3-(3-hydroxy-2-phenyl-propoxy)-2-methyl-phenyl]-2-methyl-phenyl]methoxy]phenoxy]methyl]pyridine-3-carbonitrile (300 mg, 473.84 μmol) and 1,3-diaminopropan-2-ol (85.41 mg, 947.67 μmol) in DMA (1 mL) was added $K_2CO_3$ (130.97 mg, 947.67 μmol) and $I_2$ (360.79 mg, 1.42 mmol) in one portion at 0° C. under $N_2$. The mixture was stirred at 15° C. for 12 h. The mixture was combined with a 50 mg scaled batch. The mixture was purified directly without work-up by prep-HPLC (column: Phenomenex Luna C18 200*40 mm*10 μm; mobile phase: [water (0.05% HCl)-MeCN]; B %: 20%-70%, 10 min) to give 5-[[4-chloro-5-[[3-[3-(3-hydroxy-2-phenyl-propoxy)-2-methyl-phenyl]-2-methyl-phenyl]methoxy]-2-(5-hydroxy-1,4,5,6-tetrahydropyrimidin-2-yl)phenoxy]methyl]pyridine-3-carbonitrile hydrochloride salt (119.21 mg) as a yellow solid. MS: m/z found 703.2[M+H]$^+$; $^1$H NMR (400 MHz, DMSO-d$_6$): δ 9.78 (s, 2H), 9.03-9.02 (d, J=1.6 Hz, 1H), 8.97 (s, 1H), 8.42 (s, 1H), 7.61 (s, 1H), 7.49-7.47 (d, J=7.6 Hz, 1H), 7.34-7.25 (m, 6H), 7.21-7.15 (m, 2H), 7.06-7.05 (m, 1H), 6.97-6.94 (d, J=8.4 Hz, 1H), 6.64-6.62 (d, J=7.2 Hz, 1H), 5.44-5.35 (m, 4H), 4.32-4.20 (m, 3H), 3.82-3.69 (m, 13H), 3.50-3.46 (m, 2H), 3.29-3.26 (m, 2H), 3.20-3.17 (m, 1H), 2.00-1.98 (d, J=4.8 Hz, 3H), 1.71-1.67 (d, J=12 Hz, 3H). $^1$H NMR (400 MHz, CD$_3$OD): δ 9.64 (brs, 1H), 8.97-8.96 (d, J=2 Hz, 1H), 8.95-8.94 (d, J=1.6 Hz, 1H), 8.43 (s, 1H), 7.63 (s, 1H), 7.48-7.46 (d, J=7.6 Hz, 1H), 7.36-7.28 (m, 4H), 7.23-7.14 (m, 4H), 7.07 (m, 1H), 6.95-6.92 (d, J=8.4 Hz, 1H), 6.67-6.65 (d, J=7.6 Hz, 1H), 5.42 (s, 2H), 5.38 (s, 2H), 4.39-4.37 (m, 2H), 4.37-4.25 (m, 1H), 4.01-3.99 (m, 1H), 3.93-3.89 (m, 1H), 3.64-3.60 (m, 2H), 3.48-3.44 (dd, J=2.4 Hz, 2H), 3.28 (m, 1H), 2.07-2.05 (d, J=6.8 Hz, 3H), 1.77-1.75 (d, J=8 Hz, 3H). $^1$H NMR (400 MHz, DMSO-d$_6$, T=273+80 K): δ 9.70 (s, 2H), 9.00-8.98 (dd, J=2 Hz, 2H), 8.40 (s, 1H), 7.63 (s, 1H), 7.51-7.49 (d, J=7.6 Hz, 1H), 7.36-7.27 (m, 6H), 7.23-7.18 (m, 2H), 7.08 (m, H), 7.00-6.98 (d, J=8.4 Hz, 1H), 6.68-6.66 (d, J=7.6 Hz, 1H), 5.46-5.41 (m, 4H), 4.38-4.23 (m, 3H), 3.86-3.77 (m, 2H), 3.54-3.22 (m, 13H), 2.06-2.04 (d, J=5.6 Hz, 3H), 1.75-1.1.73 (d, J=8 Hz, 3H).

Example 27: (2S)-1-[[4-[[3-[3-[4-[[(2S)-2-Carboxy-1-piperidyl]methyl]-2-chloro-5-[(5-cyano-3-pyridyl)methoxy]phenoxy]methyl]-2-methyl-phenyl]-2-methyl-phenyl] methoxy]-5-chloro-2-[(5-cyano-3-pyridyl)methoxy] phenyl] methyl] piperidine-2-carboxylic acid

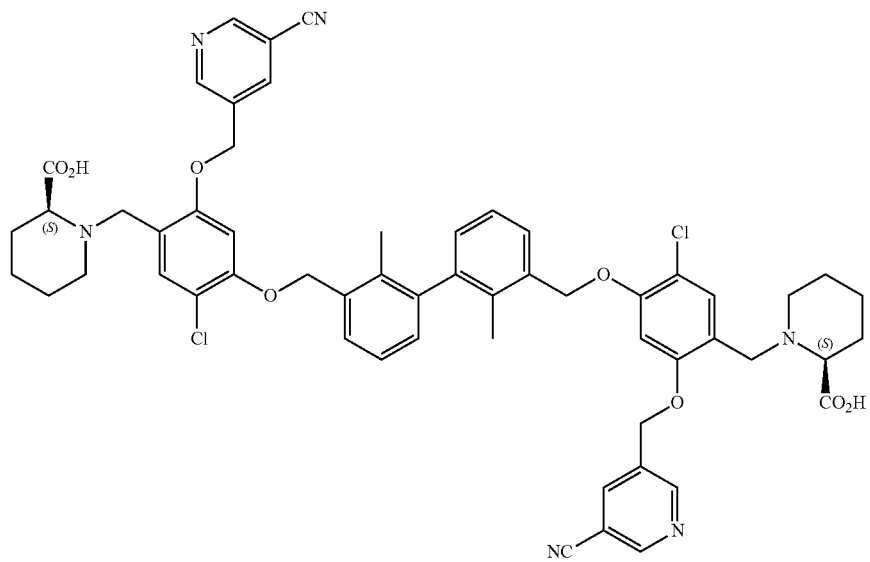

149

(a) 5-[[4-chloro-2-formyl-5-[[2-methyl-3-(4,4,5,5-tetramethyl-1,3,2-dioxaborolan-2-yl)phenyl]methoxy]phenoxy]methyl]pyridine-3-carbonitrile

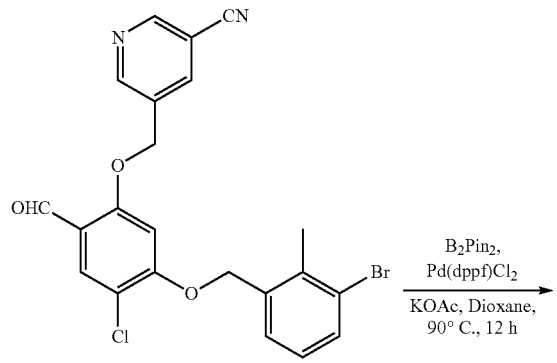

To a solution of 5-[[5-[(3-bromo-2-methyl-phenyl)methoxy]-4-chloro-2-formyl-phenoxy]methyl]pyridine-3-carbonitrile (3 g, 6.36 mmol) and 4,4,5,5-tetramethyl-2-(4,4,5,5-tetramethyl-1,3,2-dioxaborolan-2-yl)-1,3,2-dioxaborolane (2.58 g, 10.2 mmol) in dioxane (30 mL) was added Pd(dppf)Cl$_2$ (465.34 mg, 636 µmol) and KOAc (1.87 g, 19.1 mmol). The mixture was stirred at 90° C. for 12 hr. The reaction mixture was filtered and the filtrate was concentrated. The residue was purified by column chromatography (silica gel, petroleum ether:ethyl acetate=5/1 to 1:1) to give the crude product. The crude product was washed with petroleum ether (5 mL) and EtOAc (1 mL). The filter cake was concentrated to give 850 mg of 5-[[4-chloro-2-formyl-5-[[2-methyl-3-(4,4,5,5-tetramethyl-1,3,2-dioxaborolan-2-yl)phenyl]methoxy]phenoxy]methyl] pyridine-3-carbonitrile as a white solid. LCMS: m/z found 519.3 [M+H]$^+$.

150

(b) 5-[[4-chloro-5-[[3-[[2-chloro-5-[(5-cyano-3-pyridyl)methoxy]-4-formyl-phenoxy] methyl]-2-methyl-phenyl]-2-methyl-phenyl]methoxy]-2-formyl-phenoxy]methyl]pyridine-3-carbonitrile

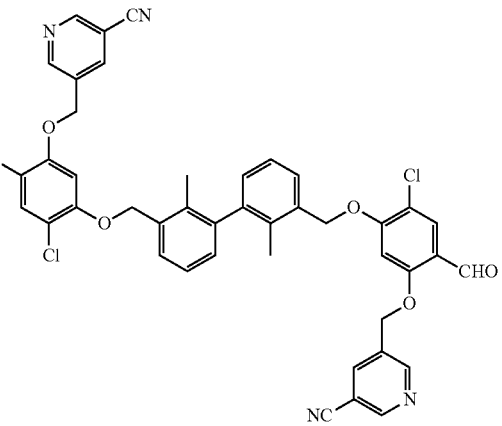

To a solution of 5-[[4-chloro-2-formyl-5-[[2-methyl-3-(4,4,5,5-tetramethyl-1,3,2-dioxaborolan-2-yl)phenyl]methoxy]phenoxy]methyl]pyridine-3-carbonitrile (200 mg, 385.51 µmol) and 5-[[5-[(3-bromo-2-methyl-phenyl)methoxy]-4-chloro-2-formyl-phenoxy]methyl]pyridine-3-carbonitrile (181.86 mg, 385 µmol) in THF (4 mL) was added K$_3$PO$_4$ (245.50 mg, 1.16 mmol) and [1,1'-Bis(di-tert-butylphosphino)ferrocene] dichloropalladium(II) (CAS No. 95408-45-0; 25.13 mg, 38.6 µmol). The mixture was stirred at 80° C. for 12 hr. The reaction mixture (four batches) was filtered and the filtrate was concentrated. The residue was purified by column chromatography (silica gel, petroleum ether:ethyl acetate=5/1 to 1:1) to give 5-[[4-chloro-5-[[3-[3-[[2-chloro-5-[(5-cyano-3-pyridyl)methoxy]-4-formyl-phenoxy] methyl]-2-methyl-phenyl]-2-methyl-phenyl]methoxy]-2-formyl-phenoxy]methyl]pyridine-3-carbonitrile (600 mg, 49.7% yield) as a white solid. LCMS: m/z found 783.3 [M+H]$^+$.

(c) (2S)-1-[[4-[[3-[3-[[4-[[(2S)-2-carboxy-1-piperidyl]methyl]-2-chloro-5-[(5-cyano-3-pyridyl)methoxy]phenoxy]methyl]-2-methyl-phenyl]-2-methyl-phenyl]methoxy]-5-chloro-2-[(5-cyano-3-pyridyl)methoxy]phenyl]methyl]piperidine-2-carboxylic acid

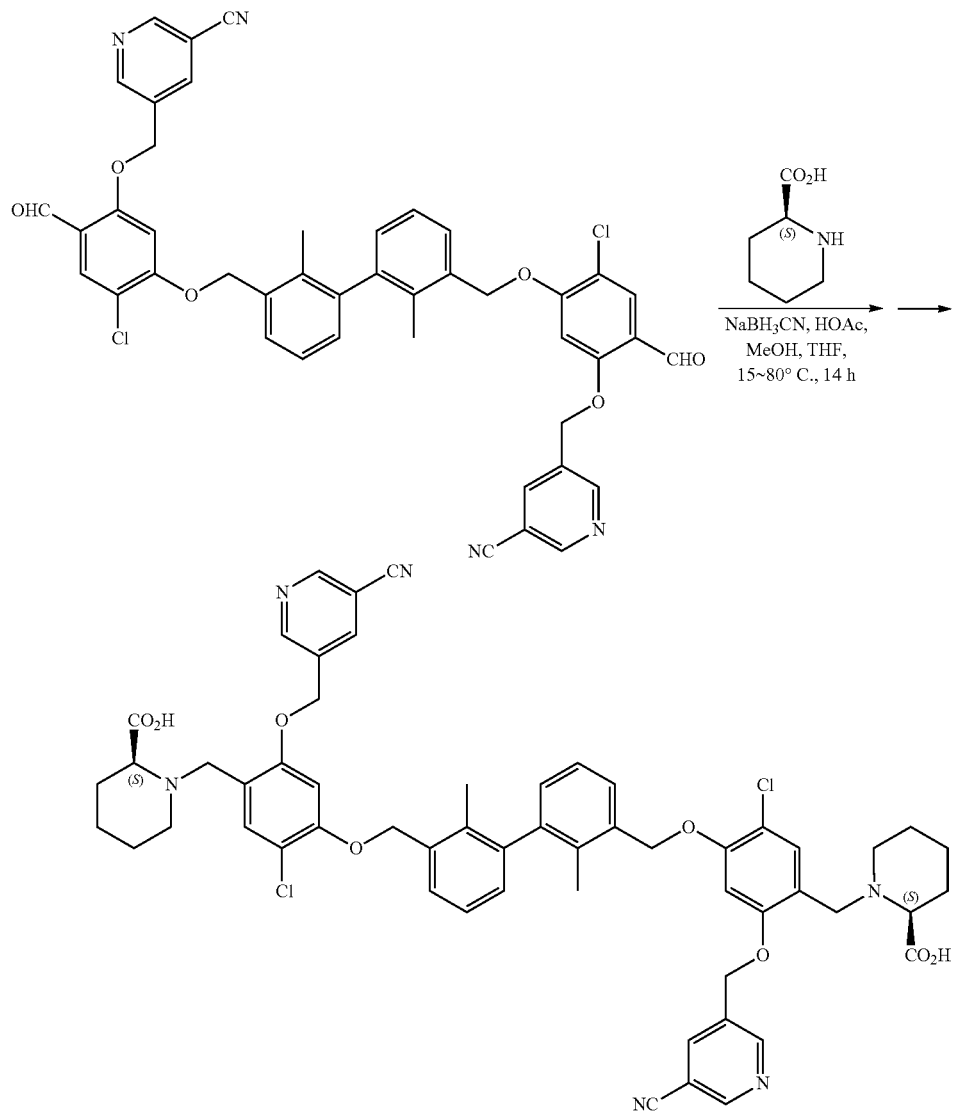

To a solution of 5-[[4-chloro-5-[[3-[3-[[2-chloro-5-[(5-cyano-3-pyridyl)methoxy]-4-formyl-phenoxy]methyl]-2-methyl-phenyl]-2-methyl-phenyl]methoxy]-2-formyl-phenoxy] methyl] pyridine-3-carbonitrile (300 mg, 383 μmol) and (2S)-piperidine-2-carboxylic acid (296.66 mg, 2.30 mmol) in MeOH/THF (5 mL/2 mL) was added acetic acid (22.99 mg, 383 μmol) and the mixture was stirred at 80° C. for 2 hr. The reaction mixture was cooled to 15° C., and NaBH$_3$CN (96.23 mg, 1.53 mmol) was added. Then the reaction mixture was stirred at 80° C. for 12 hr, and concentrated. The residue was purified by prep-HPLC (column: Phenomenex Luna C18 200*40 mm*10 μm; mobile phase: [water (0.05% HCl)-ACN]; B %: 30%-50%, 10 min) to give (2S)-1-[[4-[[3-[3-[[4-[[(2S)-2-carboxy-1-piperidyl]methyl]-2-chloro-5-[(5-cyano-3-pyridyl)methoxy]phenoxy]methyl]-2-methyl-phenyl]-2-methyl-phenyl]methoxy]-5-chloro-2-[(5-cyano-3-pyridyl)methoxy]phenyl]methyl] piperidine-2-carboxylic acid di-hydrochloride salt (80.37 mg) as a white solid. MS: m/z found 1009.4 [M+H]$^+$; $^1$H NMR (400 MHz, DMSO-d$_6$): δ 9.94 (br, 2H), 9.12-9.10 (m, 4H), 8.56 (s, 2H), 7.60 (m, 4H), 7.40-7.36 (m, 2H), 7.31 (s, 2H), 7.22-7.19 (d, 2H), 5.51-5.38 (m, 8H), 4.43-4.40 (m, 2H), 4.33-4.29 (m, 2H), 4.09 (m, 2H), 3.38-3.17 (m, 2H), 2.97 (m, 1H), 2.25-2.22 (m, 3H), 2.11 (s, 6H), 1.76 (m, 7H), 1.55 (m, 2H). $^1$H NMR (400 MHz, MeOD-d$_6$): δ 8.99-8.96 (m, 4H), 8.44 (s, 2H), 7.56 (s, 2H), 7.51-7.48 (m, 2H), 7.30-7.26 (m, 2H), 7.15-7.11 (m, 4H), 5.40 (s, 4H), 5.34 (s, 4H), 4.47-4.43 (m, 2H), 4.36-4.32 (m, 2H), 4.03-4.00 (m, 2H), 3.48-3.41 (m, 2H), 3.03-2.97 (m, 2H), 2.34-2.30 (m, 2H), 2.09 (s, 6H), 1.88-1.56 (m, 10H).

Example 28: 5-[[4-chloro-5-[[3-[3-[[2-Chloro-5-[(5-cyano-3-pyridyl)methoxy]-4-(5-hydroxy-1,4,5,6-tetrahydropyrimidin-2-yl)phenoxy]methyl]-2-methyl-phenyl]-2-methyl-phenyl]methoxy]-2-(5-hydroxy-1,4,5,6-tetrahydropyrimidin-2-yl)phenoxy]methyl]pyridine-3-carbonitrile

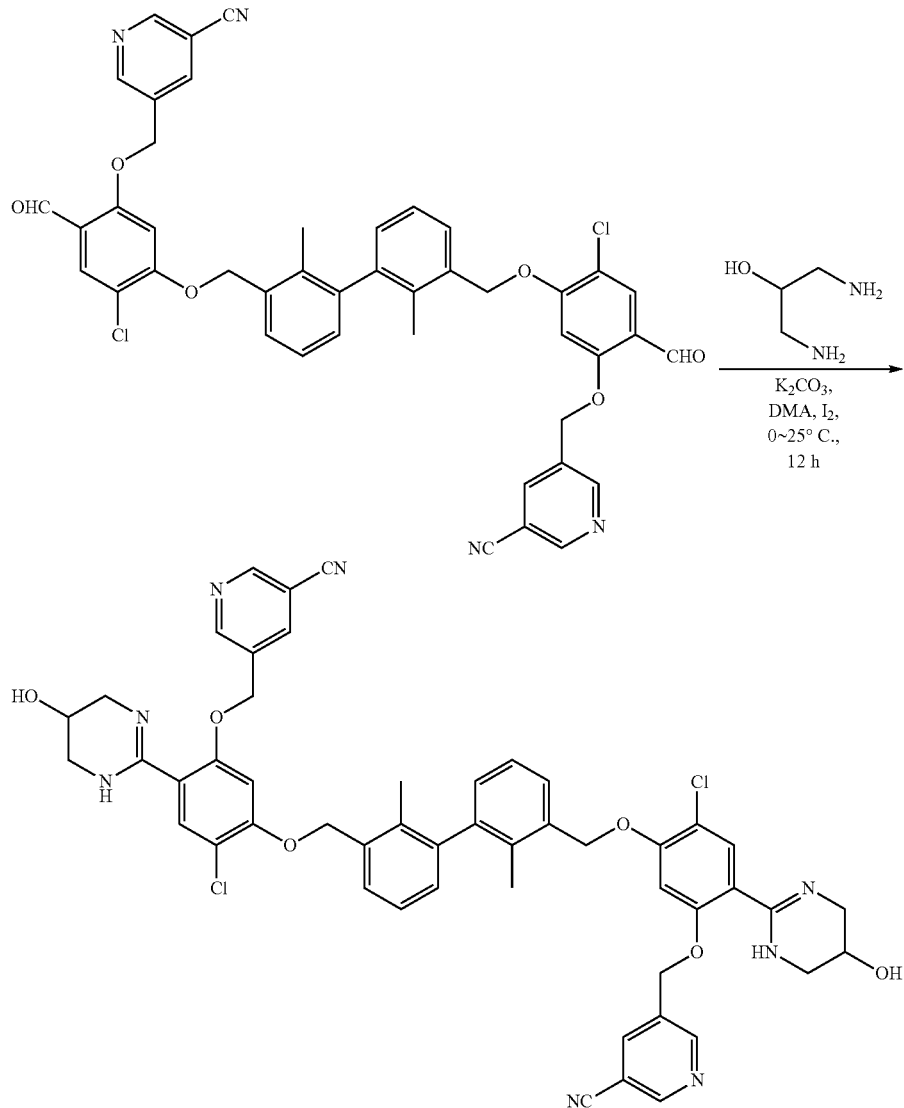

To a solution of 5-[[4-chloro-5-[[3-[3-[[2-chloro-5-[(5-cyano-3-pyridyl)methoxy]-4-formyl-phenoxy]methyl]-2-methyl-phenyl]-2-methyl-phenyl]methoxy]-2-formyl-phenoxy] methyl] pyridine-3-carbonitrile (210 mg, 267.98 μmol) and 1,3-diaminopropan-2-ol (96.60 mg, 1.07 mmol) in 1,1-dimethoxyethane (4 mL) at 0° C. was added potassium carbonate (111.11 mg, 804 μmol) and I$_2$ (408.09 mg, 1.61 mmol). The mixture was stirred at 25° C. for 12 hr, and then filtered. The isolated solution was purified by prep-HPLC (column: Phenomenex luna C18 250*50 mm*10 μm; mobile phase: [water (0.05% HCl)-ACN]; B %: 20%-50%, 23 min) to give a solution. 50 mL of saturated NaHCO$_3$ was added to this solution, and then the solution was extracted with 100 mL of EtOAc. The solution was concentrated and lyophilized to give 5-[[4-chloro-5-[[3-[3-[[2-chloro-5-[(5-cyano-3-pyridyl)methoxy]-4-(5-hydroxy-1,4,5,6-tetrahydropyrimidin-2-yl)phenoxy]methyl]-2-methyl-phenyl]-2-methyl-phenyl]methoxy]-2-(5-hydroxy-1,4,5,6-tetrahydropyrimidin-2-yl)phenoxy]methyl]pyridine-3-carbonitrile (237.64 mg) as a yellow solid. MS: m/z found 923.2 [M+H]$^+$; $^1$H NMR (400 MHz, DMSO-d$_6$): δ 9.00 (m, 4H), 8.50 (s, 2H), 7.57 (s, 2H), 7.54-7.52 (d, J=7.6 Hz, 2H), 7.32-7.28 (m, 4H), 7.13-7.11 (d, J=7.2 Hz, 2H), 5.43 (s, 4H), 5.39 (s, 4H), 4.02 (m, 2H), 3.45-3.41 (d, J=15.2 Hz, 4H), 3.22-3.18 (d, J=12.4 Hz, 4H), 2.03 (s, 6H). $^1$H NMR (400 MHz, MeOD-d$_6$): δ8.96-8.95 (d, J=2 Hz, 2H), 8.90-8.89 (d, J=1.6 Hz, 2H), 8.41 (s, 2H), 7.63 (s, 2H), 7.54-7.51 (d, J=7.6 Hz, 2H), 7.32-7.27 (t, 2H), 7.23 (s, 2H), 7.15-7.13 (d, J=6.8 Hz, 2H), 5.45 (s, 4H), 5.42 (s, 4H), 4.39-4.37 (m, 2H), 3.65-3.61 (m, 4H), 3.49-3.45 (m, 4H), 2.10 (s, 6H).

Example 29: (2S)-1-[[4-[[3-[3-[[4-[[(2S)-2-carboxy-1-piperidyl]methyl]-2-chloro-5-methoxy-phenoxy]methyl]-2-methyl-phenyl]-2-methyl-phenyl]methoxy]-5-chloro-2-methoxy-phenyl]methyl]piperidine-2-carboxylic acid

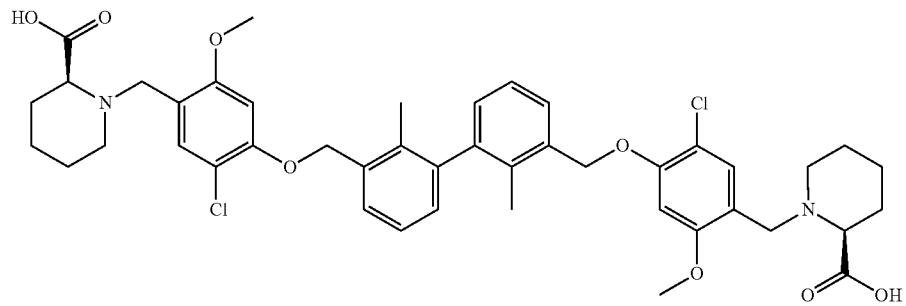

Example 30: (2S)-1-[[5-chloro-4-[[3-[3-[[2-chloro-4-(hydroxymethyl)-5-methoxy-phenoxy]methyl]-2-methyl-phenyl]-2-methyl-phenyl]methoxy]-2-methoxy-phenyl]methyl]piperidine-2-carboxylic acid

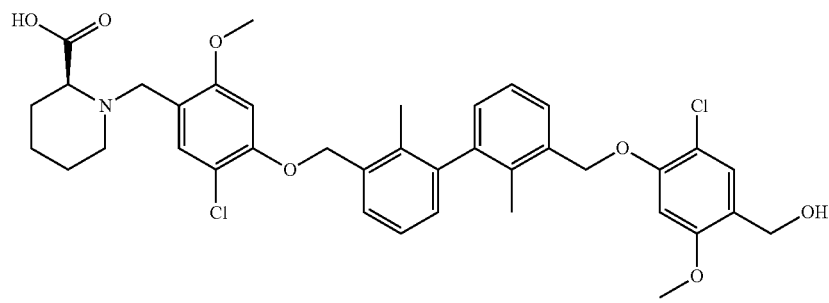

(a) 5-chloro-2,4-dihydroxy-benzaldehyde

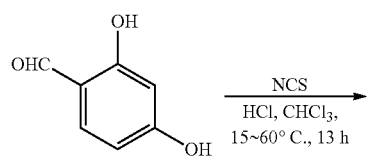

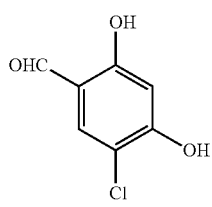

To a solution of 2,4-dihydroxybenzaldehyde (40 g, 290 mmol) in chloroform (1200 mL) was added N-chlorosuccuninamide (NCS; 38.67 g, 290 mmol) at 15° C. The mixture was stirred at 60° C. for 1 h. Then concentrated HCl (5.2 mL) was added to the mixture carefully. The mixture was stirred at 60° C. for 12 h, and separated. The CHCl₃ layer was washed with water (300 mL) and brine (300 mL), dried over Na₂SO₄, and filtered. The precipitate was dissolved in 300 mL of EtOAc, washed with 300 mL of water and 300 mL of brine, dried over Na₂SO₄, and filtered. The CHCl₃ layer and EtOAc layer were combined, and concentrated. The crude product was purified by prep-MPLC (TFA condition). Then the mixture was concentrated to remove MeOH, and the aqueous phase was extracted with EtOAc (3000 mL). The combined organic layer was dried over Na₂SO₄, filtered, and evaporated to give 5-chloro-2,4-dihydroxy-benzaldehyde (24.8 g, 139.26 mmol, 48.1% yield) as a light yellow solid. LCMS: m/z found 173.1 [M+H]⁺; ¹H NMR (400 MHz, DMSO-d₆): δ=11.40 (s, 1H), 10.87 (s, 1H), 9.9 (s, 1H), 7.58 (s, 1H), 6.58 (s, 1H).

(b) 4-[(3-bromo-2-methyl-phenyl)methoxy]-5-chloro-2-hydroxy-benzaldehyde

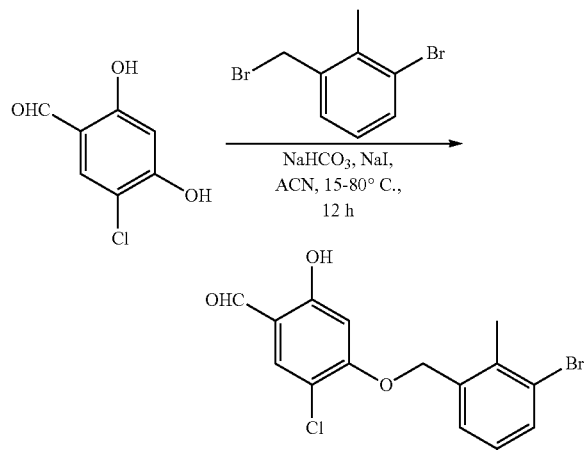

To a mixture of 5-chloro-2,4-dihydroxy-benzaldehyde (8.43 g, 48.85 mmol), NaHCO$_3$ (8.21 g, 97.70 mmol) and NaI (1.46 g, 9.77 mmol) in acetonitrile (200 mL) was added 1-bromo-3-(bromomethyl)-2-methyl-benzene (12.25 g, 46.41 mmol) at 15° C. Then the mixture was heated to 80° C. and stirred for 12 h. The mixture was filtered to give the crude product, which was washed with acetonitrile (2×100 mL) and water (2×100 mL), and filtered. The filter cake was washed with MeCN:CH$_2$Cl$_2$ (1:1, 160 mL) to give 4-[(3-bromo-2-methyl-phenyl)methoxy]-5-chloro-2-hydroxy-benzaldehyde (14 g, 38.54 mmol, 78.9% yield) as a white solid. LCMS: m/z found 357.1 [M+H]$^+$; $^1$H NMR (400 MHz, DMSO-d$_6$) δ=10.04 (s, 1H), 7.59 (d, J=7.9 Hz, 1H), 7.52 (s, 1H), 7.48-7.40 (m, 1H), 7.18-7.12 (m, 1H), 6.60 (s, 1H), 5.17 (s, 2H), 2.34 (s, 3H).

(c) 4-[(3-bromo-2-methyl-phenyl)methoxy]-5-chloro-2-methoxy-benzaldehyde

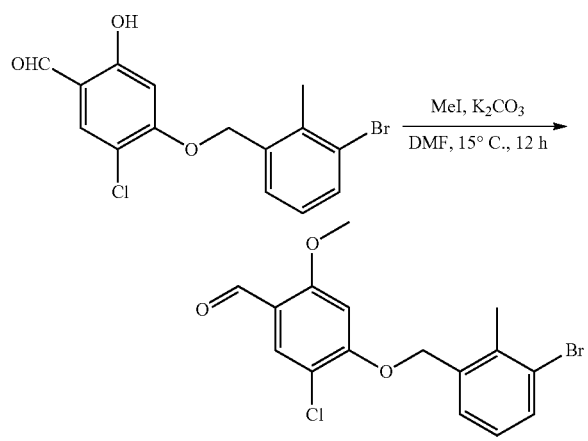

To a mixture of 4-[(3-bromo-2-methyl-phenyl)methoxy]-5-chloro-2-hydroxy-benzaldehyde (20 g, 56.24 mmol) and K$_2$CO$_3$ (23.32 g, 168.72 mmol) in DMF (200 mL) was added MeI (15.97 g, 112.48 mmol, 7.00 mL) at 0° C. The mixture was stirred at 15° C. for 12 h. The reaction mixture was cooled to 10° C., and to the mixture was added water (200 mL) with stirring (more solid precipitated). The suspension was filtered, and the solid was washed with water (3×100 mL) and petroleum ether (40 mL) to give 4-[(3-bromo-2-methyl-phenyl) methoxy]-5-chloro-2-methoxy-benzaldehyde (23.3 g) as a white solid. LCMS: m/z found 371.1 [M+H]$^+$; $^1$H NMR (400 MHz, DMSO-d$_6$) δ=10.16 (s, 1H), 7.68 (s, 1H), 7.65 (d, J=7.9 Hz, 1H), 7.56 (d, J=7.5 Hz, 1H), 7.22 (t, J=7.8 Hz, 1H), 7.11 (s, 1H), 5.43 (s, 2H), 4.00 (s, 3H), 2.42 (s, 3H).

(d) 5-chloro-2-methoxy-4-[[2-methyl-3-(4,4,5,5-tetramethyl-1,3,2-dioxaborolan-2-yl)phenyl]methoxy]benzaldehyde

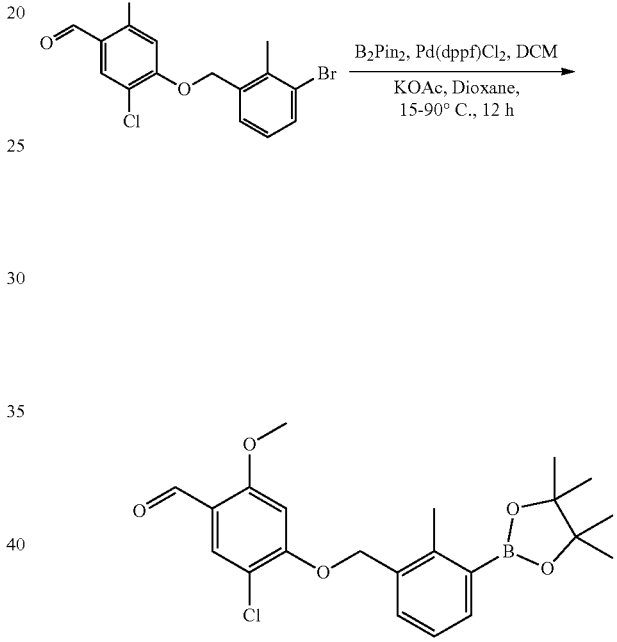

To a mixture of 4-[(3-bromo-2-methyl-phenyl)methoxy]-5-chloro-2-methoxy-benzaldehyde (7 g, 18.94 mmol) in dioxane (100 mL) was added 4,4,5,5-tetramethyl-2-(4,4,5,5-tetramethyl-1,3,2-dioxaborolan-2-yl)-1,3,2-dioxaborolane (7.69 g, 30.3 mmol), potassium acetate (5.58 g, 56.8 mmol), and Pd(dppf)Cl$_2$·CH$_2$Cl$_2$ (1.55 g, 1.89 mmol) at 15° C. The mixture was heated to 90° C. and stirred for 12 h. The mixture was poured into ice water (100 mL) and extracted with EtOAc (2×100 mL). The organic layer was washed with brine (100 mL), dried over Na$_2$SO$_4$, filtered, and evaporated. The residue was purified by flash silica gel chromatography (ISCO®; 80 g SEPAFLASH® Silica Flash Column, Eluent of 0-26% ethyl acetate:petroleum ether gradient @ 80 mL/min) to give 5-chloro-2-methoxy-4-[[2-methyl-3-(4,4,5,5-tetramethyl-1,3,2-dioxaborolan-2-yl)phenyl]methoxy]benzaldehyde (4.9 g, 9.29 mmol, 49.1% yield) as a yellow solid. LCMS: m/z found 417.3 [M+H]$^+$; $^1$H NMR (400 MHz, CDCl$_3$) δ=10.30-10.22 (m, 1H), 7.86 (s, 1H), 7.79 (dd, J=1.0, 7.4 Hz, 1H), 7.52 (d, J=6.8 Hz, 1H), 7.26-7.21 (m, 1H), 6.56 (s, 1H), 5.22 (s, 2H), 3.91 (s, 3H), 2.60 (s, 3H), 1.37 (s, 12H).

(e) 5-chloro-4-[[3-[3-[(2-chloro-4-formyl-5-methoxy-phenoxy)methyl]-2-methyl-phenyl]-2-methyl-phenyl]methoxy]-2-methoxy-benzaldehyde

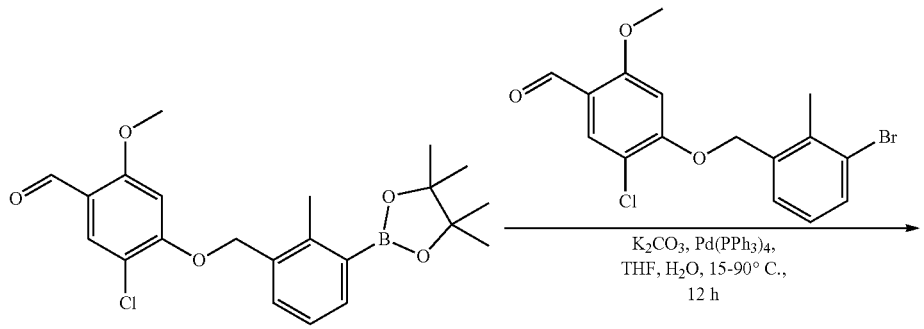

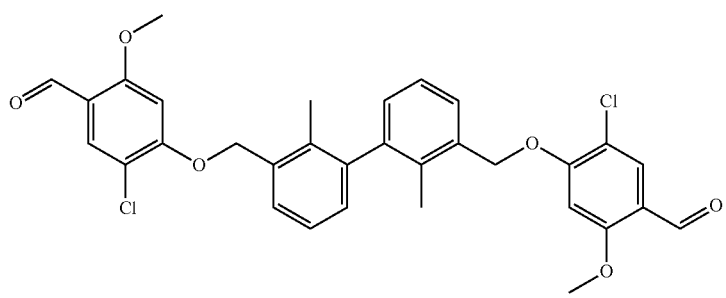

To a mixture of 5-chloro-2-methoxy-4-[[2-methyl-3-(4,4,5,5-tetramethyl-1,3,2-dioxaborolan-2-yl)phenyl]methoxy]benzaldehyde (2.5 g, 6.00 mmol) and 4-[(3-bromo-2-methyl-phenyl)methoxy]-5-chloro-2-methoxy-benzaldehyde (3.55 g, 9.60 mmol) in THF/water (30 mL/15 mL) was added $K_2CO_3$ (2.49 g, 18.0 mmol) and $Pd(PPh_3)_4$ (693.28 mg, 600 μmol) at 15° C. The mixture was heated to 90° C. and stirred for 12 h. The mixture was poured into ice water (100 mL) and extracted with EtOAc (4×100 mL) and THF (100 mL). The organic layer was washed with brine (200 mL), dried over $Na_2SO_4$, filtered, and evaporated. The residue was purified by flash silica gel chromatography (ISCO®; 40 g SEPAFLASH® Silica Flash Column, eluent of 0-50% ethyl acetate:petroleum ether gradient @75 mL/min) to give 5-chloro-4-[[3-[3-[(2-chloro-4-formyl-5-methoxy-phenoxy)methyl]-2-methyl-phenyl]-2-methyl-phenyl]methoxy]-2-methoxy-benzaldehyde (1 g, 1.21 mmol, 20.2% yield, 70% purity) as a light yellow solid. MS: m/z found 579.0 [M+H]$^+$; $^1$H NMR (400 MHz, DMSO-$d_6$) δ=10.16 (s, 2H), 7.68 (s, 2H), 7.65-7.52 (m, 6H), 7.45-7.39 (m, 2H), 7.38-7.27 (m, 4H), 7.15 (d, J=7.5 Hz, 2H), 7.13 (s, 2H), 5.49-5.41 (m, 4H), 4.00 (s, 6H), 2.03 (s, 6H).

(f) (2S)-1-[[4-[[3-[3-[[4-[[(2S)-2-carboxy-1-piperidyl]methyl]-2-chloro-5-methoxy-phenoxy]methyl]-2-methyl-phenyl]-2-methyl-phenyl]methoxy]-5-chloro-2-methoxy-phenyl]methyl]piperidine-2-carboxylic acid (2S)-1-[[5-chloro-4-[[3-[3-[[2-chloro-4-(hydroxymethyl)-5-methoxy-phenoxy]methyl]-2-methyl-phenyl]-2-methyl-phenyl]methoxy]-2-methoxy-phenyl]methyl]piperidine-2-carboxylic acid

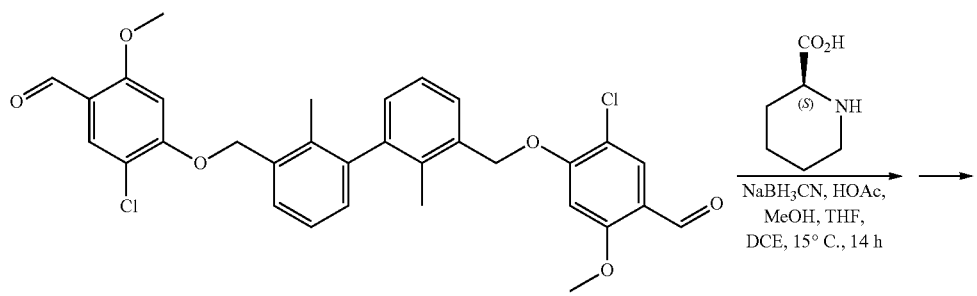

-continued

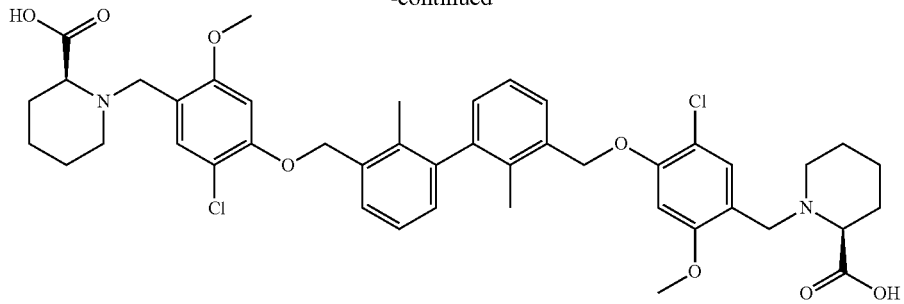

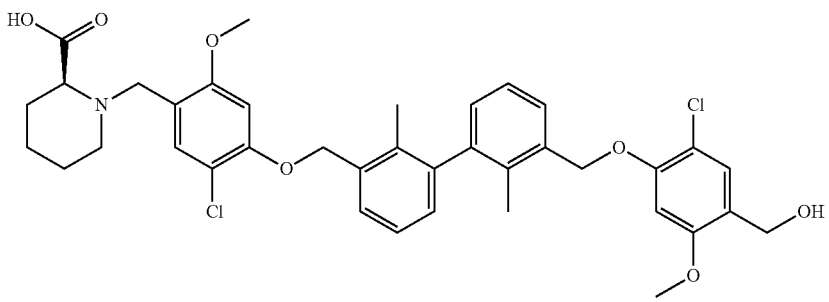

To a mixture of 5-chloro-4-[[3-[3-[(2-chloro-4-formyl-5-methoxy-phenoxy) methyl]-2-methyl-phenyl]-2-methyl-phenyl]methoxy]-2-methoxy-benzaldehyde (200 mg, 345 μmol) and (2S)-piperidine-2-carboxylic acid (356.62 mg, 2.76 mmol) in MeOH/DCE/THF (5 mL/5 mL/5 mL) was added AcOH (41.45 mg, 690 μmol, 39.48 μL) at 15° C. The mixture was stirred for 2 h. Then NaBH$_3$CN (108.45 mg, 1.73 mmol) was added to the mixture at 15° C. The mixture was stirred at 15° C. for 12 h and concentrated. The residue was purified by prep-HPLC (column: Nano-Micro Unisil 8-120 c18 Ultra Plus 250*50 mm; mobile phase: [water (10 mM NH$_4$HCO$_3$)-ACN]; B %: 20%-50%, 20 min) to give:

(2S)-1-[[4-[[3-[3-[[4-[[(2S)-2-carboxy-1-piperidyl] methyl]-2-chloro-5-methoxy-phenoxy]methyl]-2-methyl-phenyl]-2-methyl-phenyl]methoxy]-5-chloro-2-methoxy-phenyl]methyl]piperidine-2-carboxylic acid (29) (21.66 mg, 6.25 μmol, 7.6% yield) as a white solid. MS: m/z found 805.2 [M+H]$^+$; $^1$H NMR (400 MHz, DMSO-d$_6$) δ=7.54 (d, J=7.5 Hz, 2H), 7.41 (s, 2H), 7.31 (t, J=7.6 Hz, 2H), 7.12 (d, J=7.3 Hz, 2H), 6.95 (s, 2H), 5.34-5.26 (m, 4H), 3.83 (s, 6H), 3.77-3.72 (m, 4H), 3.12 (br s, 2H), 2.91 (br d, J=11.0 Hz, 2H), 2.37-2.26 (m, 2H), 2.02 (s, 6H), 1.81 (br s, 2H), 1.69 (br d, J=10.1 Hz, 2H), 1.50 (br s, 6H), 1.41-1.28 (m, 2H); $^1$H NMR (400 MHz, methanol-d$_4$) δ=7.55 (s, 2H), 7.52 (d, J=7.7 Hz, 2H), 7.29 (t, J=7.6 Hz, 2H), 7.13 (d, J=7.5 Hz, 2H), 6.93 (s, 2H), 5.32 (s, 4H), 4.41-4.35 (m, 2H), 4.31-4.23 (m, 2H), 3.93 (s, 6H), 3.50-3.41 (m, 2H), 2.93 (br t, J=10.9 Hz, 2H), 2.21 (br s, 2H), 2.07 (s, 6H), 1.89-1.61 (m, 8H), 1.52 (br d, J=10.4 Hz, 2H). SFC, Rt=1.48 min on OJ-3_MeOH, 100% ee; and (2S)-1-[[5-chloro-4-[[3-[3-[[2-chloro-4-(hydroxymethyl)-5-methoxy-phenoxy]methyl]-2-methyl-phenyl]-2-methyl-phenyl]methoxy]-2-methoxy-phenyl]methyl]piperidine-2-carboxylic acid (30) (29.43 mg, 41.7 μmol, 12.1% yield) as a white solid. MS: m/z found 694.0 [M+H]$^+$; $^1$H NMR (400 MHz, DMSO-d$_6$) δ=7.54 (dd, J=2.4, 7.3 Hz, 2H), 7.40 (s, 1H), 7.34-7.28 (m, 3H), 7.11 (d, J=7.5 Hz, 2H), 6.95 (d, J=9.0 Hz, 2H), 5.30 (d, J=5.1 Hz, 4H), 4.40 (s, 2H), 3.83 (d, J=1.3 Hz, 6H), 3.78-3.70 (m, 2H), 3.65 (br d, J=14.1 Hz, 2H), 3.12 (br d, J=3.5 Hz, 1H), 2.90 (br d, J=11.2 Hz, 1H), 2.03 (s, 6H), 1.88-1.78 (m, 1H), 1.76-1.62 (m, 1H), 1.50 (br s, 3H), 1.42-1.29 (m, 1H). $^1$H NMR (400 MHz, methanol-d$_4$) δ=7.55 (s, 1H), 7.53-7.48 (m, 2H), 7.32 (s, 1H), 7.28 (dt, J=5.0, 7.6 Hz, 2H), 7.12 (t, J=6.7 Hz, 2H), 6.93 (s, 1H), 6.80 (s, 1H), 5.33 (s, 2H), 5.26 (s, 2H), 4.53 (s, 2H), 4.42-4.36 (m, 1H), 4.31-4.24 (m, 1H), 3.93 (s, 3H), 3.85 (s, 3H), 3.50-3.42 (m, 1H), 2.98-2.88 (m, 1H), 2.23 (br d, J=11.7 Hz, 1H), 2.09 (s, 6H), 1.93-1.61 (m, 4H), 1.53 (br d, J=11.2 Hz, 1H). SFC, Rt=2.17 min on AS-3 MeOH, 93.52% ee.

Example 31: 2,2'-((((((2,2'-Dimethyl-[1,1'-biphenyl]-3,3'-diyl)bis(methylene))bis(oxy))bis (5-chloro-2-methoxy-4,1-phenylene))bis(methylene))bis (azanediyl))bis(ethan-1-ol)

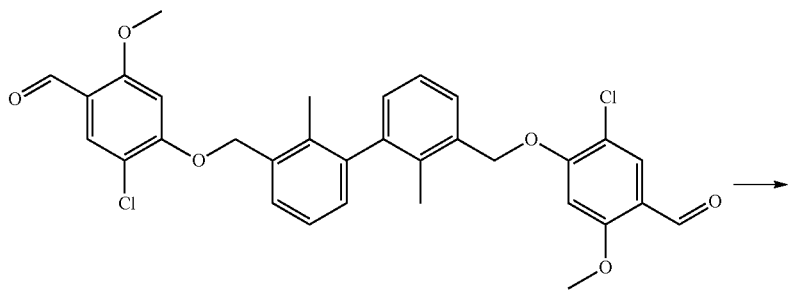

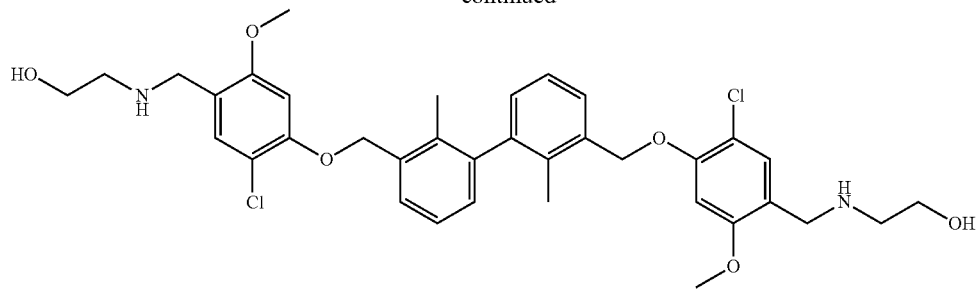

5-chloro-4-[[3-[3-[(2-chloro-4-formyl-5-methoxy-phenoxy)methyl]-2-methyl-phenyl]-2-methyl-phenyl]methoxy]-2-methoxy-benzaldehyde (50.00 mg, 0.09 mmol) and 2-aminoethanol (11.07 mg, 0.18 mmol) were dissolved in MeOH/THF (2 ml, 1:1), and the mixture was stirred at room temperature for 30 minutes. The reaction was then cooled to 0° C., and sodium cyanoborohydride (12.47 mg, 0.20 mmol) was added portionwise. The resulting mixture was warmed to room temperature and stirred overnight. The reaction was diluted with ethyl acetate (30 ml), and the organic solution was washed with water and brine. The organic phase was dried over sodium sulfate, then filtered and concentrated. Crude product mixture was purified by reverse phase HPLC to afford 2-[[5-chloro-4-[[3-[3-[[2-chloro-4-[(2-hydroxyethylamino) methyl]-5-methoxy-phenoxy]methyl]-2-methyl-phenyl]-2-methyl-phenyl]methoxy]-2-methoxy-phenyl] methylamino]ethanol (3.90 mg, 6.7%) as a clear film. MS obsd. (ESI$^+$) [(M+H)$^+$]: 669.4/671.4; $^1$H NMR (400 MHz, chloroform-d) δ 7.50 (dd, J=7.7, 1.4 Hz, 1H), 7.27 (d, J=5.1 Hz, 1H), 7.22 (d, J=5.4 Hz, 1H), 7.14 (dd, J=7.6, 1.4 Hz, 1H), 6.57 (s, 1H), 5.17 (s, 2H), 3.81 (d, J=6.8 Hz, 3H), 3.72 (s, 2H), 3.68-3.61 (m, 2H), 2.80-2.68 (m, 2H), 2.11-2.04 (m, 3H).

Example 32: 5-(Hydroxymethyl)-N-[3-[3-[[5-(hydroxymethyl)pyridine-2-carbonyl]amino]-2-methyl-phenyl]-2-methyl-phenyl]pyridine-2-carboxamide

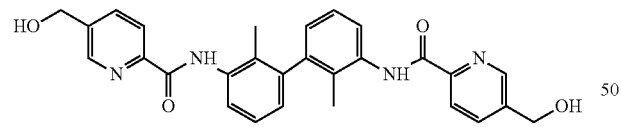

(a) 2-methyl-3-(4,4,5,5-tetramethyl-1,3,2-dioxaborolan-2-yl)aniline

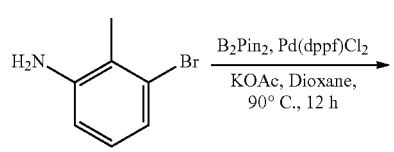

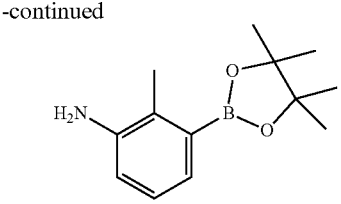

To a mixture of 3-bromo-2-methyl-aniline (10 g, 53.75 mmol) and 4,4,5,5-tetramethyl-2-(4,4,5,5-tetramethyl-1,3,2-dioxaborolan-2-yl)-1,3,2-dioxaborolane (27.30 g, 107.50 mmol) in dioxane (300 mL) were added KOAc (10.55 g, 107.50 mmol) and Pd(dppf)Cl$_2$ (3.93 g, 5.37 mmol) under N$_2$. The mixture was stirred at 90° C. for 12 h, and then concentrated. The residue was purified by flash silica gel chromatography (ISCO®; 120 g SEPAFLASH® Silica Flash Column, Eluent of 0-15% Ethyl acetate/Petroleum ether gradient @ 100 mL/min) to give 2-methyl-3-(4,4,5,5-tetramethyl-1,3,2-dioxaborolan-2-yl)aniline (8 g, 56.82% yield) as a yellow solid. LCMS: m/z found 234.2 [M+H]$^+$.

(b) 3-(3-amino-2-methyl-phenyl)-2-methyl-aniline

To a mixture of 2-methyl-3-(4,4,5,5-tetramethyl-1,3,2-dioxaborolan-2-yl)aniline (8.3 g, 35.60 mmol) and 3-bromo-2-methyl-aniline (7.95 g, 42.73 mmol) in THF (80 mL) and H$_2$O (40 mL) were added K$_2$CO$_3$ (9.84 g, 71.21 mmol) and Pd(PPh$_3$)$_4$ (2.06 g, 1.78 mmol) under N$_2$. The mixture was stirred at 80° C. for 12 h. The mixture was cooled to room temperature and extracted with EtOAc (100 mL×2). The combined EtOAc layers were washed with water (50 mL×2) and dried over anhydrous Na$_2$SO$_4$. The solvent was removed and the residue was purified by flash silica gel chromatography (ISCO®; 120 g SEPAFLASH® Silica Flash Column, Eluent of 0-22% Ethyl acetate/Petroleum ether gradient @ 100 mL/min) to give 3-(3-amino-2-methyl-phenyl)-2-methyl-aniline (4.5 g, 57.75% yield) as a yellow solid. LCMS: m/z found 213.2 [M+H]+.

(c) methyl 6-[[3-[3-[(5-methoxycarbonylpyridine-2-carbonyl)amino]-2-methyl-phenyl]-2-methyl-phenyl]carbamoyl]pyridine-3-carboxylate

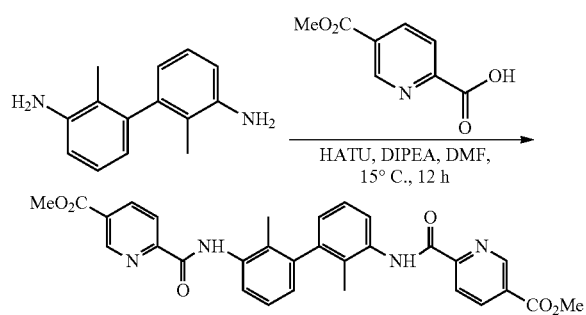

To a mixture of 3-(3-amino-2-methyl-phenyl)-2-methyl-aniline (4.5 g, 21.20 mmol) and 5-methoxycarbonylpyridine-2-carboxylic acid (15.36 g, 84.79 mmol) in DMF (200 mL) were added HATU (32.24 g, 84.79 mmol) and DIPEA (13.70 g, 105.99 mmol). The mixture was stirred at 15° C. for 12 h. The solid was collected by filtration and washed with water (50 mL) to yield methyl 6-[[3-[3-[(5-methoxycarbonylpyridine-2-carbonyl)amino]-2-methyl-phenyl]-2-methyl-phenyl]carbamoyl]pyridine-3-carboxylate (6.8 g, 51.82% yield) as a gray solid. LCMS: m/z found 539.0 [M+H]+. The product was used for next step without further purification.

(d) 5-(hydroxymethyl)-N-[3-[3-[[5-(hydroxymethyl)pyridine-2-carbonyl]amino]-2-methyl-phenyl]-2-methyl-phenyl] pyridine-2-carboxamide To a mixture of LiAlH4 (352.34 mg, 9.28 mmol) in THF (30 mL) was added dropwise a solution of methyl 6-[[3-[3-[(5-methoxycarbonylpyridine-2-carbonyl)amino]-2-methyl-phenyl]-2-methyl-phenyl]carbamoyl]pyridine-3-carboxylate (1 g, 1.86 mmol) in THF (30 mL) at −50° C. under N2. The mixture was stirred at 15° C. for 12 h. Then to the reaction mixture was added dropwise water (1 mL) at −50° C. The mixture was filtered, and the filtrate was extracted with EtOAc (20 mL×2). The combined EtOAc layers were washed with (10 mL×2) and dried over anhydrous Na2SO4. The solvent was removed to yield 5-(hydroxymethyl)-N-[3-[3-[[5-(hydroxymethyl)pyridine-2-carbonyl]amino]-2-methyl-phenyl]-2-methyl-phenyl]pyridine-2-carboxamide (0.4 g). 0.2 g of the product was further purified by prep-HPLC (column: YMC-Actus Triart C18 100*30 mm*5 μm; mobile phase: [water (10 mM NH4HCO3)-ACN]; B %: 35%-55%, 12 min) to yield 40 mg of analytically pure sample of 5-(hydroxymethyl)-N-[3-[3-[[5-(hydroxymethyl)pyridine-2-carbonyl]amino]-2-methyl-phenyl]-2-methyl-phenyl]pyridine-2-carboxamide as a white solid. MS: m/z found 483.1 [M+H]t 1H NMR (400 MHz, DMSO-d6): δ 10.33 (s, 2H), 8.67 (s, 2H), 8.17-8.15 (d, J=8 Hz, 2H), 8.01-7.99 (d, J=8 Hz, 2H), 7.90-7.88 (d, J=8 Hz, 2H), 7.35-7.31 (t, J=7.8 Hz, 2H), 7.00-6.99 (d, J=7.2 Hz, 2H), 5.51-5.49 (t, J=5.6 Hz, 2H), 4.67-4.66 (d, J=5.6 Hz, 4H), 2.03 (s, 6H).

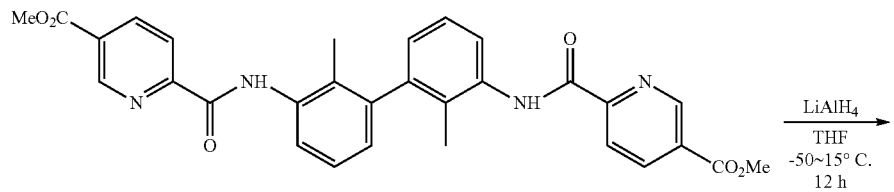

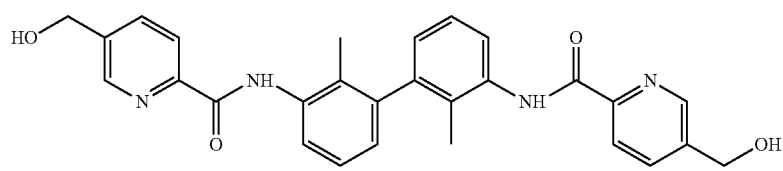

Example 33. 5-[(2-hydroxyethylamino)methyl]-N-[3-[3-[3-(4-hydroxy-1-piperidyl) propoxy]-2-methyl-phenyl]-2-methyl-phenyl]pyridine-2-carboxamide

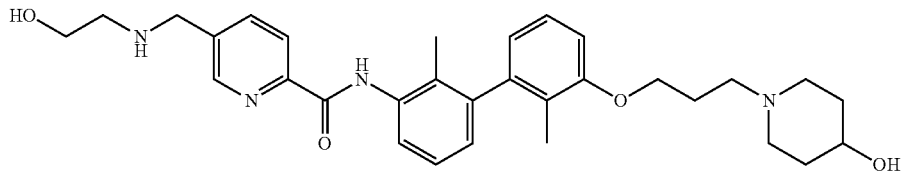

(a) methyl 6-[(3-bromo-2-methyl-phenyl)carbamoyl]pyridine-3-carboxylate

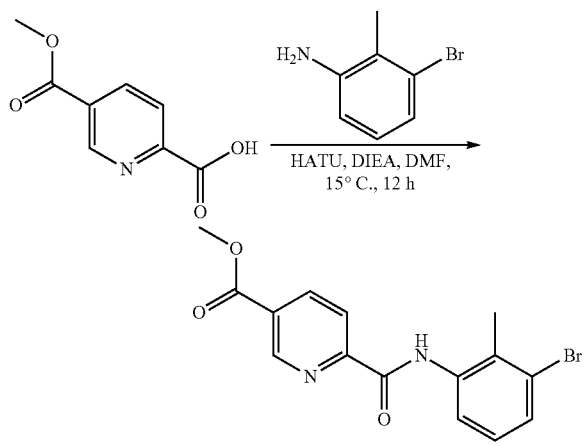

To a mixture of 5-methoxycarbonylpyridine-2-carboxylic acid (6 g, 33.12 mmol) and 3-bromo-2-methyl-aniline (6.16 g, 33.12 mmol) in DMF (60 mL) were added HATU (18.89 g, 49.68 mmol) and DIPEA (10.70 g, 82.81 mmol) under $N_2$. The mixture was stirred at 15° C. for 12 h, treated with $NaHCO_3$ (sat. 50 mL×2), and extracted with ethyl acetate (50 mL×2). The combined organic phase was dried with anhydrous $Na_2SO_4$, filtered, and concentrated. The residue was purified by flash silica gel chromatography (ISCO®; 120 g SEPAFLASH® Silica Flash Column, Eluent of 0-30% ethyl acetate/petroleum ether gradient @ 100 mL/min) to give methyl 6-[(3-bromo-2-methyl-phenyl)carbamoyl]pyridine-3-carboxylate (8.5 g, 49% yield) as a yellow solid. LCMS: m/z found 349.0, 351.0 [M+H]⁺.

(b) N-(3-bromo-2-methyl-phenyl)-5-(hydroxymethyl)pyridine-2-carboxamide

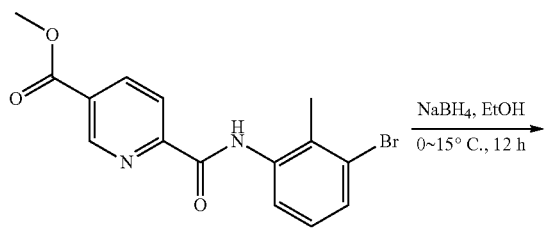

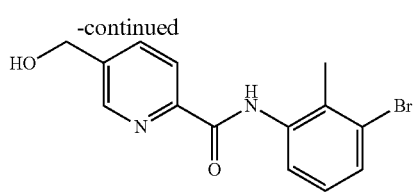

To a mixture of methyl 6-[(3-bromo-2-methyl-phenyl) carbamoyl] pyridine-3-carboxylate (3.9 g, 11.17 mmol) in EtOH (30 mL) was added $NaBH_4$ (845.05 mg, 22.34 mmol) at 0° C. under $N_2$. The mixture was stirred at 15° C. for 12 h. The mixture was concentrated, and the residue was purified by column chromatography (silica gel, petroleum ether/ethyl acetate=1:1 to ethyl acetate/methanol=1:1) to give N-(3-bromo-2-methyl-phenyl)-5-(hydroxymethyl)pyridine-2-carboxamide (2.4 g, 66% yield) as a yellow solid. LCMS: m/z found 321.1, 323.0 [M+H]⁺.

(c) N-(3-bromo-2-methyl-phenyl)-5-formyl-pyridine-2-carboxamide

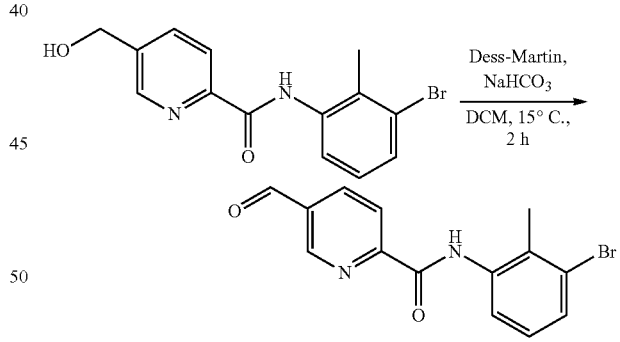

To a mixture of N-(3-bromo-2-methyl-phenyl)-5-(hydroxymethyl)pyridine-2-carboxamide (2.4 g, 7.47 mmol) in dichloromethane (60 mL) was added Dess-Martin reagent (3.80 g, 8.97 mmol) and $NaHCO_3$ (1.57 g, 18.68 mmol). The mixture was stirred at 15° C. for 2 h. The mixture was concentrated, and the residue was purified by flash silica gel chromatography (ISCO®; 20 g SEPAFLASH® Silica Flash Column, Eluent of 0-20% ethyl acetate/petroleum ether gradient @45 mL/min) to give N-(3-bromo-2-methyl-phenyl)-5-formyl-pyridine-2-carboxamide (1.1 g, 45% yield) as a yellow solid. LCMS: m/z found 319.0, 321.0 [M+H]⁺; ¹H NMR (400 MHz, DMSO-$d_6$): δ 10.67 (s, 1H), 10.22 (s, 1H), 9.21 (s, 1H), 8.50-8.48 (d, J=8 Hz, 1H), 8.33-8.30 (d, J=8

Hz, 1H), 7.59-7.57 (d, J=8 Hz, 1H), 7.53-7.52 (d, J=7.6 Hz, 1H), 7.21-7.14 (t, J=8 Hz, 1H), 2.32 (s, 3H).

(d) 1-[3-(3-bromo-2-methyl-phenoxy)propyl]piperidin-4-ol

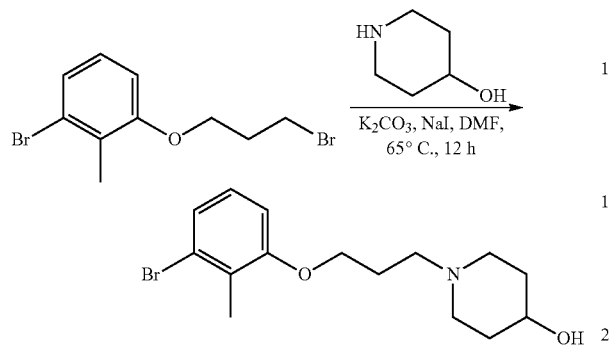

To a mixture of 1-bromo-3-(3-bromopropoxy)-2-methylbenzene (10 g, 32.47 mmol) and piperidin-4-ol (4.60 g, 45.45 mmol) in dimethylformamide (25 mL) was added K$_2$CO$_3$ (13.46 g, 97.40 mmol) and NaI (0.8 g, 5.34 mmol). The mixture was stirred at 65° C. for 12 h, and extracted with EtOAc (50 mL×2). The combined EtOAc layers were washed with water (50 mL×3) and dried over anhydrous Na$_2$SO$_4$. The solvent was removed to yield 1-[3-(3-bromo-2-methyl-phenoxy)propyl]piperidin-4-ol (10 g, 78.82% yield) as a yellow oil. LCMS: m/z found 328.2[M+H]$^+$. The product was used for next step without purification.

(e) 1-[3-[2-methyl-3-(4,4,5,5-tetramethyl-1,3,2-dioxaborolan-2-yl)phenoxy]propyl]piperidin-4-ol

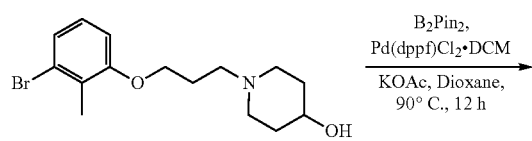

To a mixture of 1-[3-(3-bromo-2-methyl-phenoxy)propyl]piperidin-4-ol (9 g, 27.42 mmol) in dioxane (100 mL) were added 4,4,5,5-tetramethyl-2-(4,4,5,5-tetramethyl-1,3,2-dioxaborolan-2-yl)-1,3,2-dioxaborolane (13.93 g, 54.84 mmol), KOAc (5.38 g, 54.84 mmol) and Pd(dppf)Cl$_2$·CH$_2$Cl$_2$ (2.24 g, 2.74 mmol) under N$_2$. The mixture was stirred at 90° C. for 12 h. The mixture was combined with another batch of same scale. The combined mixture was filtered. The filtrate was concentrated, and the residue was purified by column chromatography (silica gel, Petroleum ether/Ethyl acetate=1/1 to Ethyl acetate/MeOH=5:1) to give a semi-purified product, which was further purified by prep-HPLC (column: Phenomenex luna(2) C18 250*50*10μ; mobile phase: [water (0.1% TFA)-ACN]; B %: 10%-40%, 20 min) to yield 1-[3-[2-methyl-3-(4,4,5,5-tetramethyl-1,3,2-dioxaborolan-2-yl)phenoxy]propyl]piperidin-4-ol (7.5 g) as a yellow oil. LCMS: m/z found 375.4 [M+H]$^+$.

(f) 5-formyl-N-[3-[3-[3-(4-hydroxy-1-piperidyl) propoxy]-2-methyl-phenyl]-2-methyl-phenyl]pyridine-2-carboxamide

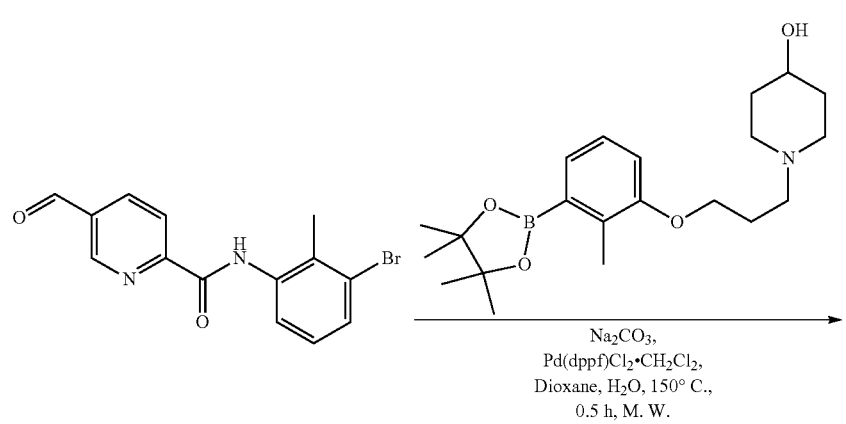

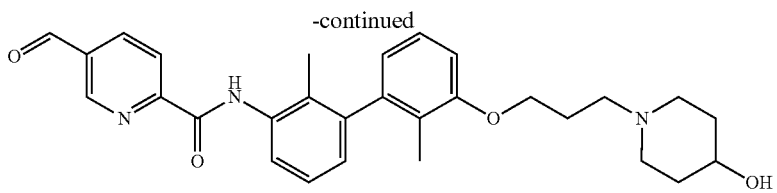

A mixture of N-(3-bromo-2-methyl-phenyl)-5-formyl-pyridine-2-carboxamide (400 mg, 1.25 mmol), 1-[3-[2-methyl-3-(4,4,5,5-tetramethyl-1,3,2-dioxaborolan-2-yl)phenoxy]propyl] piperidin-4-ol (282.23 mg, 751.99 umol), Na₂CO₃ (398.51 mg, 3.76 mmol) and Pd(dppf)Cl₂·CH₂Cl₂ (204.70 mg, 250.66 umol) in dioxane (9 mL) and H₂O (4 mL) was sealed into a microwave tube. The sealed tube was heated at 150° C. for 0.5 h under microwave. The mixture was combined with another batch at same scale. The combined mixture was concentrated. The residue was purified by column chromatography (Al₂O₃, ethyl acetate/methanol=1:0 to 10:1) to yield 5-formyl-N-[3-[3-[3-(4-hydroxy-1-piperidyl)propoxy]-2-methyl-phenyl]-2-methyl-phenyl] pyridine-2-carboxamide (250 mg) as a yellow solid. LCMS: m/z found 488.3 [M+H]⁺.

(g) 5-[(2-hydroxyethylamino)methyl]-N-[3-[3-[3-(4-hydroxy-1-piperidyl)propoxy]-2-methyl-phenyl]-2-methyl-phenyl]pyridine-2-carboxamide

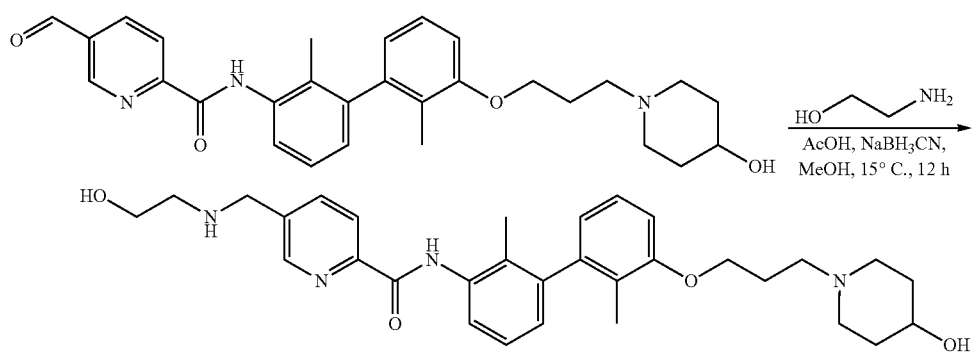

To a mixture of 5-formyl-N-[3-[3-[3-(4-hydroxy-1-piperidyl) propoxy]-2-methyl-phenyl]-2-methyl-phenyl]pyridine-2-carboxamide (180 mg, 369.16 umol) and 2-aminoethanol (67.65 mg, 1.11 mmol) in MeOH (2 mL) was added AcOH (11.08 mg, 184.58 μmol). The mixture was stirred at 15° C. for 2 h. To the mixture was added NaBH₃CN (69.59 mg, 1.11 mmol). The mixture was stirred at 15° C. for 10 h. The mixture was purified directly by prep-HPLC (column: Waters Xbridge 150*25 5μ; mobile phase: [water (10 mM NH₄HCO₃)-ACN]; B %: 20%-50%, 12 min) to give 5-[(2-hydroxyethylamino)methyl]-N-[3-[3-[3-(4-hydroxy-1-piperidyl)propoxy]-2-methyl-phenyl]-2-methyl-phenyl]pyridine-2-carboxamide (33.22 mg, 16% yield) as a yellow solid. LCMS: m/z found 533.1 [M+H]⁺; ¹H NMR (400 MHz, MeOD-d₄): δ 8.68 (s, 1H), 8.20-8.18 (d, J=8.4 Hz, 1H), 8.03-8.01 (m, 1H), 7.89-7.87 (d, J=7.2 Hz, 1H), 7.31-7.26 (t, J=8 Hz, 1H), 7.20-7.16 (t, J=8 Hz, 1H), 6.99-6.96 (d, J=7.6 Hz, 1H), 6.94-6.91 (d, J=8 Hz, 1H), 6.72-6.69 (d, J=7.6 Hz, 1H), 4.10-4.07 (m, 2H), 3.93 (s, 2H), 3.70-3.65 (m, 3H), 2.91-2.88 (m, 2H), 2.77-2.73 (t, J=5.6 Hz, 1H), 2.66-2.60 (m, 2H), 2.27-2.24 (m, 2H), 2.07-2.01 (m, 5H), 1.92-1.86 (m, 5H), 1.64-1.57 (m, 2H).

Example 34. 5-[(2-Hydroxyethylamino)methyl]-N-[3-[3-[[5-[(2-hydroxyethylamino)methyl]pyridine-2-carbonyl]amino]-2-methyl-phenyl]-2-methyl-phenyl] pyridine-2-carboxamide

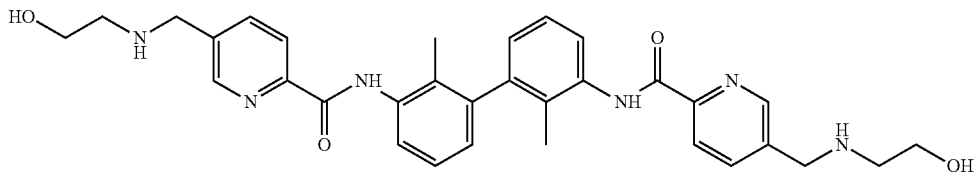

(a) 5-formyl-N-[3-[3-[(5-formylpyridine-2-carbonyl)amino]-2-methyl-phenyl]-2-methyl-phenyl]pyridine-2-carboxamide

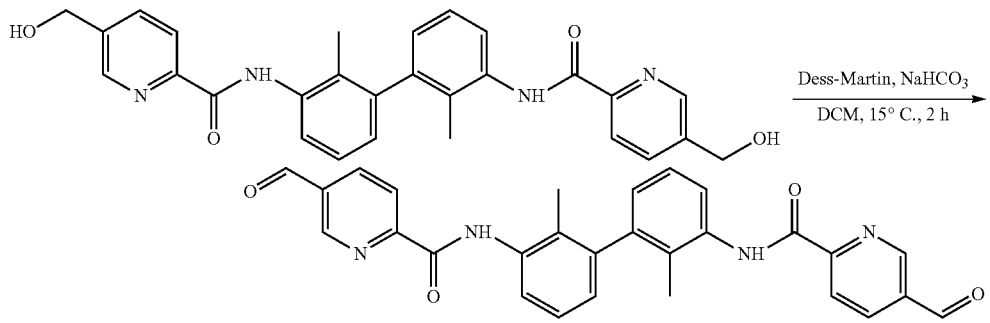

To a mixture of 5-(hydroxymethyl)-N-[3-[3-[[5-(hydroxymethyl)pyridine-2-carbonyl]amino]-2-methyl-phenyl]-2-methyl-phenyl]pyridine-2-carboxamide (2.25 g, 4.66 mmol) in dichloromethane (20 mL) was added Dess-Martin reagent (4.94 g, 11.66 mmol) and NaHCO₃ (1.96 g, 23.31 mmol) under $N_2$. The mixture was stirred at 15° C. for 2 h. The mixture was concentrated, and the residue was purified by flash silica gel chromatography (ISCO®; 25 g SEPA-FLASH® Silica Flash Column, eluent of 40-100% ethyl acetate/petroleum ether gradient @ 25 mL/min) to give 5-formyl-N-[3-[3-[(5-formylpyridine-2-carbonyl)amino]-2-methyl-phenyl]-2-methyl-phenyl]pyridine-2-carboxamide (0.8 g, 15% yield) as a yellow solid. LCMS: m/z found 479.2[M+H]⁺.

(b) 5-[(2-hydroxyethylamino)methyl]-N-[3-[3-[[5-[(2-hydroxyethylamino)methyl]pyridine-2-carbonyl]amino]-2-methyl-phenyl]-2-methyl-phenyl]pyridine-2-carboxamide

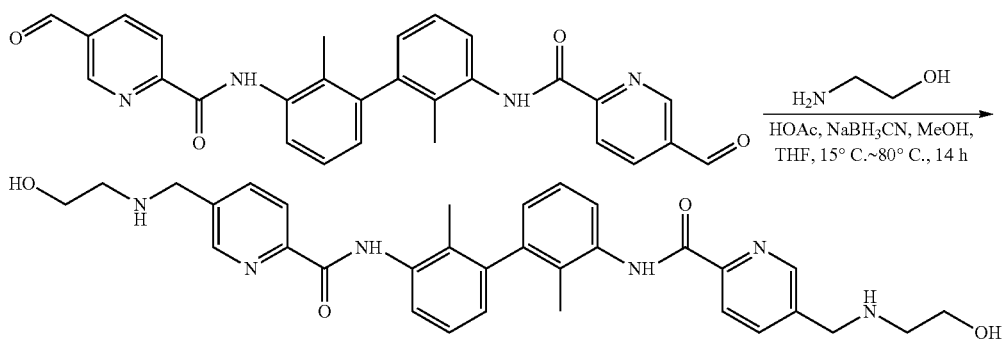

To a mixture of 5-formyl-N-[3-[3-[(5-formylpyridine-2-carbonyl)amino]-2-methyl-phenyl]-2-methyl-phenyl]pyridine-2-carboxamide (300 mg, 626.96 umol) and 2-aminoethanol (229.78 mg, 3.76 mmol) in THF/MeOH (3 mL/1 mL) was added HOAc (37.65 mg, 626.96 umol). The mixture was stirred at 80° C. for 2 h. The mixture was cooled to 15° C., and NaBH₃CN (236.40 mg, 3.76 mmol) was added. The resulting mixture was stirred at 15° C. for 12 h. The mixture was purified directly without work-up by prep-HPLC (column: Nano-Micro UniSil 5-100 C18 ULTRA 100*250 mm Sum; mobile phase: [water (0.05% HCl)-MeCN]; B %: 5%-35%, 11 min) to give 5-[(2-hydroxyethylamino)methyl]-N-[3-[3-[[5-[(2-hydroxyethylamino) methyl]pyridine-2-carbonyl]amino]-2-methyl-phenyl]-2-methyl-phenyl]pyridine-2-carboxamide hydrochloride salt (35.09 mg, 9% yield) as a yellow solid. MS: m/z found 569.2[M+H]⁺; ¹H NMR (400 MHz, DMSO-d₆): δ 10.38 (s, 2H), 9.45 (brs, 4H), 8.88 (s, 2H), 8.27-8.24 (m, 2H), 8.21-8.19 (d, J=8 Hz, 2H), 7.79-7.77 (d, J=7.6 Hz, 2H), 7.34-7.30 (t, J=7.8 Hz, 2H), 7.00-6.99 (d, J=7.2 Hz, 2H), 4.80 (brs, 7H), 4.34-4.31 (t, J=5.4 Hz, 4H), 3.71-3.68 (m, 4H), 3.00 (m, 4H), 2.00 (s, 6H). ¹H NMR (400 MHz, MeOD-d₄): δ 8.85 (s, 2H), 8.33-8.31 (d, J=8 Hz, 2H), 8.23-8.20 (dd, J=2 Hz, 2H), 7.87-7.85 (d, J=7.2 Hz, 2H), 7.36-7.32 (t, J=7.8 Hz, 2H), 7.08-7.06 (d, J=6.8 Hz, 2H), 4.44 (s, 4H), 3.87-3.84 (t, J=5.2 Hz, 4H), 3.25-3.22 (t, J=5.2 Hz, 4H), 2.09 (s, 6H).

Example 35. 2-[6-[[3-[3-[[5-(4-Carboxy-1,4,5,6-tetrahydropyrimidin-2-yl)pyridine-2-carbonyl]amino]-2-methyl-phenyl]-2-methyl-phenyl]carbamoyl]-3-pyridyl]-1,4,5,6-tetrahydropyrimidine-4-carboxylic acid

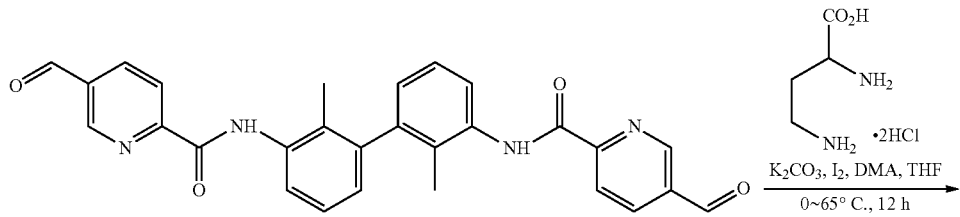

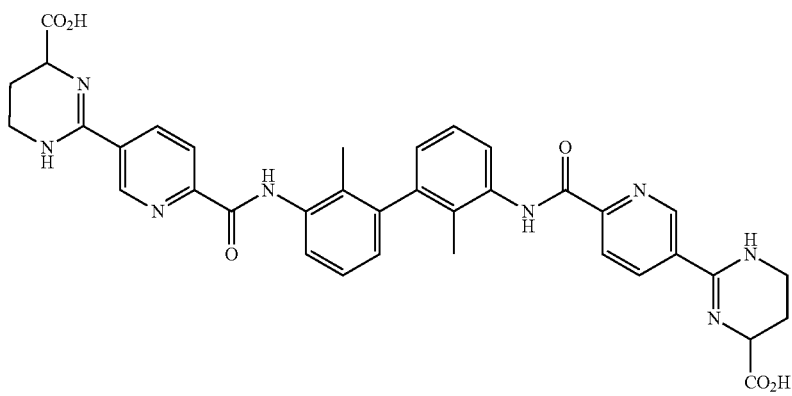

To a mixture of 5-formyl-N-[3-[3-[(5-formylpyridine-2-carbonyl)amino]-2-methyl-phenyl]-2-methyl-phenyl]pyridine-2-carboxamide (200 mg, 0.42 mmol) and 2,4-diaminobutanoic acid as dihydrochloride salt (319.43 mg, 1.67 mmol) in DMA/THF (2 mL/7 mL) was added $K_2CO_3$ (288.83 mg, 2.09 mmol) and $I_2$ (636.51 mg, 2.51 mmol) at 0° C. under $N_2$. The mixture was stirred at 65° C. for 12 h. The mixture was concentrated. The residue was purified directly with prep-HPLC (column: YMC-Actus Triart C18 100*30 mm*5 μm; mobile phase: [water (10 mM $NH_4HCO_3$)-MeCN]; B %: 5%-30%, 12 min) to yield 2-[6-[[3-[3-[[5-(4-carboxy-1,4,5,6-tetrahydropyrimidin-2-yl)pyridine-2-carbonyl]amino]-2-methyl-phenyl]-2-methyl-phenyl]carbamoyl]-3-pyridyl]-1,4,5,6-tetrahydropyrimidine-4-carboxylic acid (27.43 mg, 9% yield) as a yellow solid. MS: m/z found 675.2[M+H]$^+$; $^1$H NMR (400 MHz, DMSO-d$_6$): δ 10.51 (s, 2H), 9.01 (s, 2H), 8.40-8.34 (m, 4H), 7.74-7.72 (d, J=8 Hz, 2H), 7.37-7.32 (t, J=7.8 Hz, 2H), 7.05-7.03 (d, J=7.2 Hz, 2H), 4.09 (brs, 2H), 3.58-3.36 (m, 46H), 2.13 (m, 4H), 2.00 (s, 6H). $^1$H NMR (400 MHz, MeOD-d$_4$): δ 9.07 (s, 2H), 8.46-8.40 (m, 4H), 7.88-7.86 (d, J=7.6 Hz, 2H), 7.40-7.35 (t, J=7.8 Hz, 2H), 7.12-7.10 (d, J=6.8 Hz, 2H), 4.36-4.33 (m, 2H), 3.74-3.69 (m, 2H), 3.62-3.55 (m, 2H), 2.42-2.32 (m, 4H), 2.12 (s, 6H).

Example 36. 5-(((1,3-dihydroxypropan-2-yl)amino)methyl)-N-(3'-(5-(((2-hydroxyethyl)amino)methyl)picolinamido)-2,2'-dimethyl-[1,1'-biphenyl]-3-yl)picolinamide

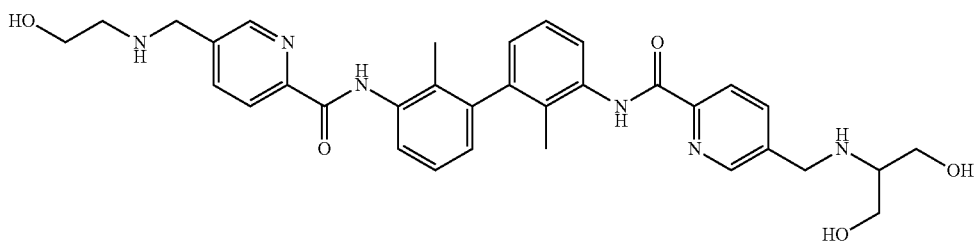

(a) N-(3-bromo-2-methylphenyl)-5-formylpicolinamide

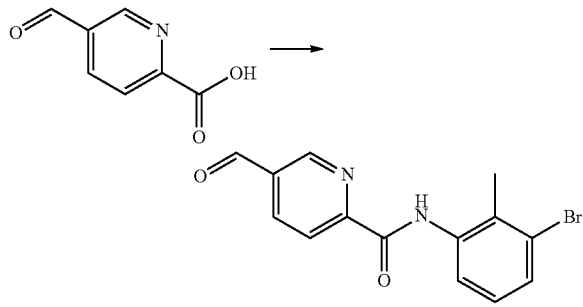

HATU (1225.48 mg, 3.22 mmol), 5-formylpyridine-2-carboxylic acid (421.37 mg, 2.79 mmol), and 1.5 equivalent of DIEA were dissolved in 5 ml DMF and the mixture was stirred at rt for 20 minutes. This solution was then added dropwise to a solution of 3-bromo-2-methyl-aniline (400.00 mg, 2.15 mmol) and 1.5 equivalent of DIEA in 10 ml DMF. The resulting mixture was stirred at rt overnight. The reaction was subsequently added dropwise to an ice water solution with vigorous stirring. The precipitate was filtered, washed with water, then dried to afford N-(3-bromo-2-methyl-phenyl)-5-formyl-pyridine-2-carboxamide (618.00 mg, 90.1%) as a light brown solid. MS obsd. (ESI$^+$) [(M+H)$^+$]: 320.2.

(b) N-(3-bromo-2-methylphenyl)-5-(((2-hydroxyethyl)-amino)-methyl)-picolinamide

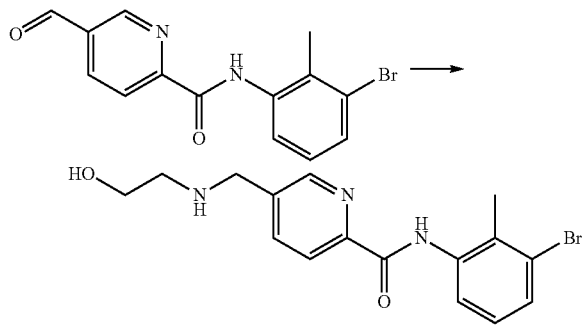

2-aminoethanol (114.83 mg, 1.88 mmol), acetic acid (73.38 mg, 1.22 mmol), and N-(3-bromo-2-methyl-phenyl)-5-formyl-pyridine-2-carboxamide (300.00 mg, 0.94 mmol) were dissolved in 6 ml MeOH/THF mix and the mixture was stirred at 70° C. for 2 hours. The reaction was then cooled to 0° C. and NaBH$_3$CN (88.60 mg, 1.41 mmol) was added portionwise. The resulting mixture was stirred at 70° C. overnight. The reaction was diluted with 20 ml EtOAc and the solution was washed with water and brine. The organic phase was dried over sodium sulfate, then filtered and concentrated to afford N-(3-bromo-2-methyl-phenyl)-5-[(2-hydroxyethylamino)-methyl]-pyridine-2-carboxamide (300.00 mg, 87.6%) as a yellow solid. Material was used as-is for the next step. MS obsd. (ESI$^+$) [(M+H)$^+$]: 365.2.

(c) tert-butyl ((6-((3-bromo-2-methylphenyl)-carbamoyl)-pyridin-3-yl)-methyl)-(2-hydroxyethyl)carbamate

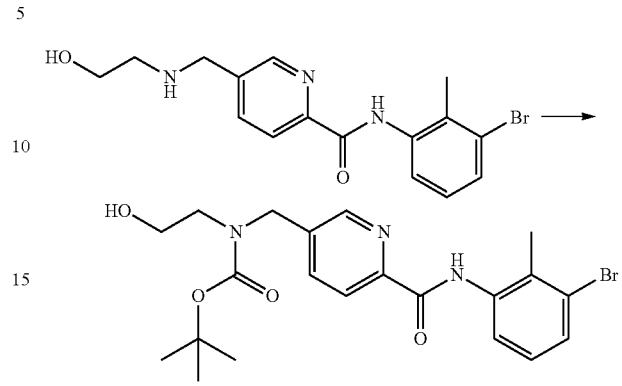

N-(3-bromo-2-methyl-phenyl)-5-[(2-hydroxyethyl-amino)-methyl]-pyridine-2-carboxamide (300.00 mg, 0.82 mmol) and DIEA (429.58 μL, 318.75 mg, 2.47 mmol) were dissolved in 7 ml DCM and tert-butoxycarbonyl tert-butyl carbonate (233.68 mg, 1.07 mmol) was added portionwise. The resulting mixture was stirred at rt for 3 hours. The reaction was subsequently diluted with DCM (30 ml) and the resulting organic solution was washed with saturated aqueous NaHCO$_3$ (20 ml×2), then brine (20 ml×2). The organic layer was dried under sodium sulfate, concentrated, and the crude mixture was purified by silica column, eluting with 10-90% EtOAc gradient in hexane to afford tert-butyl N-[[6-[(3-bromo-2-methyl-phenyl)-carbamoyl]-3-pyridyl]-methyl]-N-(2-hydroxyethyl)-carbamate (305.00 mg, 79.7%) as a white foam. MS obsd. (ESI$^+$) [(M+H)$^+$]: 465.4.

(d) tert-butyl ((6-((3'-amino-2,2'-dimethyl-[1,1'-biphenyl]-3-yl)carbamoyl)pyridin-3-yl)methyl)(2-hydroxyethyl)carbamate

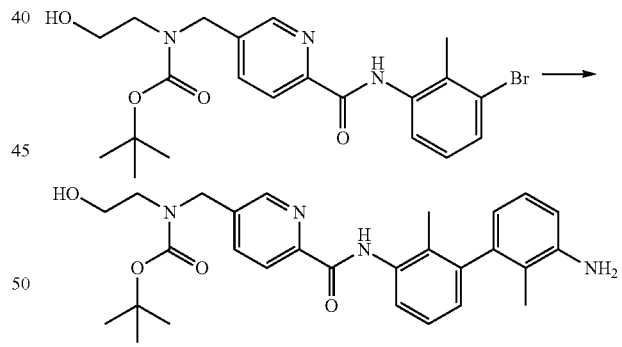

Potassium carbonate, (226.61 mg, 1.64 mmol), Pd(PPh$_3$)$_4$, (75.86 mg, 0.07 mmol), tert-butyl N-[[6-[(3-bromo-2-methyl-phenyl)carbamoyl]-3-pyridyl]methyl]-N-(2-hydroxyethyl) carbamate, (305.00 mg, 0.66 mmol), and 2-methyl-3-(4,4,5,5-tetramethyl-1,3,2-dioxaborolan-2-yl) aniline, (199.05 mg, 0.85 mmol) were suspended in 10 ml dioxane/water (4:1 mix) and the mixture was heated at 105° C. for 1 hour. The reaction was diluted with water and extracted with EtOAc (3×30 ml). The combined organic layers were washed with water, brine, then dried over sodium sulfate and concentrated. The crude product was purified by silica gel column, eluting with 10-90% EtOAc gradient in hexane to afford tert-butyl N-[[6-[[3-(3-amino-2-methyl-phenyl)-2-methyl-phenyl]-carbamoyl]-3-pyridyl]-methyl]-N-(2-hydroxyethyl)-carbamate (312.00 mg, 96.8%) as a yellow foam. MS obsd. (ESI$^+$) [(M+H)$^+$]: 491.6.

(e) tert-butyl ((6-((3'-(5-formylpicolinamido)-2,2'-dimethyl-[1,1'-biphenyl]-3-yl)carbamoyl)-pyridin-3-yl)methyl)(2-hydroxyethyl)carbamate

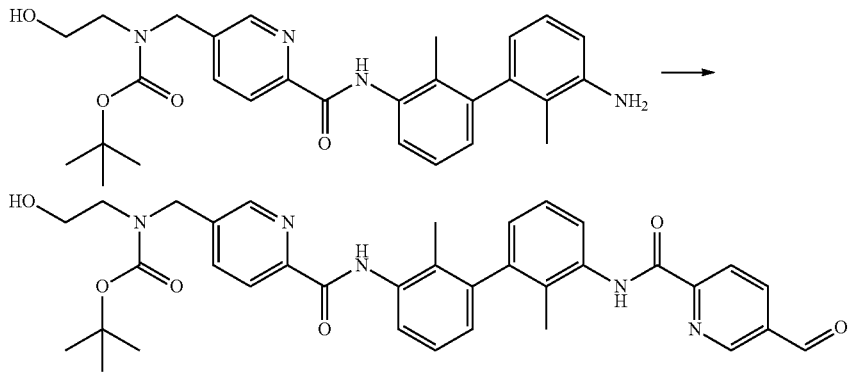

HATU (362.50 mg, 0.95 mmol), 5-formylpyridine-2-carboxylic acid (124.94 mg, 0.83 mmol), and 1.5 equivalent of DIEA were dissolved in 5 ml DMF and the mixture was stirred at rt for 20 minutes. This solution was then added dropwise to a solution of tert-butyl N-[[6-[[3-(3-amino-2-methyl-phenyl)-2-methyl-phenyl]-carbamoyl]-3-pyridyl]-methyl]-N-(2-hydroxyethyl)-carbamate (312.00 mg, 0.64 mmol) and 2 equivalents of DIEA in 10 ml DMF. The resulting mixture was stirred at rt overnight. The reaction was added dropwise to an ice water solution with vigorous stirring. The precipitates were filtered, washed with water, then dried to afford a crude solid, which was further purified by silica gel column, eluting with 10-100% EtOAc gradient in hexane to afford tert-butyl N-[[6-[[3-[3-[(5-formylpyridine-2-carbonyl)amino]-2-methyl-phenyl]-2-methyl-phenyl]carbamoyl]-3-pyridyl]methyl]-N-(2-hydroxyethyl)carbamate (339.00 mg, 76.9%) as a yellow foam. MS obsd. (ESI$^+$) [(M+H)$^+$]: 624.7.

(f) tert-butyl ((6-((3'-(5-(((1,3-dihydroxypropan-2-yl)amino)-methyl)picolinamido)-2,2'-dimethyl-[1,1'-biphenyl]-3-yl)carbamoyl)pyridin-3-yl)methyl)(2-hydroxyethyl)carbamate

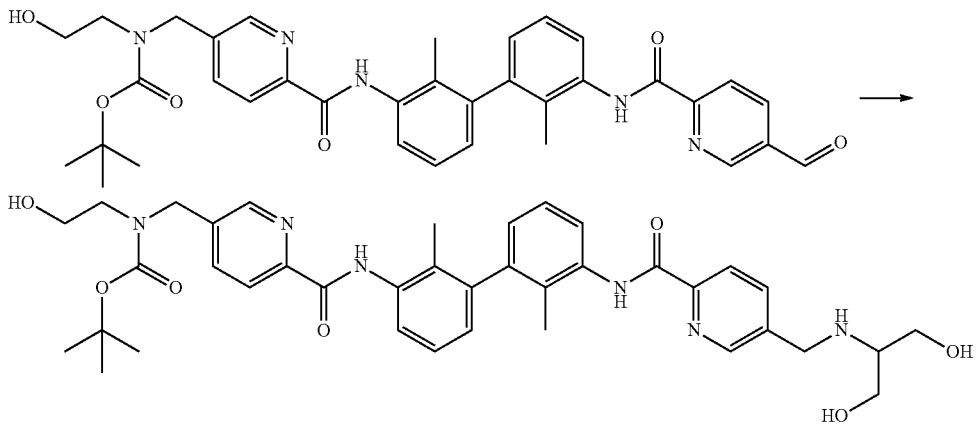

Tert-butyl N-[[6-[[3-[3-[(5-formylpyridine-2-carbonyl)amino]-2-methyl-phenyl]-2-methyl-phenyl]carbamoyl]-3-pyridyl]methyl]-N-(2-hydroxyethyl)carbamate (30.00 mg, 0.05 mmol), 2-aminopropane-1,3-diol (13.15 mg, 0.14 mmol), and acetic acid (3.76 mg, 0.06 mmol) were dissolved in 1 ml MeOH/THF (1:1) mix and the mixture was stirred at 70° C. for 2 hours. The reaction was cooled to 0° C. and NaBH$_3$CN (6.05 mg, 0.10 mmol) was added in one portion, then the resulting mixture was stirred at 70° C. overnight. The reaction was concentrated and crude product was purified by reverse phase HPLC. The product fractions were combined, basified with saturated NaHCO$_3$ solution, then extracted with EtOAc. The combined organic portions were dried over sodium sulfate, filtered and concentrated to afford tert-butyl N-(2-hydroxyethyl)-N-[[6-[[3-[3-[[5-[[[2-hydroxy-1-(hydroxymethyl)ethyl] amino]methyl]pyridine-2-carbonyl]amino]-2-methyl-phenyl]-2-methyl-phenyl]carbamoyl]-3-pyridyl]methyl]carbamate (22.60 mg, 67.2%) as a white foam. MS obsd. (ESI$^+$) [(M+H)$^+$]: 699.8.

(g) 5-(((1,3-dihydroxypropan-2-yl)amino)methyl)-N-(3'-(5-(((2-hydroxyethyl)amino)methyl)picolinamido)-2,2'-dimethyl-[1,1'-biphenyl]-3-yl)picolinamide

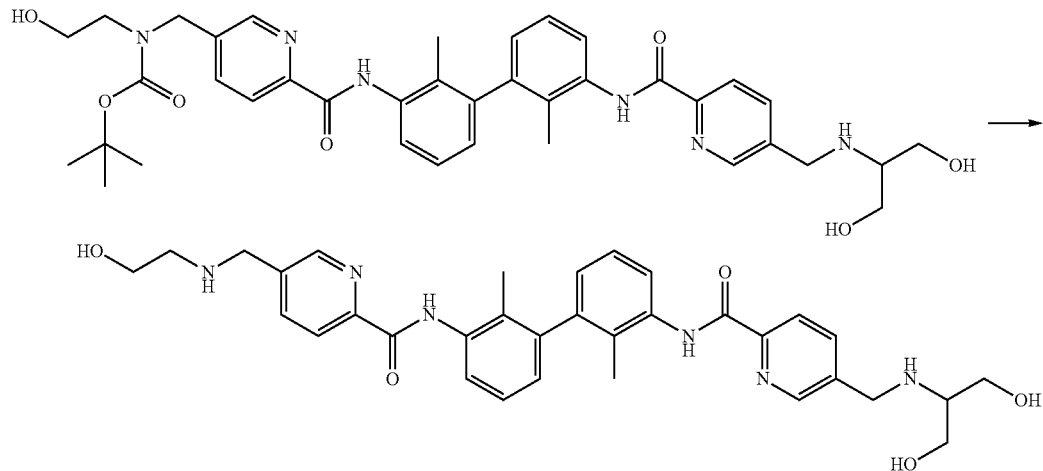

Tert-butyl N-(2-hydroxyethyl)-N-[[6-[[3-[3-[[5-[[[2-hydroxy-1-(hydroxymethyl)ethyl] amino]methyl]pyridine-2-carbonyl]amino]-2-methyl-phenyl]-2-methyl-phenyl] carbamoyl]-3-pyridyl]methyl]carbamate (21.00 mg, 0.03 mmol) was dissolved in 1 ml DCM and 4M hydrogen chloride solution in dioxane (75.13 μL, 10.96 mg, 0.30 mmol) was added dropwise. The resulting mixture was stirred at rt for 30 minutes. The precipitate was filtered, washed with DCM, then dried, to afford 5-[(2-hydroxyethylamino)methyl]-N-[3-[3-[[5-[[[2-hydroxy-1-(hydroxymethyl)ethyl]amino]methyl]pyridine-2-carbonyl]amino]-2-methyl-phenyl]-2-methyl-phenyl]pyridine-2-carboxamide (23.10 mg, 70.0%) as a white solid (HCl salt). MS obsd. (ESI⁺) [(M+H)⁺]: 599.7. ¹H NMR (400 MHz, Methanol-d₄) δ 8.87 (dd, J=4.3, 2.1 Hz, 2H), 8.32 (dd, J=8.1, 1.0 Hz, 2H), 8.28-8.21 (m, 2H), 7.87 (dt, J=8.2, 1.5 Hz, 2H), 7.34 (td, J=7.8, 1.7 Hz, 2H), 7.07 (dt, J=7.6, 1.6 Hz, 2H), 4.53 (s, 2H), 4.45 (s, 2H), 3.95-3.79 (m, 6H), 3.40 (p, J=5.5 Hz, 1H), 3.28-3.21 (m, 2H), 2.09 (d, J=1.8 Hz, 6H).

Example 37. (R)-5-(((2-hydroxyethyl)amino)methyl)-N-(3'-(5-((3-hydroxypyrrolidin-1-yl)methyl)picolinamido)-2,2'-dimethyl-[1,1'-biphenyl]-3-yl)picolinamide

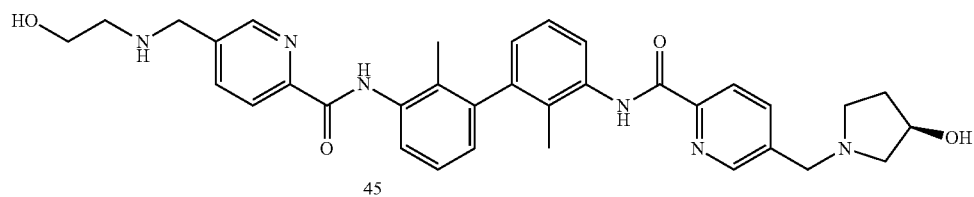

(a) tert-butyl (R)-(2-hydroxyethyl)((6-((3'-(5-((3-hydroxypyrrolidin-1-yl)methyl)picolinamido)-2,2'-dimethyl-[1,1'-biphenyl]-3-yl)carbamoyl)pyridin-3-yl)methyl)carbamate

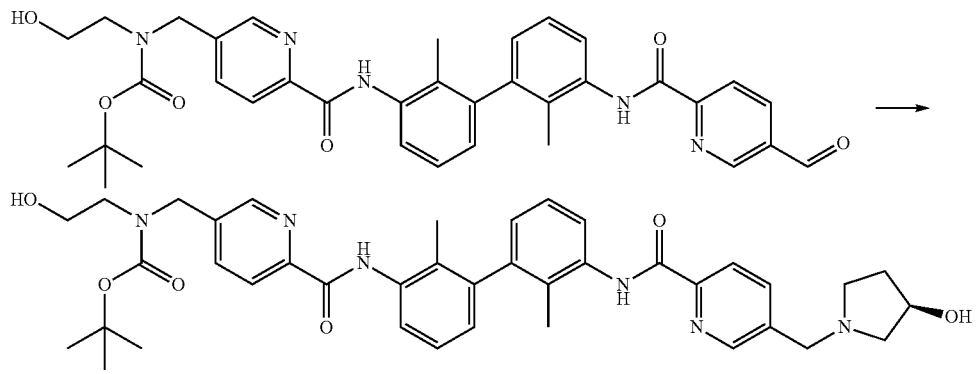

Tert-butyl N-[[6-[[3-[3-[(5-formylpyridine-2-carbonyl)amino]-2-methyl-phenyl]-2-methyl-phenyl]carbamoyl]-3-pyridyl]methyl]-N-(2-hydroxyethyl)carbamate (30.00 mg, 0.05 mmol), (3R)-pyrrolidin-3-ol (12.57 mg, 0.14 mmol), and acetic acid (3.76 mg, 0.06 mmol) were dissolved in 1 ml MeOH/THF (1:1) mix and the mixture was stirred at 70° C. for 2 hours. The reaction was cooled to 0° C. and NaBH$_3$CN (6.05 mg, 0.10 mmol) was added in one portion, then the resulting mixture was stirred at 70° C. overnight. The reaction was concentrated and crude product was purified by reverse phase HPLC. The product fractions were combined, basified with saturated NaHCO$_3$ solution, then extracted with EtOAc. The combined organic portions were dried over sodium sulfate, filtered and concentrated to afford tert-butyl N-(2-hydroxyethyl)-N-[[6-[[3-[3-[[5-[[(3R)-3-hydroxypyrrolidin-1-yl]methyl]pyridine-2-carbonyl]amino]-2-methyl-phenyl]-2-methyl-phenyl]carbamoyl]-3-pyridyl]methyl]carbamate (16.60 mg, 49.7%) as a clear oil. MS obsd. (ESI$^+$) [(M+H)$^+$]: 695.8.

(b) (R)-5-(((2-hydroxyethyl)amino)methyl)-N-(3'-(5-((3-hydroxypyrrolidin-1-yl)methyl)picolinamido)-2,2'-dimethyl-[1,1'-biphenyl]-3-yl)picolinamide

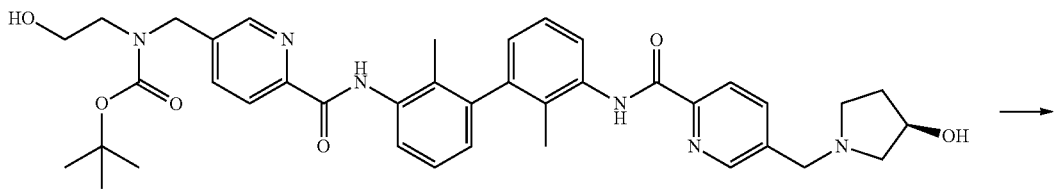

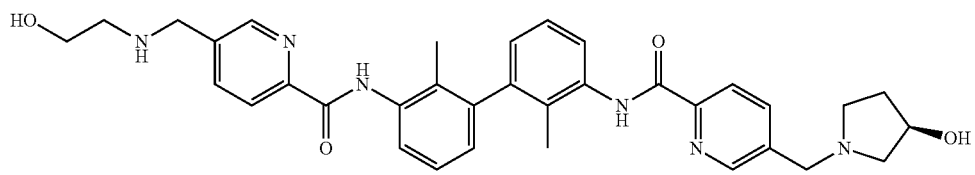

Tert-butyl N-(2-hydroxyethyl)-N-[[6-[[3-[3-[[5-[[(3R)-3-hydroxypyrrolidin-1-yl]methyl]pyridine-2-carbonyl]amino]-2-methyl-phenyl]-2-methyl-phenyl]carbamoyl]-3-pyridyl]methyl]carbamate (16.60 mg, 0.02 mmol) was dissolved in 1 ml DCM and 4M hydrogen chloride solution in dioxane (59.73 µL, 0.01 g, 0.24 mmol) was added dropwise. The resulting mixture was stirred at rt for 30 minutes. The precipitate was filtered, washed with DCM, then dried to afford 5-[(2-hydroxyethylamino)methyl]-N-[3-[3-[[5-[[(3R)-3-hydroxypyrrolidin-1-yl]methyl]pyridine-2-carbonyl]amino]-2-methyl-phenyl]-2-methyl-phenyl]pyridine-2-carboxamide (15.90 mg, 111.9%) as an off-white solid (HCl salt). MS obsd. (ESI$^+$) [(M+H)$^+$]: 595.7; $^1$H NMR (400 MHz, Methanol-d$_4$) δ 9.03-8.86 (m, 2H), 8.45-8.28 (m, 4H), 7.83 (d, J=8.7 Hz, 2H), 7.34 (t, J=7.7 Hz, 2H), 7.08 (d, J=7.7 Hz, 2H), 4.66 (dd, J=24.1, 7.9 Hz, 3H), 4.48 (s, 2H), 3.93-3.84 (m, 2H), 3.82-3.35 (m, 4H), 3.26 (t, J=5.4 Hz, 2H), 2.09 (s, 8H).

Example 38. 5-(((2-hydroxyethyl)-(methyl)amino)methyl)-N-(3'-(5-(((2-hydroxyethyl)amino)methyl)picolinamido)-2,2'-dimethyl-[1,1'-biphenyl]-3-yl)picolinamide

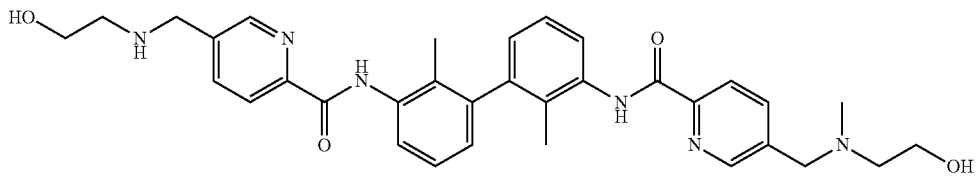

(a) tert-butyl (2-hydroxyethyl)-((6-((3'-(5-(((2-hydroxyethyl)(methyl)amino)methyl) picolinamido)-2,2'-dimethyl-[1,1'-biphenyl]-3-yl)carbamoyl)pyridin-3-yl)methyl) carbamate

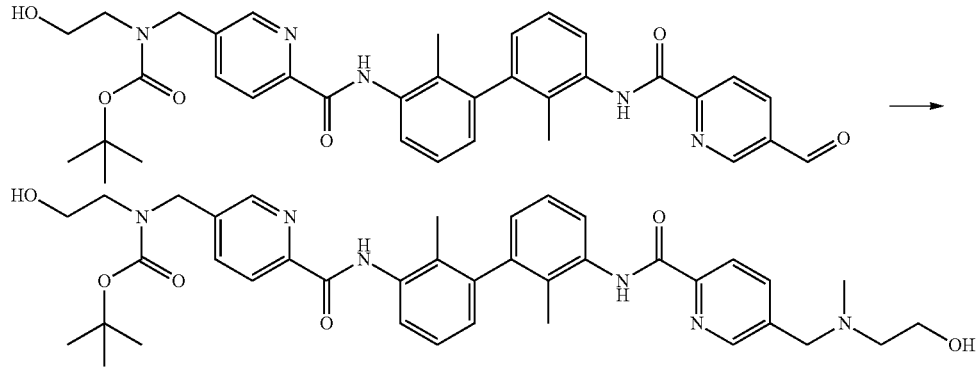

Tert-butyl N-[[6-[[3-[3-[(5-formylpyridine-2-carbonyl)amino]-2-methyl-phenyl]-2-methyl-phenyl]carbamoyl]-3-pyridyl]methyl]-N-(2-hydroxyethyl)carbamate (30.00 mg, 0.05 mmol), 2-(methylamino)ethanol (10.84 mg, 0.14 mmol), and acetic acid (3.76 mg, 0.06 mmol) were dissolved in 1 ml MeOH/THF (1:1) mix and the mixture was stirred at 70° C. for 2 hours. The reaction was cooled to 0° C. and NaBH₃CN (6.05 mg, 0.10 mmol) was added in one portion, then the resulting mixture was stirred at 70° C. overnight. The reaction was concentrated and the crude product was purified by reverse phase HPLC. The product fractions were combined, basified with saturated NaHCO₃ solution, then extracted with EtOAc. The combined organic portions were dried over sodium sulfate, filtered and concentrated to afford tert-butyl N-(2-hydroxyethyl)-N-[[6-[[3-[3-[[5-[[2-hydroxyethyl(methyl)amino]methyl]pyridine-2-carbonyl]amino]-2-methyl-phenyl]-2-methyl-phenyl]carbamoyl]-3-pyridyl]methyl]carbamate (29.00 mg, 88.3%) as a white foam. MS obsd. (ESI⁺) [(M+H)⁺]: 683.8.

(b) 5-(((2-hydroxyethyl)-(methyl)amino)methyl)-N-(3'-(5-(((2-hydroxyethyl)amino)methyl)picolinamido)-2,2'-dimethyl-[1,1'-biphenyl]-3-yl)picolinamide

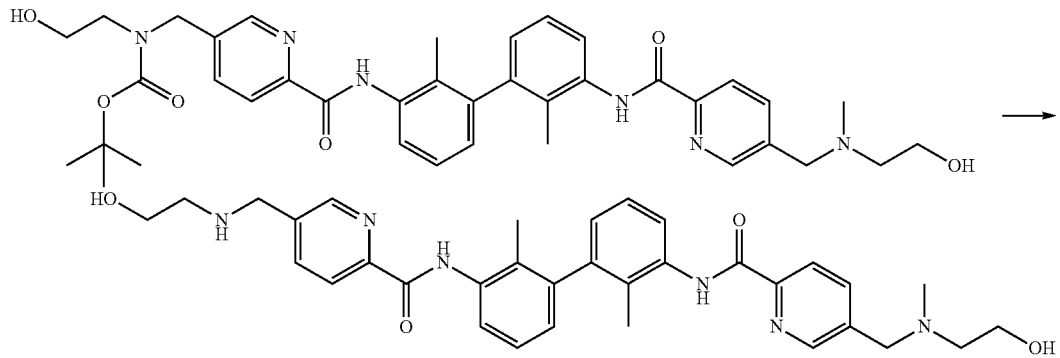

Tert-butyl N-(2-hydroxyethyl)-N-[[6-[[3-[3-[[5-[[2-hydroxyethyl(methyl)amino]methyl] pyridine-2-carbonyl]amino]-2-methyl-phenyl]-2-methyl-phenyl]carbamoyl]-3-pyridyl]methyl] carbamate (29.00 mg, 0.04 mmol) was dissolved in 1 ml DCM and 4M hydrogen chloride solution in dioxane (106.18 μL, 15.49 mg, 0.42 mmol) was added dropwise. The resulting mixture was stirred at rt for 30 minutes. The precipitate was filtered, washed with DCM, then dried to afford 5-[(2-hydroxyethylamino)-methyl]-N-[3-[3-[[5-[[2-hydroxyethyl(methyl)amino]-methyl]-pyridine-2-carbonyl]-amino]-2-methyl-phenyl]-2-methyl-phenyl]-pyridine-2-carboxamide (24.20 mg, 97.8%) as an off-white solid (HCl salt). MS obsd. (ESI⁺) [(M+H)⁺]: 583.7. ¹H NMR (400 MHz, Methanol-d₄) δ 8.96 (s, 2H), 8.43-8.38 (m, 4H), 7.81 (t, J=8.3 Hz, 2H), 7.34 (t, J=7.8 Hz, 2H), 7.08 (dt, J=7.7, 1.4 Hz, 2H), 4.74 (d, J=13.0 Hz, 1H), 4.53 (d, J=30.5 Hz, 3H), 3.95 (t, J=4.8 Hz, 2H), 3.91-3.82 (m, 2H), 3.41 (d, J=12.2 Hz, 1H), 3.34 (s, 1H), 3.29-3.24 (m, 2H), 2.95 (s, 3H), 2.08 (s, 6H).

Examples 39-66 can be prepared according to the synthetic routes described elsewhere herein and/or methods known to those skilled in the art in view of the teachings provided elsewhere herein.

Example 67. HTRF Assay

PD-L1 His protein was prepared and added at the final concentration of 6 nM in the White opaque 384 well plate (Corning cat #3824BC). PD-L1 small molecule inhibitors were diluted by 3-fold starting from 20 μM and a final concentration of 0.001 μM and added to the well. PD-1 Fc protein was added at the final concentration of 6 nM. PD-L1 His protein, PD-L1 small molecule inhibitors, and PD1 Fc proteins were added to the well in this order, with each 5 μl volume, and were incubated for 15 minutes at room temperature. PAb anti-Human IgG-XL665 (Cisbio, cat #61HFCXLA) and Mab anti-6HIS Tb cryptate Gold (Cisbio, cat #61HI2TLA) were mixed at 6.7 nM and 0.35 nM respectively, and total 5 μl volume of mixture was added to the well and incubated at room temperature for 1 hour. The plate was read using PerkinElmer Envision plate reader and data was analyzed by Prism 6 software. Results are illustrated in Table 1

TABLE 1

| Ex. No. | COMPOUND | PD-L1 HTRF IC$_{50}$ (μM) |
|---|---|---|
| 1 | 3-((2-(4,5-dihydro-1H-imidazol-2-yl)-5-((2-methyl-[1,1'-biphenyl]-3-yl)methoxy)phenoxy)methyl)benzonitrile | 0.28 |
| 2 | 3-((2-(1H-imidazol-2-yl)-5-((2-methyl-[1,1'-biphenyl]-3-yl)methoxy)phenoxy)methyl)benzonitrile | 20 |
| 3 | | 0.32 |

TABLE 1-continued

| Ex. No. | COMPOUND | PD-L1 HTRF IC$_{50}$ (μM) |
|---|---|---|
| | 3-((2-(1-methyl-4,5-dihydro-1H-imidazol-2-yl)-5-((2-methyl-[1,1'-biphenyl]-3-yl)methoxy)phenoxy)methyl)benzonitrile | |
| 4 | 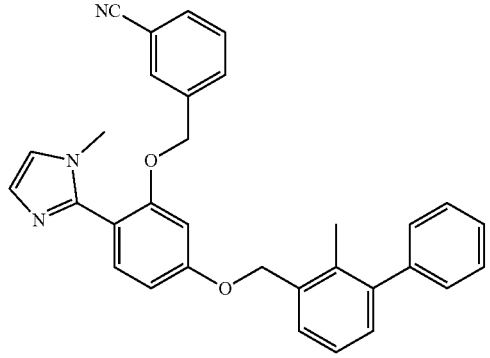 3-((2-(1-methyl-1H-imidazol-2-yl)-5-((2-methyl-[1,1'-biphenyl]-3-yl)methoxy)phenoxy)methyl)benzonitrile | 5.4 |
| 5 | 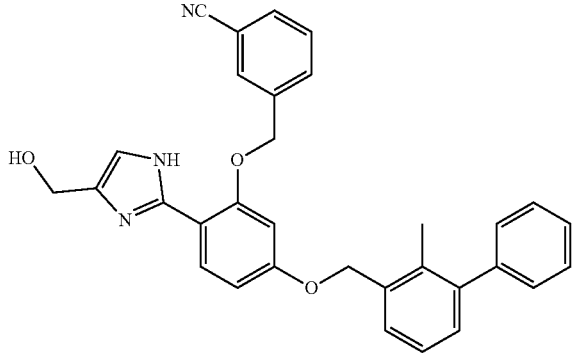 3-((2-(4-(hydroxymethyl)-1H-imidazol-2-yl)-5-((2-methyl-[1,1'-biphenyl]-3-yl)methoxy)phenoxy)methyl)benzonitrile | 16 |
| 6 | 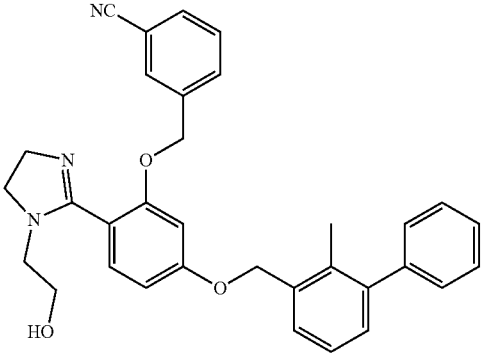 3-((2-(1-(2-hydroxyethyl)-4,5-dihydro-1H-imidazol-2-yl)-5-((2-methyl-[1,1'-biphenyl]-3-yl)methoxy)phenoxy)methyl)benzonitrile | 0.053 |

TABLE 1-continued
| Ex. No. | COMPOUND | PD-L1 HTRF IC$_{50}$ (μM) |
|---|---|---|
| 7 | 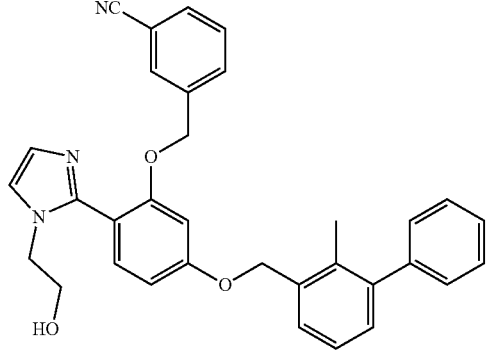 3-((2-(1-(2-hydroxyethyl)-1H-imidazol-2-yl)-5-((2-methyl-[1,1'-biphenyl]-3-yl)methoxy)phenoxy)methyl)benzonitrile | 1.8 |
| 8 | 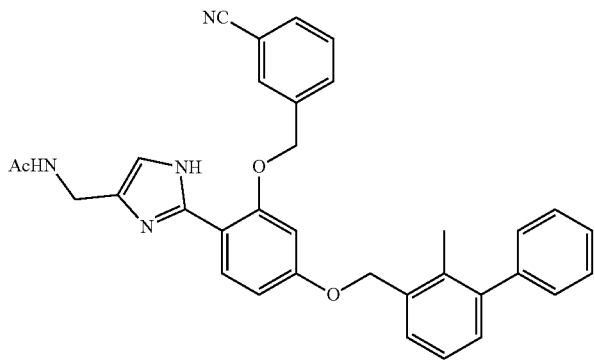 N-((2-(2-((3-cyanobenzyl)oxy)-4-((2-methyl-[1,1'-biphenyl]-3-yl)methoxy)phenyl)-1H-imidazol-4-yl)methyl)acetamide | 19 |
| 9 | 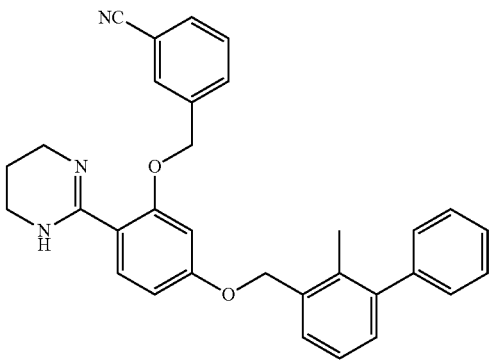 3-((5-((2-methyl-[1,1'-biphenyl]-3-yl)methoxy)-2-(1,4,5,6-tetrahydropyrimidin-2-yl)phenoxy)methyl)benzonitrile | 0.15 |

TABLE 1-continued
| Ex. No. | COMPOUND | PD-L1 HTRF IC$_{50}$ (μM) |
|---|---|---|
| 10 | 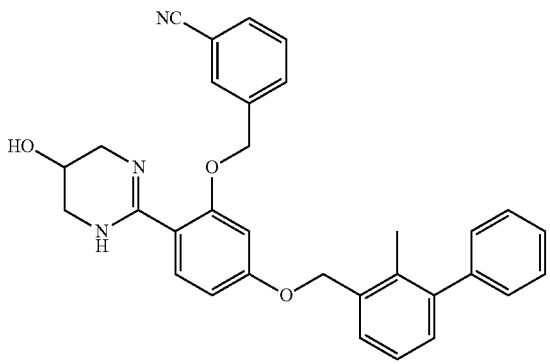 3-((2-(5-hydroxy-1,4,5,6-tetrahydropyrimidin-2-yl)-5-((2-methyl-[1,1'-biphenyl]-3-yl)methoxy)phenoxy)methyl)benzonitrile | 0.10 |
| 11 | 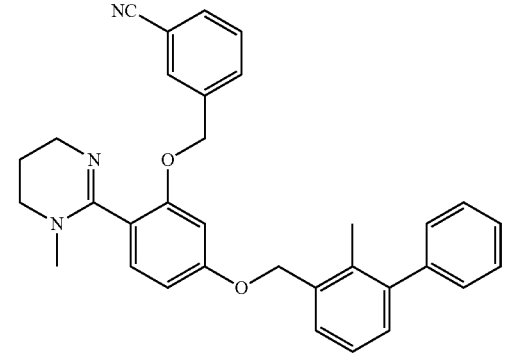 3-((2-(1-methyl-1,4,5,6-tetrahydropyrimidin-2-yl)-5-((2-methyl-[1,1'-biphenyl]-3-yl)methoxy)phenoxy)methyl)benzonitrile | 0.30 |
| 12 | 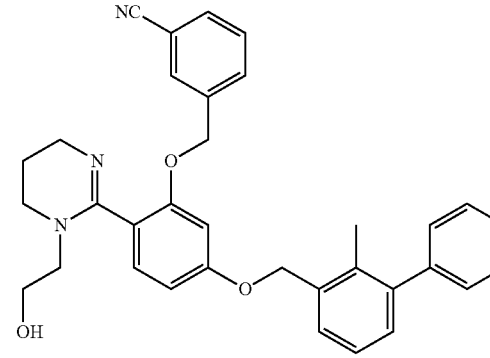 3-((2-(1-(2-hydroxyethyl)-1,4,5,6-tetrahydropyrimidin-2-yl)-5-((2-methyl-[1,1'-biphenyl]-3-yl)methoxy)phenoxy)methyl)benzonitrile | 0.11 |

TABLE 1-continued
| Ex. No. | COMPOUND | PD-L1 HTRF IC$_{50}$ (μM) |
|---|---|---|
| 13 | 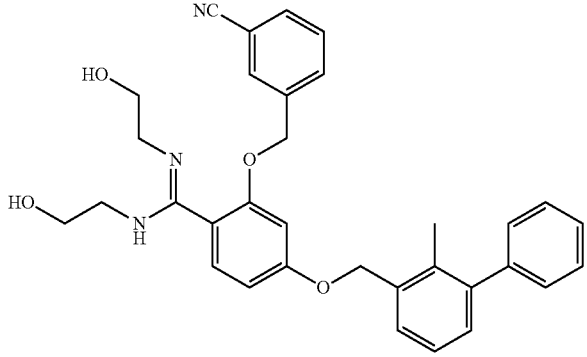 2-((3-cyanobenzyl)oxy)-N,N'-bis(2-hydroxyethyl)-4-((2-methyl-[1,1'-biphenyl]-3-yl)methoxy)benzimidamide | 0.17 |
| 14 | 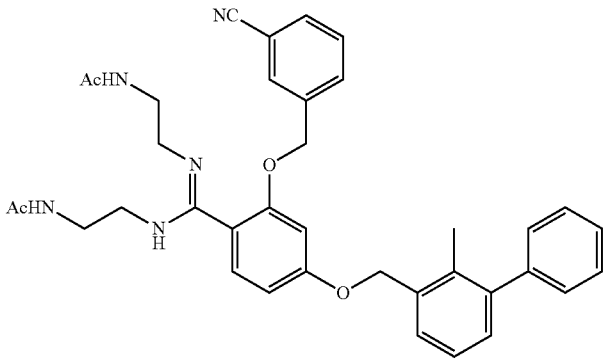 N-(2-(N'-(2-acetamidoethyl)-2-((3-cyanobenzyl)oxy)-4-((2-methyl-[1,1'-biphenyl]-3-yl)methoxy)benzimidamido)ethyl)acetamide | 0.33 |
| 15 | 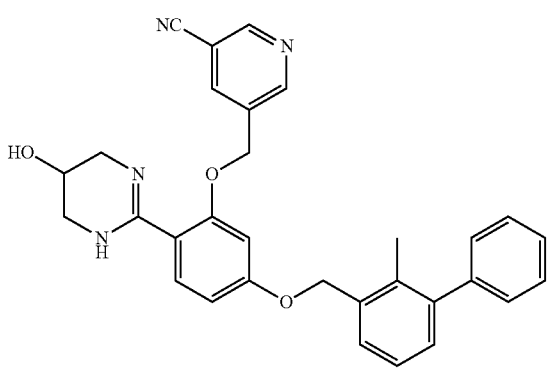 5-((2-(5-hydroxy-1,4,5,6-tetrahydropyrimidin-2-yl)-5-((2-methyl-[1,1'-biphenyl]-3-yl)methoxy)phenoxy)methyl)nicotinonitrile | 0.015 |

TABLE 1-continued

| Ex. No. | COMPOUND | PD-L1 HTRF IC$_{50}$ (μM) |
|---|---|---|
| 16 | 5-((4-chloro-2-(5-hydroxy-1,4,5,6-tetrahydropyrimidin-2-yl)-5-((3'-(3-(4-hydroxypiperidin-1-yl)propoxy)-2,2'-dimethyl-[1,1'-biphenyl]-3-yl)methoxy)phenoxy)methyl)nicotinonitrile | 0.0012 |
| 17 | 5-((4-chloro-2-(1-(2-hydroxyethyl)-1,4,5,6-tetrahydropyrimidin-2-yl)-5-((3'-(3-(4-hydroxypiperidin-1-yl)propoxy)-2,2'-dimethyl-[1,1'-biphenyl]-3-yl)methoxy)phenoxy)methyl)nicotinonitrile | 0.0015 |
| 18 | 2-(5-chloro-2-((5-cyanopyridin-3-yl)methoxy)-4-((3'-(3-(4-hydroxypiperidin-1-yl)propoxy)-2,2'-dimethyl-[1,1'-biphenyl]-3-yl)methoxy)phenyl)-1,4,5,6-tetrahydropyrimidine-4-carboxylic acid | 0.0012 |

TABLE 1-continued

| Ex. No. | COMPOUND | PD-L1 HTRF IC$_{50}$ (μM) |
|---|---|---|
| 19 | 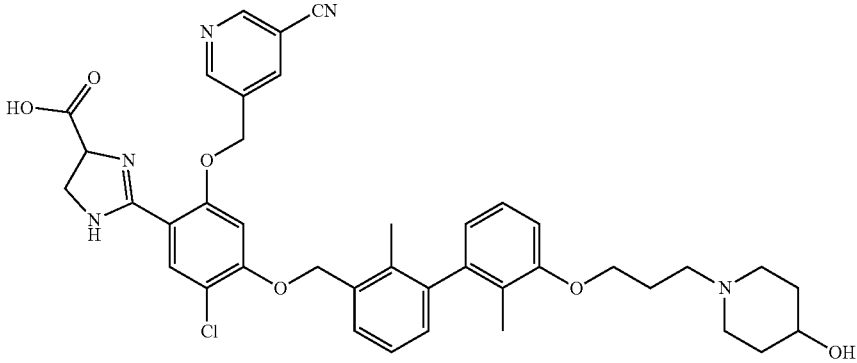<br>2-(5-chloro-2-((5-cyanopyridin-3-yl)methoxy)-4-((3'-(3-(4-hydroxypiperidin-1-yl)propoxy)-2,2'-dimethyl-[1,1'-biphenyl]-3-yl)methoxy)phenyl)-4,5-dihydro-1H-imidazole-4-carboxylic acid | 0.0012 |
| 20 | 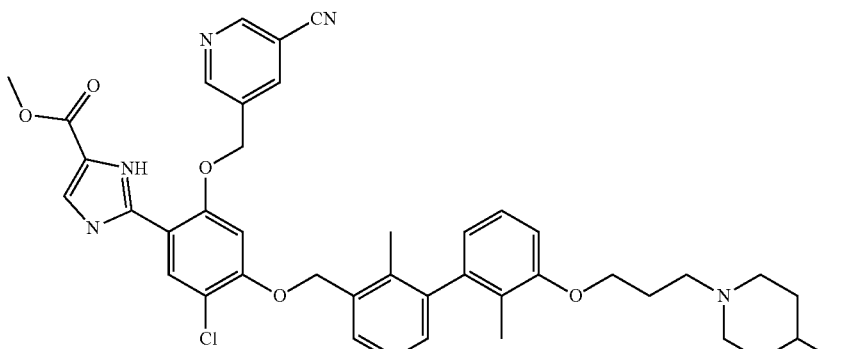<br>methyl 2-(5-chloro-2-((5-cyanopyridin-3-yl)methoxy)-4-((3'-(3-(4-hydroxypiperidin-1-yl)propoxy)-2,2'-dimethyl-[1,1'-biphenyl]-3-yl)methoxy)phenyl)-1H-imidazole-5-carboxylate | 0.010 |
| 21 | 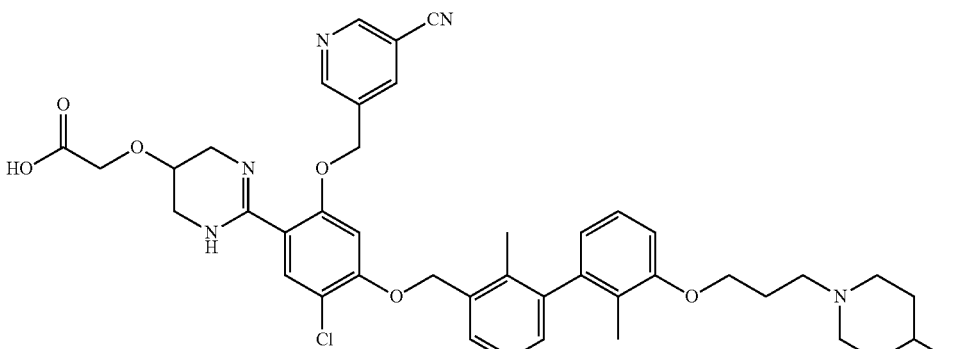<br>2-((2-(5-chloro-2-((5-cyanopyridin-3-yl)methoxy)-4-((3'-(3-(4-hydroxypiperidin-1-yl)propoxy)-2,2'-dimethyl-[1,1'-biphenyl]-3-yl)methoxy)phenyl)-1,4,5,6-tetrahydropyrimidin-5-yl)oxy)acetic acid | 0.0008 |

TABLE 1-continued

| Ex. No. | COMPOUND | PD-L1 HTRF IC$_{50}$ (μM) |
|---|---|---|
| 22 | 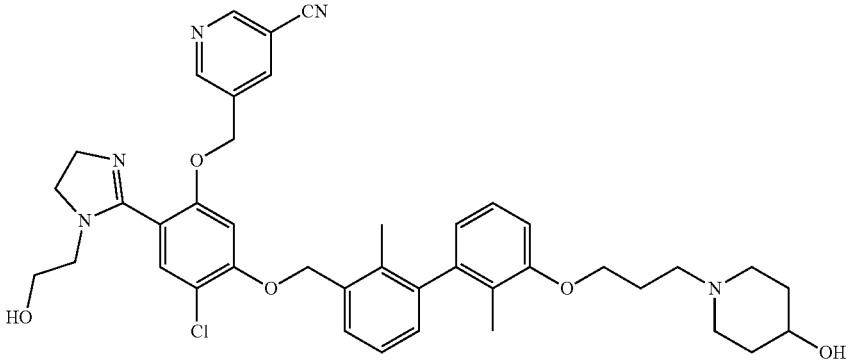<br>5-((4-chloro-2-(1-(2-hydroxyethyl)-4,5-dihydro-1H-imidazol-2-yl)-5-((3'-(3-(4-hydroxypiperidin-1-yl)propoxy)-2,2'-dimethyl-[1,1'-biphenyl]-3-yl)methoxy)phenoxy)methyl)nicotinonitrile | 0.0038 |
| 23 | 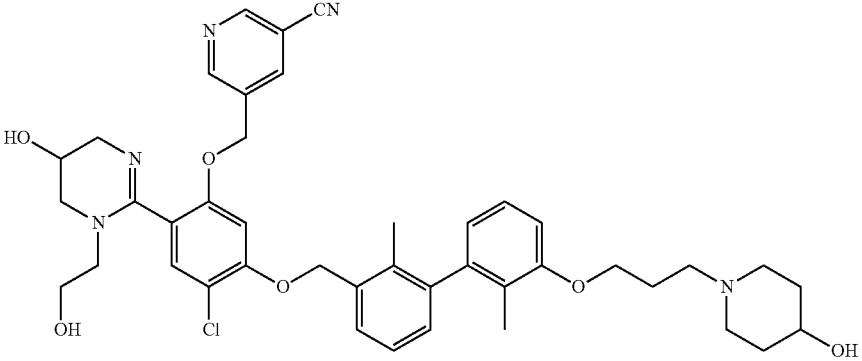<br>5-((4-chloro-2-(5-hydroxy-1-(2-hydroxyethyl)-1,4,5,6-tetrahydropyrimidin-2-yl)-5-((3'-(3-(4-hydroxypiperidin-1-yl)propoxy)-2,2'-dimethyl-[1,1'-biphenyl]-3-yl)methoxy)phenoxy)methyl)nicotinonitrile | 0.014 |
| 24 | 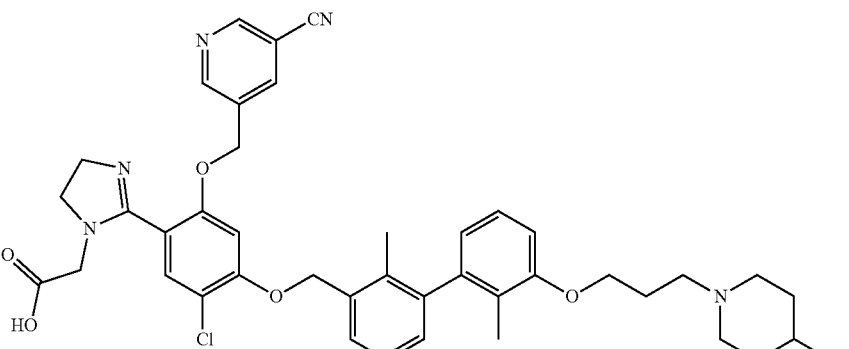<br>2-(2-(5-chloro-2-((5-cyanopyridin-3-yl)methoxy)-4-((3'-(3-(4-hydroxypiperidin-1-yl)propoxy)-2,2'-dimethyl-[1,1'-biphenyl]-3-yl)methoxy)phenyl)-4,5-dihydro-1H-imidazol-1-yl)acetic acid | 0.0011 |

TABLE 1-continued
| Ex. No. | COMPOUND | PD-L1 HTRF IC$_{50}$ (μM) |
|---|---|---|
| 25 | 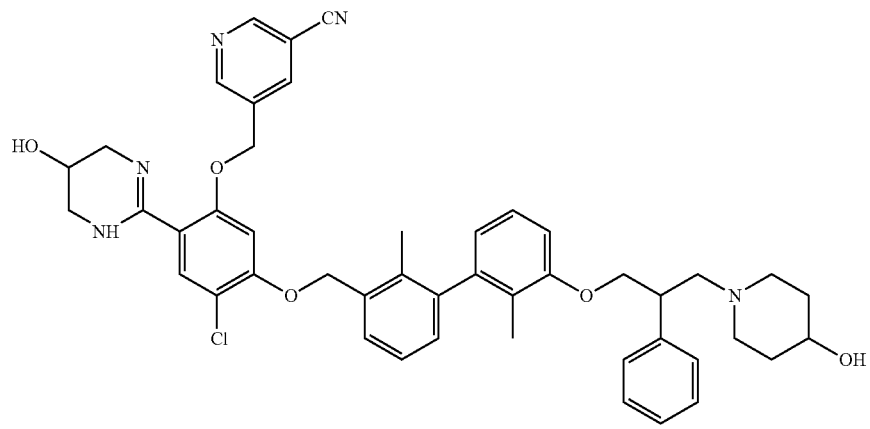<br>5-((4-chloro-2-(5-hydroxy-1,4,5,6-tetrahydropyrimidin-2-yl)-5-((3'-(3-(4-hydroxypiperidin-1-yl)-2-phenylpropoxy)-2,2'-dimethyl-[1,1'-biphenyl]-3-yl)methoxy)phenoxy)methyl)nicotinonitrile | 0.030 |
| 26 | 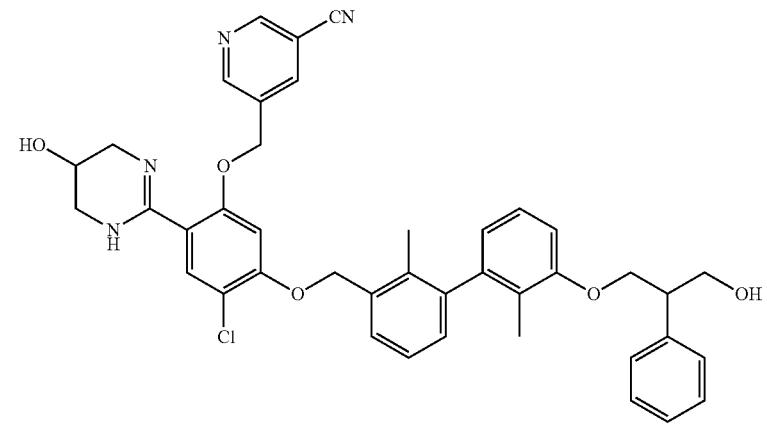<br>5-((4-chloro-2-(5-hydroxy-1,4,5,6-tetrahydropyrimidin-2-yl)-5-((3'-(3-hydroxy-2-phenylpropoxy)-2,2'-dimethyl-[1,1'-biphenyl]-3-yl)methoxy)phenoxy)methyl)nicotinonitrile | 0.0074 |

TABLE 1-continued

| Ex. No. | COMPOUND | PD-L1 HTRF IC$_{50}$ (μM) |
|---|---|---|
| 27 | (2S,2'S)-1,1'-(((((2,2'-dimethyl-[1,1'-biphenyl]-3,3'-diyl)bis(methylene))bis(oxy))bis(5-chloro-2-((5-cyanopyridin-3-yl)methoxy)-4,1-phenylene))bis(methylene))bis(piperidine-2-carboxylic acid) | 0.0013 |
| 28 | 5,5'-((((((2,2'-dimethyl-[1,1'-biphenyl]-3,3'-diyl)bis(methylene))bis(oxy))bis(4-chloro-6-(5-hydroxy-1,4,5,6-tetrahydropyrimidin-2-yl)-3,1-phenylene))bis(oxy))bis(methylene))dinicotinonitrile | 0.0067 |

TABLE 1-continued

| Ex. No. | COMPOUND | PD-L1 HTRF IC$_{50}$ (μM) |
|---|---|---|
| 29 | (2S,2'S)-1,1'-(((((2,2'-dimethyl-[1,1'-biphenyl]-3,3'-diyl)bis(methylene))bis(oxy))bis(5-chloro-2-methoxy-4,1-phenylene))bis(methylene))bis(piperidine-2-carboxylic acid) | 0.0012 |
| 30 | (S)-1-(5-chloro-4-((3'-((2-chloro-4-(hydroxymethyl)-5-methoxyphenoxy)methyl)-2,2'-dimethyl-[1,1'-biphenyl]-3-yl)methoxy)-2-methoxybenzyl)piperidine-2-carboxylic acid | 0.0040 |
| 31 | 2,2'-((((((2,2'-dimethyl-[1,1'-biphenyl]-3,3'-diyl)bis(methylene))bis(oxy))bis(5-chloro-2-methoxy-4,1-phenylene))bis(methylene))bis(azanediyl))bis(ethan-1-ol) | 0.0010 |
| 32 | N,N'-(2,2'-dimethyl-[1,1'-biphenyl]-3,3'-diyl)bis(5-(hydroxymethyl)picolinamide) | 0.0032 |
| 33 | | 0.0037 |

TABLE 1-continued

| Ex. No. | COMPOUND | PD-L1 HTRF IC$_{50}$ (μM) |
|---|---|---|
| 34 | 5-(((2-hydroxyethyl)amino)methyl)-N-(3'-(3-(4-hydroxypiperidin-1-yl)propoxy)-2,2'-dimethyl-[1,1'-biphenyl]-3-yl)picolinamide | 0.001 |
| 35 | N,N'-(2,2'-dimethyl-[1,1'-biphenyl]-3,3'-diyl)bis(5-(((2-hydroxyethyl)amino)methyl)picolinamide) | 0.0003 |
|  | 2,2'-((((2,2'-dimethyl-[1,1'-biphenyl]-3,3'-diyl)bis(azanediyl))bis(carbonyl))bis(pyridine-6,3-diyl))bis(3,4,5,6-tetrahydropyrimidine-4-carboxylic acid) |  |
| 36 | 5-((bis(2-hydroxyethyl)amino)methyl)-N-(3'-(5-(((2-hydroxyethyl)amino)methyl)picolinamido)-2,2'-dimethyl-[1,1'-biphenyl]-3-yl)picolinamide | 0.0004 |
| 37 | (R)-5-(((2-hydroxyethyl)amino)methyl)-N-(3'-(5-(((3-hydroxypyrrolidin-1-yl)methyl)picolinamido)-2,2'-dimethyl-[1,1'-biphenyl]-3-yl)picolinamide | 0.0008 |
| 38 |  | 0.0009 |

TABLE 1-continued

| Ex. No. | COMPOUND | PD-L1 HTRF IC$_{50}$ (μM) |
|---|---|---|
| | 5-(((2-hydroxyethyl)-(methyl)amino)methyl)-N-(3'-(5-(((2-hydroxyethyl)amino)methyl)picolinamido)-2,2'-dimethyl-[1,1'-biphenyl]-3-yl)picolinamide | |
| 39 | (2S,2'S)-1,1'-(((((2,2'-dimethyl-[1,1'-biphenyl]-3,3'-diyl)bis(azanediyl))bis(carbonyl))bis(pyridine-6,3-diyl))bis(methylene))bis(piperidine-2-carboxylic acid) | |
| 40 | 2-(6-((3'-(5-(((2-hydroxyethyl)amino)methyl)picolinamido)-2,2'-dimethyl-[1,1'-biphenyl]-3-yl)carbamoyl)pyridin-3-yl)-3,4,5,6-tetrahydropyrimidine-4-carboxylic acid | |
| 41 | (2S,2'S)-2,2'-((((((2,2'-dimethyl-[1,1'-biphenyl]-3,3'-diyl)bis(azanediyl))bis(carbonyl))bis(pyridine-6,3-diyl))bis(methylene))bis(azanediyl))bis(3-hydroxypropanoic acid) | |

TABLE 1-continued

| Ex. No. | COMPOUND | PD-L1 HTRF IC$_{50}$ (μM) |
|---|---|---|
| 42 | (2R,2'R)-2,2'-((((((2,2'-dimethyl-[1,1'-biphenyl]-3,3'-diyl)bis(azanediyl))bis(carbonyl))bis(pyridine-6,3-diyl))bis(methylene))bis(azanediyl))bis(3-hydroxypropanoic acid) | |
| 43 | (2S,2'S)-2,2'-((((((2,2'-dimethyl-[1,1'-biphenyl]-3,3'-diyl)bis(azanediyl))bis(carbonyl))bis(pyridine-6,3-diyl))bis(methylene))bis(azanediyl))bis(4-hydroxybutanoic acid) | |
| 44 | (2R,2'R)-2,2'-((((((2,2'-dimethyl-[1,1'-biphenyl]-3,3'-diyl)bis(azanediyl))bis(carbonyl))bis(pyridine-6,3-diyl))bis(methylene))bis(azanediyl))bis(4-hydroxybutanoic acid) | |
| 45 | 2-(6-((3'-(5-(((2-hydroxyethyl)amino)methyl)picolinamido)-2,2'-dimethyl-[1,1'-biphenyl]-3-yl)carbamoyl)pyridin-3-yl)-4,5-dihydro-1H-imidazole-5-carboxylic acid | |

TABLE 1-continued

| Ex. No. | COMPOUND | PD-L1 HTRF IC$_{50}$ (μM) |
|---|---|---|
| 46 | N,N'-(2,2'-dimethyl-[1,1'-biphenyl]-3,3'-diyl)bis(5-(((2-acetamidoethyl)amino)methyl)picolinamide) | |
| 47 | N,N'-(2,2'-dimethyl-[1,1'-biphenyl]-3,3'-diyl)bis(5-((((1,3-dihydroxypropan-2-yl)amino)methyl)picolinamide) | |
| 48 | (2S,2'S)-1,1'-(((((2,2'-dimethyl-[1,1'-biphenyl]-3,3'-diyl)bis(azanediyl))bis(carbonyl))bis(pyridine-6,3-diyl))bis(methylene))bis(azetidine-2-carboxylic acid) | |
| 49 | N,N'-(2,2'-dimethyl-[1,1'-biphenyl]-3,3'-diyl)bis(5-(((R)-3-hydroxypyrrolidin-1-yl)methyl)picolinamide) | |
| 50 | | |

TABLE 1-continued

| Ex. No. | COMPOUND | PD-L1 HTRF IC$_{50}$ (μM) |
|---|---|---|
| 51 | 2-(6-((3'-(5-(((R)-3-hydroxypyrrolidin-1-yl)methyl)picolinamido)-2,2'-dimethyl-[1,1'-biphenyl]-3-yl)carbamoyl)pyridin-3-yl)-4,5-dihydro-1H-imidazole-5-carboxylic acid 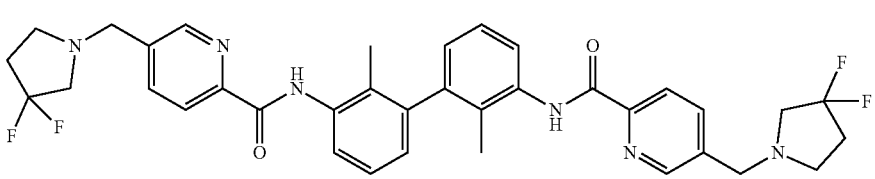 N,N'-(2,2'-dimethyl-[1,1'-biphenyl]-3,3'-diyl)bis(5-((3,3-difluoropyrrolidin-1-yl)methyl)picolinamide) | |
| 52 | 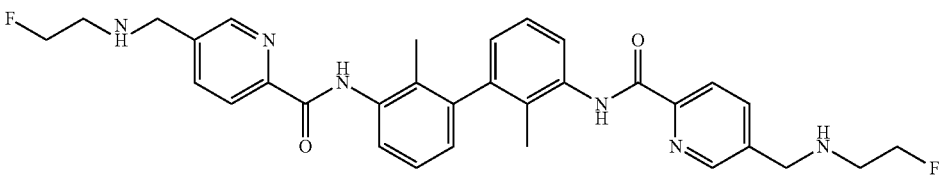 N,N'-(2,2'-dimethyl-[1,1'-biphenyl]-3,3'-diyl)bis(5-(((2-fluoroethyl)amino)methyl)picolinamide) | |
| 53 | 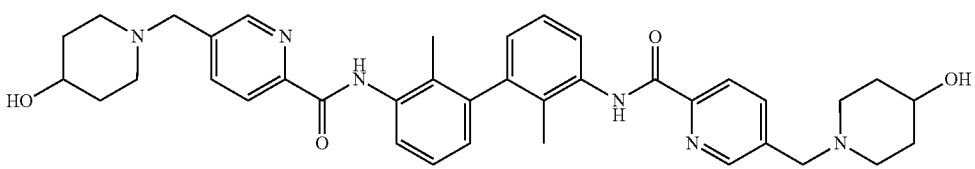 N,N'-(2,2'-dimethyl-[1,1'-biphenyl]-3,3'-diyl)bis(5-((4-hydroxypiperidin-1-yl)methyl)picolinamide) | |
| 54 | 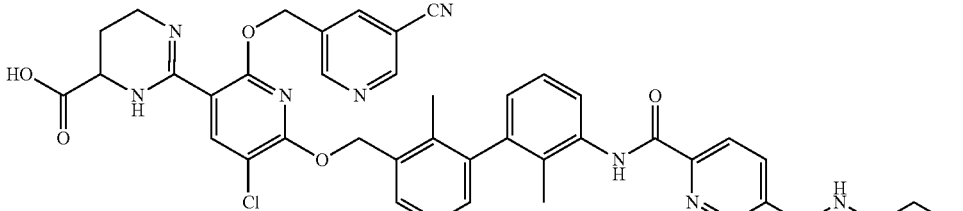 2-(5-chloro-2-((5-cyanopyridin-3-yl)methoxy)-4-((3'-(5-(((2-hydroxyethyl)amino)methyl)picolinamido)-2,2'-dimethyl-[1,1'-biphenyl]-3-yl)methoxy)phenyl)-3,4,5,6-tetrahydropyrimidine-4-carboxylic acid | |
| 55 |  N,N'-(2-chloro-2'-methyl-[1,1'-biphenyl]-3,3'-diyl)bis(5-(((2-hydroxyethyl)amino)methyl)picolinamide) | |

TABLE 1-continued

| Ex. No. | COMPOUND | PD-L1 HTRF IC$_{50}$ (μM) |
|---|---|---|
| 56 | N,N'-(2-bromo-2'-methyl-[1,1'-biphenyl]-3,3'-diyl)bis(5-(((2-hydroxyethyl)amino)methyl)picolinamide) | |
| 57 | N,N'-(2,2'-dimethyl-[1,1'-biphenyl]-3,3'-diyl)bis(5-((bis(2-hydroxyethyl)amino)methyl)picolinamide) | |
| 58 | 2-(2-((5-cyanopyridin-3-yl)methoxy)-6-((3'-(5-(((2-hydroxyethyl)amino)methyl)picolinamido)-2,2'-dimethyl-[1,1'-biphenyl]-3-yl)carbamoyl)pyridin-3-yl)-3,4,5,6-tetrahydropyrimidine-4-carboxylic acid | |
| 59 | N,N'-(2,2'-dimethyl-[1,1'-biphenyl]-3,3'-diyl)bis(5-(((2-(methylsulfonyl)ethyl)amino)methyl)picolinamide) | |
| 60 | | |

TABLE 1-continued

| Ex. No. | COMPOUND | PD-L1 HTRF IC$_{50}$ (μM) |
|---|---|---|
| 61 | N³,N³'-bis(5-((((2-hydroxyethyl)amino)methyl)pyridin-2-yl)-2,2'-dimethyl-[1,1'-biphenyl]-3,3'-dicarboxamide 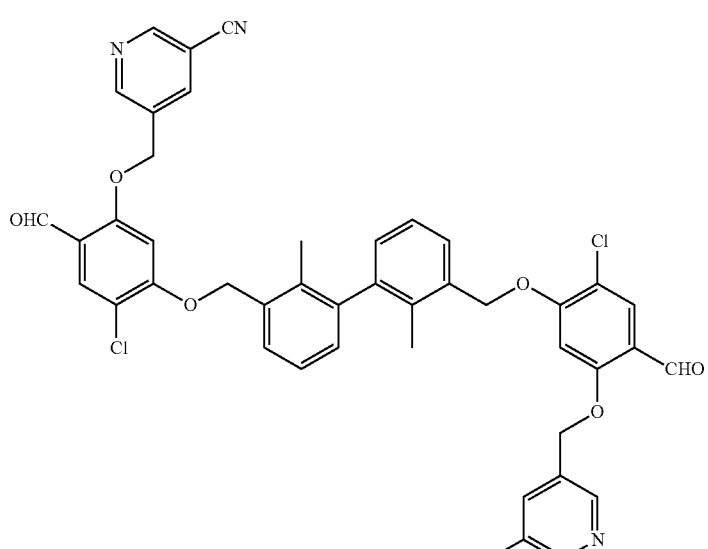 5,5'-((((((2,2'-dimethyl-[1,1'-biphenyl]-3,3'-diyl)bis(methylene))bis(oxy))bis(4-chloro-6-formyl-3,1-phenylene))bis(oxy))bis(methylene)) dinicotinonitrile | |
| 62 | 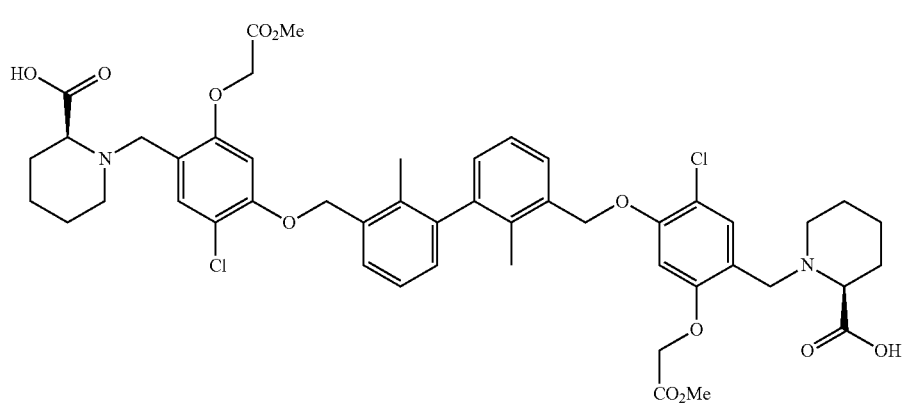 [SMILES: COC(=O)COc1cc(OCc2cccc(-c3cccc(COc4cc(OCC(=O)OC)c(CN5CCCC[C@H]5C(=O)O)cc4Cl)c3C)c2C)c(Cl)cc1CN1CCCC[C@H]1C(=O)O] (2S,2'S)-1,1'-(((((2,2'-dimethyl-[1,1'-biphenyl]-3,3'-diyl)bis(methylene))bis(oxy))bis(5-chloro-2-(2-methoxy-2-oxoethoxy)-4,1-phenylene))bis(methylene))bis(piperidine-2-carboxylic acid) | |
| 63 | 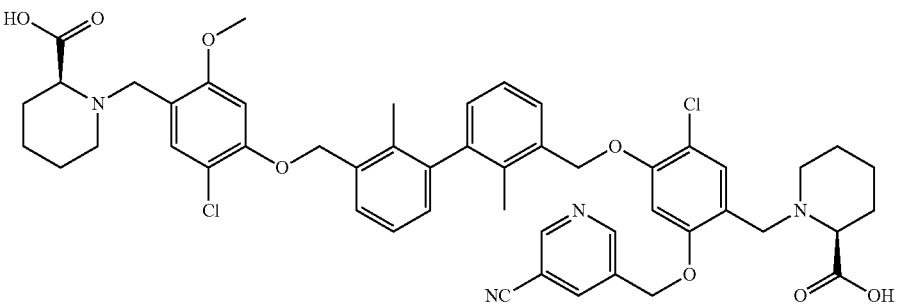 [SMILES: COc1cc(OCc2cccc(-c3cccc(COc4cc(OCc5cncc(C#N)c5)c(CN5CCCC[C@H]5C(=O)O)cc4Cl)c3C)c2C)c(Cl)cc1CN1CCCC[C@H]1C(=O)O] | |

| Ex. No. | COMPOUND | PD-L1 HTRF IC$_{50}$ (μM) |
|---|---|---|
| | 5-chloro-4-((3'-((2-chloro-5-((5-cyanopyridin-3-yl)methoxy)-4-(((2-hydroxyethyl)amino)methyl)phenoxy)methyl)-2,2'-dimethyl-[1,1'-biphenyl]-3-yl)methoxy)-2-((5-cyanopyridin-3-yl)methoxy)-N-(2-hydroxyethyl)benzamide | |
| 64 | 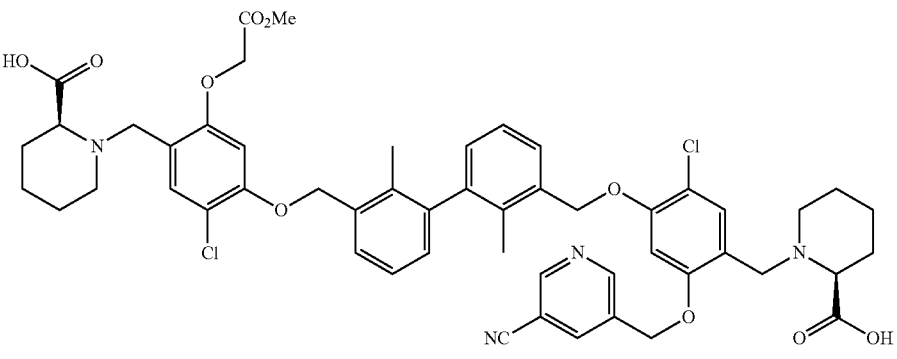 [SMILES: COC(=O)COc1cc(OCc2cccc(-c3cccc(COc4cc(OCc5cncc(C#N)c5)c(CN5CCCC[C@H]5C(=O)O)cc4Cl)c3C)c2C)c(Cl)cc1CN1CCCC[C@H]1C(=O)O] (S)-1-(4-((3'-((4-(((S)-2-carboxypiperidin-1-yl)methyl)-2-chloro-5-((5-cyanopyridin-3-yl)methoxy)phenoxy)methyl)-2,2'-dimethyl-[1,1'-biphenyl]-3-yl)methoxy)-5-chloro-2-(2-methoxy-2-oxoethoxy)benzyl)piperidine-2-carboxylic acid | |
| 65 | 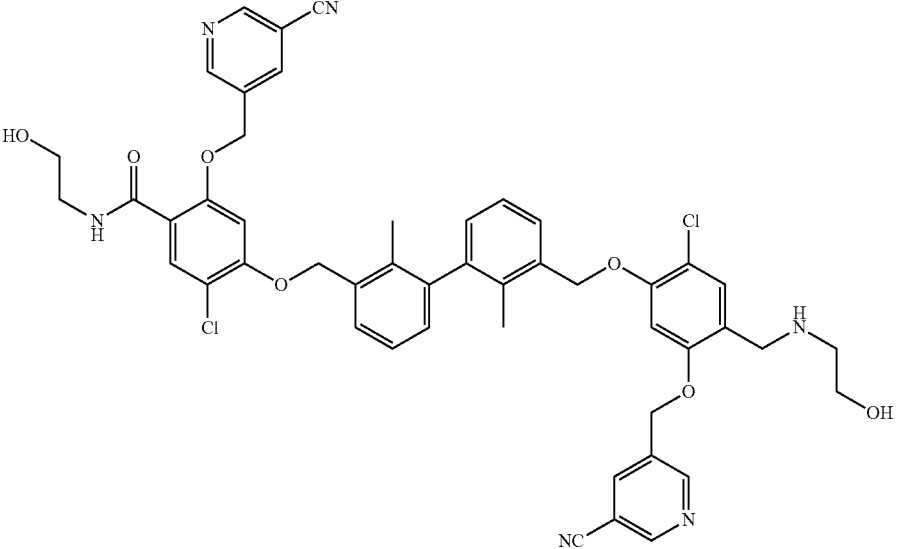 [SMILES: Cc1c(COc2cc(OCc3cncc(C#N)c3)c(CNCCO)cc2Cl)cccc1-c1cccc(COc2cc(OCc3cncc(C#N)c3)c(C(=O)NCCO)cc2Cl)c1C] 5-chloro-4-((3'-((2-chloro-5-((5-cyanopyridin-3-yl)methoxy)-4-(((2-hydroxyethyl)amino)methyl)phenoxy)methyl)-2,2'-dimethyl-[1,1'-biphenyl]-3-yl)methoxy)-2-((5-cyanopyridin-3-yl)methoxy)-N-(2-hydroxyethyl)benzamide | |
| 66 | 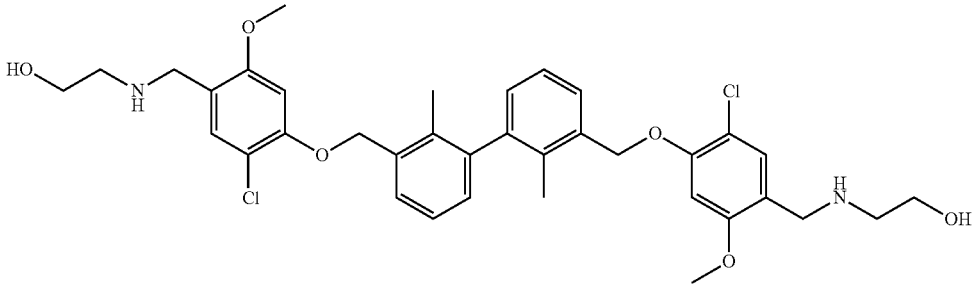 [SMILES: COc1cc(OCc2cccc(-c3cccc(COc4cc(OC)c(CNCCO)cc4Cl)c3C)c2C)c(Cl)cc1CNCCO] | |

TABLE 1-continued

| Ex. No. | COMPOUND | PD-L1 HTRF IC$_{50}$ (μM) |
|---|---|---|
| | 2,2'-((((((2,2'-dimethyl-[1,1'-biphenyl]-3,3'-diyl)bis(methylene))bis(oxy))bis(5-chloro-2-methoxy-4,1-phenylene))bis(methylene))bis(azanediyl))bis(ethan-1-ol) | |

ENUMERATED EMBODIMENTS

The following enumerated embodiments are provided, the numbering of which is not to be construed as designating levels of importance.

Embodiment 1 provides a compound of formula (I):

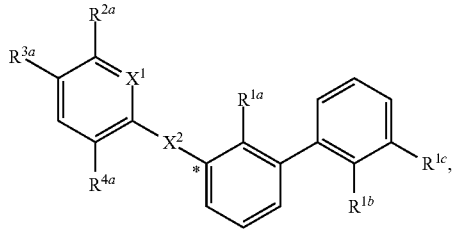

wherein: $X^1$ is selected from the group consisting of CH and N; $X^2$ is selected from the group consisting —OCH$_2$—, —CH$_2$O—, —C(═O)NH—, and —NHC(═O)—, wherein the bond marked with *** is to the phenyl ring carbon marked with *; $R^{1a}$ is selected from the group consisting of H, C$_1$-C$_3$ alkyl, C$_1$-C$_3$ alkoxy, cyano, halogen, and C$_1$-C$_3$ haloalkyl; $R^{1b}$ is selected from the group consisting of H, C$_1$-C$_3$ alkyl, C$_1$-C$_3$ alkoxy, cyano, halogen, and C$_1$-C$_3$ haloalkyl; $R^{1c}$ is selected from the group consisting of H, C$_1$-C$_6$ alkyl, —OH, C$_1$-C$_6$ alkoxy optionally substituted with at least one selected from the group consisting of OH, C$_1$-C$_6$ alkoxy, phenyl, and optionally substituted heterocyclyl (such as but not limited to piperidinyl, pipyrolidinyl, or morpholinyl, and hydroxylated derivatives thereof),

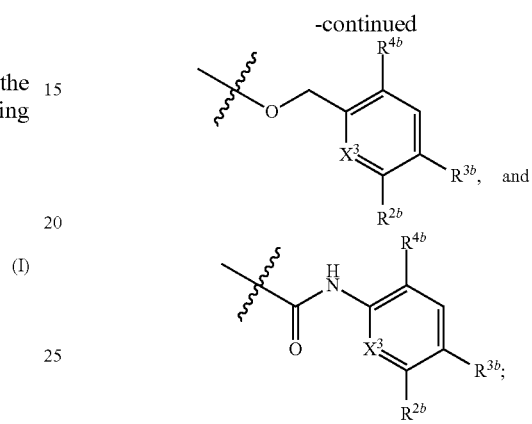

$X^3$ is selected from the group consisting of CH and N; $R^{2a}$ is selected from the group consisting of C$_1$-C$_6$ alkyl, C$_1$-C$_6$ alkoxy, —(CH$_2$)$_{1-3}$ (optionally substituted phenyl), —(CH$_2$)$_{1-3}$ (optionally substituted heteroaryl), —O(CH$_2$)$_{1-3}$ (optionally substituted phenyl), —O(CH$_2$)$_{1-3}$ (optionally substituted heteroaryl), —(CH$_2$)$_{1-3}$C(═O)OR$^I$, —(CH$_2$)$_{1-3}$C(═O)NR$^I$R$^I$, —O(CH$_2$)$_{1-3}$C(═O)OR$^I$, and —O(CH$_2$)$_{1-3}$C(═O)NR$^I$R$^I$, wherein each occurrence of R$^I$ is independently H or C$_1$-C$_6$ alkyl optionally substituted with halogen, —OH, C$_1$-C$_6$ alkoxy, —NH$_2$, —NH(C$_1$-C$_6$ alkyl), and —N(C$_1$-C$_6$ alkyl)(C$_1$-C$_6$ alkyl, or two R$^I$ can combine with the N atom to which they are bound to form 3-8 membered optionally substituted heterocyclyl; $R^{2b}$ is selected from the group consisting of C$_1$-C$_6$ alkyl, C$_1$-C$_6$ alkoxy, —(CH$_2$)$_{1-3}$ (optionally substituted phenyl), —(CH$_2$)$_{1-3}$ (optionally substituted heteroaryl), —O(CH$_2$)$_{1-3}$ (optionally substituted phenyl), —O(CH$_2$)$_{1-3}$ (optionally substituted heteroaryl), —(CH$_2$)$_{1-3}$C(═O)OR$^{II}$, —(CH$_2$)$_{1-3}$C(═O)NR$^{II}$R$^{II}$, —O(CH$_2$)$_{1-3}$C(═O)OR$^{II}$, and —O(CH$_2$)$_{1-3}$C(═O)NR$^{II}$R$^{II}$, wherein each occurrence of R$^{II}$ is independently H or C$_1$-C$_6$ alkyl optionally substituted with halogen, —OH, C$_1$-C$_6$ alkoxy, —NH$_2$, —NH(C$_1$-C$_6$ alkyl), and —N(C$_1$-C$_6$ alkyl)(C$_1$-C$_6$ alkyl), or two R$^{II}$ can combine with the N atom to which they are bound to form 3-8 membered optionally substituted heterocyclyl, $R^{3a}$ is selected from the group consisting of —CHO, —C(O)OR$^{III}$, —C(═O)NR$^{III}$R$^{III}$, —C(═NR$^5$)NR$^{III}$R$^{III}$, optionally substituted heterocyclyl, —(CH$_2$)$_{1-3}$ (optionally substituted heterocyclyl), optionally substituted C$_1$-C$_6$ alkoxy, optionally substituted C$_1$-C$_6$ aminoalkyl, and optionally substituted C$_1$-C$_6$ hydroxyalkyl, wherein each occurrence of R$^5$ is independently H or C$_1$-C$_6$ alkyl optionally substituted with halogen, —OH, C$_1$-C$_6$ alkoxy, —NH$_2$, —NH(C$_1$-C$_6$ alkyl), and —N(C$_1$-C$_6$ alkyl)(C$_1$-C$_6$ alkyl), wherein each occurrence of R$^5$ is independently H or C$_1$-C$_6$ alkyl optionally substituted with halogen, —OH, C$_1$-C$_6$ alkoxy, —NH$_2$, —NH(C$_1$-C$_6$ alkyl), and —N(C$_1$-C$_6$ alkyl)(C$_1$-C$_6$ alkyl), or two R$^{III}$ can combine with the N atom to which they are bound to form 3-8 membered optionally substituted heterocyclyl, or, if $R^{3a}$ is —C(=NR$^5$)NR$^{III}$R$^{III}$, then $R^5$ and one R$^{III}$ can combine to form 4-8 membered optionally substituted heterocyclyl; $R^{3b}$ is selected from the group consisting of —CHO, —C(O)OR$^{IV}$, —C(=O)NR$^{IV}$R$^{IV}$, —C(=NR$^5$)NR$^{IV}$R$^{IV}$, optionally substituted heterocyclyl, —(CH$_2$)$_{1-3}$ (optionally substituted heterocyclyl), optionally substituted C$_1$-C$_6$ alkoxy, optionally substituted C$_1$-C$_6$ aminoalkyl, and optionally substituted C$_1$-C$_6$ hydroxyalkyl, wherein each occurrence of R$^{IV}$ is independently H or C$_1$-C$_6$ alkyl optionally substituted with halogen, —OH, C$_1$-C$_6$ alkoxy, —NH$_2$, —NH(C$_1$-C$_6$ alkyl), and —N(C$_1$-C$_6$ alkyl)(C$_1$-C$_6$ alkyl), wherein each occurrence of $R^5$ is independently H or C$_1$-C$_6$ alkyl optionally substituted with halogen, —OH, C$_1$-C$_6$ alkoxy, —NH$_2$, —NH(C$_1$-C$_6$ alkyl), and —N(C$_1$-C$_6$ alkyl)(C$_1$-C$_6$ alkyl), or two R$^{IV}$ can combine with the N atom to which they are bound to form 3-8 membered optionally substituted heterocyclyl, or, if $R^{3b}$ is —C(=NR$^5$)NR$^{IV}$R$^{IV}$, then $R^5$ and one R$^{IV}$ can combine to form 4-8 membered optionally substituted heterocyclyl; $R^{4a}$ is selected from the group consisting of halogen, cyano, and C$_1$-C$_3$ alkyl; and $R^{4b}$ is selected from the group consisting of halogen, cyano, and C$_1$-C$_3$ alkyl; or a salt, solvate, geometric isomer, stereoisomer, tautomer and any mixtures thereof.

Embodiment 2 provides the compound of Embodiment 1, wherein $R^{1a}$ is identical to $R^{1b}$.

Embodiment 3 provides the compound of any of Embodiments 1-2, wherein $R^{1b}$ is H.

Embodiment 4 provides the compound of any of Embodiments 1-3, wherein $R^{1c}$ is H.

Embodiment 5 provides the compound of any of Embodiments 1-4, wherein $R^{1a}$ is methyl and $R^{1b}$ is methyl.

Embodiment 6 provides the compound of any of Embodiments 1-5, wherein $R^{2a}$ is identical to $R^{2b}$.

Embodiment 7 provides the compound of any of Embodiments 1-6, wherein $R^{2a}$ is selected from the group consisting of C$_1$-C$_6$ alkoxy, —CH$_2$ (optionally substituted pyridinyl), —O(CH$_2$)$_{1-3}$C(=O)OH, and —O(CH$_2$)$_{1-3}$C(=O)O(C$_1$-C$_6$ alkyl).

Embodiment 8 provides the compound of any of Embodiments 1-7, wherein $R^{2b}$ is selected from the group consisting of C$_1$-C$_6$ alkoxy, —CH$_2$ (optionally substituted pyridinyl), —O(CH$_2$)$_{1-3}$C(=O)OH, and —O(CH$_2$)$_{1-3}$C(=O)O(C$_1$-C$_6$ alkyl).

Embodiment 9 provides the compound of any of Embodiments 1-8, wherein $R^{3a}$ is identical to $R^{3b}$.

Embodiment 10 provides the compound of any of Embodiments 1-9, wherein $R^{3a}$ is selected from the group consisting of —CHO, —CH$_2$OH, —C(=NH)NH$_2$, —(CH$_2$)$_{0-1}$ (optionally substituted piperidinyl), —(CH$_2$)$_{0-1}$ (optionally substituted tetrahydropyrimidinyl), —(CH$_2$)$_{0-1}$ (optionally substituted imidazolyl), —(CH$_2$)$_{0-1}$ (optionally substituted dihydroimidazolyl), —C(=O)NH(C$_1$-C$_6$ hydroxyalkyl), CH$_2$NH(C$_1$-C$_6$ haloalkyl), —CH$_2$NH(C$_1$-C$_6$ hydroxyalkyl), CH$_2$N(C$_1$-C$_6$ hydroalkyl)(C$_1$-C$_6$ hydroalkyl), —CH$_2$NH(C$_1$-C$_6$ aminoalkyl), —CH$_2$NH(C$_1$-C$_6$ acetamidoalkyl), —CH$_2$NH—CH[C(=O)OH](CH$_2$)$_{1-6}$OH, and —CH$_2$NH—CH[C(=O)OC$_1$-C$_6$alkyl](CH$_2$)$_{1-6}$OH.

Embodiment 11 provides the compound of any of Embodiments 1-10, wherein $R^{3a}$ is selected from the group consisting of —C(=NH)NH$_2$, —(CH$_2$)$_{0-1}$ (optionally substituted piperidinyl), —(CH$_2$)$_{0-1}$ (optionally substituted tetrahydropyrimidinyl), —(CH$_2$)$_{0-1}$ (optionally substituted imidazolyl), and —(CH$_2$)$_{0-1}$ (optionally substituted dihydroimidazolyl).

Embodiment 12 provides the compound of any of Embodiments 1-11, wherein in $R^{3a}$ the —C(=NH)NH$_2$, piperidinyl, tetrahydropyrimidinyl, imidazolyl, or dihydroimidazolyl is optionally substituted with at least one selected from the group consisting of C$_1$-C$_6$ alkyl, C$_1$-C$_6$ hydroxyalkyl, C$_1$-C$_6$ aminoalkyl, C$_1$-C$_6$N-acylaminoalkyl, —(CH$_2$)$_{0-3}$C(=O)OH, —(CH$_2$)$_{0-3}$C(=O)O(C$_1$-C$_6$ alkyl), —OH, C$_1$-C$_6$ alkoxy, —O(CH$_2$)$_{0-3}$C(=O)OH, or —O(CH$_2$)$_{0-3}$C(=O)O(C$_1$-C$_6$ alkyl).

Embodiment 13 provides the compound of any of Embodiments 1-12, wherein $R^{3b}$ is selected from the group consisting of —CHO, —CH$_2$OH, —C(=NH)NH$_2$, —(CH$_2$)$_{0-1}$ (optionally substituted piperidinyl), —(CH$_2$)$_{0-1}$ (optionally substituted tetrahydropyrimidinyl), —(CH$_2$)$_{0-1}$ (optionally substituted imidazolyl), —(CH$_2$)$_{0-1}$ (optionally substituted dihydroimidazolyl), —C(=O)NH(C$_1$-C$_6$ hydroxyalkyl), CH$_2$NH(C$_1$-C$_6$ haloalkyl), —CH$_2$NH(C$_1$-C$_6$ hydroxyalkyl), —CH$_2$N(C$_1$-C$_6$ hydroalkyl)(C$_1$-C$_6$ hydroalkyl), —CH$_2$NH(C$_1$-C$_6$ aminoalkyl), —CH$_2$NH(C$_1$-C$_6$ acetamidoalkyl), —CH$_2$NH—CH[C(=O)OH](CH$_2$)$_{1-6}$OH, and —CH$_2$NH—CH[C(=O)OC$_1$-C$_6$alkyl](CH$_2$)$_{1-6}$OH.

Embodiment 14 provides the compound of any of Embodiments 1-13, wherein $R^{3b}$ is selected from the group consisting of —C(=NH)NH$_2$, —(CH$_2$)$_{0-1}$ (optionally substituted piperidinyl), —(CH$_2$)$_{0-1}$ (optionally substituted tetrahydropyrimidinyl), —(CH$_2$)$_{0-1}$ (optionally substituted imidazolyl), and —(CH$_2$)$_{0-1}$ (optionally substituted dihydroimidazolyl).

Embodiment 15 provides the compound of any of Embodiments 1-14, wherein in $R^{3b}$ the —C(=NH)NH$_2$, piperidinyl, tetrahydropyrimidinyl, imidazolyl, or dihydroimidazolyl is optionally substituted with at least one selected from the group consisting of C$_1$-C$_6$ alkyl, C$_1$-C$_6$ hydroxyalkyl, C$_1$-C$_6$ aminoalkyl, C$_1$-C$_6$N-acylaminoalkyl, —(CH$_2$)$_{0-3}$C(=O)OH, —(CH$_2$)$_{0-3}$C(=O)O(C$_1$-C$_6$ alkyl), —OH, C$_1$-C$_6$ alkoxy, —O(CH$_2$)$_{0-3}$C(=O)OH, or —O(CH$_2$)$_{0-3}$C(=O)O(C$_1$-C$_6$ alkyl).

Embodiment 16 provides the compound of any of Embodiments 1-15, wherein $R^{4a}$ is identical to $R^{4b}$.

Embodiment 17 provides the compound of any of Embodiments 1-16, wherein $R^{4a}$ is chloro and $R^{4b}$ is chloro.

Embodiment 18 provides the compound of any of Embodiments 1-17, which is

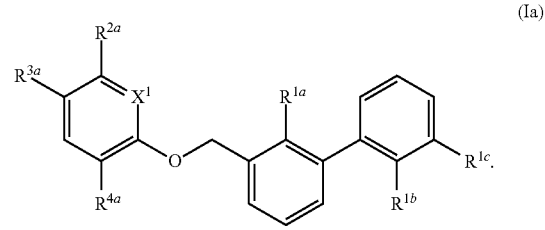

(Ia)

Embodiment 19 provides the compound of any of Embodiments 1-18, which is

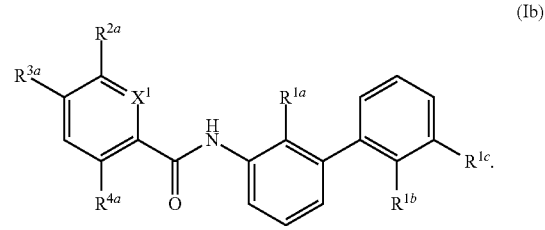

(Ib)

Embodiment 20 provides the compound of any of Embodiments 1-19, which is

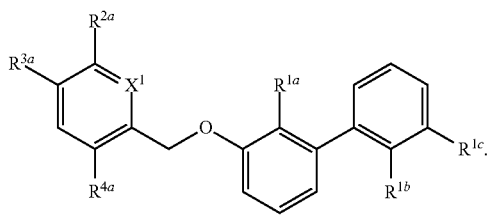

(Ic)

Embodiment 21 provides the compound of any of Embodiments 1-20, which is

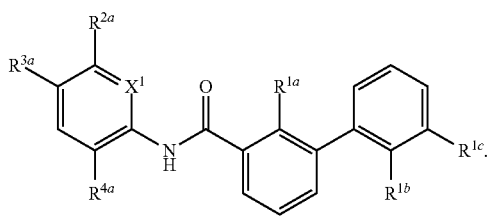

(Id)

Embodiment 22 provides the compound of any of Embodiments 1-21, which is any one of 1-66, or any combinations thereof.

Embodiment 23 provides a pharmaceutical composition comprising any compound of Embodiments 1-22 and at least one pharmaceutically acceptable carrier.

Embodiment 24 provides the pharmaceutical composition of Embodiment 23, further comprising at least one additional agent that treats or prevents hepatitis virus infection.

Embodiment 25 provides the pharmaceutical composition of Embodiment 24, wherein the at least one additional agent comprises at least one selected from the group consisting of reverse transcriptase inhibitor; capsid inhibitor; cccDNA formation inhibitor; sAg secretion inhibitor; oligomeric nucleotide targeted to the Hepatitis B genome; immunostimulator; and RNA destabilizer.

Embodiment 26 provides the pharmaceutical composition of any of Embodiments 24-25, wherein the hepatitis virus is at least one selected from the group consisting of hepatitis B virus (HBV) and hepatitis D virus (HDV).

Embodiment 27 provides a method of treating or preventing hepatitis virus infection in a subject, the method comprising administering to the subject in need thereof a therapeutically effective amount of the compound of any of Embodiments 1-22 and/or composition of any of Embodiments 23-26, or a salt, solvate, prodrug, stereoisomer, tautomer, or any mixtures thereof.

Embodiment 28 provides the method of Embodiment 27, wherein the subject is infected with hepatitis B virus (HBV).

Embodiment 29 provides the method of any of Embodiments 27-28, wherein the subject is infected with hepatitis D virus (HDV).

Embodiment 30 provides the method of any of Embodiments 27-29, wherein the subject is infected with HBV and HDV.

Embodiment 31 provides the method of any of Embodiments 27-30, wherein the subject is further administered at least one additional agent useful for treating the hepatitis virus infection.

Embodiment 32 provides the method of Embodiment 31, wherein the at least one additional agent comprises at least one selected from the group consisting of reverse transcriptase inhibitor; capsid inhibitor; cccDNA formation inhibitor; sAg secretion inhibitor; oligomeric nucleotide targeted to the Hepatitis B genome; immunostimulator; and RNA destabilizer.

Embodiment 33 provides the method of any of Embodiments 31-32, wherein the subject is co-administered the at least one compound and the at least one additional agent.

Embodiment 34 provides the method of any of Embodiments 31-33, wherein the at least one compound and the at least one additional agent are coformulated.

Embodiment 35 provides the method of any of Embodiments 27-34, wherein the subject is a mammal.

Embodiment 36 provides the method of Embodiment 35, wherein the mammal is human.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of formula (I):

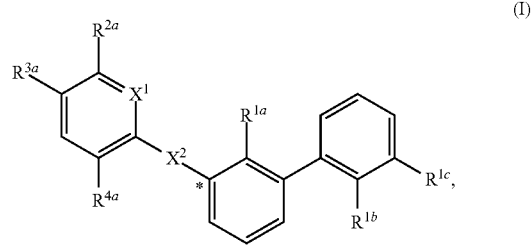

(I)

wherein:
  $X^1$ is selected from the group consisting of CH and N;
  $X^2$ is selected from the group consisting —OCH$_2$—, —CH$_2$O—, —C(=O)NH—, and —NHC(=O)—, wherein the bond marked with ** is to the phenyl ring carbon marked with *;
  $R^{1a}$ is selected from the group consisting of H, $C_1$-$C_3$ alkyl, $C_1$-$C_3$ alkoxy, cyano, halogen, and $C_1$-$C_3$ haloalkyl;
  $R^{1b}$ is selected from the group consisting of H, $C_1$-$C_3$ alkyl, $C_1$-$C_3$ alkoxy, cyano, halogen, and $C_1$-$C_3$ haloalkyl;
  $R^{1c}$ is selected from the group consisting of $C_1$-$C_6$ alkyl, —OH, $C_1$-$C_6$ alkoxy optionally substituted with at least one selected from the group consisting of OH, $C_1$-$C_6$ alkoxy, phenyl, and optionally substituted heterocyclyl,

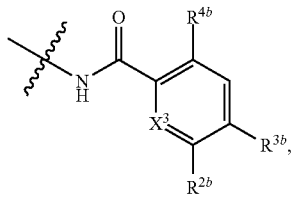

-continued

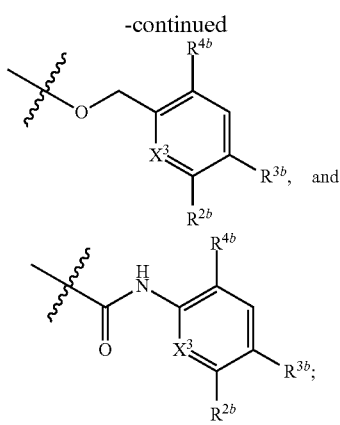

$X^3$ is selected from the group consisting of CH and N;
$R^{2a}$ is selected from the group consisting of $C_1$-$C_6$ alkyl, $C_1$-$C_6$ alkoxy, —$(CH_2)_{1-3}$ (optionally substituted phenyl), —$(CH_2)_{1-3}$ (optionally substituted heteroaryl), —$O(CH_2)_{1-3}$ (optionally substituted phenyl), —$O(CH_2)_{1-3}$ (optionally substituted heteroaryl), —$(CH_2)_{1-3}C(=O)OR$, —$(CH_2)_{1-3}C(=O)NR^I R^I$, —$O(CH_2)_{1-3}C(=O)OR^I$, and —$O(CH_2)_{1-3}C(=O)NR^I R^I$,
wherein each occurrence of R is independently H or $C_1$-$C_6$ alkyl optionally substituted with halogen, —OH, $C_1$-$C_6$ alkoxy, —$NH_2$, —$NH(C_1$-$C_6$ alkyl), or —$N(C_1$-$C_6$ alkyl)($C_1$-$C_6$ alkyl),
or two $R^I$ can combine with the N atom to which they are bound to form a 3-8 membered optionally substituted heterocyclyl;
$R^{2b}$ is selected from the group consisting of $C_1$-$C_6$ alkyl, $C_1$-$C_6$ alkoxy, —$(CH_2)_{1-3}$ (optionally substituted phenyl), —$(CH_2)_{1-3}$ (optionally substituted heteroaryl), —$O(CH_2)_{1-3}$ (optionally substituted phenyl), —$O(CH_2)_{1-3}$ (optionally substituted heteroaryl), —$(CH_2)_{1-3}C(=O)OR^{II}$, —$(CH_2)_{1-3}C(=O)NR^{II}R^{II}$, —$O(CH_2)_{1-3}C(=O)OR^{II}$, and —$O(CH_2)_{1-3}C(=O)NR^{II}R^{II}$,
wherein each occurrence of $R^{II}$ is independently H or $C_1$-$C_6$ alkyl optionally substituted with halogen, —OH, $C_1$-$C_6$ alkoxy, —$NH_2$, —$NH(C_1$-$C_6$ alkyl), or —$N(C_1$-$C_6$ alkyl)($C_1$-$C_6$ alkyl),
or two $R^{II}$ can combine with the N atom to which they are bound to form a 3-8 membered optionally substituted heterocyclyl,
$R^{3a}$ is selected from the group consisting of —CHO, —C(O)$OR^{III}$, —C(=O)$NR^{III}R^{III}$, —C(=$NR^5$)$NR^{III}R^{III}$, optionally substituted heterocyclyl, —$(CH_2)_{1-3}$ (optionally substituted heterocyclyl), optionally substituted $C_1$-$C_6$ alkoxy, optionally substituted $C_1$-$C_6$ aminoalkyl, and optionally substituted $C_1$-$C_6$ hydroxyalkyl,
wherein each occurrence of $R^{III}$ is independently H or $C_1$-$C_6$ alkyl optionally substituted with halogen, —OH, $C_1$-$C_6$ alkoxy, —$NH_2$, —$NH(C_1$-$C_6$ alkyl), or —$N(C_1$-$C_6$ alkyl)($C_1$-$C_6$ alkyl),
wherein each occurrence of $R^5$ is independently H or $C_1$-$C_6$ alkyl optionally substituted with halogen, —OH, $C_1$-$C_6$ alkoxy, —$NH_2$, —$NH(C_1$-$C_6$ alkyl), or —$N(C_1$-$C_6$ alkyl)($C_1$-$C_6$ alkyl),
or two $R^{III}$ can combine with the N atom to which they are bound to form a 3-8 membered optionally substituted heterocyclyl,
or, if $R^{3a}$ is —C(=$NR^5$)$NR^{III}R^{III}$, then $R^5$ and one $R^{III}$ can combine to form a 4-8 membered optionally substituted heterocyclyl;
$R^{3b}$ is selected from the group consisting of —CHO, —C(O)$OR^{IV}$, —C(=O)$NR^{IV}R^{IV}$C(=$NR^5$)$NR^{IV}R^{IV}$, optionally substituted heterocyclyl, —$(CH_2)_{1-3}$ (optionally substituted heterocyclyl), optionally substituted $C_1$-$C_6$ alkoxy, optionally substituted $C_1$-$C_6$ aminoalkyl, and optionally substituted $C_1$-$C_6$ hydroxyalkyl,
wherein each occurrence of $R^{IV}$ is independently H or $C_1$-$C_6$ alkyl optionally substituted with halogen, —OH, $C_1$-$C_6$ alkoxy, —$NH_2$, —$NH(C_1$-$C_6$ alkyl), or —$N(C_1$-$C_6$ alkyl)($C_1$-$C_6$ alkyl),
wherein each occurrence of $R^5$ is independently H or $C_1$-$C_6$ alkyl optionally substituted with halogen, —OH, $C_1$-$C_6$ alkoxy, —$NH_2$, —$NH(C_1$-$C_6$ alkyl), or —$N(C_1$-$C_6$ alkyl)($C_1$-$C_6$ alkyl),
or two $R^{IV}$ can combine with the N atom to which they are bound to form a 3-8 membered optionally substituted heterocyclyl,
or, if $R^{3b}$ is —C(=$NR^5$)$NR^{IV}R^{IV}$, then $R^5$ and one $R^{IV}$ can combine to form a 4-8 membered optionally substituted heterocyclyl;
$R^{4a}$ is selected from the group consisting of H, halogen, cyano, and $C_1$-$C_3$ alkyl; and
$R^{4b}$ is selected from the group consisting of H, halogen, cyano, and $C_1$-$C_3$ alkyl;
or a salt, solvate, geometric isomer, stereoisomer, tautomer, and any mixtures thereof.

2. The compound of claim 1, wherein at least one of the following applies:
(i) $R^{1a}$ is identical to $R^{1b}$,
(ii) $R^{2a}$ is identical to $R^{2b}$,
(iii) $R^{3a}$ is identical to $R^{3b}$, and
(iv) $R^{4a}$ is identical to $R^{4b}$.

3. The compound of claim 1, wherein $R^{1b}$ is H.

4. The compound of claim 1, wherein $R^{1a}$ is methyl and $R^{1b}$ is methyl.

5. The compound of claim 1, wherein at least one of $R^{2a}$ and $R^{2b}$ is selected from the group consisting of $C_1$-$C_6$ alkoxy, —$CH_2$ (optionally substituted pyridinyl), —$O(CH_2)_{1-3}C(=O)OH$, and —$O(CH_2)_{1-3}C(=O)O(C_1$-$C_6$ alkyl).

6. The compound of claim 1, wherein $R^{3a}$ is selected from the group consisting of —CHO, —$CH_2OH$, —C(=NH)$NH_2$, —$(CH_2)_{0-1}$ (optionally substituted piperidinyl), —$(CH_2)_{0-1}$ (optionally substituted tetrahydropyrimidinyl), —$(CH_2)_{0-1}$ (optionally substituted imidazolyl), —$(CH_2)_{0-1}$ (optionally substituted dihydroimidazolyl), —C(=O)NH($C_1$-$C_6$ hydroxyalkyl), —$CH_2NH(C_1$-$C_6$ haloalkyl), —$CH_2NH(C_1$-$C_6$ hydroxyalkyl), —$CH_2N(C_1$-$C_6$ hydroalkyl)($C_1$-$C_6$ hydroalkyl), —$CH_2NH(C_1$-$C_6$ aminoalkyl), —$CH_2NH(C_1$-$C_6$ acetamidoalkyl), —$CH_2NH$—CH[C(=O)OH]($CH_2)_{1-6}OH$, and —$CH_2NH$—CH[C(=O)O($C_1$-$C_6$ alkyl)]($CH_2)_{1-6}OH$.

7. The compound of claim 1, wherein $R^{3a}$ is selected from the group consisting of —C(=NH)$NH_2$, —$(CH_2)_{0-1}$ (optionally substituted piperidinyl), —$(CH_2)_{0-1}$ (optionally substituted tetrahydropyrimidinyl), —$(CH_2)_{0-1}$ (optionally substituted imidazolyl), and —$(CH_2)_{0-1}$ (optionally substituted dihydroimidazolyl).

8. The compound of claim 6, wherein in $R^{3a}$ the —C(=NH)$NH_2$, piperidinyl, tetrahydropyrimidinyl, imidazolyl, or dihydroimidazolyl is optionally substituted with at least one selected from the group consisting of $C_1$-$C_6$ alkyl, $C_1$-$C_6$ hydroxyalkyl, $C_1$-$C_6$ aminoalkyl, $C_1$-$C_6$ N-acylaminoalkyl, —$(CH_2)_{0-3}C(=O)OH$, —$(CH_2)_{0-3}C(=O)O(C_1$-$C_6$ alkyl), —OH, C$_1$-C$_6$ alkoxy, —O(CH$_2$)$_{0-3}$C(=O)OH, and —O(CH$_2$)$_{0-3}$C(=O)O(C$_1$-C$_6$ alkyl).

9. The compound of claim 1, wherein R$^{3b}$ is selected from the group consisting of —CHO, —CH$_2$OH, —C(=NH)NH$_2$, —(CH$_2$)$_{0-1}$ (optionally substituted piperidinyl), —(CH$_2$)$_{0-1}$ (optionally substituted tetrahydropyrimidinyl), —(CH$_2$)$_{0-1}$ (optionally substituted imidazolyl), —(CH$_2$)$_{0-1}$ (optionally substituted dihydroimidazolyl), —C(=O)NH(C$_1$-C$_6$ hydroxyalkyl), CH$_2$NH(C$_1$-C$_6$ haloalkyl), —CH$_2$NH(C$_1$-C$_6$ hydroxyalkyl), —CH$_2$N(C$_1$-C$_6$ hydroalkyl)(C$_1$-C$_6$ hydroalkyl), —CH$_2$NH(C$_1$-C$_6$ aminoalkyl), —CH$_2$NH(C$_1$-C$_6$ acetamidoalkyl), —CH$_2$NH—CH[C(=O)OH](CH$_2$)$_{1-6}$OH, and —CH$_2$NH—CH[C(=O)O(C$_1$-C$_6$ alkyl](CH$_2$)$_{1-6}$OH.

10. The compound of claim 1, wherein R$^{3b}$ is selected from the group consisting of —C(=NH)NH$_2$, —(CH$_2$)$_{0-1}$ (optionally substituted piperidinyl), —(CH$_2$)$_{0-1}$ (optionally substituted tetrahydropyrimidinyl), —(CH$_2$)$_{0-1}$ (optionally substituted imidazolyl), and —(CH$_2$)$_{0-1}$ (optionally substituted dihydroimidazolyl).

11. The compound of claim 9, wherein in R$^{3b}$ the —C(=NH)NH$_2$, piperidinyl, tetrahydropyrimidinyl, imidazolyl, or dihydroimidazolyl is optionally substituted with at least one selected from the group consisting of C$_1$-C$_6$ alkyl, C$_1$-C$_6$ hydroxyalkyl, C$_1$-C$_6$ aminoalkyl, C$_1$-C$_6$ N-acylaminoalkyl, —(CH$_2$)$_{0-3}$C(=O)OH, —(CH$_2$)$_{0-3}$C(=O)O(C$_1$-C$_6$ alkyl), —OH, C$_1$-C$_6$ alkoxy, —O(CH$_2$)$_{0-3}$C(=O)OH, or —O(CH$_2$)$_{0-3}$C(=O)O(C$_1$-C$_6$ alkyl).

12. The compound of claim 1, wherein R$^{4a}$ is chloro and R$^{4b}$ is chloro.

13. The compound of claim 1, which is:

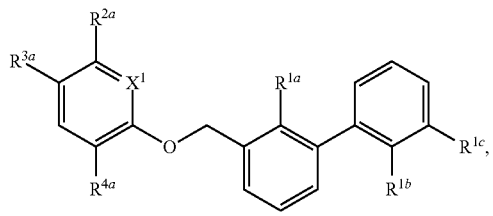

(Ia)

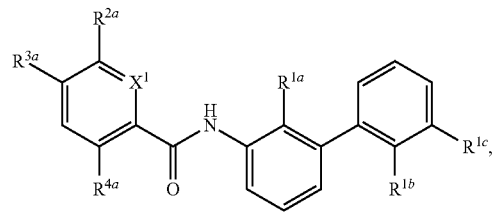

(Ib)

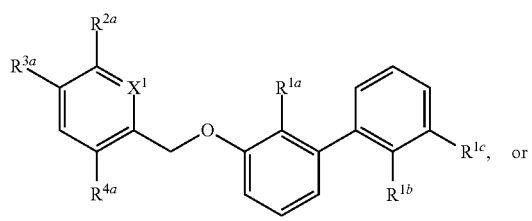

(Ic)

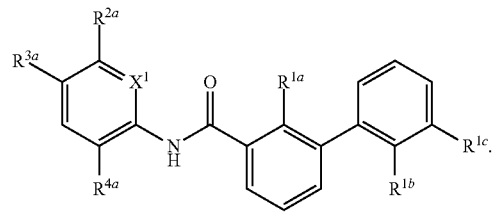

(Id)

14. A compound selected from the group consisting of:

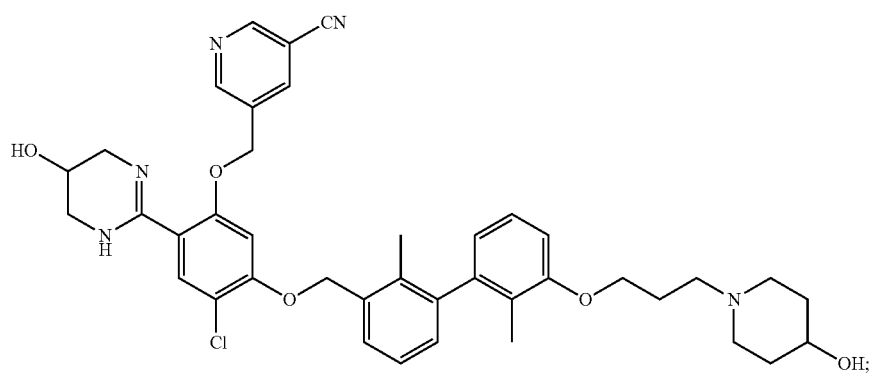

5-((4-chloro-2-(5-hydroxy-1,4,5,6-tetrahydropyrimidin-2-yl)-5-((3'-(3-(4-hydroxypiperidin-1-yl)propoxy)-2,2'-dimethyl-[1,1'-biphenyl]-3-yl)methoxy)phenoxy)methyl)nicotinonitrile

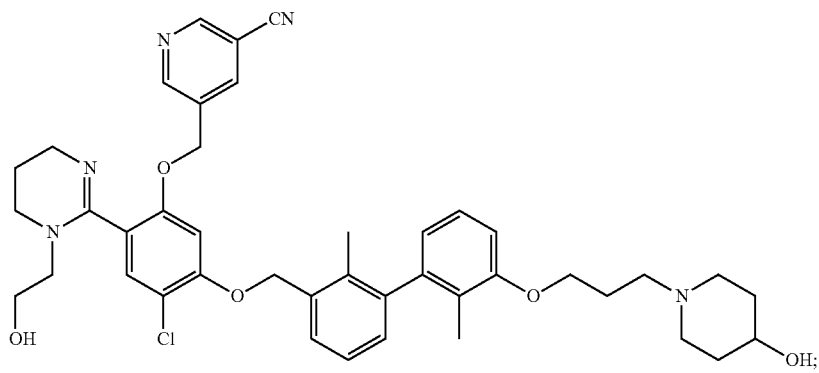

5-((4-chloro-2-(1-(2-hydroxyethyl)-1,4,5,6-tetrahydropyrimidin-2-yl)-5-((3'-(3-(4-hydroxypiperidin-1-yl)propoxy)-2,2'-dimethyl-[1,1'-biphenyl]-3-yl)methoxy)phenoxy)methyl)nicotinonitrile

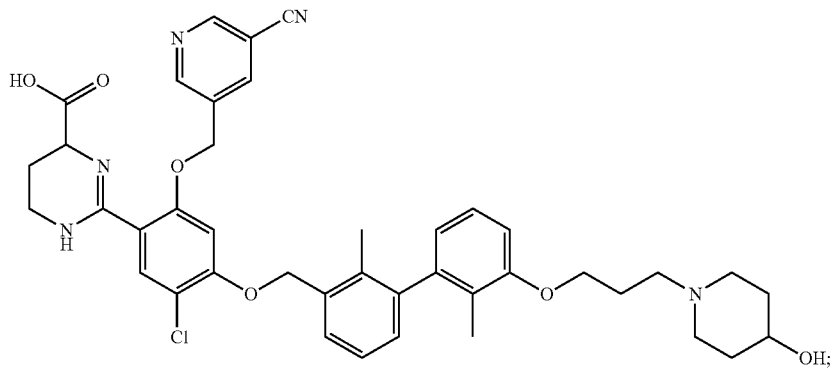

2-(5-chloro-2-((5-cyanopyridin-3-yl)methoxy)-4-((3'-(3-(4-hydroxypiperidin-1-yl)propoxy)-2,2'-dimethyl-[1,1'-biphenyl]-3-yl)methoxy)phenyl)-1,4,5,6-tetrahydropyrimidine-4-carboxylic acid

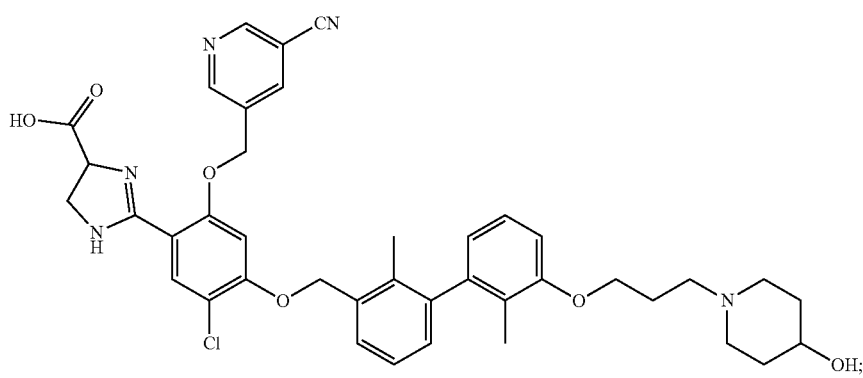

2-(5-chloro-2-((5-cyanopyridin-3-yl)methoxy)-4-((3'-(3-(4-hydroxypiperidin-1-yl)propoxy)-2,2'-dimethyl-[1,1'-biphenyl]-3-yl)methoxy)phenyl)-4,5-dihydro-1H-imidazole-4-carboxylic acid

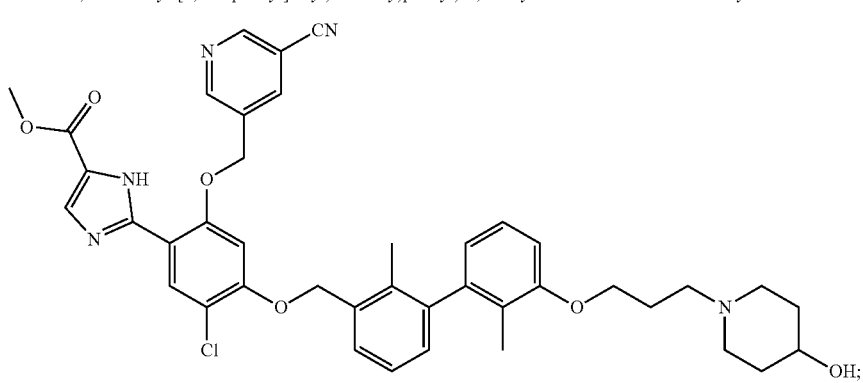

methyl 2-(5-chloro-2-((5-cyanopyridin-3-yl)methoxy)-4-((3'-(3-(4-hydroxypiperidin-1-yl)propoxy)-2,2'-dimethyl-[1,1'-biphenyl]-3-yl)methoxy)phenyl)-1H-imidazole-5-carboxylate -continued

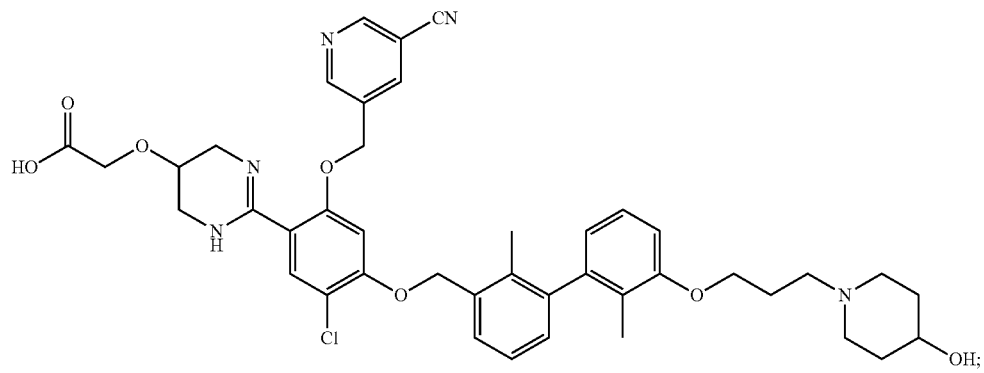

2-((2-(5-chloro-2-((5-cyanopyridin-3-yl)methoxy)-4-((3'-(3-(4-hydroxypiperidin-1-yl)propoxy)-2,2'dimethyl-[1,1'-biphenyl]-3-yl)methoxy)phenyl)-1,4,5,6-tetrahydropyrimidin-5-yl)oxy)acetic acid

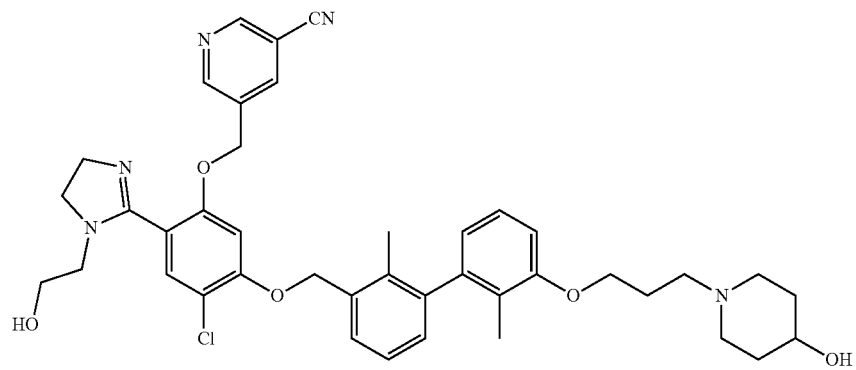

5-((4-chloro-2-(1(2-hydroxyethyl)-4,5-dihydro-1H-imidazol-2-yl)-5-((3'-(3-(4-hydroxypiperidin-1-yl)propoxy)-2,2'-dimethyl-[1,1'-biphenyl]-3-yl)methoxy)phenoxy)methyl)nicotinonitrile

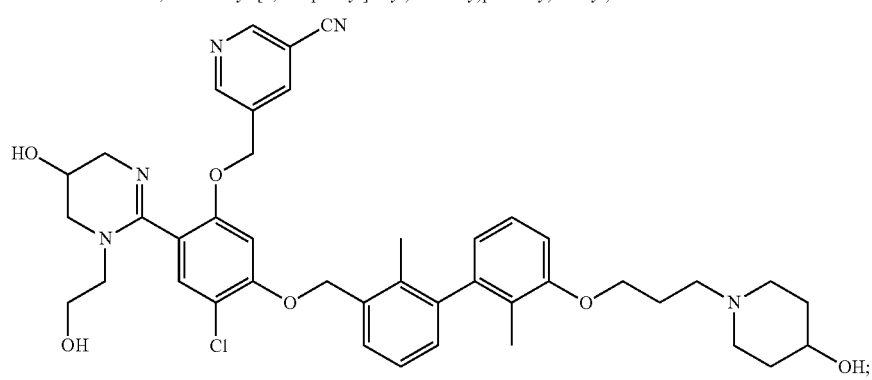

5-((4-chloro-2-(5-hydroxy-1-(2-hydroxyethyl)-1,4,5,6-tetrahydropyrimidin-2-yl)-5-((3'-(3-(4-hydroxypiperidin-1-yl)propoxy)-2,2'-dimethyl-[1,1'-biphenyl]-3-yl)methoxy)phenoxy)methyl)nicotinonitrile

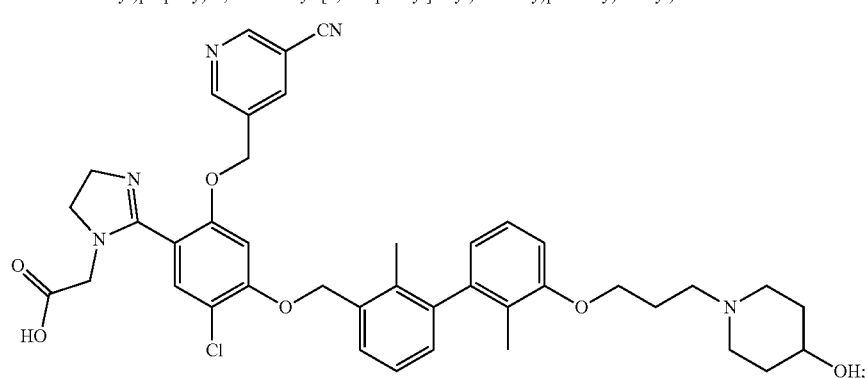

2-(2-(5-chloro-2-((5-cyanopyridin-3-yl)methoxy)-4-((3'-(3-(4-hydroxypiperidin-1-yl)propoxy)-2,2'-dimethyl-[1,1'-biphenyl]-3-yl)methoxy)phenyl)-4,5-dihyrdo-1H-imidazol-1-yl)acetic acid -continued

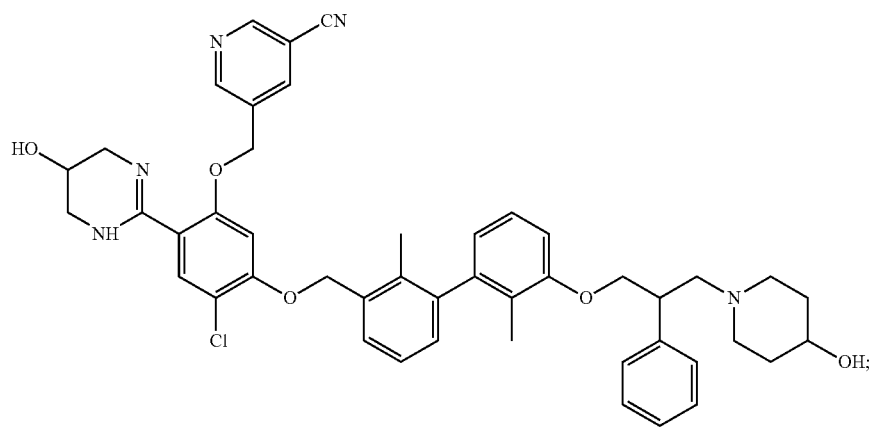

5-((4-chloro-2-(5-hydroxy-1,4,5,6-tetrahydropyrimidin-2-yl)-5-((3'-(3-(4-hydroxypiperidin-1-yl)-2-phenylpropoxy)-2,2'-dimethyl-[1,1'-biphenyl]-3-yl)methoxy)phenoxy)methyl)-nicotinonitrile

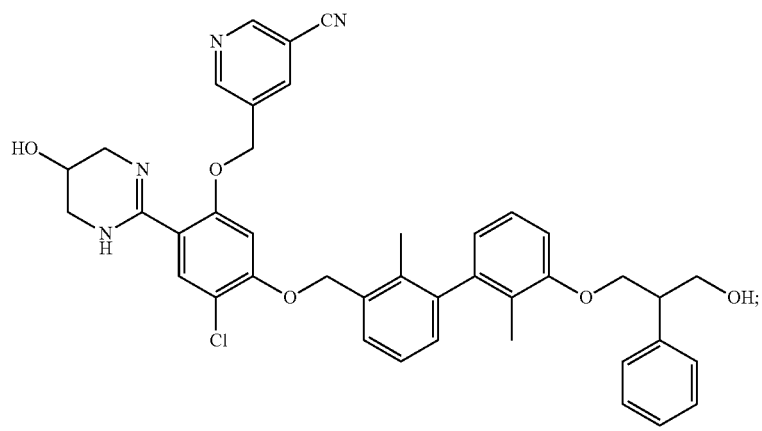

5-((4-chloro-2-((5-hydroxy-1,4,5,6-tetrahydropyrimidin-2-yl)-5-((3'-(3-hydroxy-2-phenylpropoxy)-2,2'-dimethyl-[1,1'-biphenyl]-3-yl)methoxy)phenoxy)methyl)nicotinonitrile

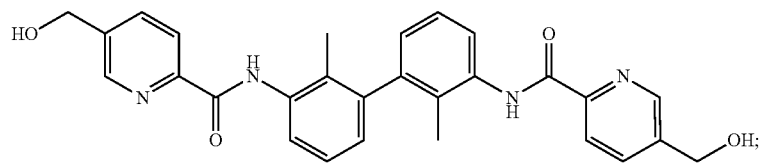

N-N'-(2,2'-dimethyl-[1,1'-biphenyl]-3,3'-diyl)bis(5-(hydroxymethyl)picolinamide)

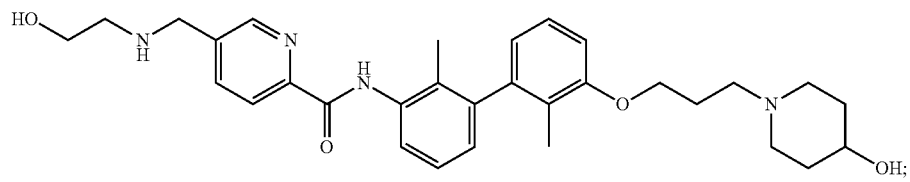

5-(((2-hydroxyethyl)amino)methyl)-N-(3'-(3-(4-(hydroxypiperidin-1-yl)propoxy)-2,2'-dimethyl-[1,1'-biphenyl]-3-yl)picolinamide

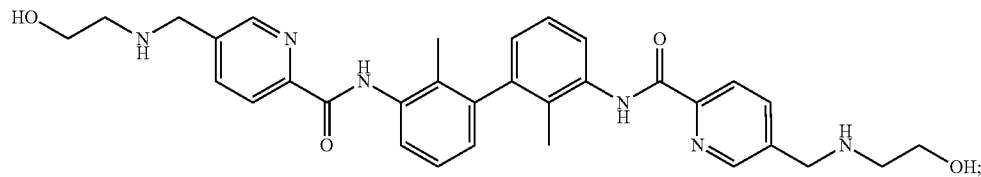

N-N'-(2,2'-dimethyl-[1,1'-biphenyl]-3,3'-diyl)bis(5-(((2-hydroxyethyl)amino)methyl-picolinamide)

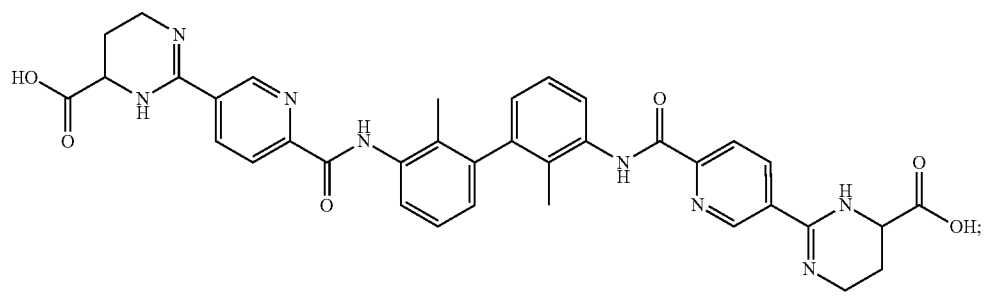

2,2'-(((((2,2'-dimethyl-[1,1'-biphenyl]-3,3'-diyl)bis(azanediyl))bis(carbonyl))bis(pyridine-6,3-diyl))bis(3,4,5,6-tetrahydropyrimidine-4-carboxylic acid)

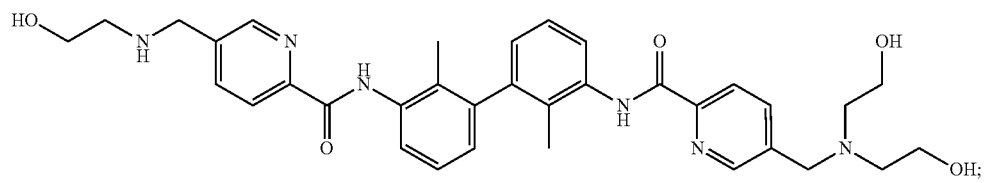

5-((bis(2-hydroxyethyl)amino)methyl)-N-(3'-(5-(((2-hydroxyethyl)amino)methyl)picoloinamido)-2,2'-dimethyl-[1,1'-biphenyl]-3-yl)-picolinamide

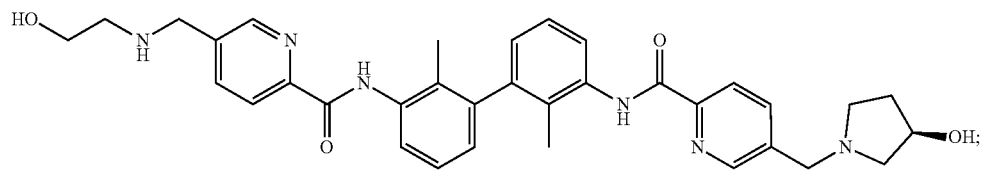

(R)-5-(((2-hydroxyethyl)amino)methyl)-N-(3'-(5-((3-hydroxypyrrolidin-1-yl)methyl)picoloinamido)-2,2'-dimethyl-[1,1'-biphenyl]-3-yl)-picolinamide

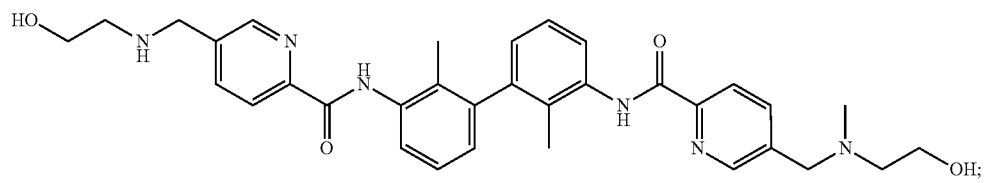

5-(((2-hydroxyethyl)-(methyl)amino)methyl)-N-(3'-(5-(((2-hydroxyethyl)amino)methyl)picoloinamido)-2,2'-dimethyl-[1,1'-biphenyl]-3-yl)-picolinamide

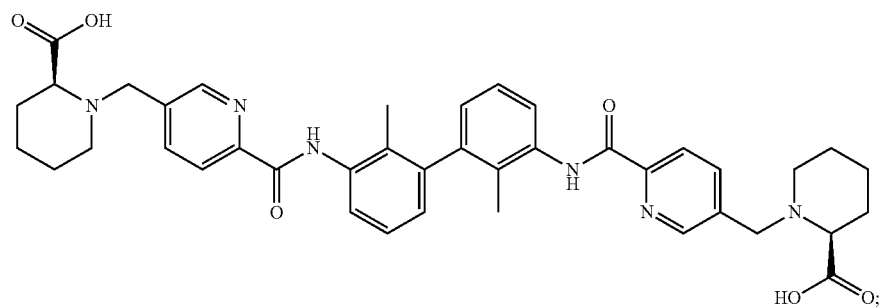

(2S,2'S)-1,1'-(((((2-2'-dimethyl-[1,1'-biphenyl]-3,3'-diyl)bis(azanediyl))bis(carbonyl))bis(pyridine-6,3-diyl))bis(methylene))bis(piperidine-2-carboxylic acid)

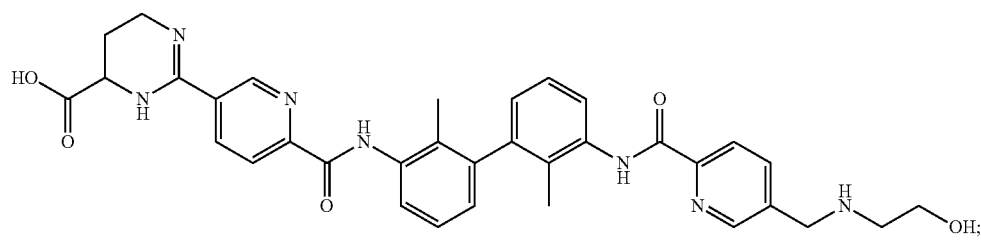

2-(6-((3'-(5-(((2-2'-hydroxyethyl)amino)methyl)picolinamido)-2,2'-dimethyl-[1,1'-biphenyl]-3-yl)carbamoyl)pyridin-3-yl)-3,4,5,6-tetrahydropyrimidine-4-carboxylic acid

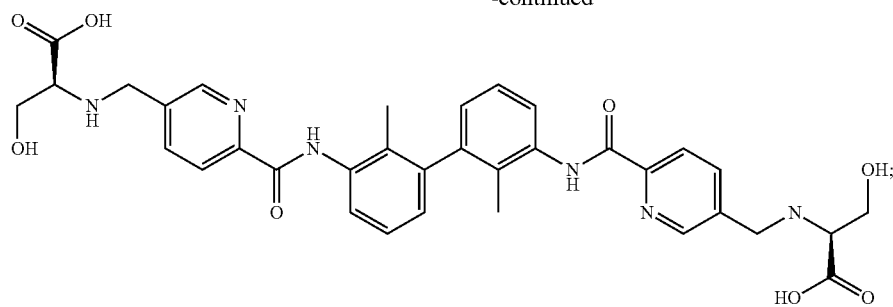

(2S,2′S)-2,2′-(((((2-2′-dimethyl-[1,1′-biphenyl]-3,3′-diyl)bis(azanediyl))bis(carbonyl))bis(pyridine-6,3-diyl))bis(methylene))bis(azanediyl))bis(3-hydroxypropanoic acid)

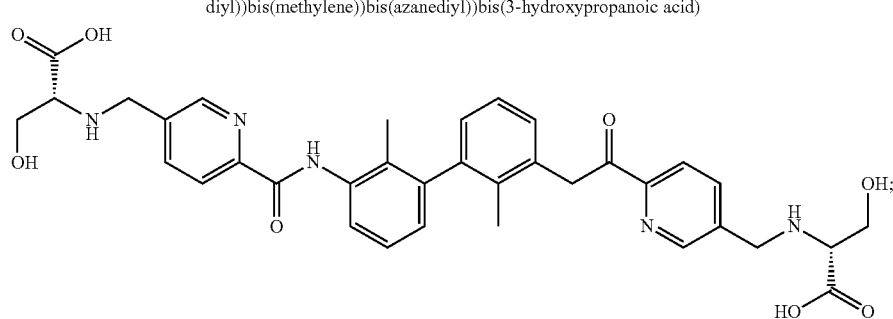

(2R,2′R)-2,2′-(((((2-2′-dimethyl-[1,1′-biphenyl]-3,3′-diyl)bis(azanediyl))bis(carbonyl))bis(pyridine-6,3-diyl))bis(methylene))bis(azanediyl))bis(3-hydroxypropanoic acid)

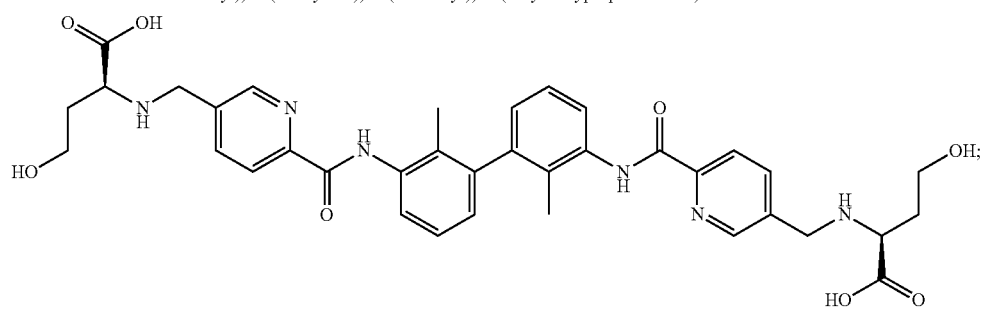

(2S,2′S)-2,2′-(((((2-2′-dimethyl-[1,1′-biphenyl]-3,3′-diyl)bis(azanediyl))bis(carbonyl))bis(pyridine-6,3-diyl))bis(methylene))bis(azanediyl))bis(4-hydroxybutanoic acid)

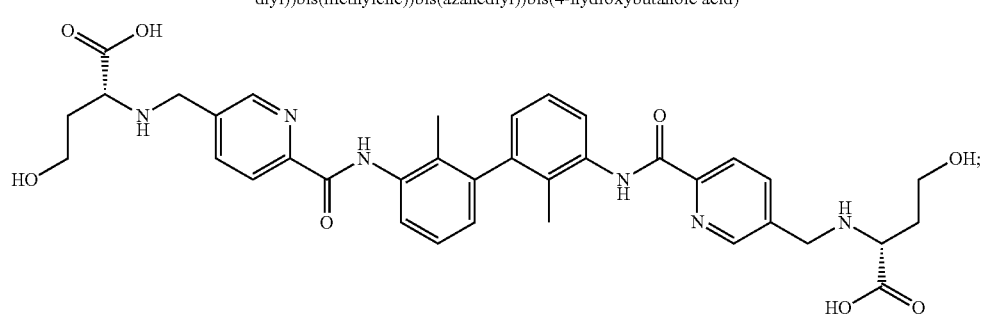

(2R,2′R)-2,2′-(((((2-2′-dimethyl-[1,1′-biphenyl]-3,3′-diyl)bis(azanediyl))bis(carbonyl))bis(pyridine-6,3-diyl))bis(methylene))bis(azanediyl))bis(4-hydroxybutanoic acid

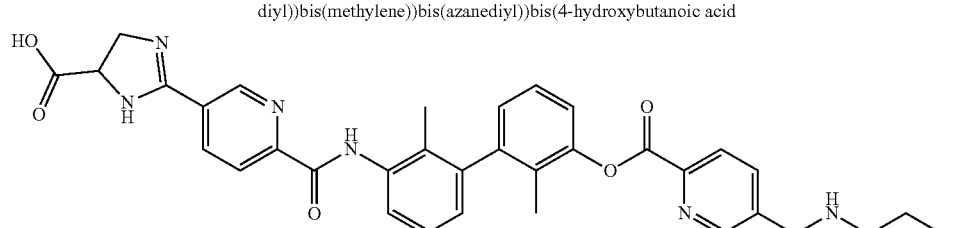

2-(6-((3′-(5-(((2-hydroxyethyl)amino)methyl)picolinamido)-2′-dimethyl-[1,1′-biphenyl]-3-yl)carbamoyl)pyridin-3-yl)-4,5-dihydro-1H-imidazole-5-carboxylic acid

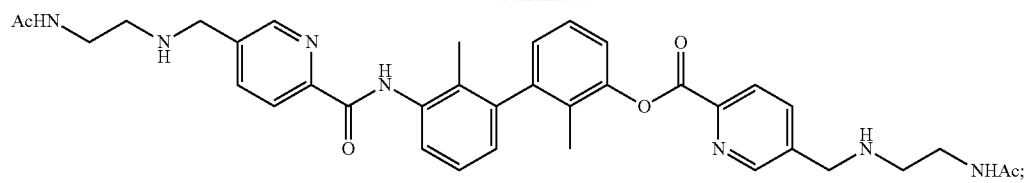

N-N'-(2,2'-dimethyl-[1,1'-biphenyl]-3,3'-diyl)bis(5-(((2-acetamidoethyl)amino)methyl)picolinamide)

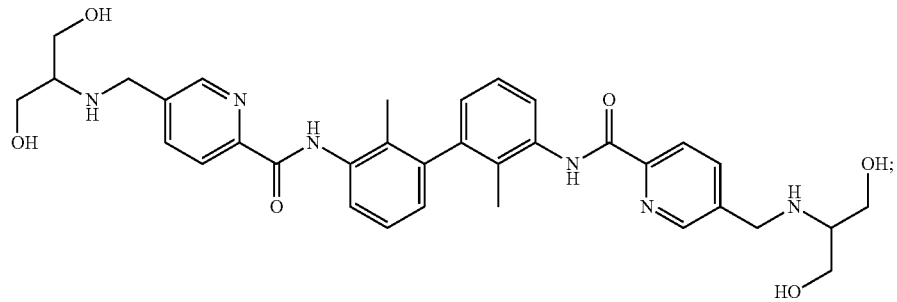

N-N'-(2,2'-dimethyl-[1,1'-biphenyl]-3,3'-diyl)bis(5-(((1,3-dihydroxypropan-2-yl)amino)methyl)picolinamide)

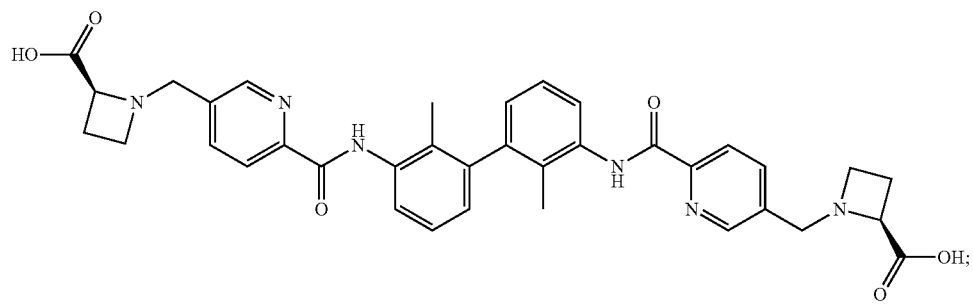

(2S,2'S)-1,1'-(((((2-2'-dimethyl-[1,1'-biphenyl]-3,3'-diyl)bis(azanediyl))bis(carbonyl))bis(pyridine-6,3-diyl))bis(methylene))bis(azetidne-2-carboxylic acid)

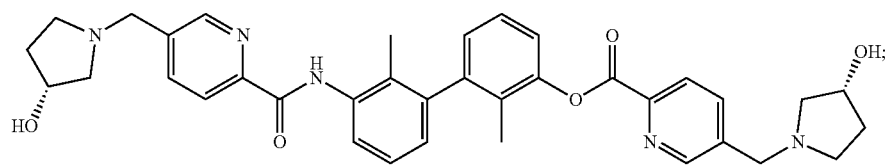

N-N'-(2,2'-dimethyl-[1,1'-biphenyl]-3,3'-diyl)bis(5-(((R)-3-hydroxypyrrolidin-1-yl)methyl)picolinamide)

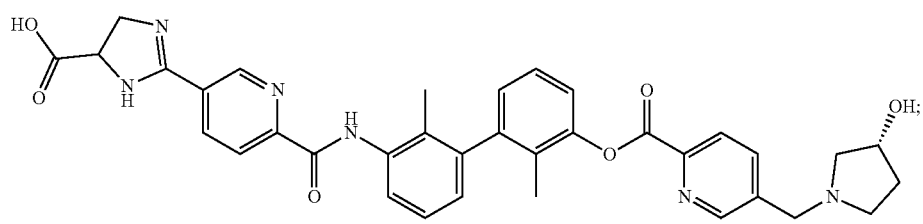

2-(6-((3'-(5-(((R)-3-hydroxpyrrolidin-1-yl)methyl)picolinamido)-2,-2'-dimethyl-[1,1'-biphenyl]-3-yl)carbamoyl)pyridin-3-yl)carbamoyl)pyridin-3-yl)-4,5-dihydro-1H-imidazole-5-carboxylic acid

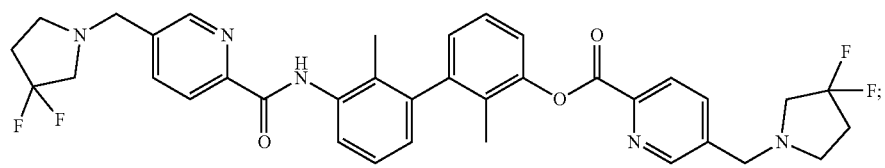

N-N'-(2,2'-dimethyl-[1,1'-biphenyl]-3,3'-diyl)bis(5-((3,3-difluuoropyrrolidin-1-yl)methyl)picolinamide)

-continued

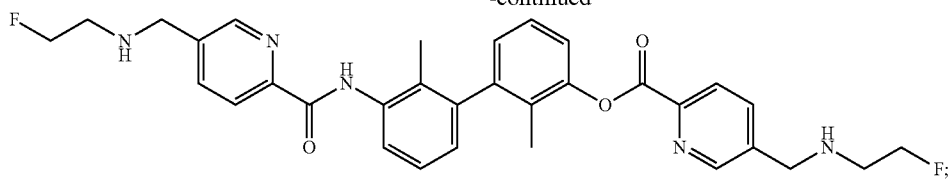

N-N'-(2,2'-dimethyl-[1,1'-biphenyl]-3,3'-diyl)bis(5-(((2-fluoroethyl)amino)methyl)picolinamide)

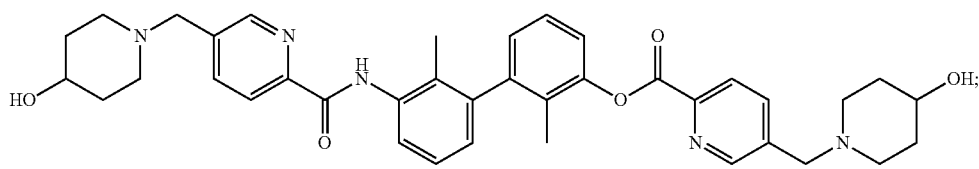

N-N'-(2,2'-dimethyl-[1,1'-biphenyl]-3,3'-diyl)bis(5-((4-hydroxypiperidin-1-yl)methyl)picolinamide)

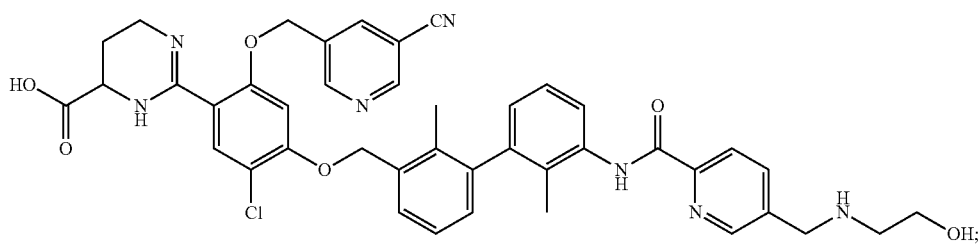

2-(5-chloro-2-((5-cyanopyridin-3-yl)methoxy)-4((3'-(5(((2-hydroxyethyl)amino)methyl)picolinamido)-2,2'-dimethyl-[1,1'-biphenyl]-3-yl)methoxy)phenyl)-3,4,5,6-tetrahydropyrimidine-4-carboxylic acid

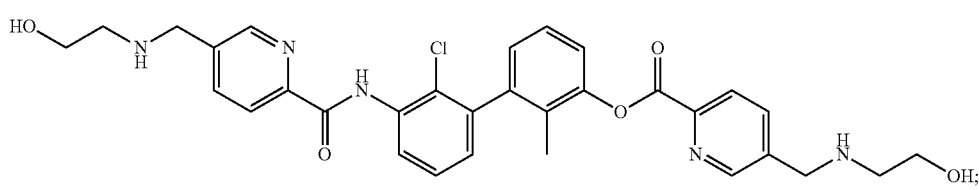

N-N'-(2-chloro-2'-methyl-[1,1'-biphenyl]-3,3'-diyl)bis(5-(((2-hydroxyethyl)amino)methyl)picolinamide)

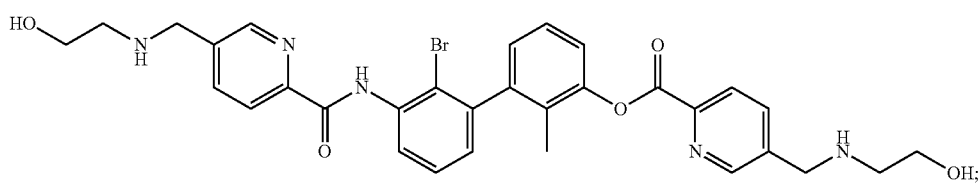

N-N'-(2-bromo-2'-methyl-[1,1'-biphenyl]-3,3'-diyl)bis(5-(((2-hydroxyethyl)amino)methyl)picolinamide)

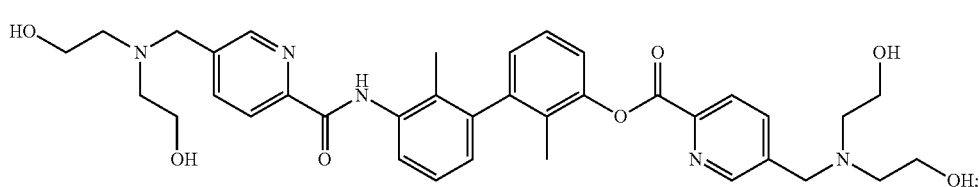

N-N'-(2-2'-dimethyl-[1,1'-biphenyl]-3,3'-diyl)bis(5-((bis(2-hydroxyethyl)amino)methyl)picolinamide)

-continued

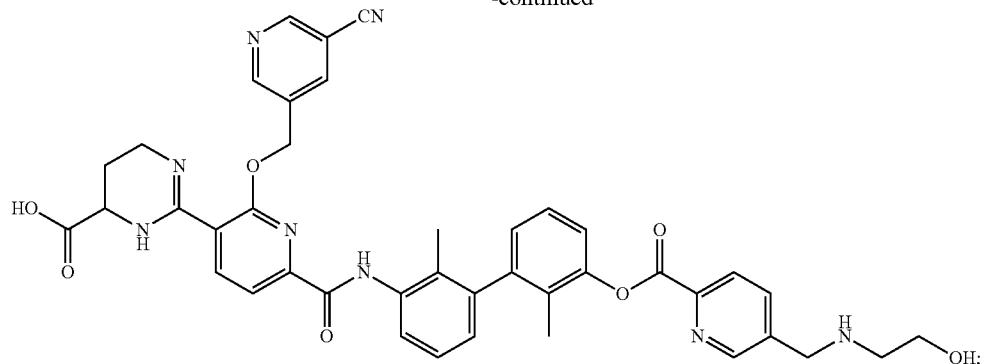

2-(2-((5-cyanopyridin-3-yl)methoxy)-6-((3'-(5(((2-hydroxyethyl)amino)mehyl)picolinamido)-2,2'-dimethyl-[1,1'-biphenyl]-3-yl)carbamoyl)pyridin-3-yl)-3,4,5,6-tetrahydropyrimidine-4-carboxylic acid

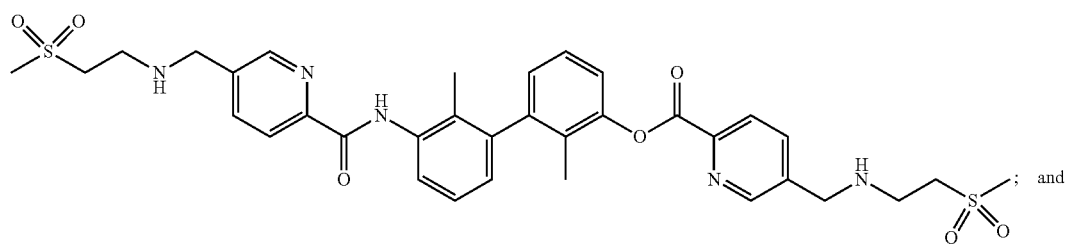

N-N'-(2,2'-dimethyl-[1,1'-biphenyl]-3,3'-diyl)bis(((2-(methylsulfonyl)ethyl)amino)methyl)picolinamide)

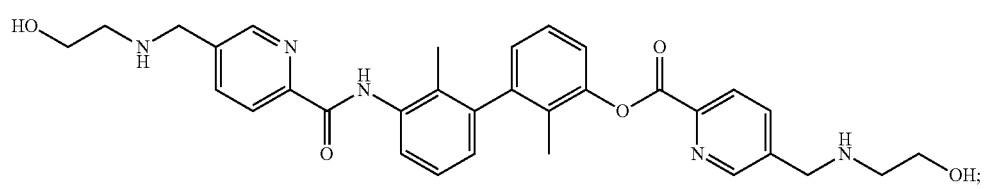

$N^3$-$N^{3'}$-bis(5-(((2-hydroxyethyl)amino)methyl)pyridin-2-yl)-2,2'-dimethyl-[1,1'-biphenyl]-3,3'-dicarboxamide or a salt, solvate, geometric isomer, stereoisomer, tautomer, and any mixtures thereof.

15. A pharmaceutical composition comprising the compound of claim 1 and at least one pharmaceutically acceptable carrier.

16. The pharmaceutical composition of claim 15, further comprising at least one additional agent that treats or prevents hepatitis virus infection, wherein the hepatitis virus is at least one selected from the group consisting of hepatitis B virus (HBV) and hepatitis D virus (HDV).

17. The pharmaceutical composition of claim 16, wherein the at least one additional agent comprises at least one selected from the group consisting of reverse transcriptase inhibitor, capsid inhibitor, cccDNA formation inhibitor, sAg secretion inhibitor, oligomeric nucleotide targeted to the Hepatitis B genome, immunostimulator, and RNA destabilizer.

18. A method of treating or ameliorating hepatitis B virus (HBV) infection in a subject, the method comprising administering to the subject in need thereof a therapeutically effective amount of the compound of claim 1, or a salt, solvate, prodrug, stereoisomer, tautomer, or any mixtures thereof.

19. The method of claim 18, wherein the subject is further infected with hepatitis D virus (HDV).

20. The method of claim 18, wherein the subject is further administered at least one additional agent useful for treating the hepatitis B virus infection.

21. The method of claim 20, wherein the at least one additional agent comprises at least one selected from the group consisting of reverse transcriptase inhibitor, capsid inhibitor, cccDNA formation inhibitor, sAg secretion inhibitor, oligomeric nucleotide targeted to the Hepatitis B genome, immunostimulator, and RNA destabilizer.

22. The method of claim 20, wherein the subject is co-administered the at least one compound and the at least one additional agent.

23. The method of claim 22, wherein the at least one compound and the at least one additional agent are coformulated.

24. The method of claim 18, wherein the subject is a mammal.

25. The method of claim 24, wherein the mammal is human.

26. A compound selected from the group consisting of:

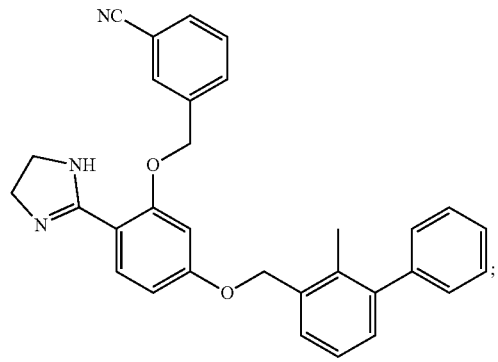

3-((2-(4,5-dihydro-1H-imidazol-2-yl)-5-((2-methyl-[1,1'-biphenyl]-3-yl)methoxy)phenoxy)methyl)benzonitrile

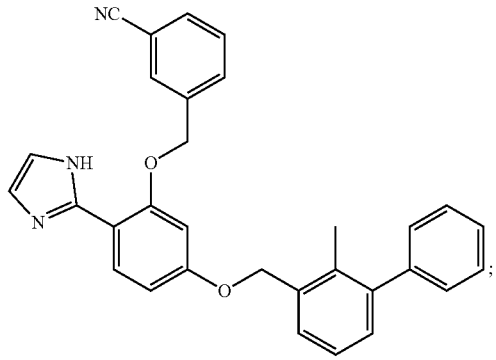

3-((2-(1H-imidazol-2-yl)-5-((2-methyl-[1,1'-biphenyl]-3-yl)methoxy)phenoxy)methyl)benzonitrile

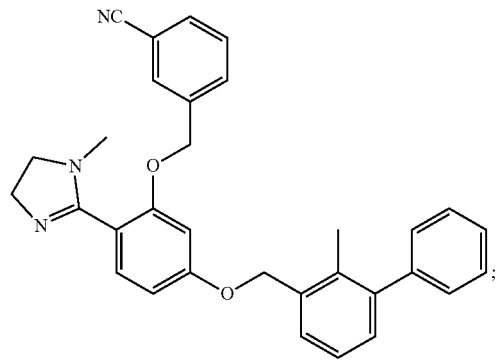

3-((2-(1-methyl-4,5-dihydro-1H-imidazol-2-yl)-5-((2-methyl-[1,1'-biphenyl]-3-yl)methoxy)phenoxy)methyl)benzonitrile

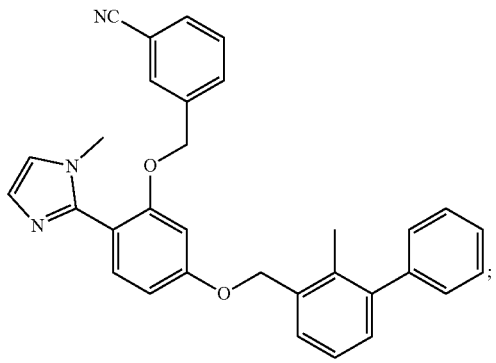

3-((2-(1-methyl-1H-imidazol-2-yl)-5-((2-methyl-[1,1'-biphenyl]-3-yl)methoxy)phenoxy)methyl)benzonitrile

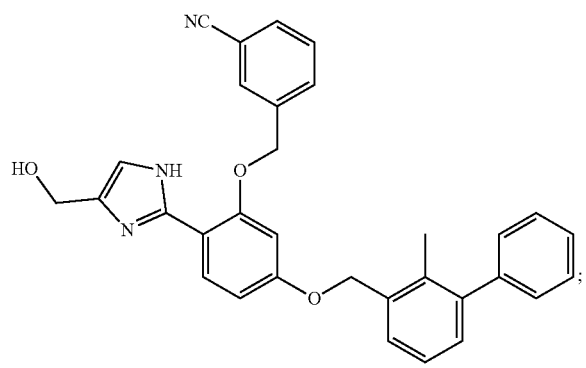

3-((2-(4-(hydroxymethyl)-1H-imidazol-2-yl)-5-((2-methyl-[1,1'-biphenyl]-3-yl)methoxy)phenoxy)methyl)benzonitrile

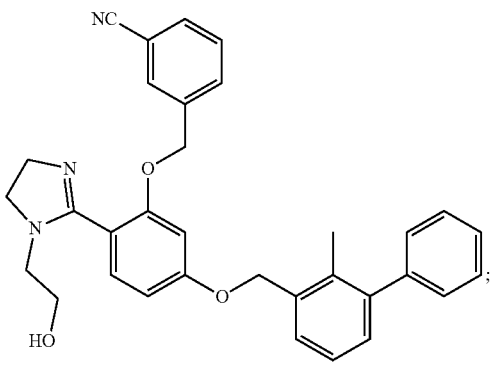

3-((2-(2-hydroxyethyl)-4,5-dihydro-1H-imidazol-2-yl)-5-((2-methyl-[1,1'-biphenyl]-3-yl)methoxy)phenoxy)methyl)benzonitrile

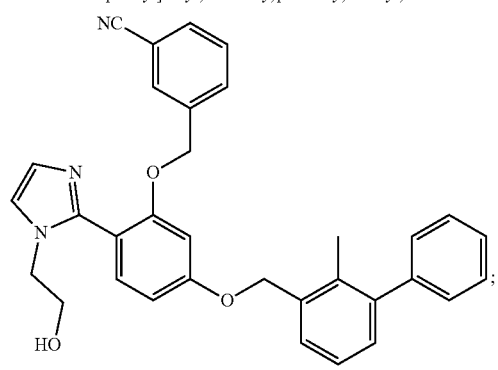

3-((2-(1-(2-hydroxyethyl)-1H-imidazol-2-yl)-5-((2-methyl-[1,1'-biphenyl]-3-yl)methoxy)phenoxy)methyl)benzonitrile

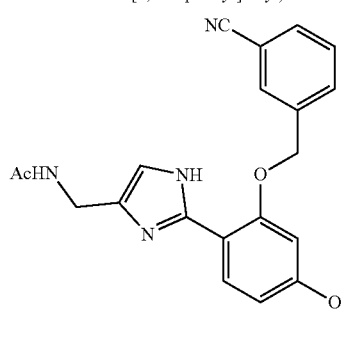

N-((2-(2-((3-cyanpbenzyl)oxy)-4-((2-methyl-[1,1'-biphenyl]-3-yl)methoxy)phenyl)-1H-imidazol-4-yl)methyl)acetamide -continued

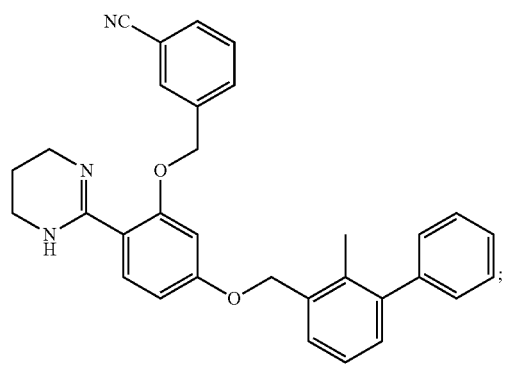

N-((5-(2-methyl-[1,1'-biphenyl]-3-yl)methoxy)-2-(1,4,5,6-tetrahydropyrimidin-2-yl)phenoxy)methyl)benzonitrile

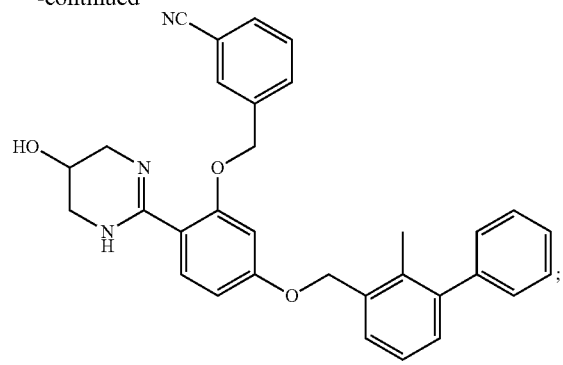

3-((2-(5-hydroxy-1,4,5,6-tetrahydropyrimidin-2-yl)-5-((2-methyl-[1,1'-biphenyl]-3-yl)methoxy)phenoxy)methyl)benzonitrile

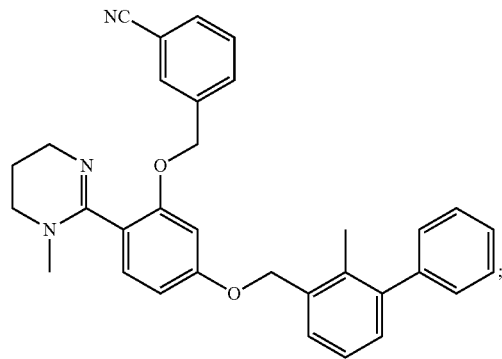

3-((2-(1-methyl-1,4,5,6-tetrahydropyrimidin-2-yl)-5-((2-methyl-[1,1'-biphenyl]-3-yl)methoxy)phenoxy)methyl)benzonitrile

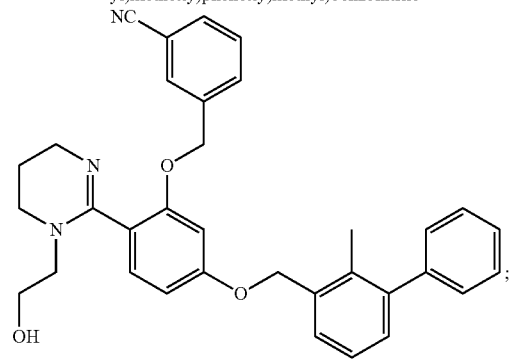

3-((2-(1-(2-hydroxyethyl-1,4,5,6-tetrahydropyrimidin-2-yl)-5-((2-methyl-[1,1'-biphenyl]-3-yl)methoxy)phenoxy)methyl)benzonitrile

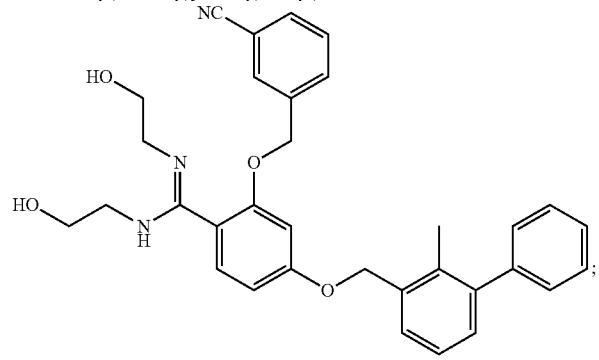

2-((3-cyanobenzyl)oxy)-N,N'-bis(2-hydroxyethyl)-4-((2-methyl-[1,1'-biphenyl]-3-yl)methoxy)benzimidamide

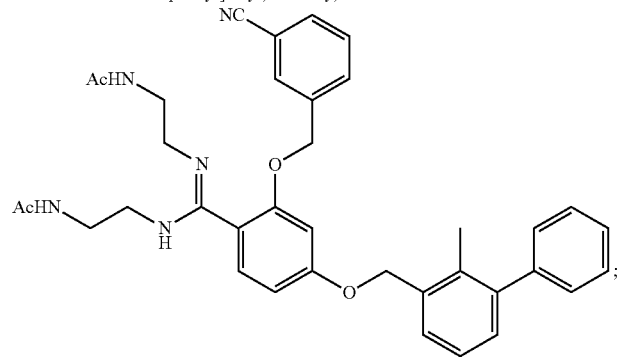

N-(2-(N'-(2-acetamidoethyl)-2-((3-cyanobenzyl)oxy)-4-((2-methyl-[1,1'-biphenyl]-3-yl)methoxy)benzimiamido)ethyl)acetamide

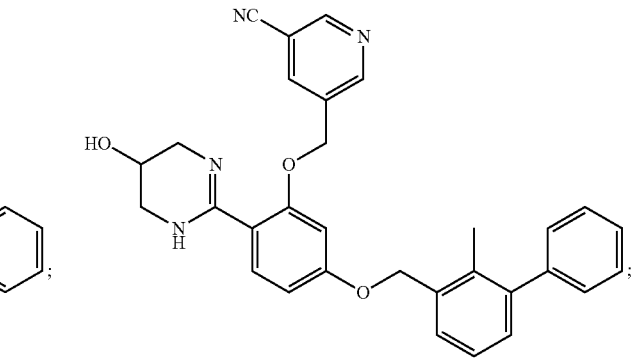

5-((2-(5-hydroxy-1,4,5,6-tetrahydropyrimidin-2-yl)-5-((2-methyl-[1,1'-biphenyl]-3-yl)methoxy)phenoxy)methyl)nicotinonitrile

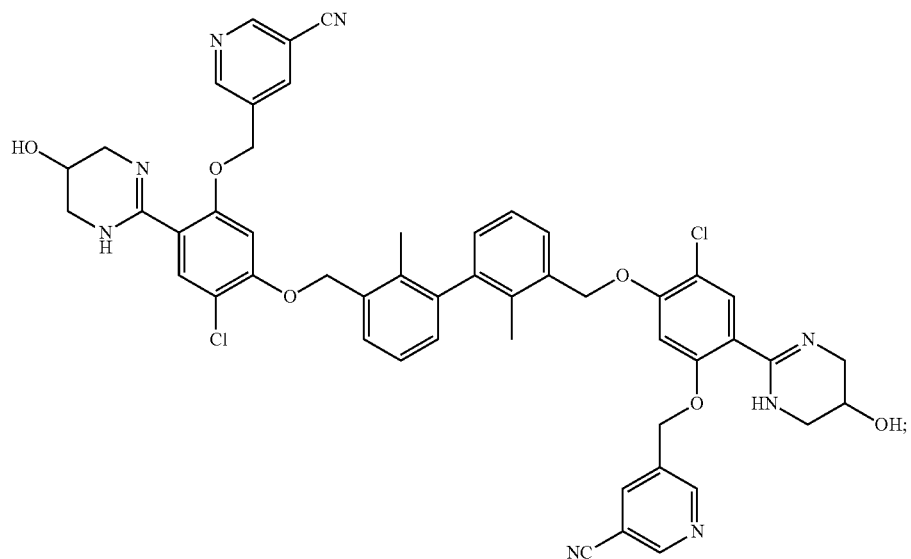

5,5'-((((((2,2'-dimethyl-[1,1'-biphenyl]-3,3'-diyl)bis(methylene)bis(oxy))bis(4-chloro-6-(5-hydroxy-1,4,5,6-tetrahydropyrimidin-2-yl)-3,1-phenylene))bis(oxy))bis(methylene))dinicotinonitrile

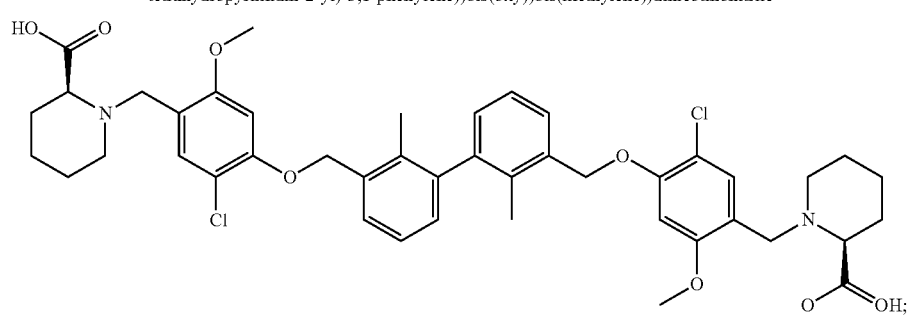

(2S,2'S)-1,1'-(((((2-2'-dimethyl-[1,1'-biphenyl]-3,3'-diyl)bis(methylene))bis(oxy))bis(5-chloro-2-methoxy-4,1-phenylene))bis(methylene))bis(piperidine-2-carboxylic acid)

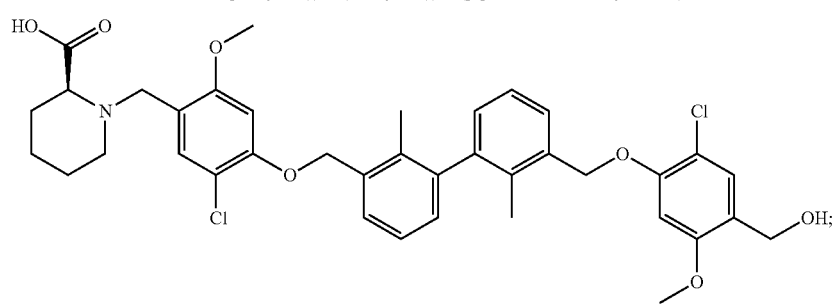

(S)-1-(5-chloro-4-((3'-((2-chloro-4-(hydroxymethyl)-5-methoxyphenoxy)methyl)-2,2'-dimethyl-[1,1'-biphenyl]-3-yl)methoxy)-2-methoxybenzyl)piperidine-2-carboxylic acid

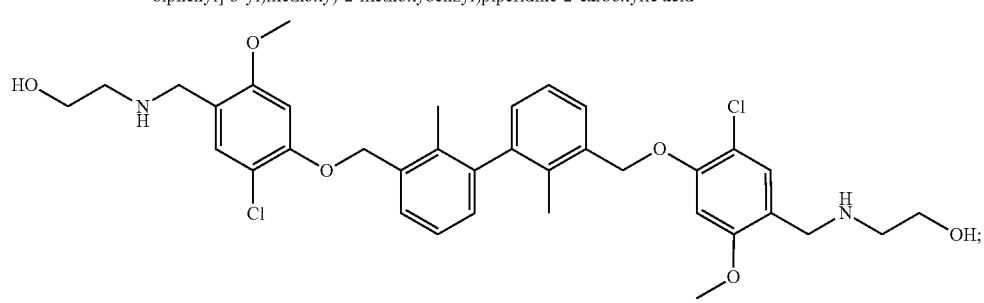

2-2'-((((((2,2'-dimethyl-[1,1'-biphenyl]-3,3'-diyl)bis)(methylene))bis(oxy))bis(5-chloro-2-methoxy-4,1-phenylene))bis(methylene))bis(azanediyl))bis(ethan-1-ol)

-continued

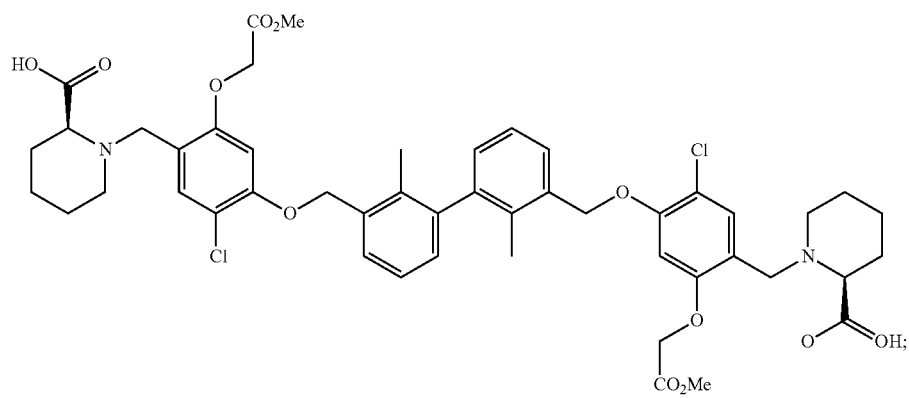

(2S,2'S)-1,1'-(((((2-2'-dimethyl-[1,1'-biphenyl]-3,3'-diyl)bis(methylene))bis(oxy)bis(5-chloro-2-(2-methoxy-2-oxoethoxy)-4,1-phenylene))bis(methylene))bis(piperidine-2-carboxylic acid)

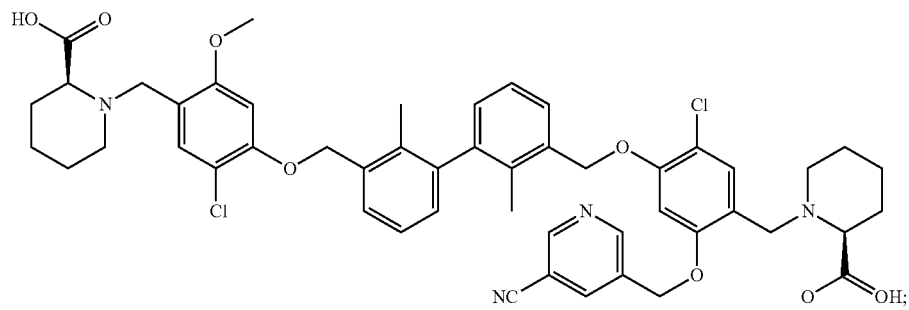

5-chloro-4-((3'-((2-chloro-5-((5-cyanopyridin-3-yl)methoxy)-4-(((2-hydroxyethyl)amino)methyl)phenoxy)methyl)-2,2'-dimethyl-[1,1'-biphenyl]-3-yl)methoxy)-2-((5-cyanopyridin-3-yl)methoxy)-N-(2-hydroxyethyl)benzamide

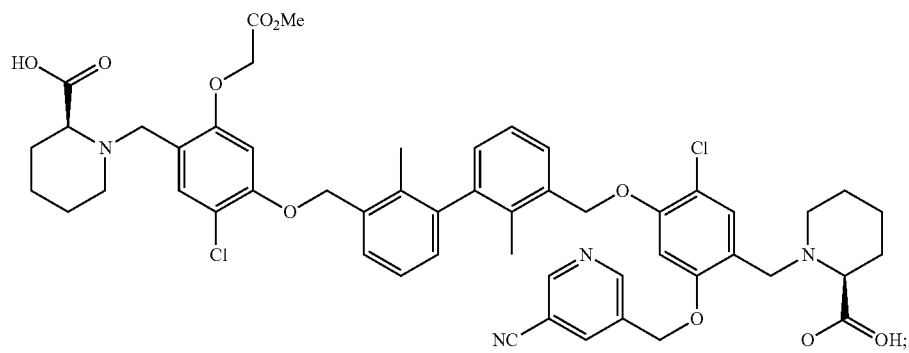

(S)-1-(4-((3'-((4-(((S)-2-carboxypiperidin-1-yl)methyl)-2-chloro-5-((5-cyanopyridin-3-yl)methoxy)phenoxy)methyl)-2,2'-dimethyl-[1,1'-biphenyl]-3-yl)methoxy)-5-chloro-2-(2-methoxy-2-oxoethyl)benzyl)piperidine-2-carboxylic acid

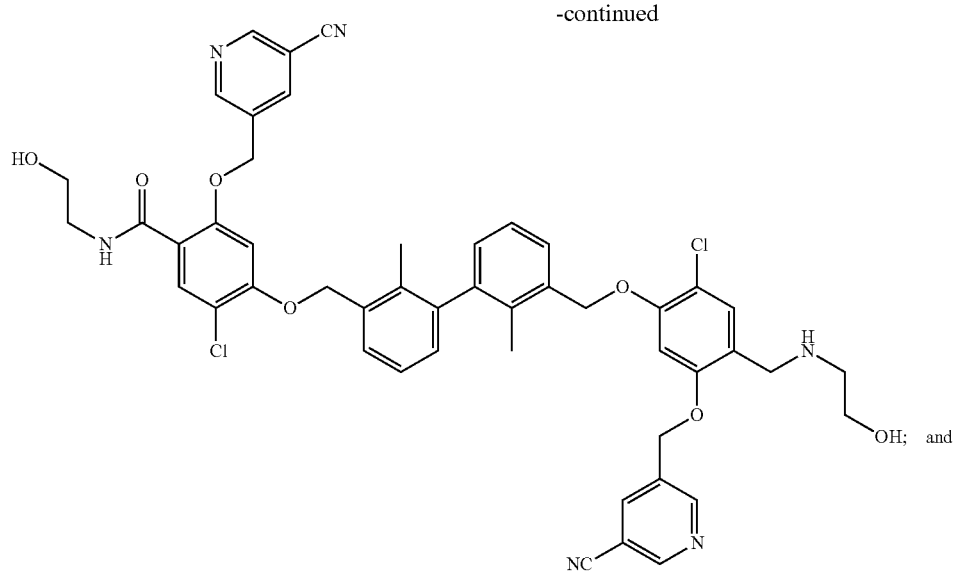

5-chloro-4-((3'-((2-chloro-5-((5-cyanopyridin-3-yl)methoxy)-4-(((2-hydroxyethyl)amino)methyl)phenoxy)methyl)-2,2'-dimethyl-[1,1'-biphenyl]-3-yl)methoxy)-2-((5-cyanopyridin-3-yl)methoxy)-N-(2-hydroxyethyl)benzamide

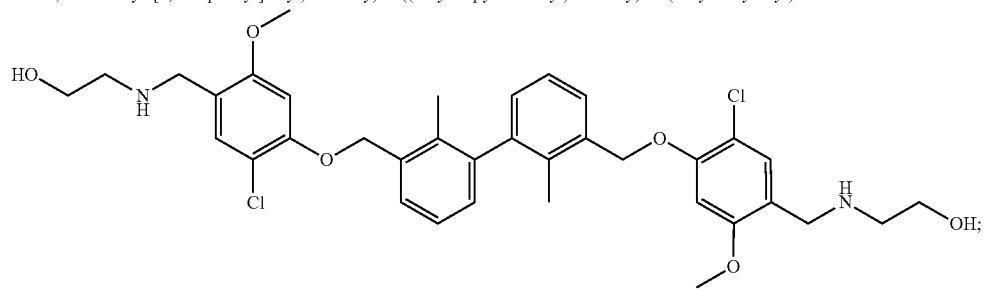

2-2'-((((((2,2'-dimethyl-[1,1'-biphenyl]-3,3'-diyl)bis(methylene))bis(oxy))bis(5-chloro-2-methoxy-4,1-phenylene))bis(methylene))bis(azanediyl))bis(ethan-1-ol)

or a salt, solvate, geometric isomer, stereoisomer, tautomer, and any mixtures thereof.

* * * * *